(12) United States Patent
So et al.

(10) Patent No.: US 10,913,975 B2
(45) Date of Patent: Feb. 9, 2021

(54) SPATIAL MAPPING OF NUCLEIC ACID SEQUENCE INFORMATION

(71) Applicant: ILLUMINA, INC., San Diego, CA (US)

(72) Inventors: Alex So, San Diego, CA (US); Li Liu, San Diego, CA (US); Min-Jui Richard Shen, San Diego, CA (US); Neeraj Salathia, San Diego, CA (US); Kathryn M. Stephens, San Diego, CA (US); Anne Jager, San Diego, CA (US); Timothy Wilson, San Diego, CA (US); Justin Fullerton, San Diego, CA (US); Sean M. Ramirez, San Diego, CA (US); Shannon Kaplan, San Diego, CA (US); Rigo Pantoja, San Diego, CA (US); Bala Murali Venkatesan, San Diego, CA (US); Steven Modiano, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 15/747,670

(22) PCT Filed: Jul. 21, 2016

(86) PCT No.: PCT/US2016/043385
§ 371 (c)(1),
(2) Date: Jan. 25, 2018

(87) PCT Pub. No.: WO2017/019456
PCT Pub. Date: Feb. 2, 2017

(65) Prior Publication Data
US 2018/0245142 A1    Aug. 30, 2018

Related U.S. Application Data

(60) Provisional application No. 62/197,389, filed on Jul. 27, 2015, provisional application No. 62/218,742,
(Continued)

(51) Int. Cl.
C12Q 1/68      (2018.01)
C12Q 1/6837    (2018.01)
(Continued)

(52) U.S. Cl.
CPC ......... *C12Q 1/6837* (2013.01); *C12Q 1/6816* (2013.01); *C12Q 1/6855* (2013.01);
(Continued)

(58) Field of Classification Search
CPC .............. C12Q 1/6837; C12Q 2543/10; C12Q 2565/514; C12Q 2565/543; C12Q 1/6816;
(Continued)

(56) References Cited

U.S. PATENT DOCUMENTS 5,985,549 A       11/1999  Singer et al.
2006/0177833 A1   8/2006   Brenner
(Continued)

FOREIGN PATENT DOCUMENTS

CN    102943107 A      2/2013
WO    2013150083 A1    10/2013
(Continued)

OTHER PUBLICATIONS

Crosetto Nicola et al: "Spatially resolved transcriptomics and beyond", Nature Reviews Genetics, vol. 16, No. 1, Jan. 2015 (Jan. 2015), pp. 57-66, XP002763989.
(Continued)

*Primary Examiner* — Betty J Forman
(74) *Attorney, Agent, or Firm* — Fletcher Yoder, PC

(57) ABSTRACT

Presented are methods and compositions for spatial detection and analysis of nucleic acids in a tissue sample. The methods can enable the characterization of transcriptomes
(Continued)

and/or genomic variations in tissues while preserving spatial information about the tissue.

7 Claims, 89 Drawing Sheets

Specification includes a Sequence Listing.

Related U.S. Application Data filed on Sep. 15, 2015, provisional application No. 62/250,329, filed on Nov. 3, 2015, provisional application No. 62/261,707, filed on Dec. 1, 2015, provisional application No. 62/269,614, filed on Dec. 18, 2015.

(51) Int. Cl.
*C12Q 1/6874* (2018.01)
*C12Q 1/6816* (2018.01)
*C12Q 1/6855* (2018.01)

(52) U.S. Cl.
CPC ...... *C12Q 1/6874* (2013.01); *C12Q 2539/115* (2013.01); *C12Q 2543/101* (2013.01); *C12Q 2565/514* (2013.01); *C12Q 2565/519* (2013.01); *C12Q 2565/543* (2013.01); *C12Q 2600/156* (2013.01)

(58) Field of Classification Search
CPC ............ C12Q 1/6874; C12Q 2539/115; C12Q 2565/519
See application file for complete search history.

(56) References Cited

U.S. PATENT DOCUMENTS

| | | | |
|---|---|---|---|
| 2010/0120098 A1 | 5/2010 | Grunenwald et al. | |
| 2011/0245111 A1* | 10/2011 | Chee | C12Q 1/6837 506/35 |
| 2012/0122737 A1* | 5/2012 | Sabot | C12Q 1/6806 506/26 |
| 2014/0066318 A1* | 3/2014 | Frisen | C12Q 1/6841 506/3 |
| 2014/0120534 A1 | 5/2014 | Bernitz et al. | |
| 2014/0194324 A1 | 7/2014 | Gormley et al. | |
| 2015/0072867 A1* | 3/2015 | Soldatov | B01J 19/0046 506/2 |
| 2015/0148239 A1 | 5/2015 | Peter et al. | |

FOREIGN PATENT DOCUMENTS

| | | |
|---|---|---|
| WO | WO2012140224 A1 | 10/2013 |
| WO | WO-2013150083 A1 * | 10/2013 |
| WO | WO2014060483 A1 | 4/2014 |
| WO | WO2014134144 A1 | 9/2014 |
| WO | WO2015058052 A1 | 4/2015 |

OTHER PUBLICATIONS

Li Song et al: "A Novel SNPs Detection Method Based on Gold Magnetic Nanoparticles Array and Single Base Extension", Theranostics, vol. 2, No. 10, 2012, pp. 967-975, XP002763990.

James Leary et al: "Nanobarcoding: detecting nanoparticles in biological samples using in situ polymerase chain reaction", International Journal of Nanomedicine, Nov. 1, 2012 (Nov. 1, 2012), p. 5625, XP055351802, DOI: 10.2147/IJN.S37433.

International Search dated May 4, 2017 in Application No. PCT/US2016/043385.

Chinese Office Action; CN Application No. 2013150083; dated Nov. 3, 2020.

Canadian Office Action; CA Application No. 2,993,463; date Nov. 12, 2020.

Australian Examination Report No. 2; AU Application No. 2019206067; dated Nov. 6, 2020.

* cited by examiner

2100

| 1 | 2 | 3 | 4 | 5 | 6 | 7 | 8 | 9 | 10 |
|---|---|---|---|---|---|---|---|---|---|
| 11 | 12 | 13 | 14 | 15 | 16 | 17 | 18 | 19 | 20 |
| 21 | 22 | 23 | 24 | 25 | 26 | 27 | 28 | 29 | 30 |
| 31 | 32 | 33 | 34 | 35 | 36 | 37 | 38 | 39 | 40 |
| 41 | 42 | 43 | 44 | 45 | 46 | 47 | 48 | 49 | 50 |
| 51 | 52 | 53 | 54 | 55 | 56 | 57 | 58 | 59 | 60 |
| 61 | 62 | 63 | 64 | 65 | 66 | 67 | 68 | 69 | 70 |
| 71 | 72 | 73 | 74 | 75 | 76 | 77 | 78 | 79 | 80 |
| 81 | 82 | 83 | 84 | 85 | 86 | 87 | 88 | 89 | 90 |
| 91 | 92 | 93 | 94 | 95 | 96 | 97 | 98 | 99 | 100 |

|  | Y1 | Y2 | Y3 | Y4 | Y5 | Y6 | Y7 | Y8 | Y9 | Y10 |
|---|---|---|---|---|---|---|---|---|---|---|
| X1 | X1+Y1 | X1+Y2 | X1+Y3 | X1+Y4 | X1+Y5 | X1+Y6 | X1+Y7 | X1+Y8 | X1+Y9 | X1+Y10 |
| X2 | X2+Y1 | X2+Y2 | X2+Y3 | X2+Y4 | X2+Y5 | X2+Y6 | X2+Y7 | X2+Y8 | X2+Y9 | X2+Y10 |
| X3 | X3+Y1 | X3+Y2 | X3+Y3 | X3+Y4 | X3+Y5 | X3+Y6 | X3+Y7 | X3+Y8 | X3+Y9 | X3+Y10 |
| X4 | X4+Y1 | X4+Y2 | X4+Y3 | X4+Y4 | X4+Y5 | X4+Y6 | X4+Y7 | X4+Y8 | X4+Y9 | X4+Y10 |
| X5 | X5+Y1 | X5+Y2 | X5+Y3 | X5+Y4 | X5+Y5 | X5+Y6 | X5+Y7 | X5+Y8 | X5+Y9 | X5+Y10 |
| X6 | X6+Y1 | X6+Y2 | X6+Y3 | X6+Y4 | X6+Y5 | X6+Y6 | X6+Y7 | X6+Y8 | X6+Y9 | X6+Y10 |
| X7 | X7+Y1 | X7+Y2 | X7+Y3 | X7+Y4 | X7+Y5 | X7+Y6 | X7+Y7 | X7+Y8 | X7+Y9 | X7+Y10 |
| X8 | X8+Y1 | X8+Y2 | X8+Y3 | X8+Y4 | X8+Y5 | X8+Y6 | X8+Y7 | X8+Y8 | X8+Y9 | X8+Y10 |
| X9 | X9+Y1 | X9+Y2 | X9+Y3 | X9+Y4 | X9+Y5 | X9+Y6 | X9+Y7 | X9+Y8 | X9+Y9 | X9+Y10 |
| X10 | X10+Y1 | X10+Y2 | X10+Y3 | X10+Y4 | X10+Y5 | X10+Y6 | X10+Y7 | X10+Y8 | X10+Y9 | X10+Y10 |

Figure 21B

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic probe"

<400> SEQUENCE: 1
caacgatcgt cgaaattcgc                                                  20

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic probe"

<400> SEQUENCE: 2
agatcggaag agcgtcgtgt a                                                21

SPATIAL MAPPING OF NUCLEIC ACID SEQUENCE INFORMATION

CROSS-REFERENCE TO RELATED APPLICATIONS

This application is a 371 National Stage Application of International Application No. PCT/US2016/043385, filed Jul. 21, 2016, which claims the benefit of Provisional Application No. 62/197,389, filed on Jul. 27, 2015, and claims the benefit of Provisional Application No. 62/218,742, filed Sep. 15, 2015, and claims the benefit of Provisional Application No. 62/250,329, filed Nov. 3, 2015, and claims the benefit of Provisional Application No. 62/261,707, filed on Dec. 1, 2015, and claims the benefit of Provisional Application No. 62/269,614, filed on Dec. 18, 2015, all of which are herein incorporated by reference in their entirety.

1. BACKGROUND

Existing techniques for the detection and analysis of nucleic acid (e.g., mRNA or genomic DNA) in a tissue sample typically provide spatial or localized information for one or limited number of genes at a time or provide information for all of the genes in the sample without the desired positional information. Recent interest has focused on the development of techniques that allow the characterization of transcriptomes and/or genomic variations in tissues while preserving spatial information about the tissue. There is a need for methods of characterizing nucleic acid in the context of a tissue sample.

2. SUMMARY

The present disclosure provides methods and compositions that facilitate the characterization of transcriptomes and/or genomic variation in tissues while preserving spatial information related to the origin of target nucleic acids in the tissue. For example, the methods disclosed herein can enable the identification of the location of a cell or a cell cluster in a tissue biopsy that carries an aberrant mutation. The methods provided herein can therefore be useful for diagnostic purposes, e.g., for the diagnosis of cancer, and possibly aid in the selection of targeted therapies.

The present disclosure provides a capture array for spatial detection and analysis of nucleic acids in a tissue sample, comprising a capture site comprising a pair of capture probes immobilized on a surface, wherein a first capture probe of the pair of capture probes comprises a first primer binding region and a spatial address region, and wherein a second capture probe of the pair of capture probes comprises a second primer binding region and a capture region.

The present disclosure also provides a method for spatial detection and analysis of nucleic acids in a tissue sample that includes (a) providing a capture array, comprising a capture site comprising a pair of capture probes immobilized on a surface, wherein a first capture probe of the pair of capture probes comprises a first primer binding region and a spatial address region, and wherein a second capture probe of the pair of capture probes comprises a second primer binding region and a capture region.

The present disclosure also provides a method for spatial detection and analysis of nucleic acids in a tissue sample that includes providing a magnetic nanoparticle comprising an immobilized capture probe comprising a capture region.

The present disclosure also provides a method for spatial detection and analysis of nucleic acids in a tissue sample that includes providing a magnetic nanoparticle comprising an immobilized capture probe comprising a capture region.

The present disclosure also provides a capture array for spatial detection and analysis of nucleic acids in a tissue sample, comprising a capture site comprising a capture probe comprising a spatial address region, and a transposon end (TE) region.

The present disclosure also provides a method for spatial detection and analysis of nucleic acids in a tissue sample that includes providing a capture array comprising a capture site comprising a capture probe comprising a spatial address region and a transposon end (TE) region.

3. BRIEF DESCRIPTION OF THE DRAWINGS

Figure 14:
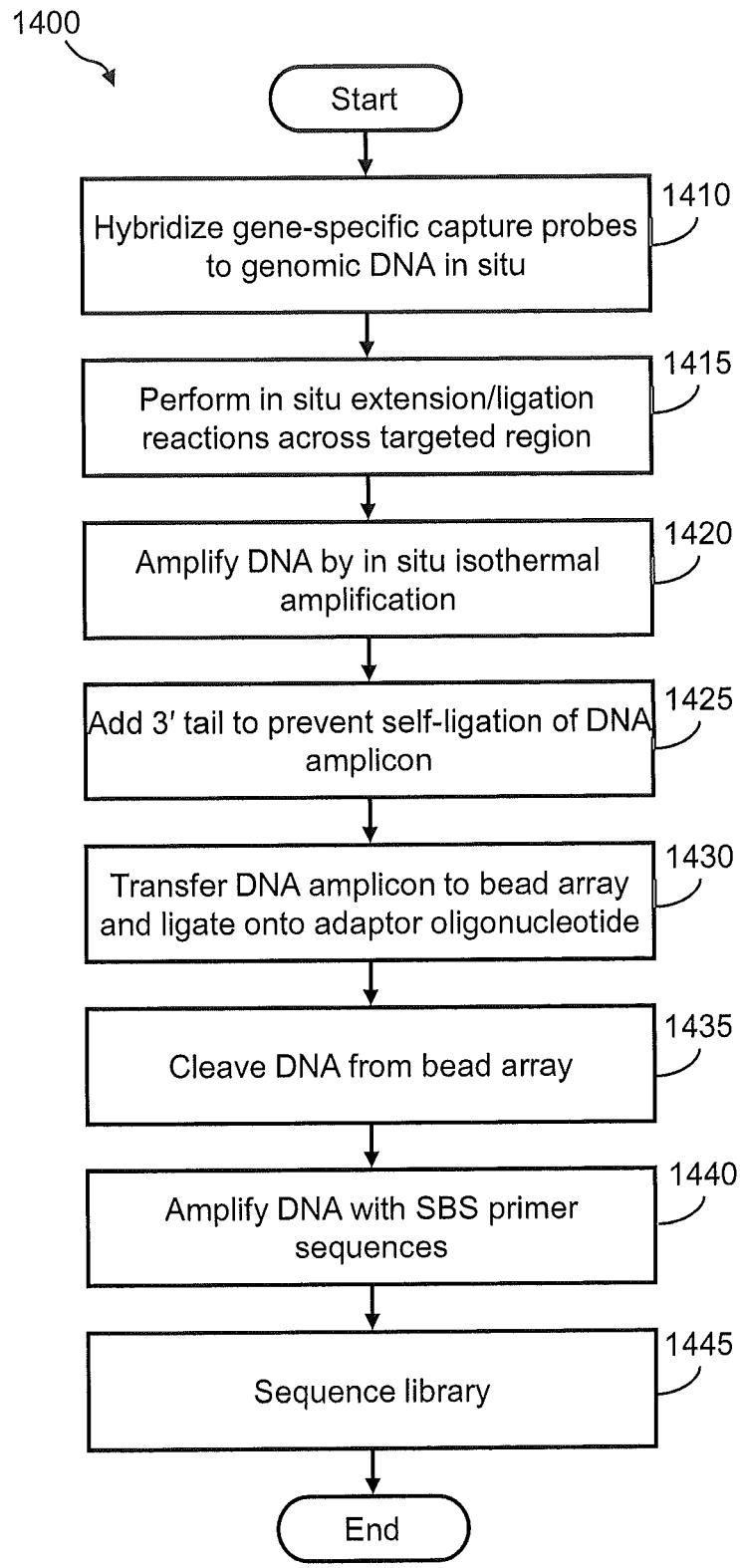
FIG. 14 illustrates a flow diagram of an exemplary embodiment of a method of capturing DNA amplicons onto an array, wherein the DNA amplicons are generated by in situ amplification of target nucleic acid.
Figure 15A:
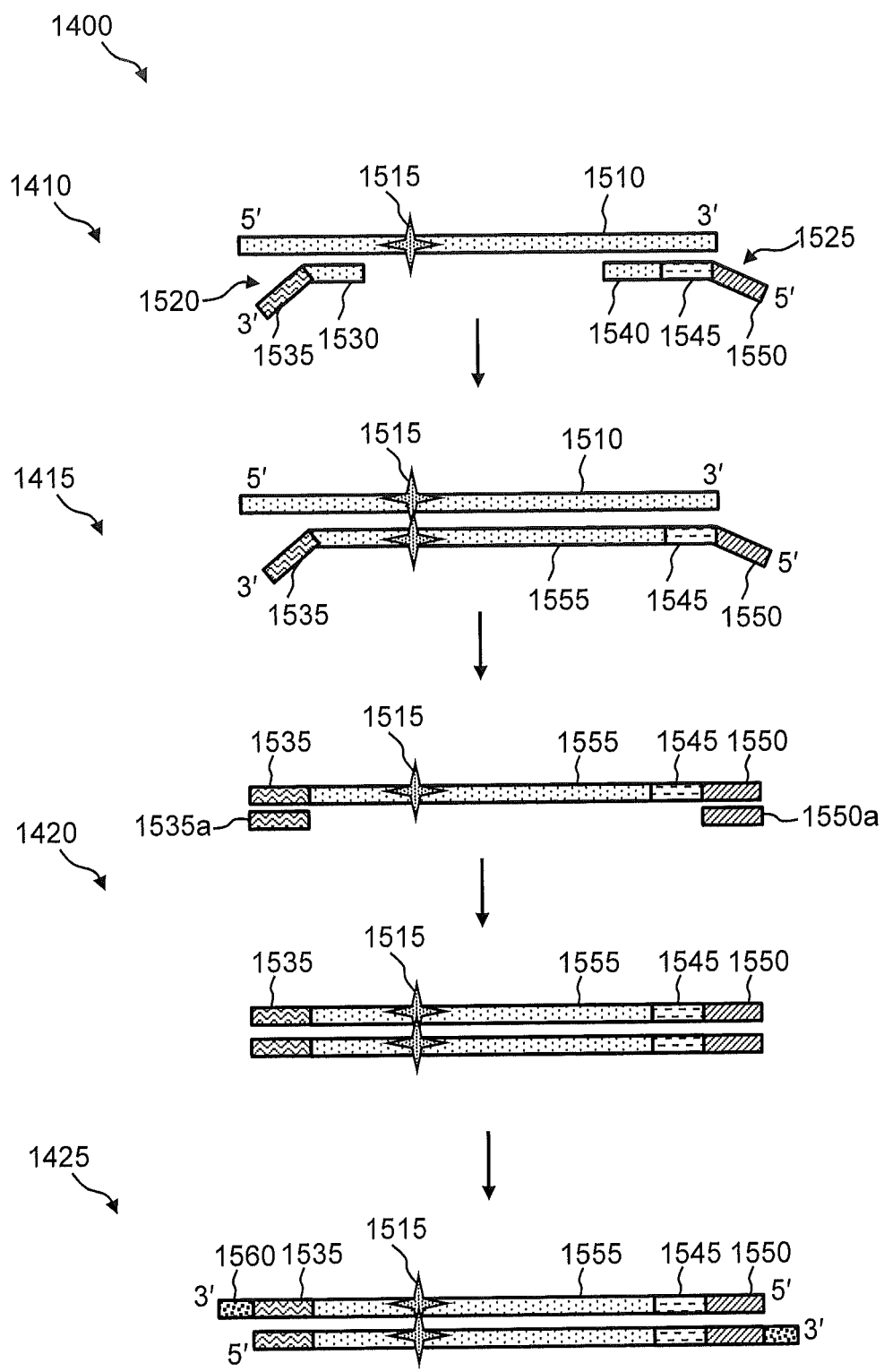
Figure 15B:
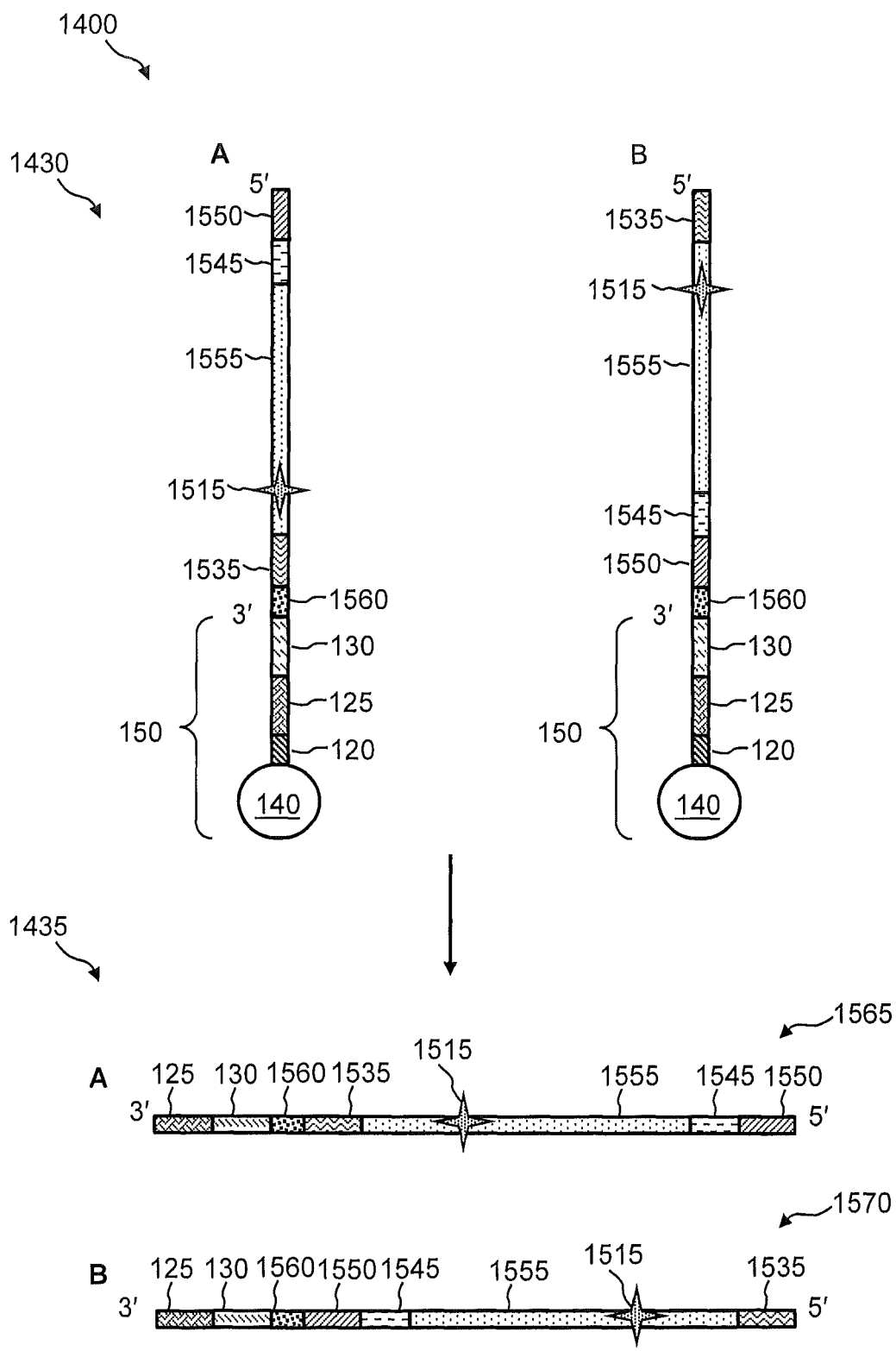
Figure 15C:
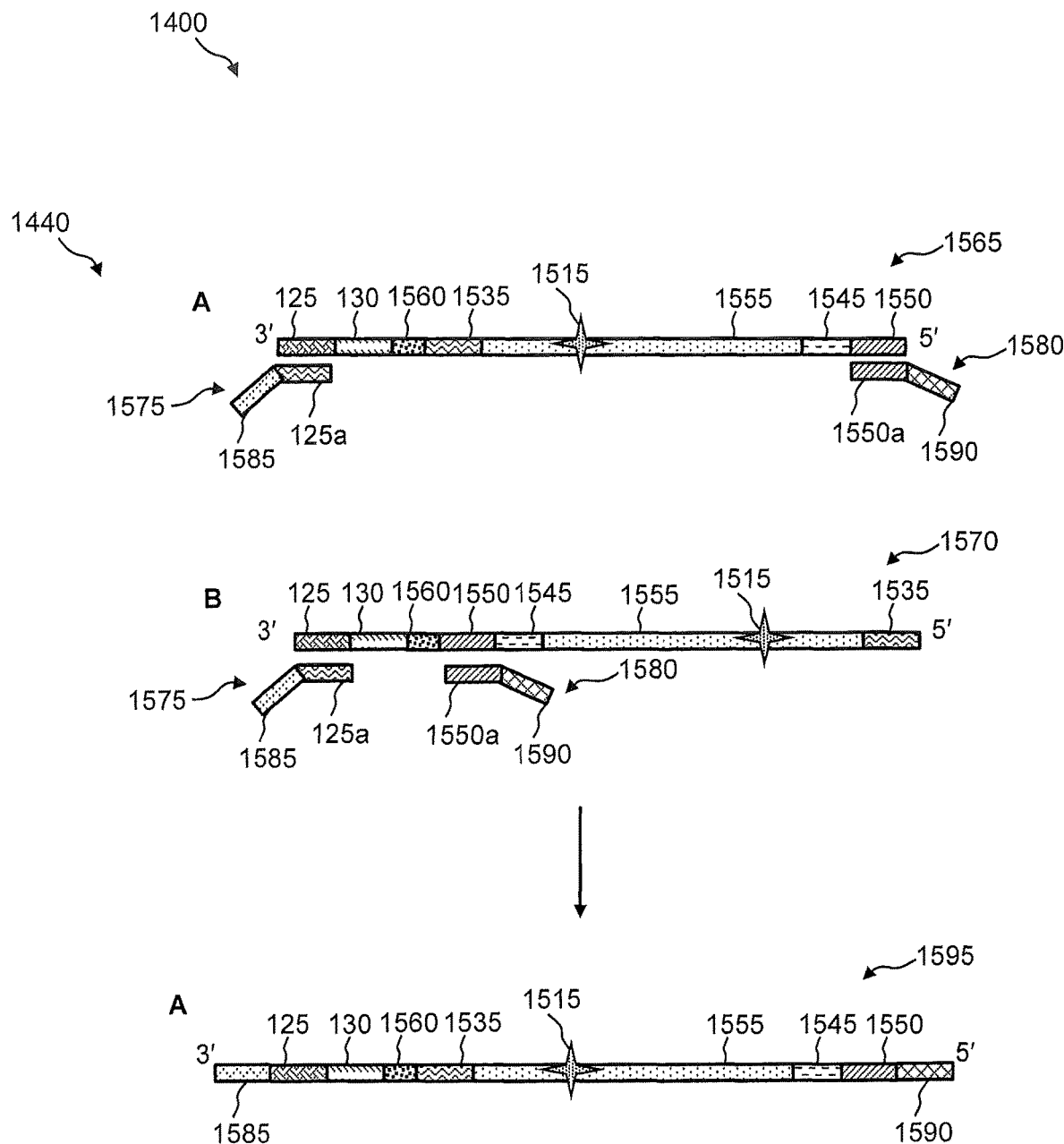

FIGS. 15A, 15B, and 15C illustrate the steps of a method of FIG. 14.

Figure 16:
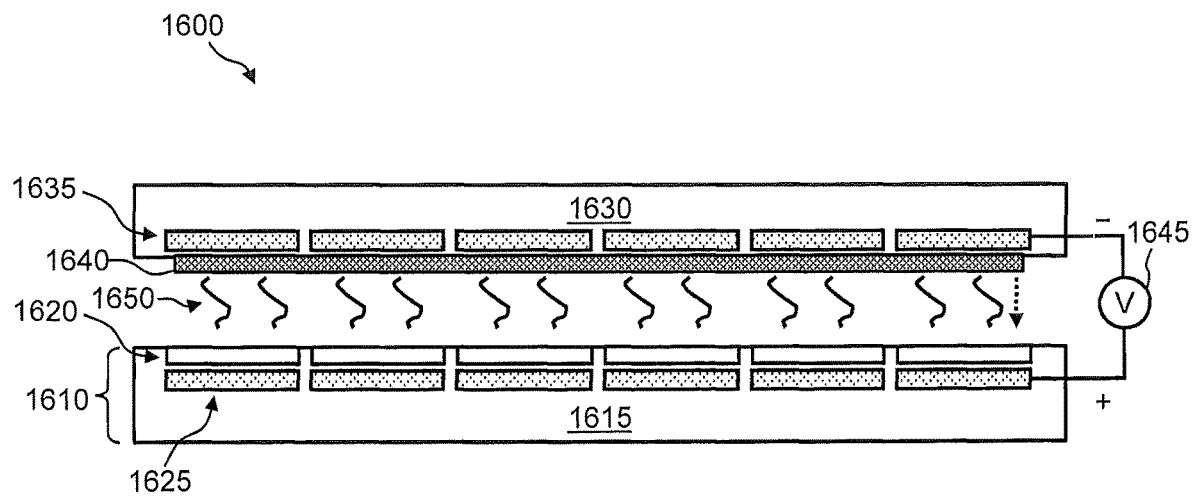

FIG. 16 illustrates a side view of a portion of an electrophoretic transfer system that is configured for spatial detection and analysis of nucleic acid in a tissue sample.

Figure 17:
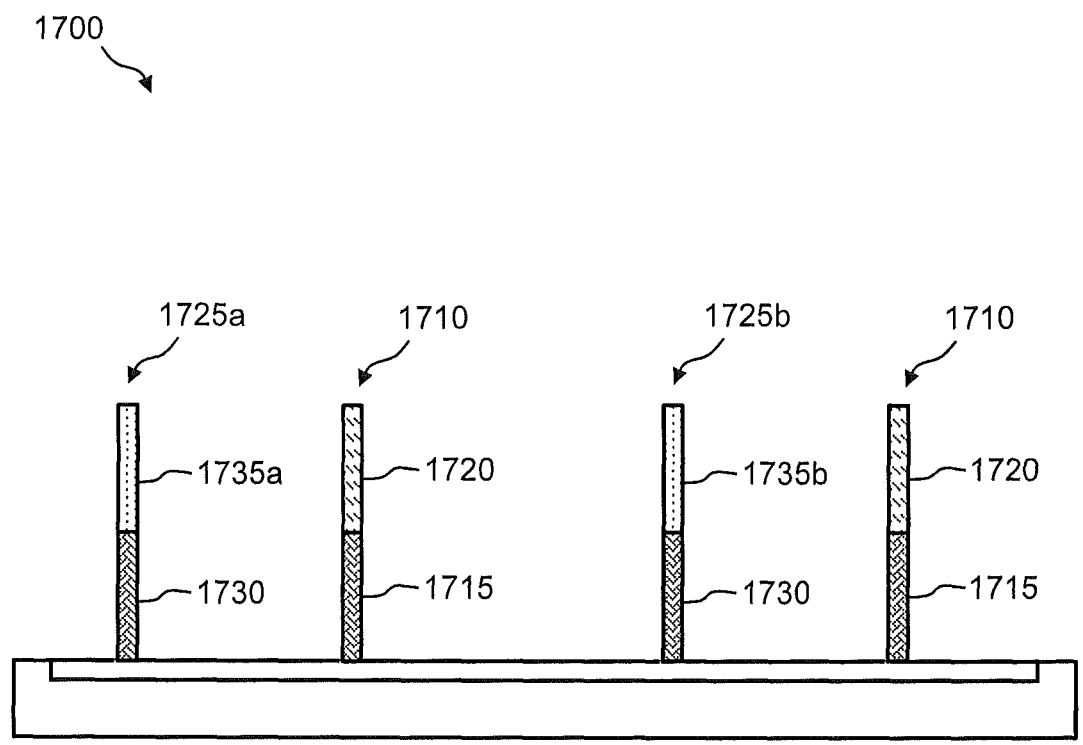

FIG. 17 illustrates a side view of one capture site on a capture array (e.g., the capture array of FIG. 1A), wherein the one capture site comprises two separate sets of immobilized capture probes.

Figure 18:
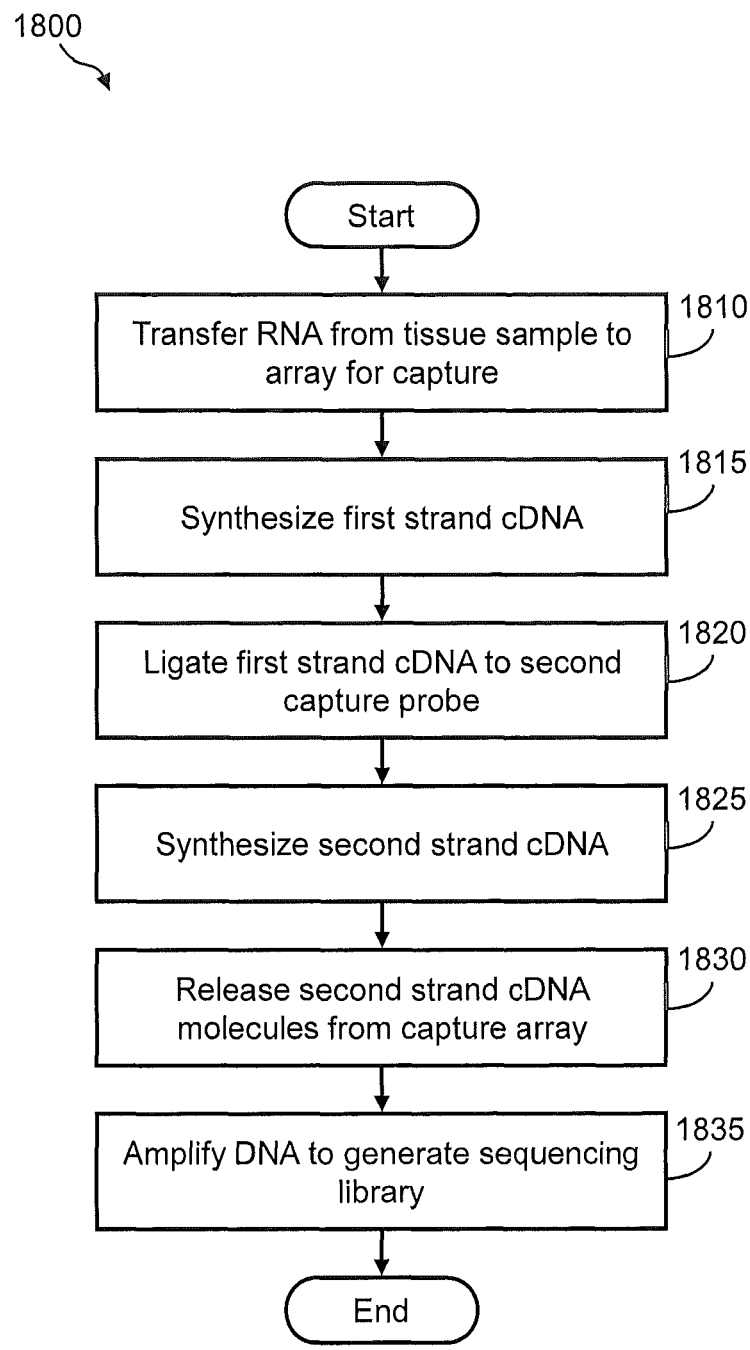
Figure 19A:
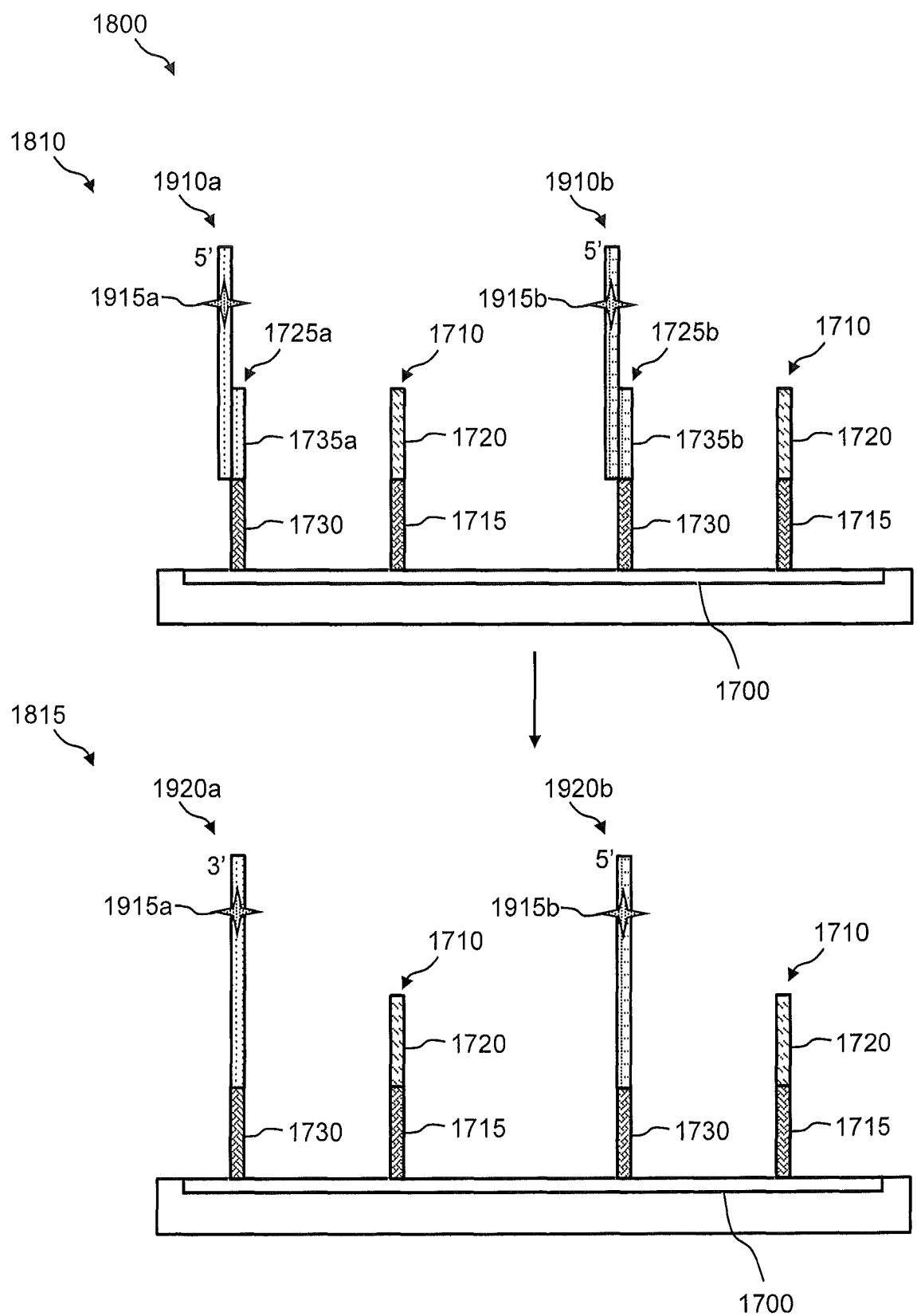
Figure 19B:
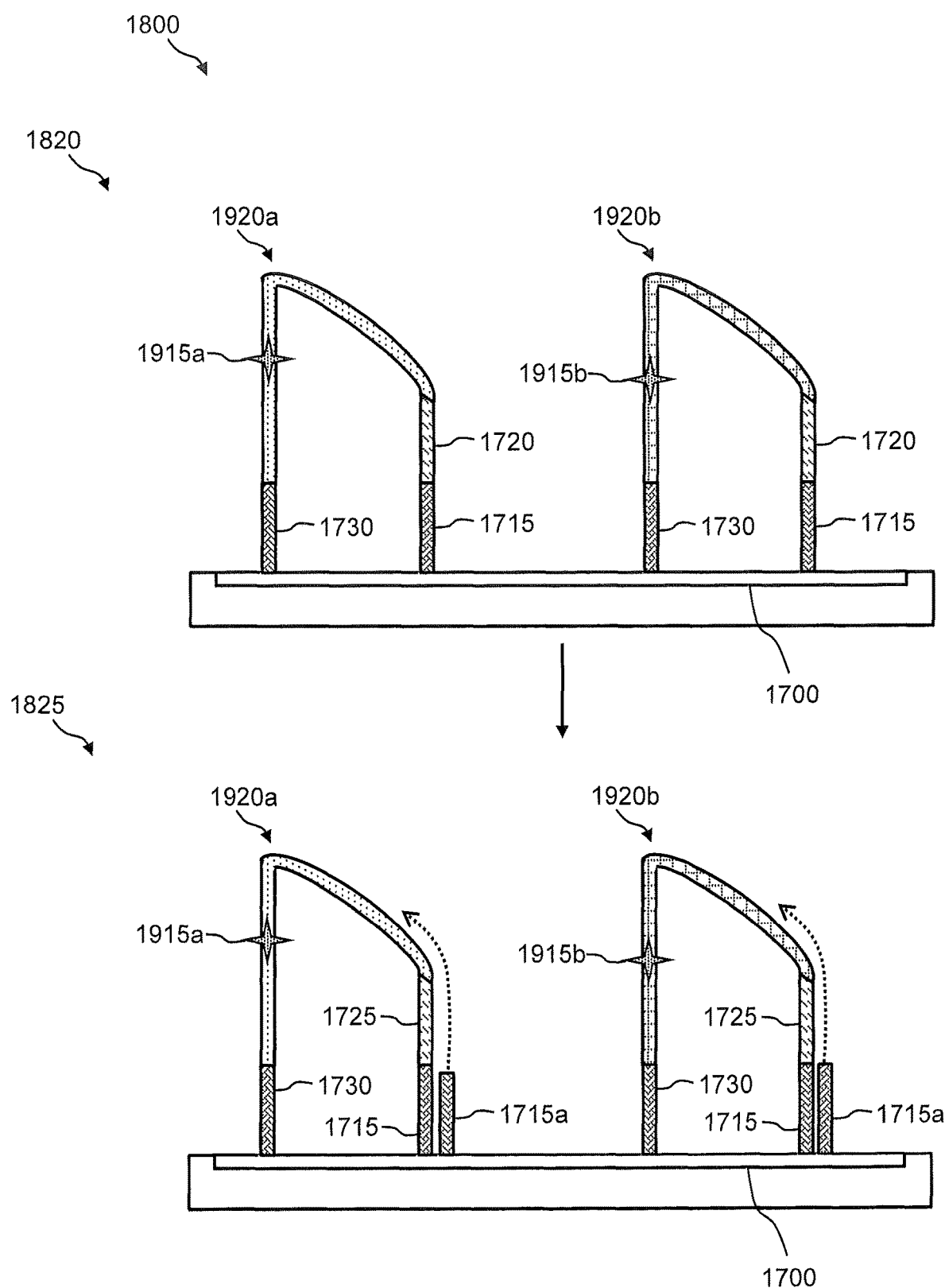
Figure 19C:
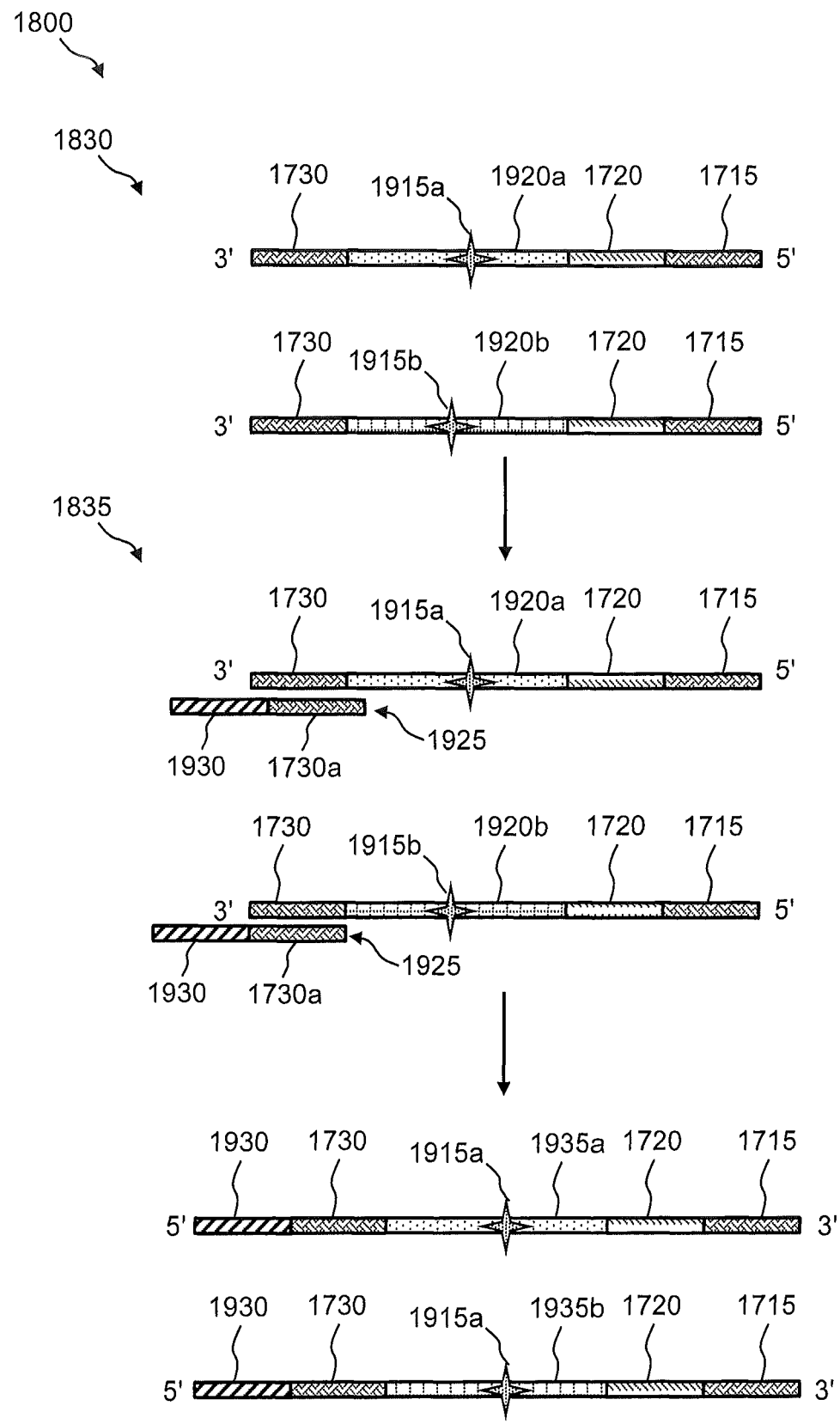
Figure 19D:
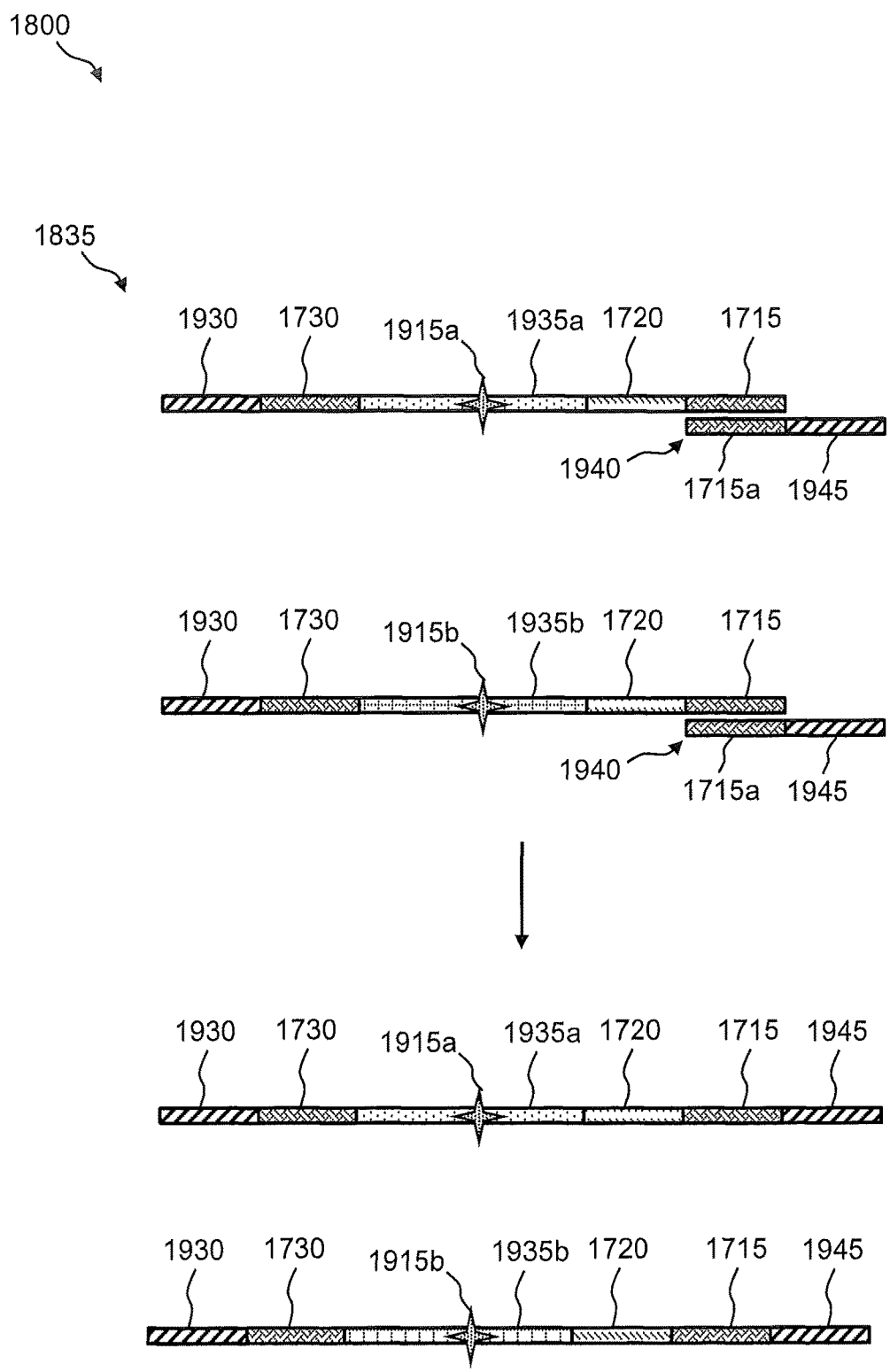

FIG. 18 illustrates a flow diagram of an embodiment of a method of transferring nucleic acids from a tissue sample to a capture array for generation of a spatially addressed sequencing library, wherein the capture array comprises capture sites that include separate pairs of immobilized capture probes, e.g., as shown in FIG. 17.

FIGS. 19A, 19B, 19C, and 19D illustrate the steps of the method of FIG. 18.

Figure 20:
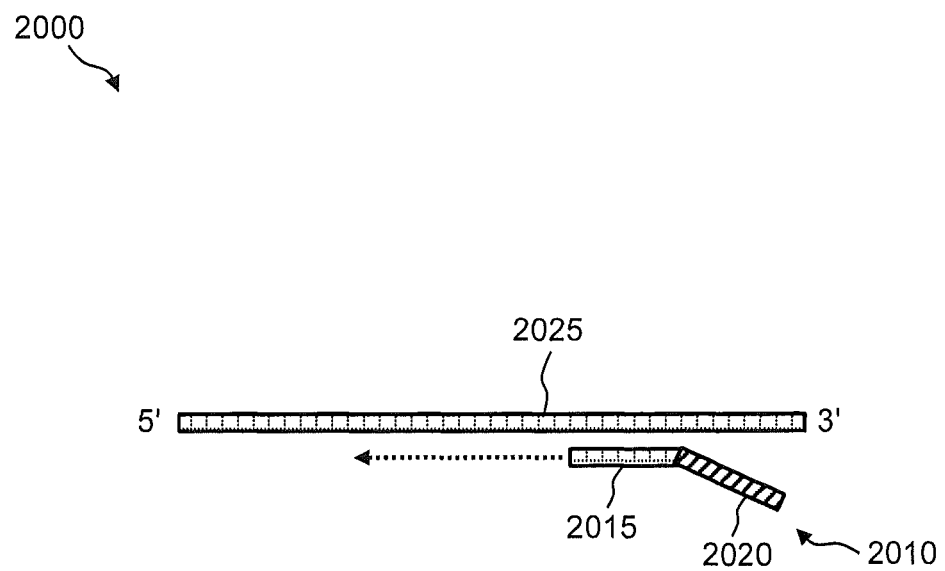

FIG. 20 shows an exemplary embodiment of a process of capturing a nucleic acid in a tissue sample for subsequent anchoring onto an array.

FIGS. 21A and 21B illustrate a grid array of a one-dimensional indexing scheme and a grid array of a two-dimensional indexing scheme, respectively, for spatial detection and analysis of nucleic acids in a tissue sample.

Figure 22:
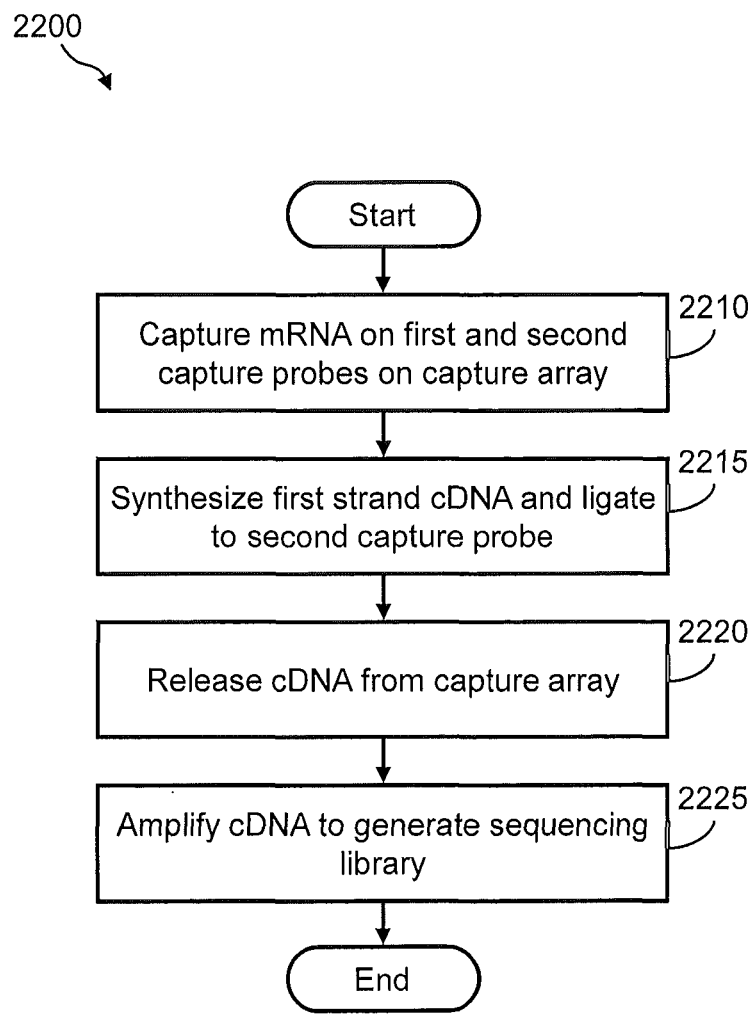

FIG. 22 illustrates a flow diagram of an exemplary embodiment of a method of using a combinatorial indexing system for generation of a spatially addressed cDNA sequencing library.

Figure 23A:
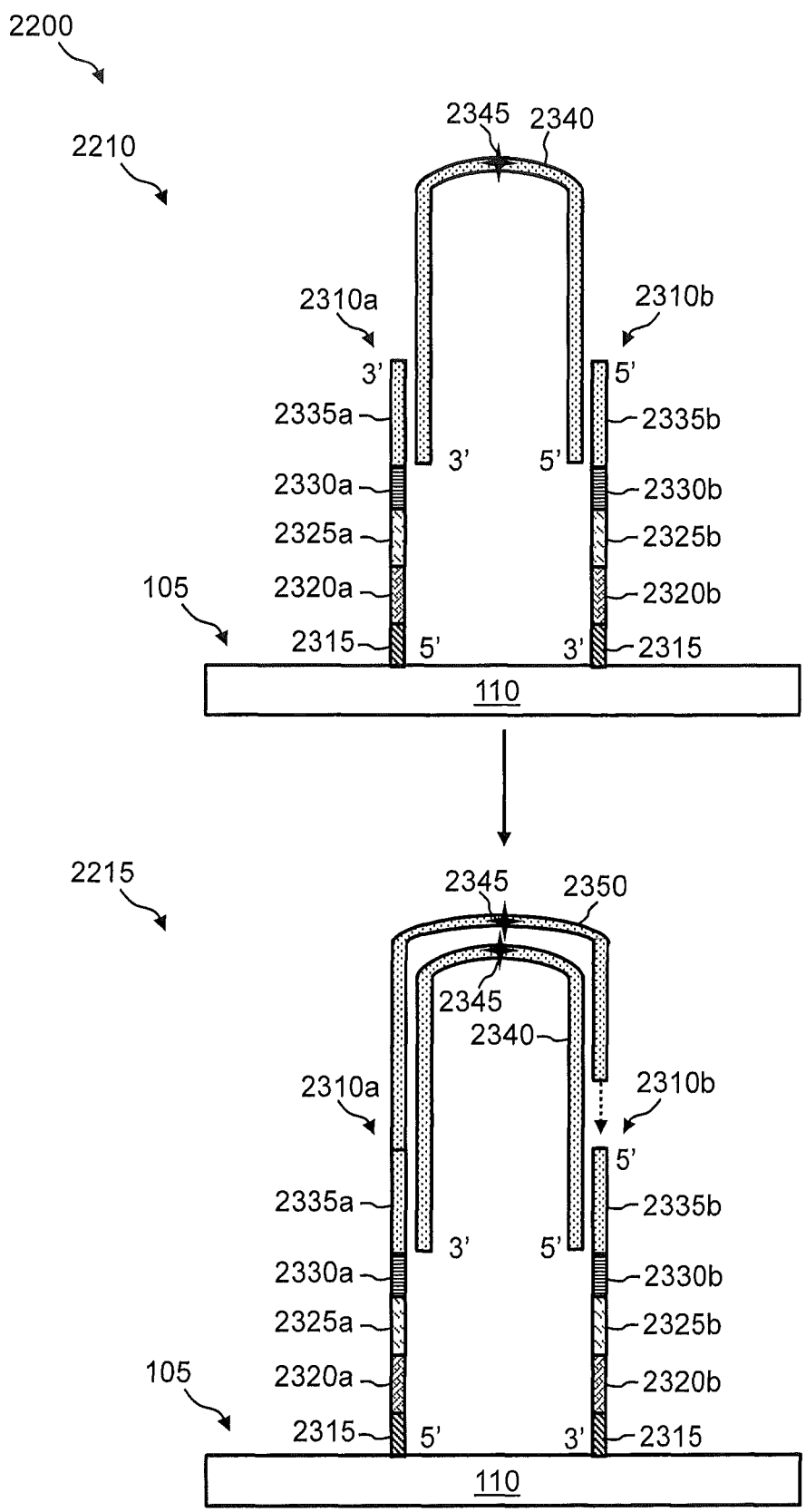
Figure 23B:
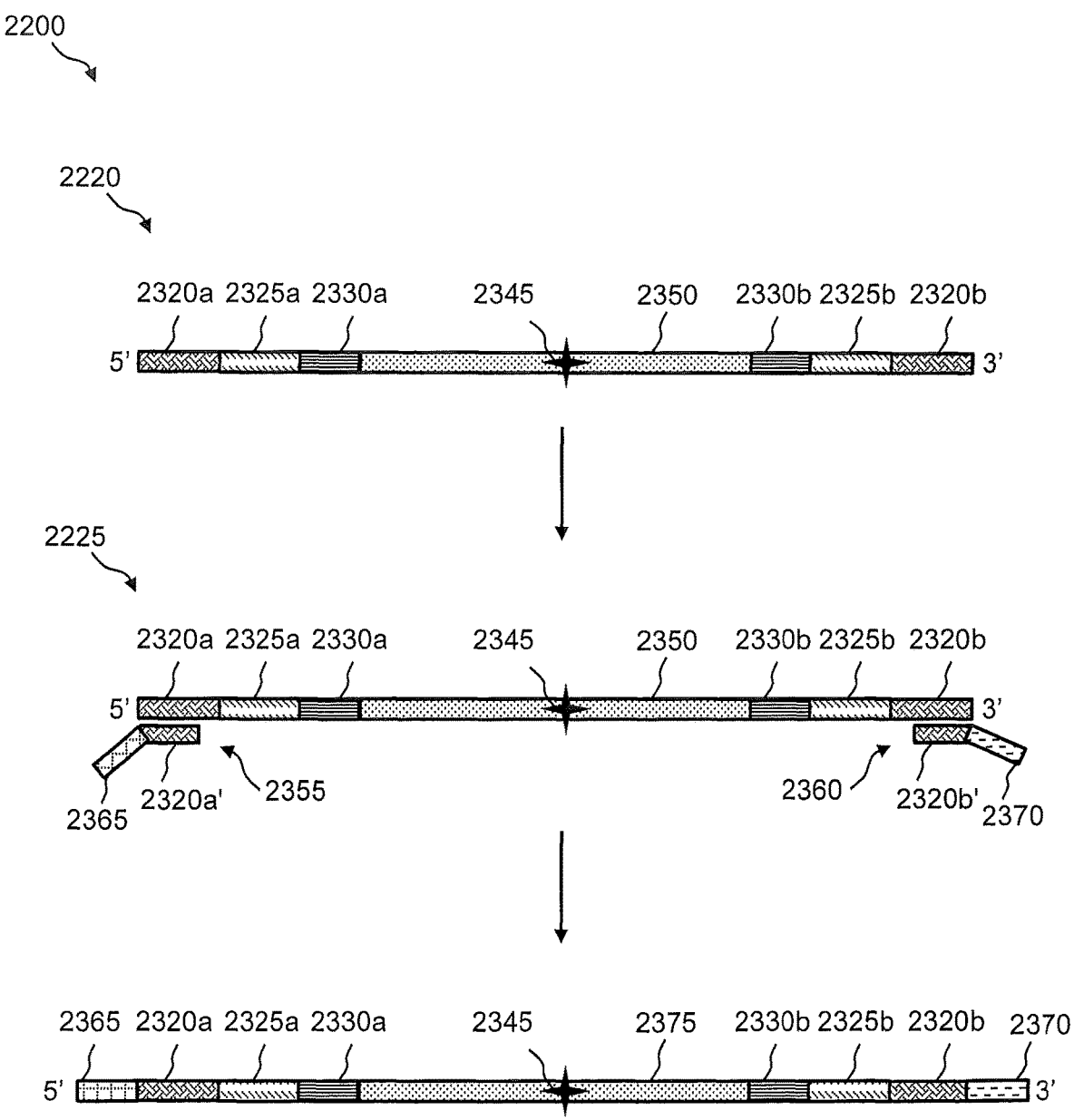

FIGS. 23A and 23B illustrate the steps of a method of FIG. 21.

Figure 24:
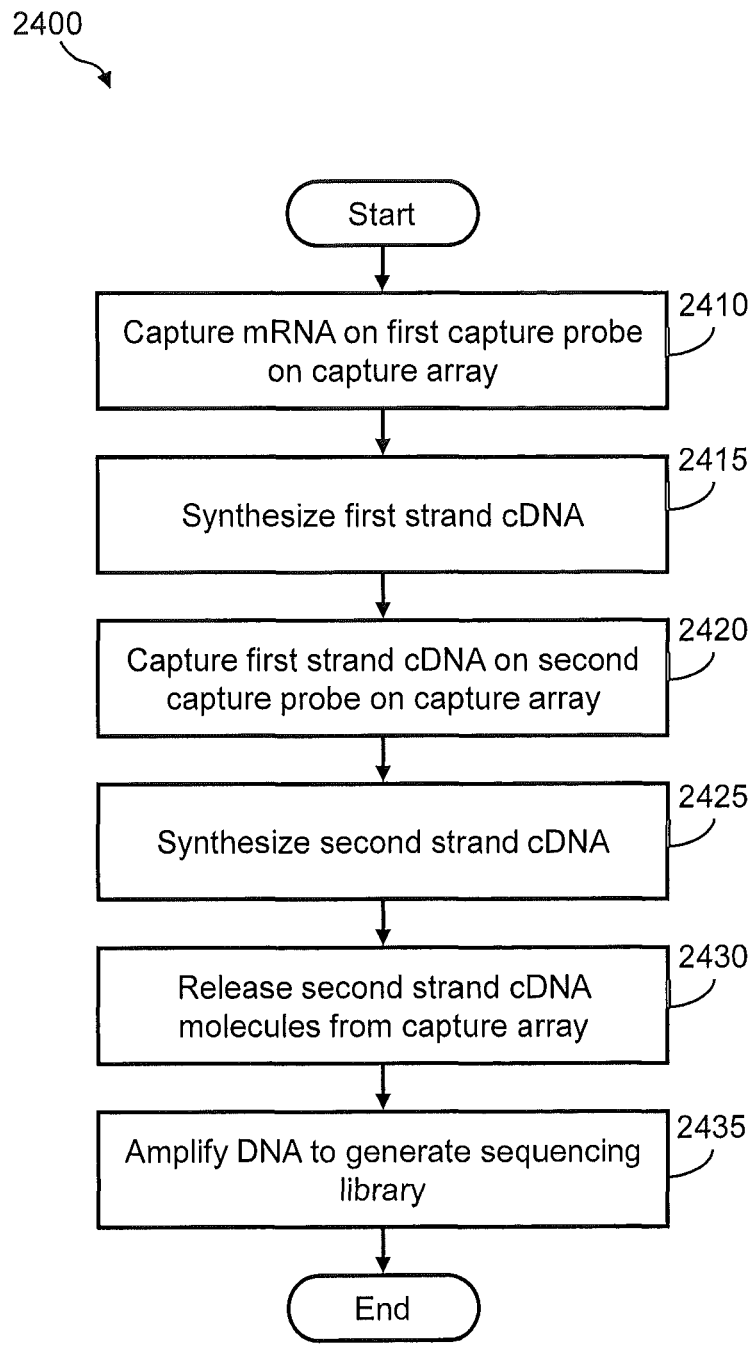

FIG. 24 illustrates a flow diagram of an exemplary embodiment of an alternative method of using a combinatorial indexing system for generation of a spatially addressed cDNA sequencing library.

Figure 25A:
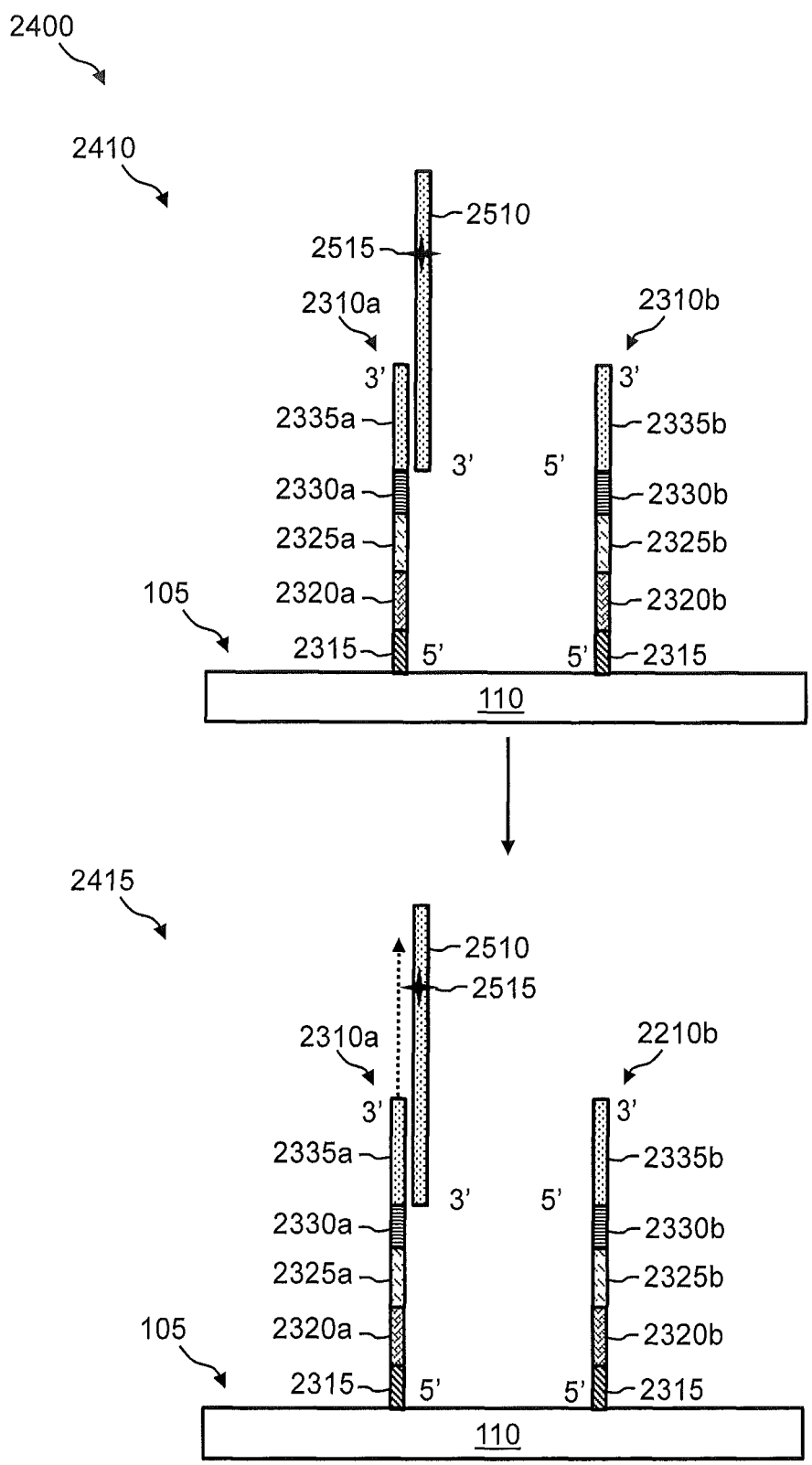
Figure 25B:
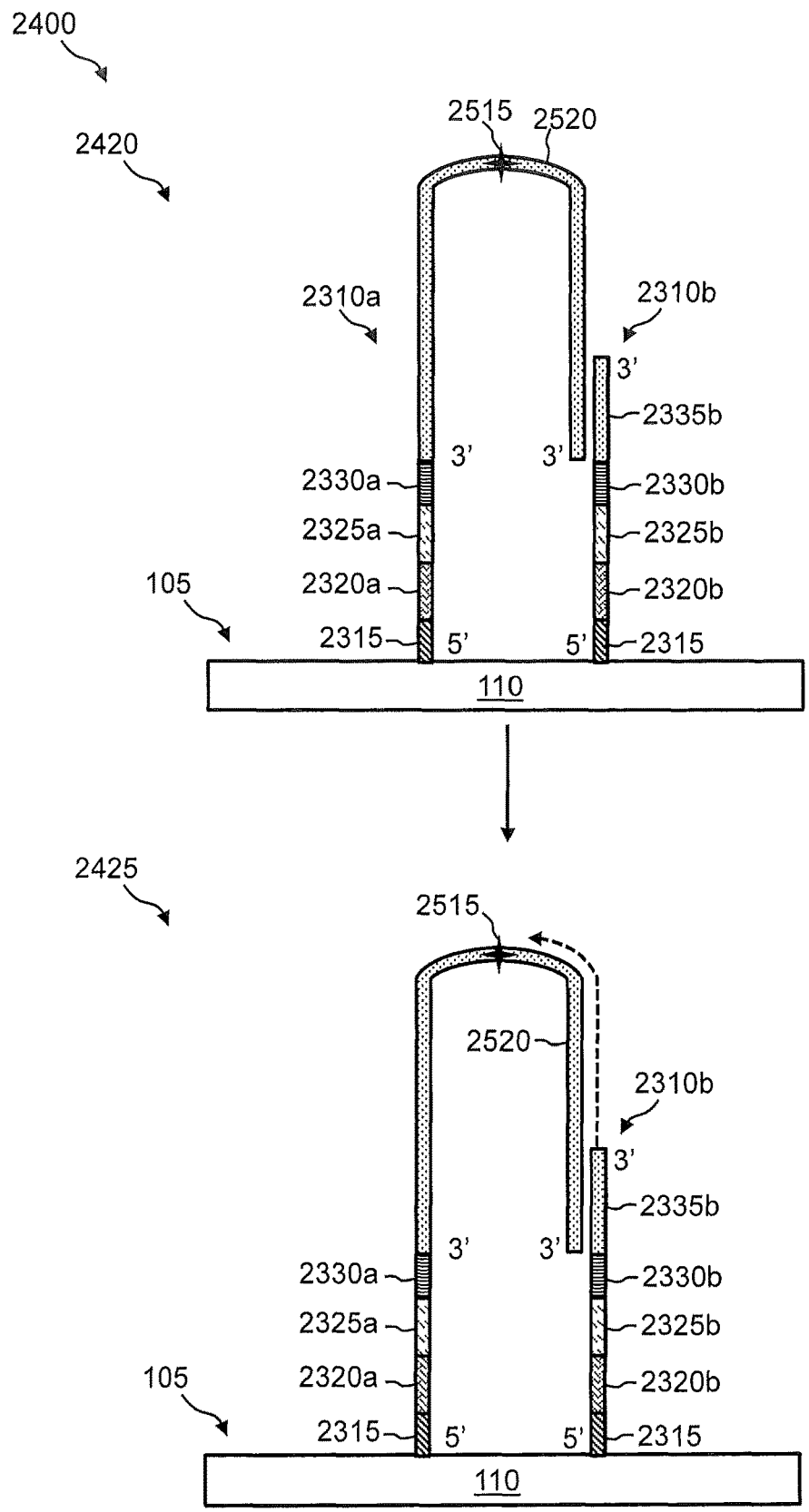
Figure 25C:
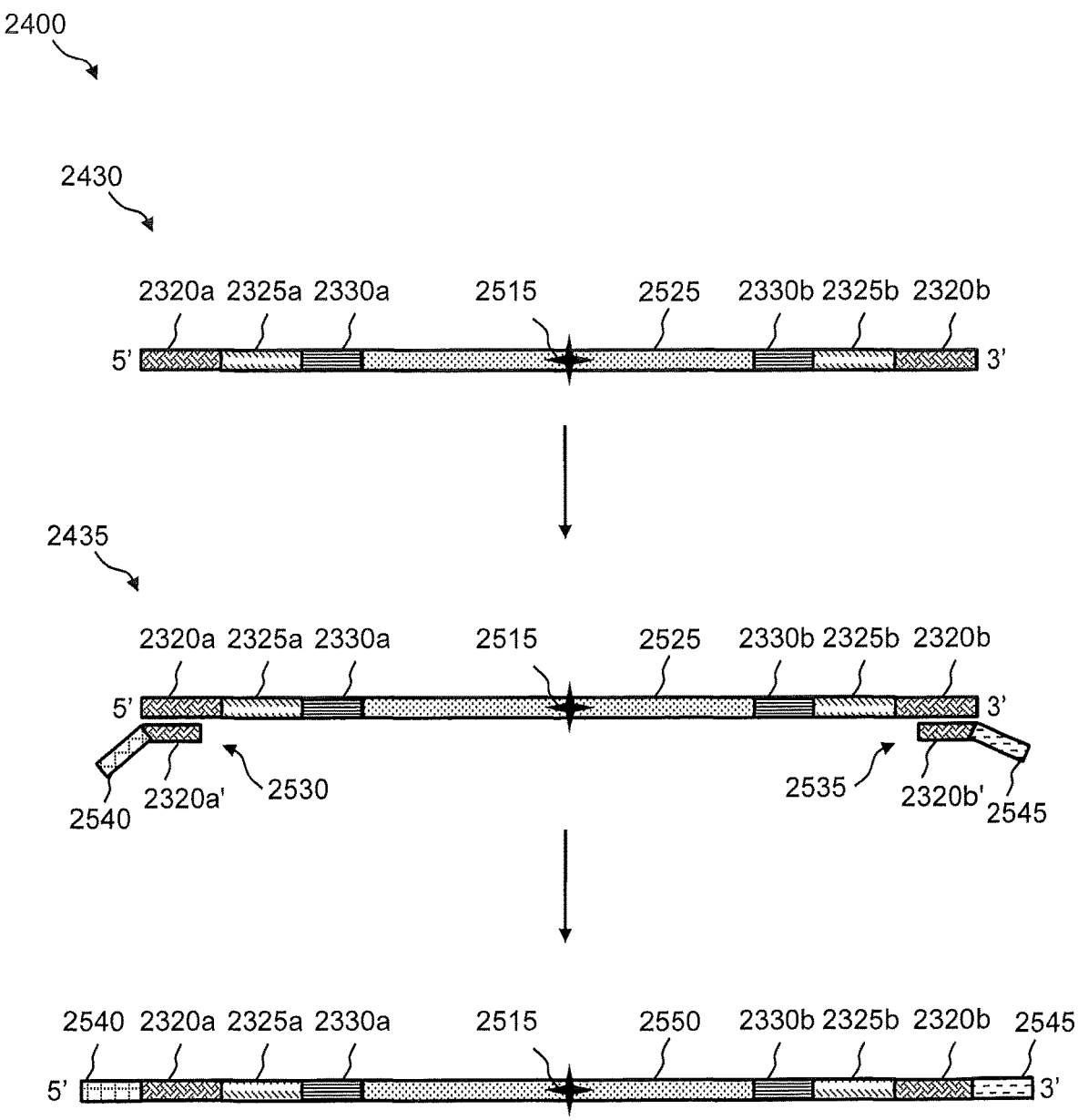

FIGS. 25A, 25B, and 25C illustrate the steps of a method of FIG. 24.

Figure 26A:
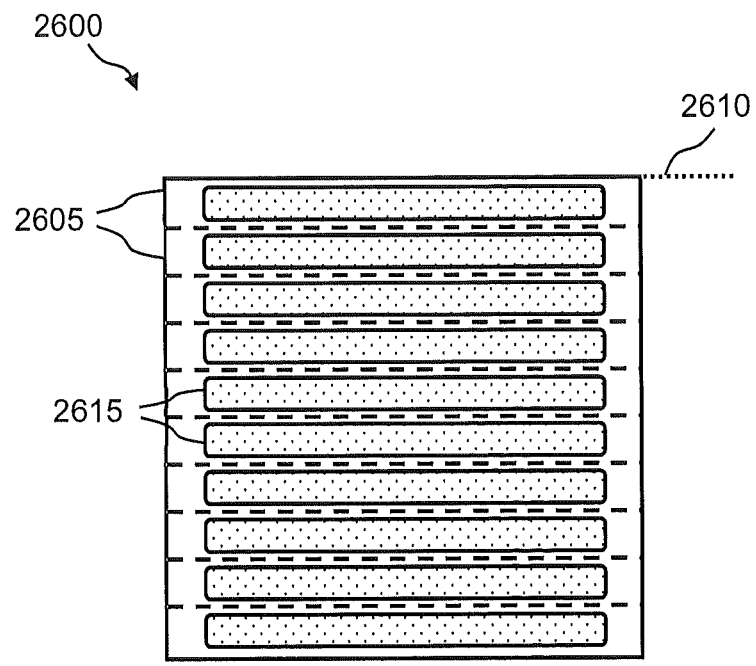

FIG. 26A illustrates a plan view of an exemplary embodiment of an array for delivery of reverse transcription (RT) primers to a tissue sample for in situ synthesis of cDNA.

Figure 26B:
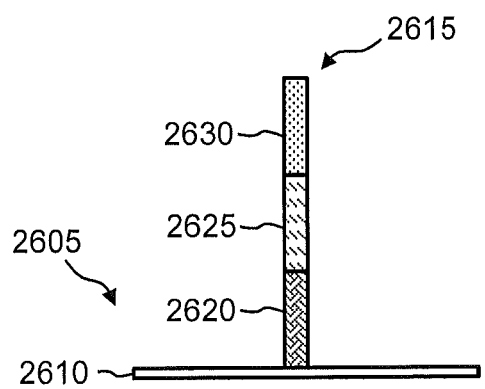

FIG. 26B illustrates a side view of a portion of one delivery site of the array of FIG. 26A, wherein the portion of the delivery site comprises at least one RT primer for synthesis of cDNA from mRNA in a tissue sample.

Figure 27A:
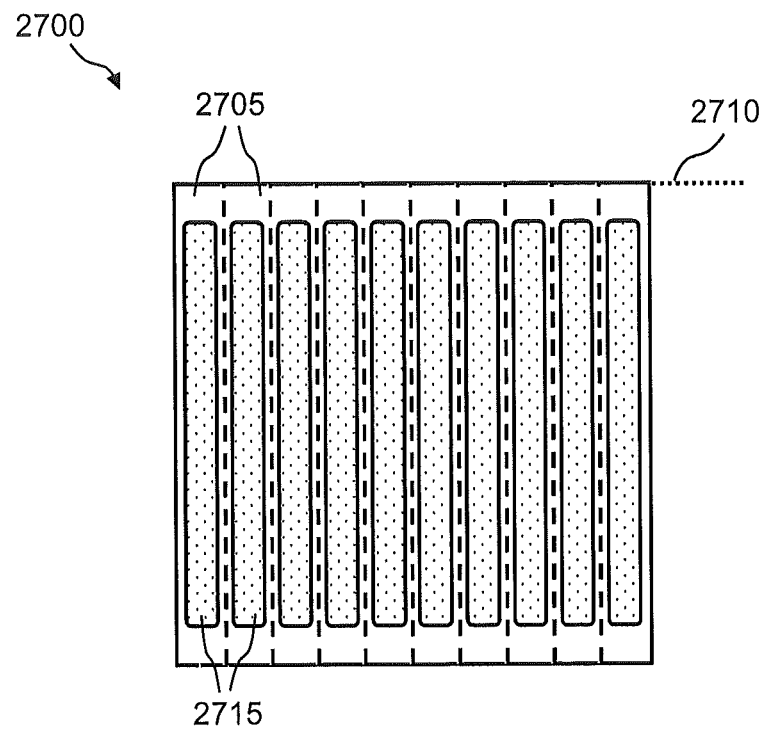

FIG. 27A illustrates a plan view of an exemplary embodiment of a capture array for the capture of cDNA synthesized in situ using the RT primers of FIG. 26B.

Figure 27B:
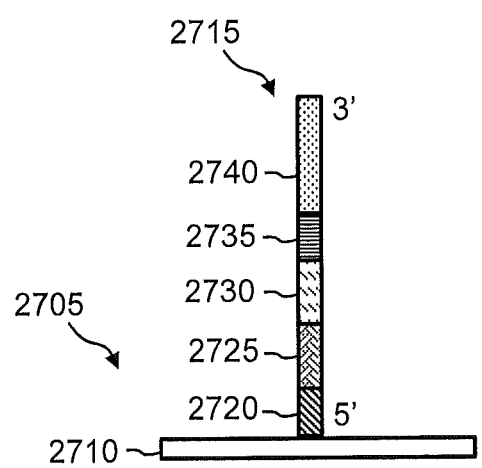

FIG. 27B illustrates a side view of a portion of one capture site of the capture array of FIG. 27A, wherein the portion of the capture site comprises at least one capture probe for capture of cDNA synthesized.

Figure 28:
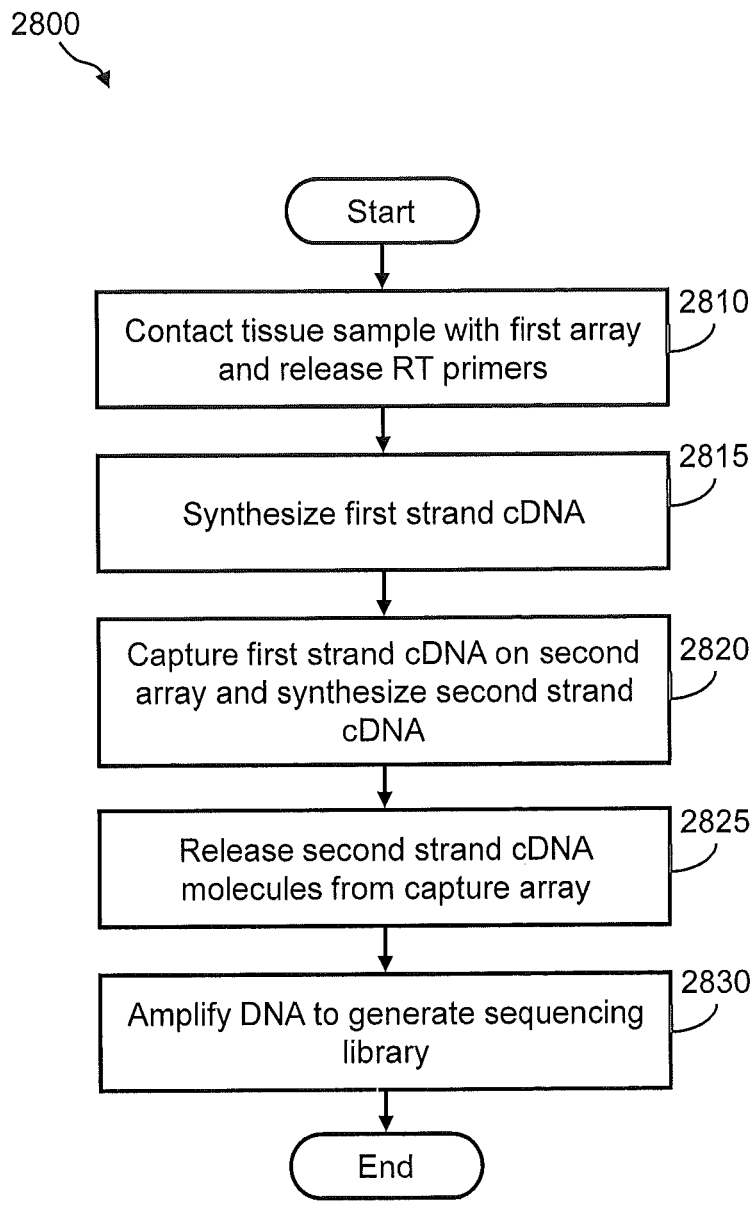

FIG. 28 illustrates a flow diagram of an exemplary embodiment of a method of generating a spatially addressed sequencing library, wherein a first array is used for in situ synthesis of first strand cDNA and a second array is used to capture the cDNA for subsequent library generation.

Figure 29A:
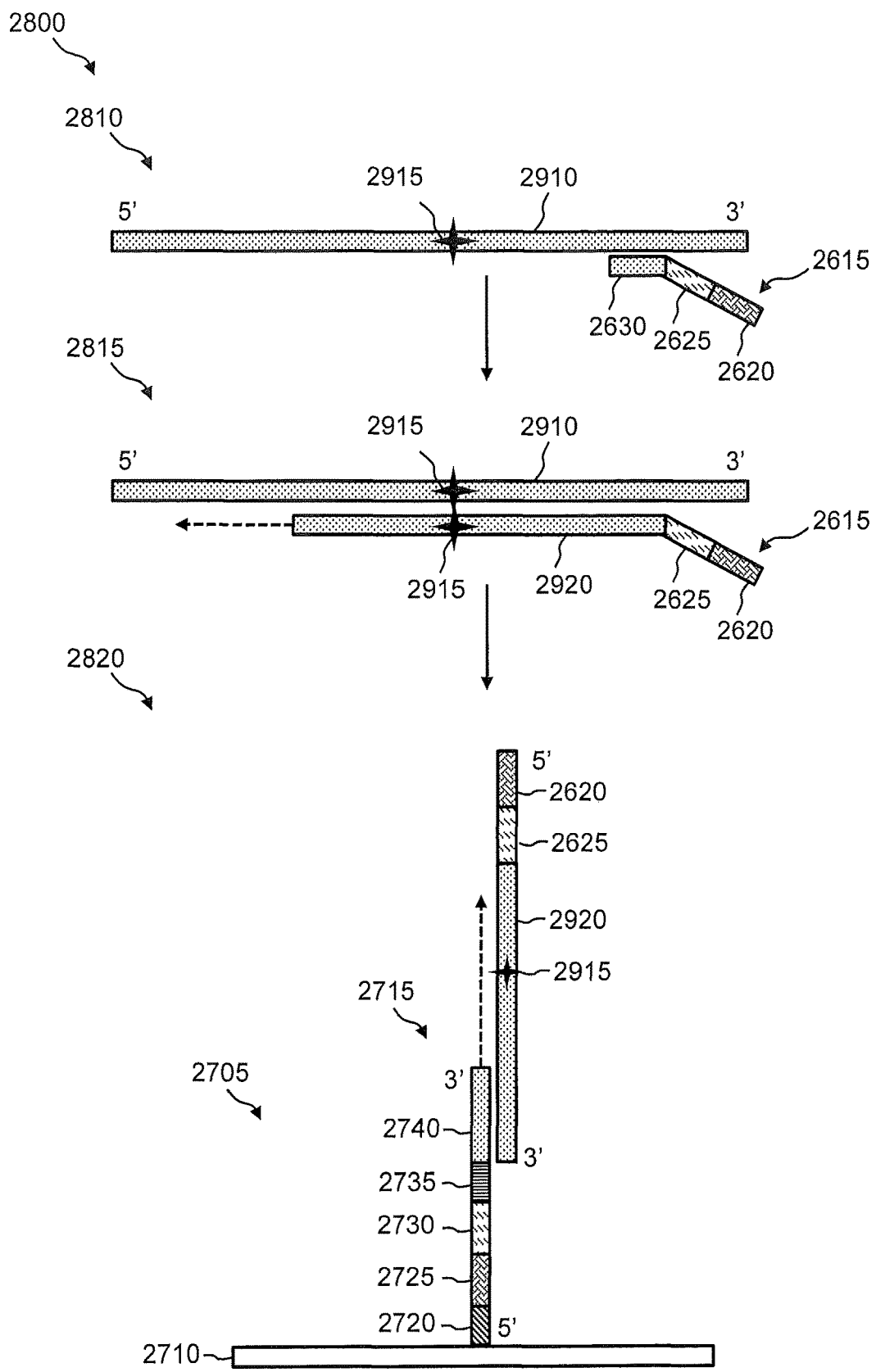
Figure 29B:
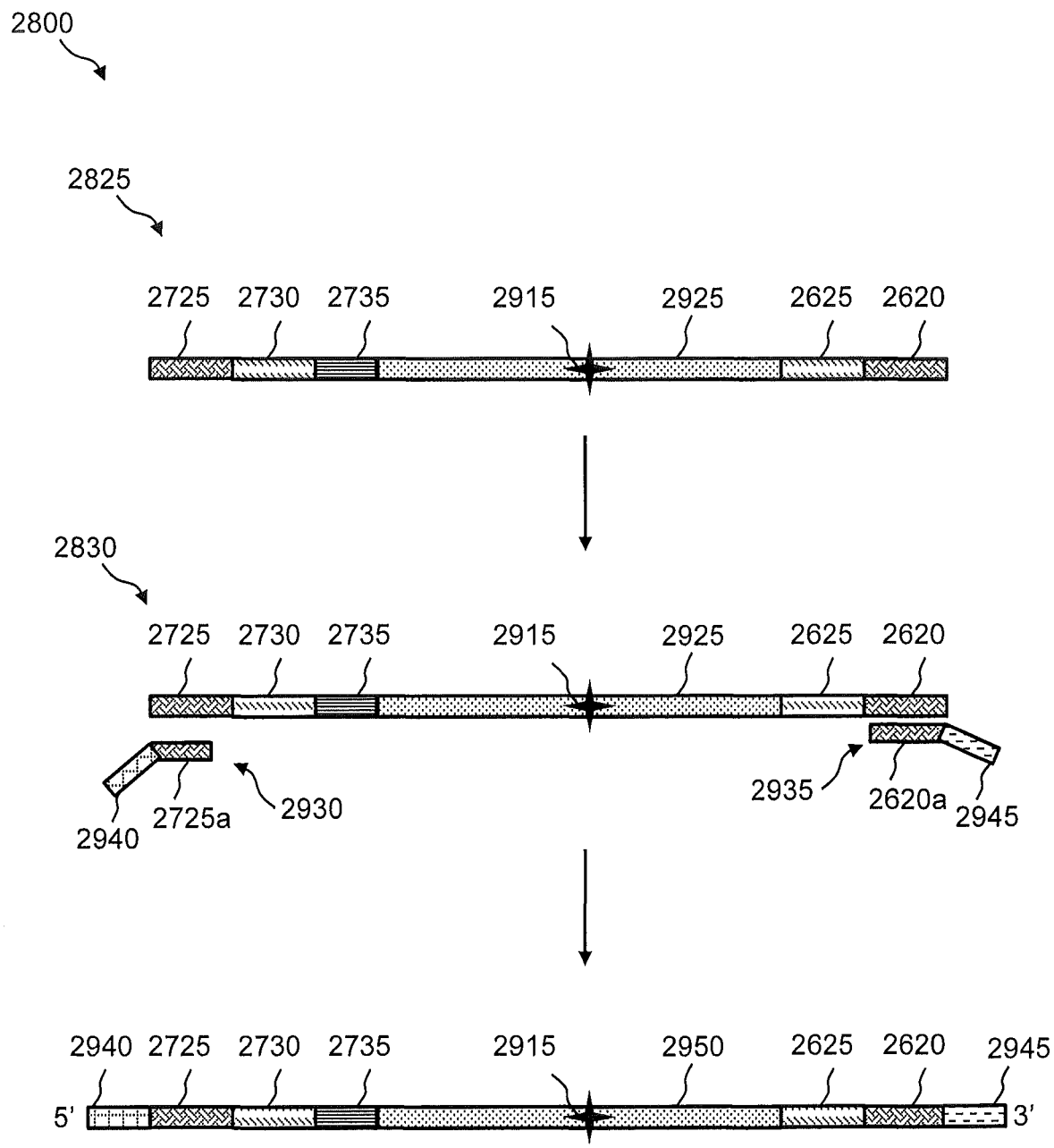

FIGS. 29A and 29B illustrate the steps of a method of FIG. 28.

Figure 30:
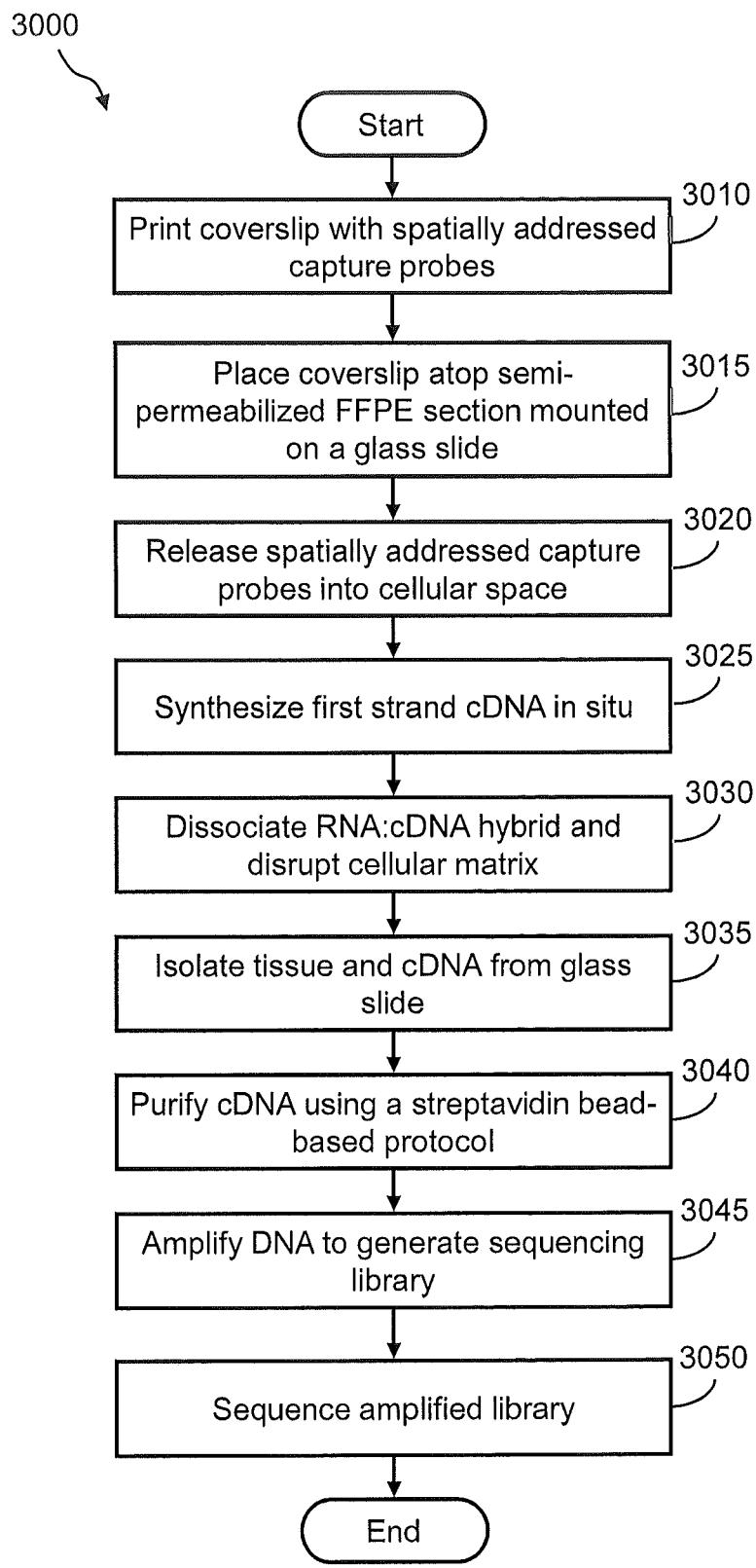

FIG. 30 illustrates a flow diagram of an exemplary embodiment of a method of generating a spatially addressed cDNA library using releasable capture probes.

Figure 31A:
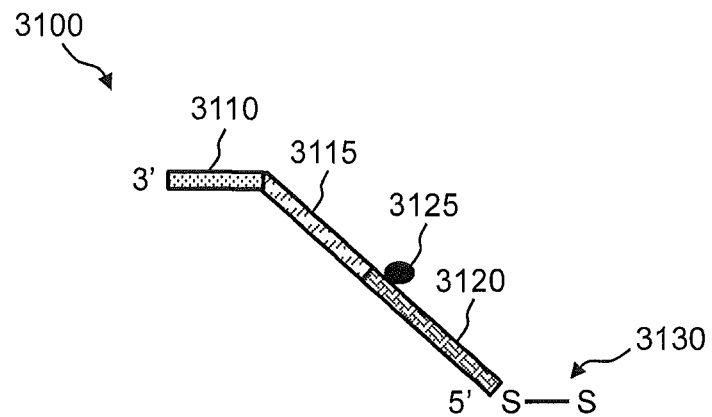
Figure 31B:
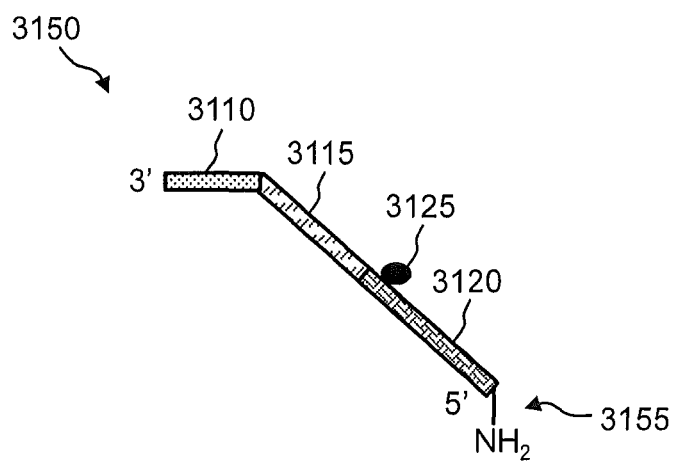

FIGS. 31A and 31B illustrate exemplary schematic diagrams of a spatially addressed capture probe that comprises a 5' disulfide modification and a spatially addressed capture probe that comprises a 5' photocleavable linker, respectively.

Figure 32A:
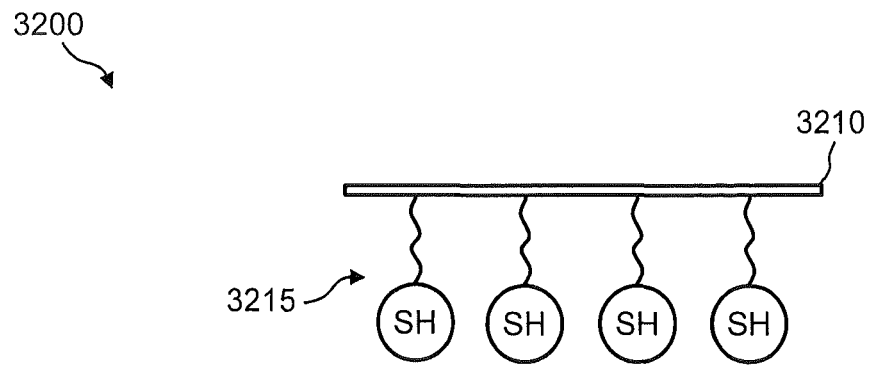
Figure 32B:
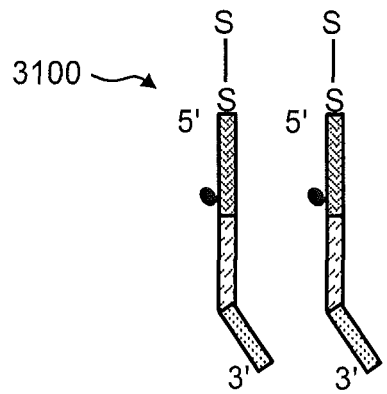
Figure 32C:
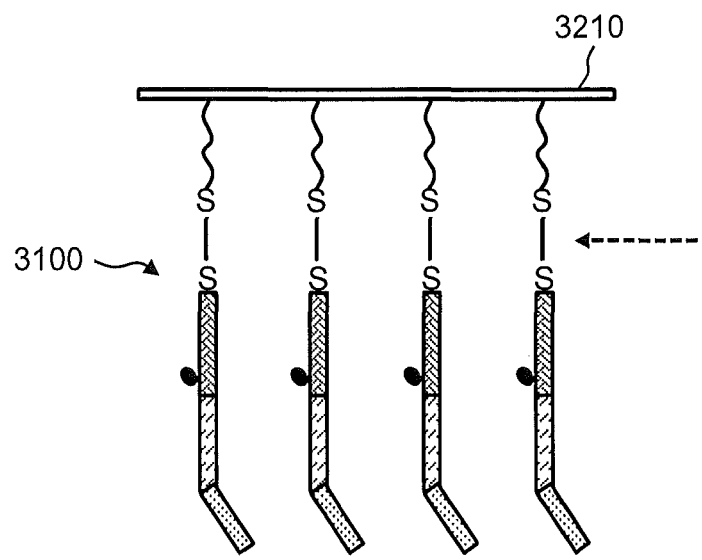

FIGS. 32A, 32B, and 32C illustrate an exemplary embodiment of a process of reversibly anchoring the spatially addressed capture probe of FIG. 31A onto the surface of a glass coverslip.

Figure 33A:
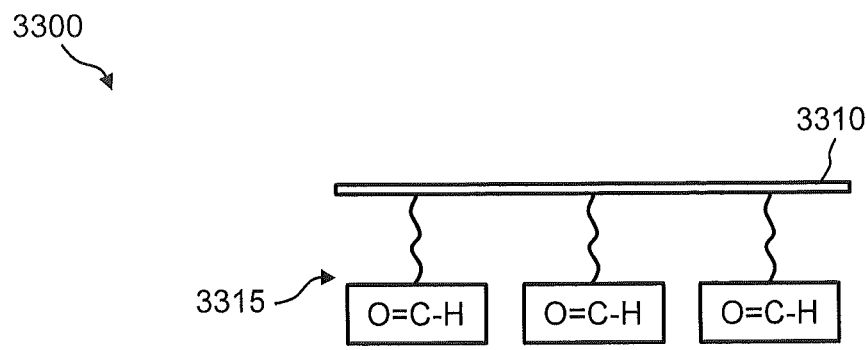
Figure 33B:
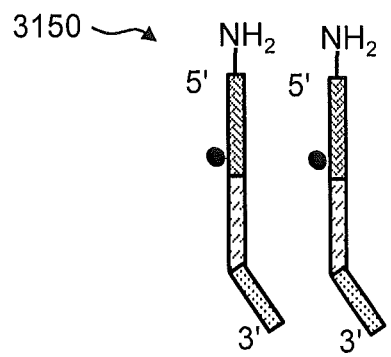
Figure 33C:
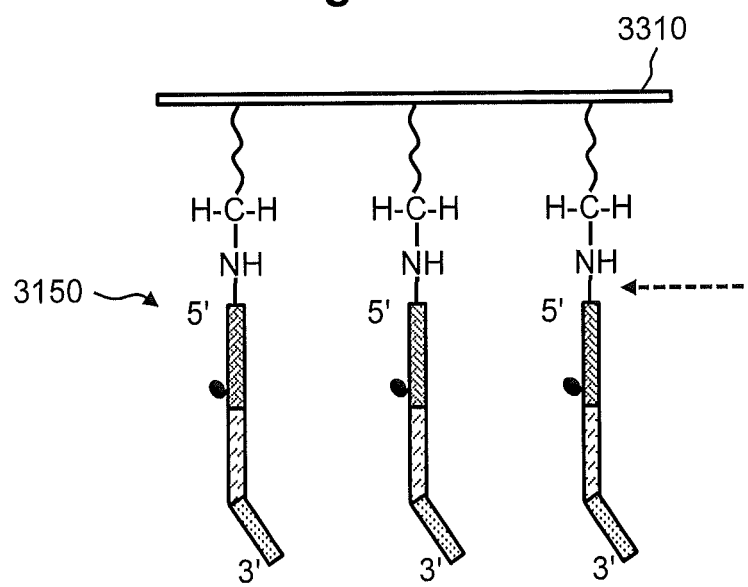

FIGS. 33A, 33B, and 33C illustrate an exemplary embodiment of a process of reversibly anchoring the spatially addressed capture probes of FIG. 31B onto the surface of a glass coverslip.

Figure 34A:
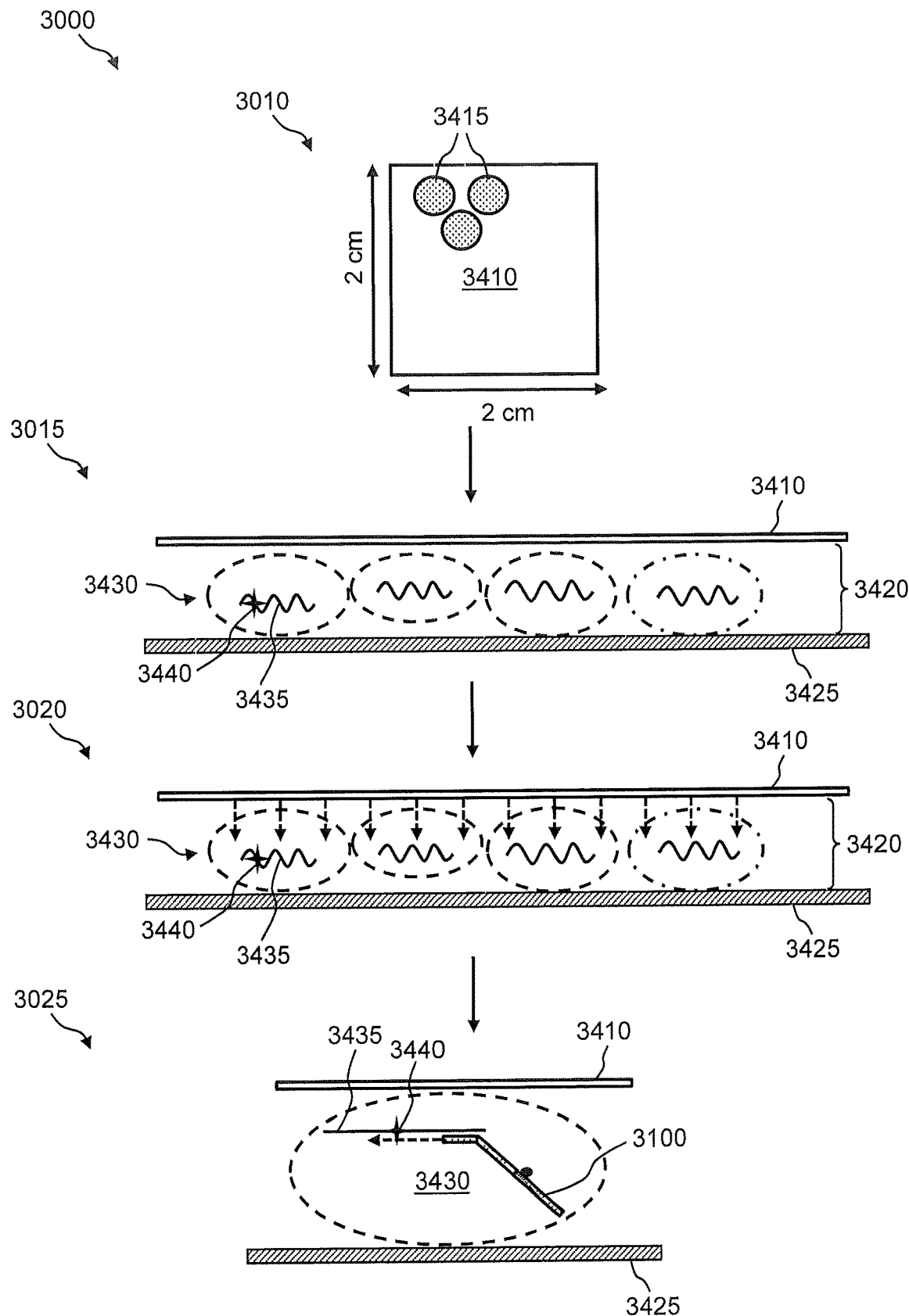
Figure 34B:
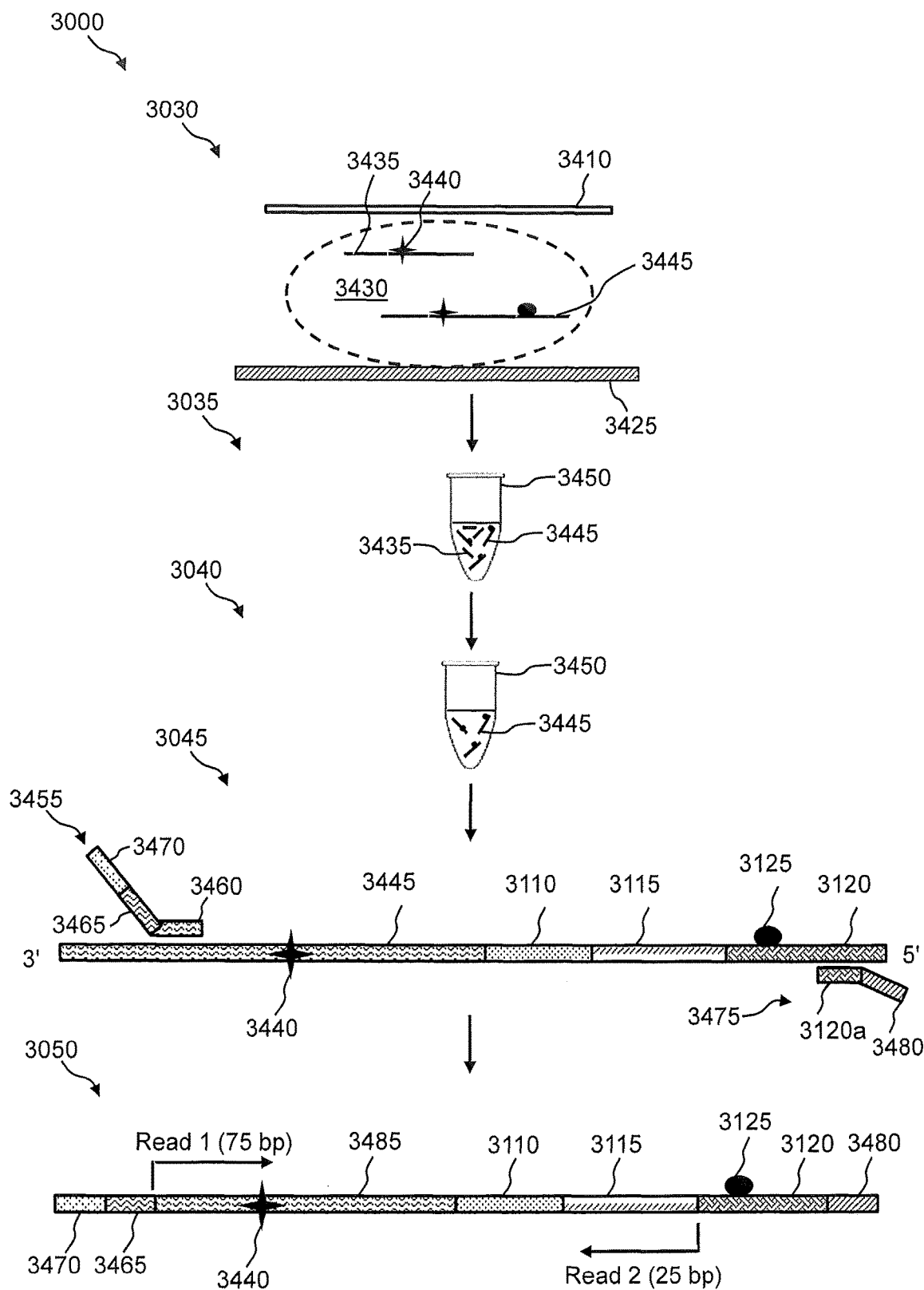

FIGS. 34A and 34B illustrate the steps of the method of FIG. 30.

Figure 35:
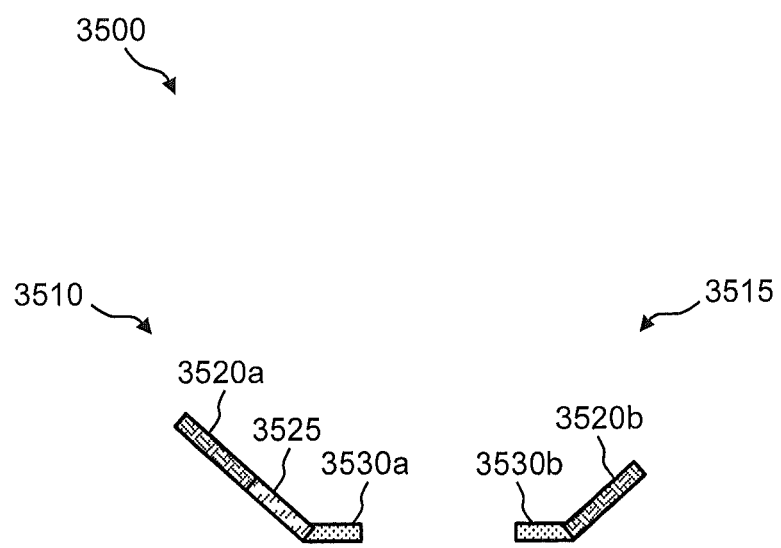

FIG. 35 illustrates a schematic diagram of an exemplary embodiment of a capture probe pair for capturing a genomic DNA region of interest.

Figure 36:
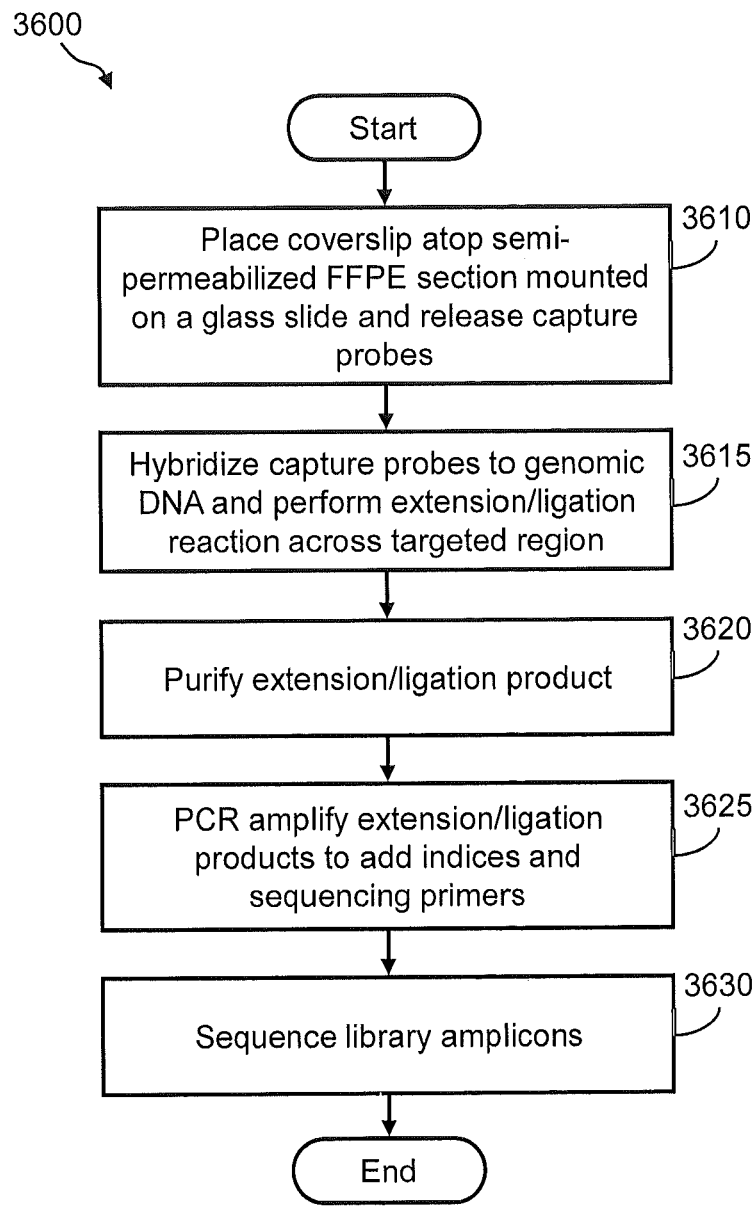

FIG. 36 illustrates a flow diagram of an exemplary embodiment of a method of generating a spatially addressed genomic amplicon library using releasable capture probes.

Figure 37:
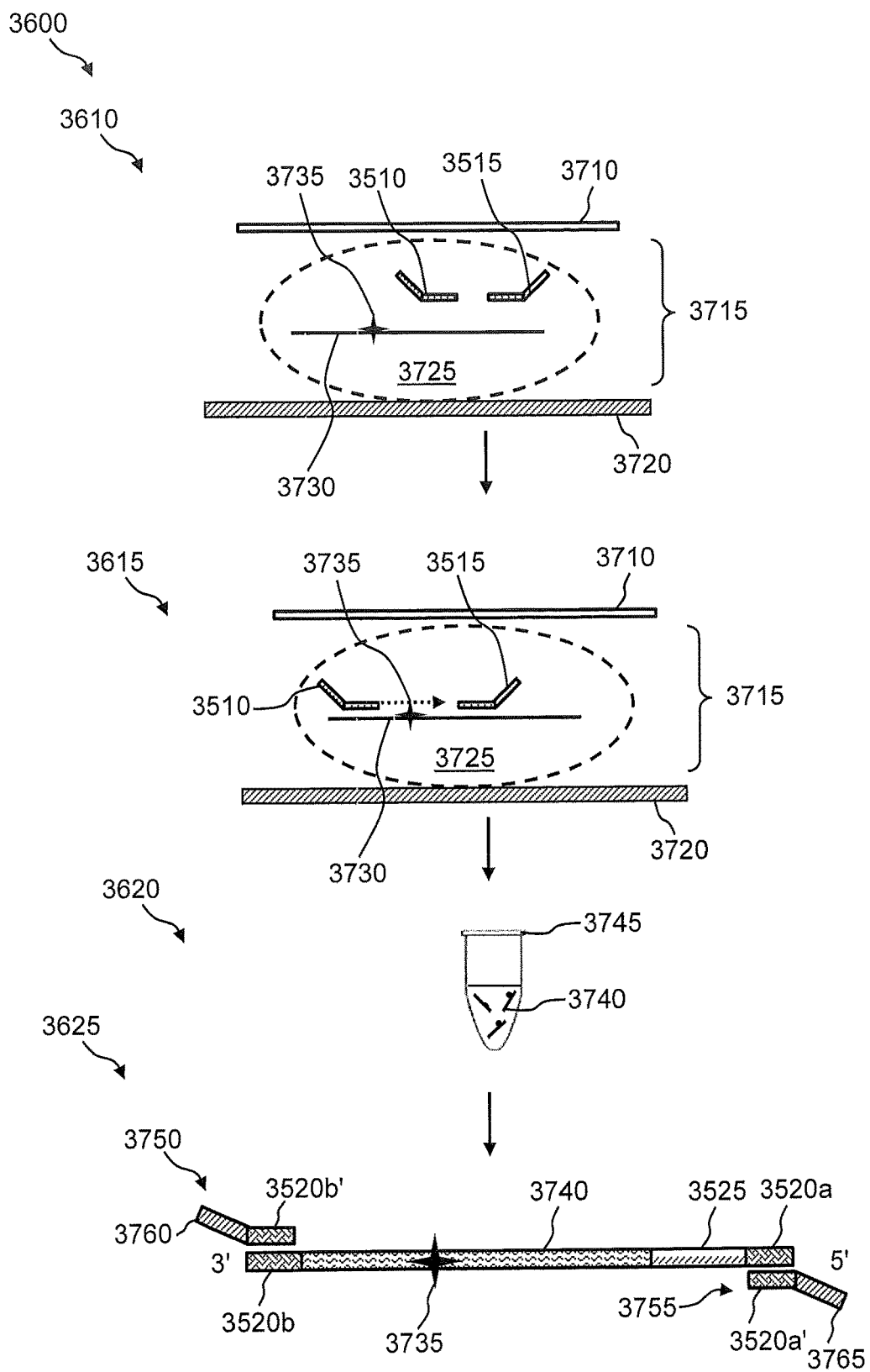

FIG. 37 illustrates the steps of a method of FIG. 36.

Figure 38:
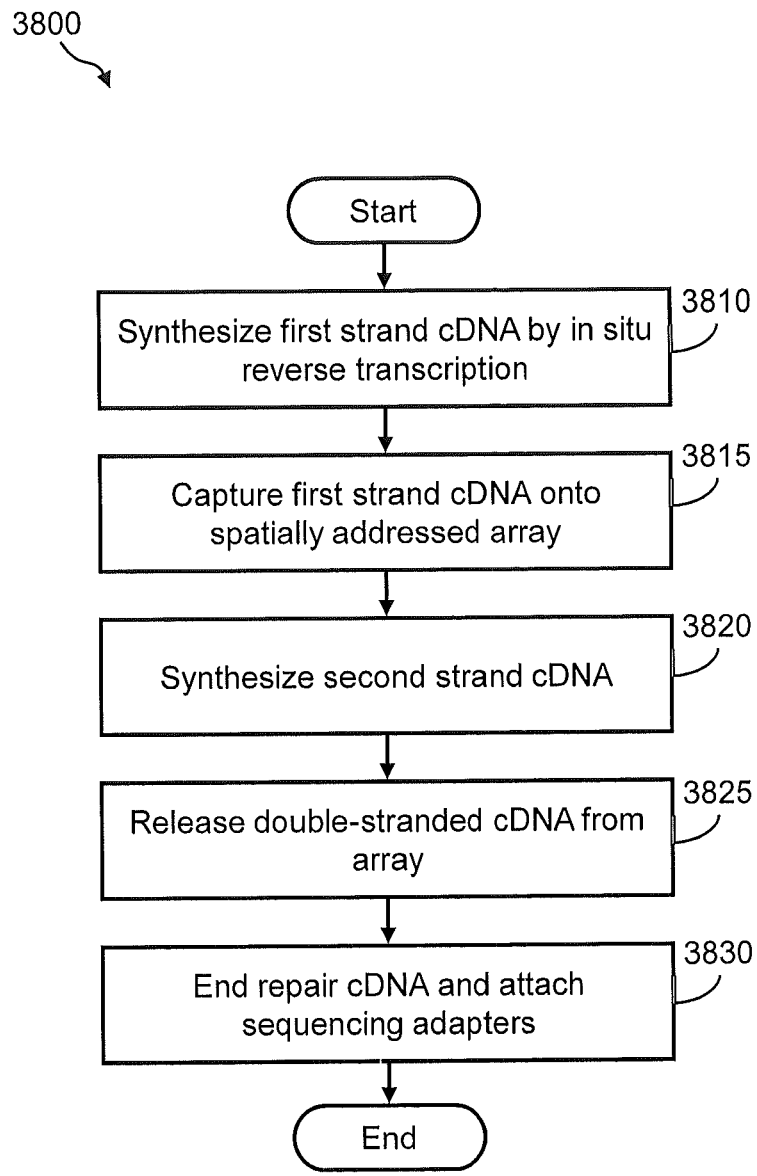

FIG. 38 illustrates a flow diagram of an exemplary embodiment of a method of generating a spatially addressed sequencing library using magnetic nanoparticles to capture nucleic acid from a tissue sample.

Figure 39:
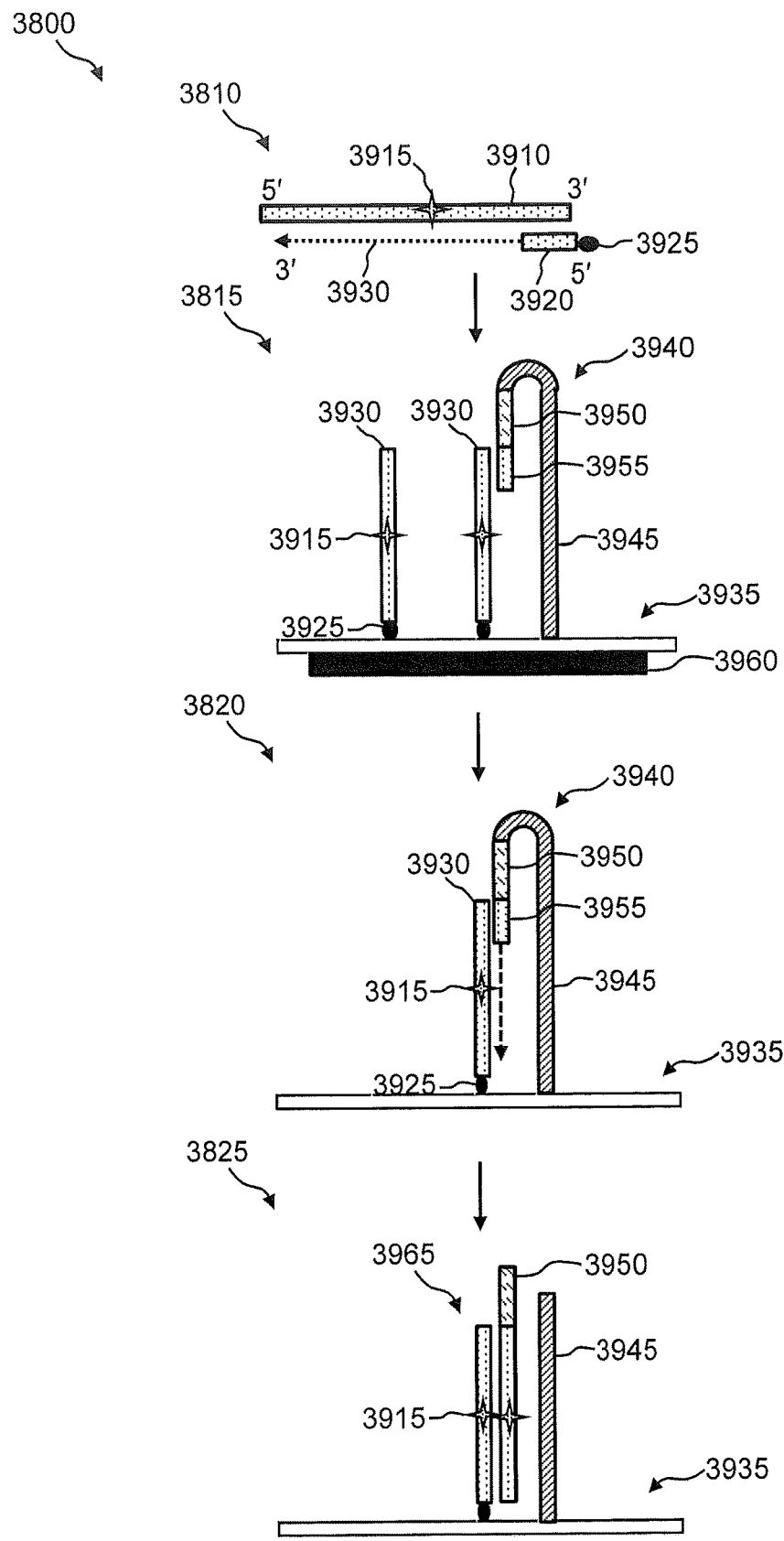

FIG. 39 illustrates the steps of a method of FIG. 38.

Figure 40A:
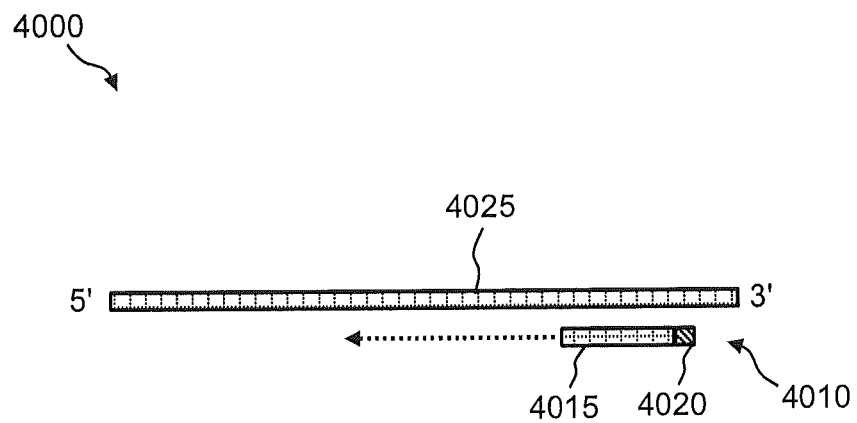
Figure 40B:
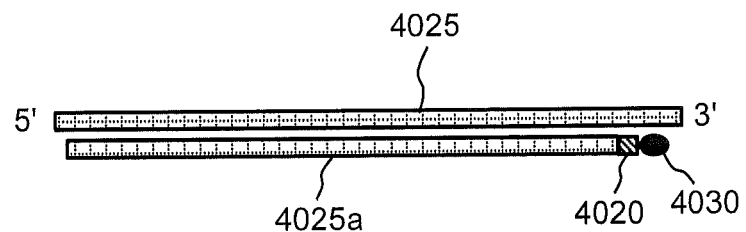

FIGS. 40A and 40B illustrate an example of a process of using a capture probe to form a complementary nucleic acid in a tissue sample and subsequently immobilizing the complementary nucleic acid to a nanoparticle.

Figure 41A:
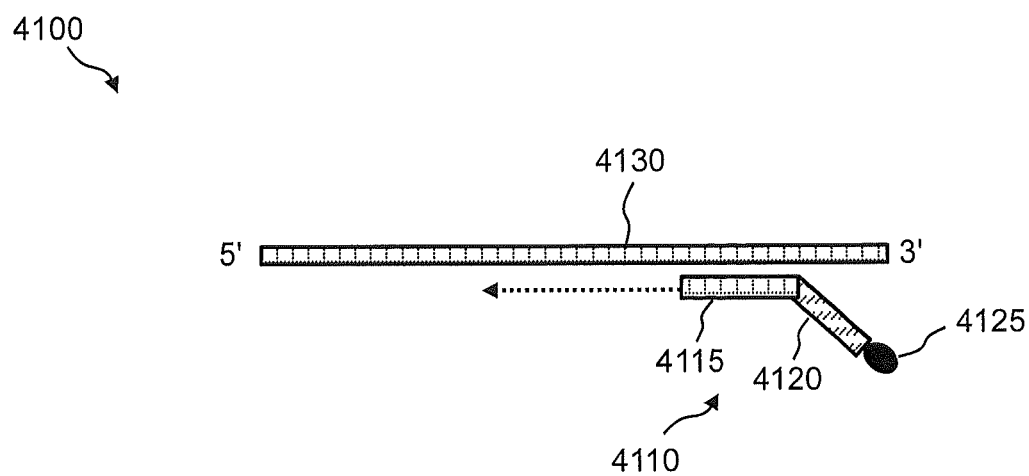
Figure 41B:
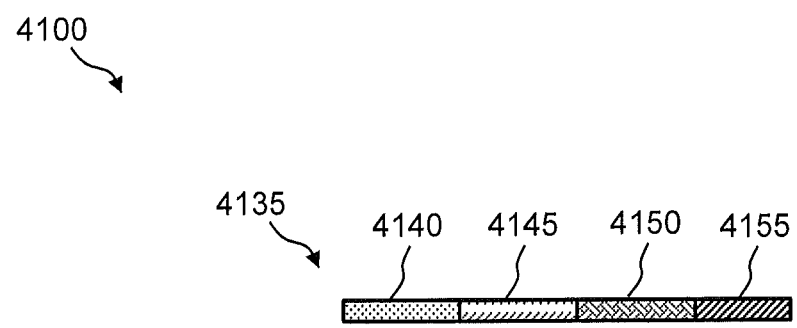

FIGS. 41A and 41B illustrate schematic diagrams of an example of a particle-associated capture probe comprising a first partial spatial address region and a second array capture probe comprising a second partial address region, respectively, for spatial detection and analysis of nucleic acids in a tissue sample.

Figure 42A:
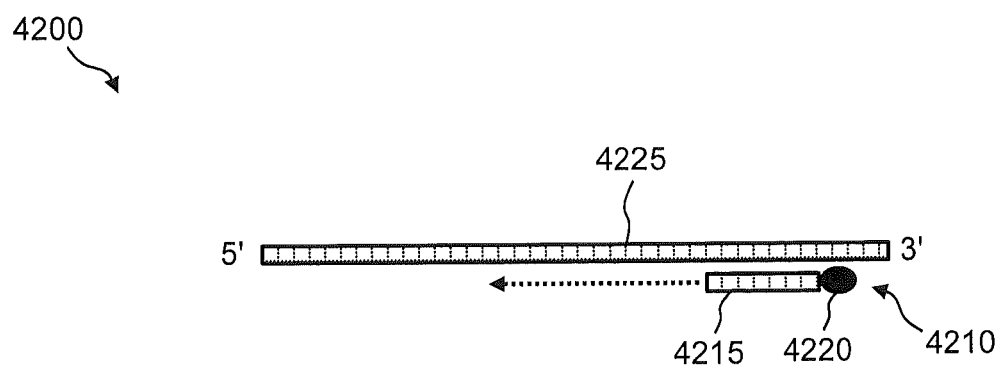
Figure 42B:
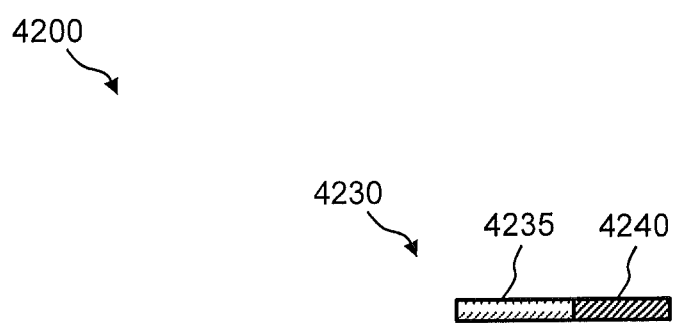

FIGS. 42A and 42B illustrate schematic diagrams of an example of a particle-associated capture probe and a second array capture probe comprising a spatial address region, respectively, for spatial detection and analysis of nucleic acids in a tissue sample.

Figure 43A:
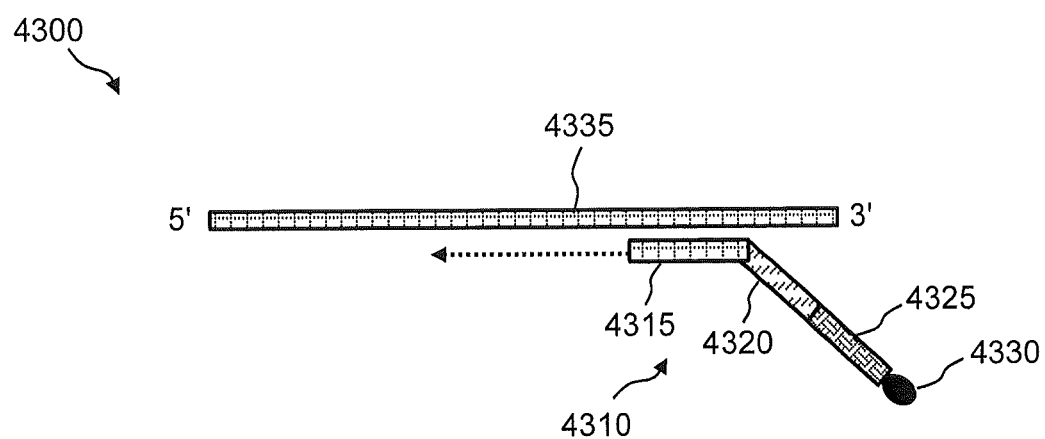
Figure 43B:
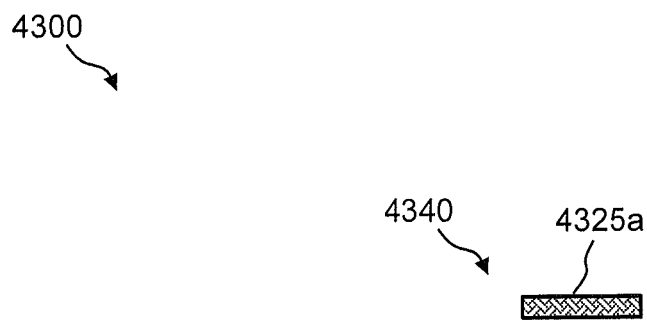

FIGS. 43A and 43B illustrate schematic diagrams of an example of a particle-associated capture probe and a second array capture probe, respectively, for spatial detection and analysis of nucleic acids from a tissue sample.

Figure 44:
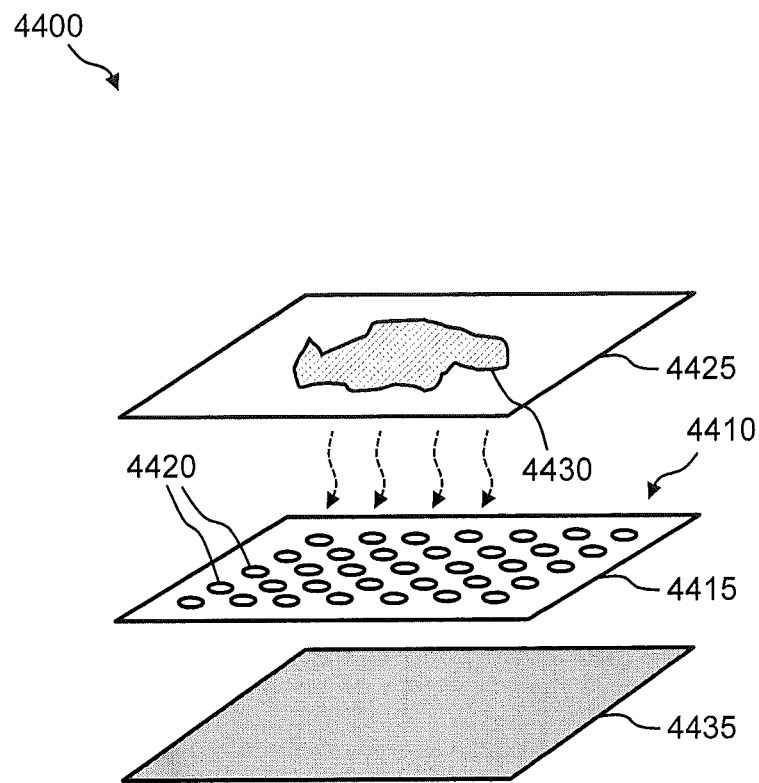

FIG. 44 illustrates a perspective view of a magnetic-based transfer system that is configured for spatial detection and analysis of nucleic acid in a tissue sample.

Figure 45:
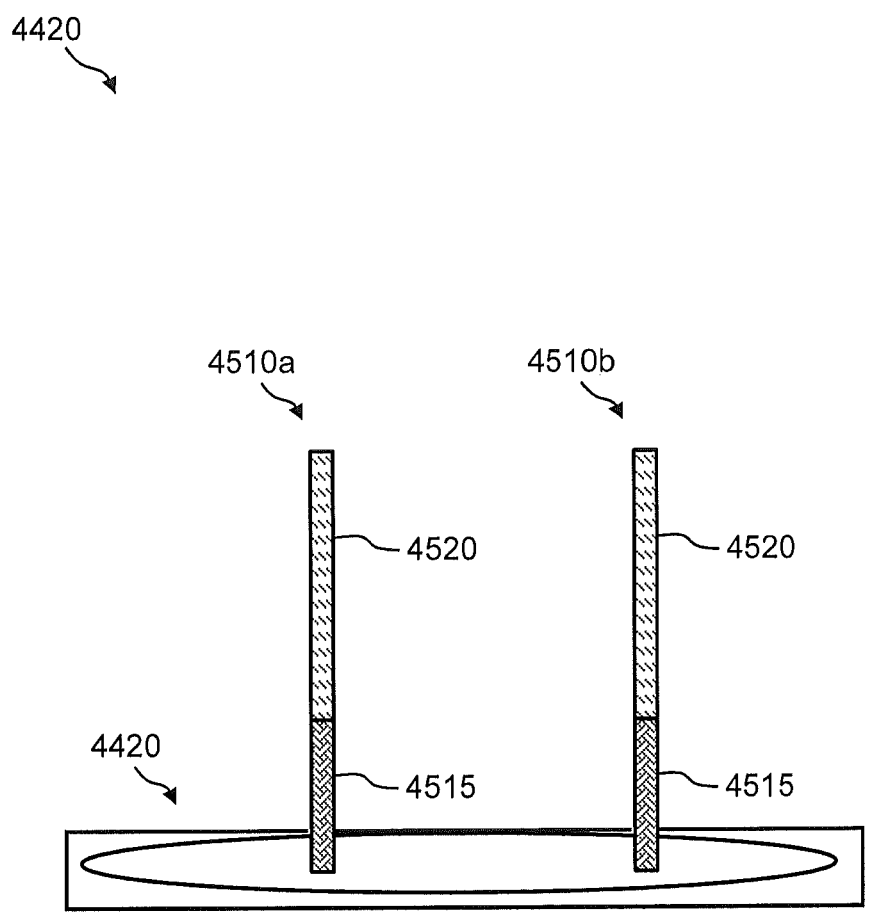

FIG. 45 illustrates a side view of one capture site on the capture array of FIG. 44, wherein the one capture site includes a plurality of capture probes.

Figure 46:
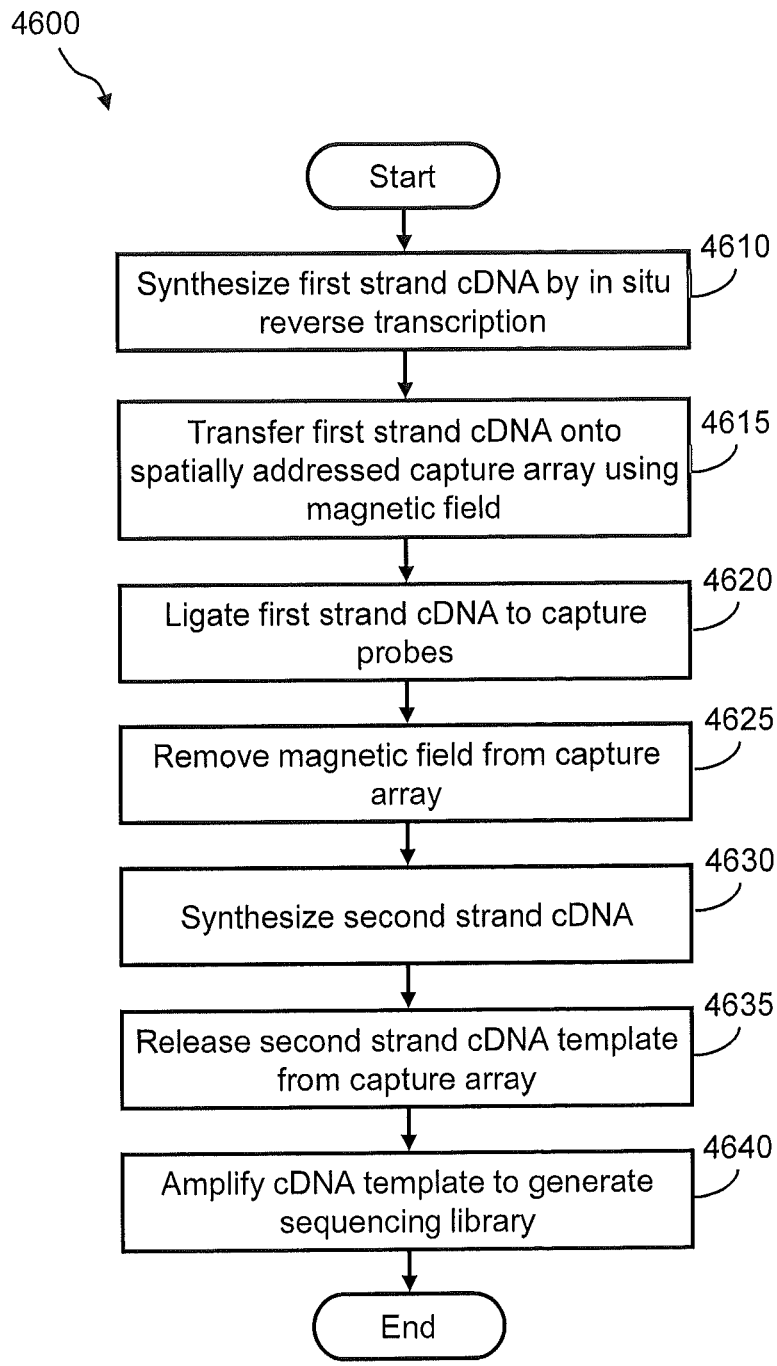

FIG. 46 illustrates a flow diagram of an example of a method of transferring cDNA from a tissue sample to a capture array for generation of a spatially addressed sequencing library using the magnetic-based transfer system of FIG. 44 and FIG. 45.

Figure 47A:
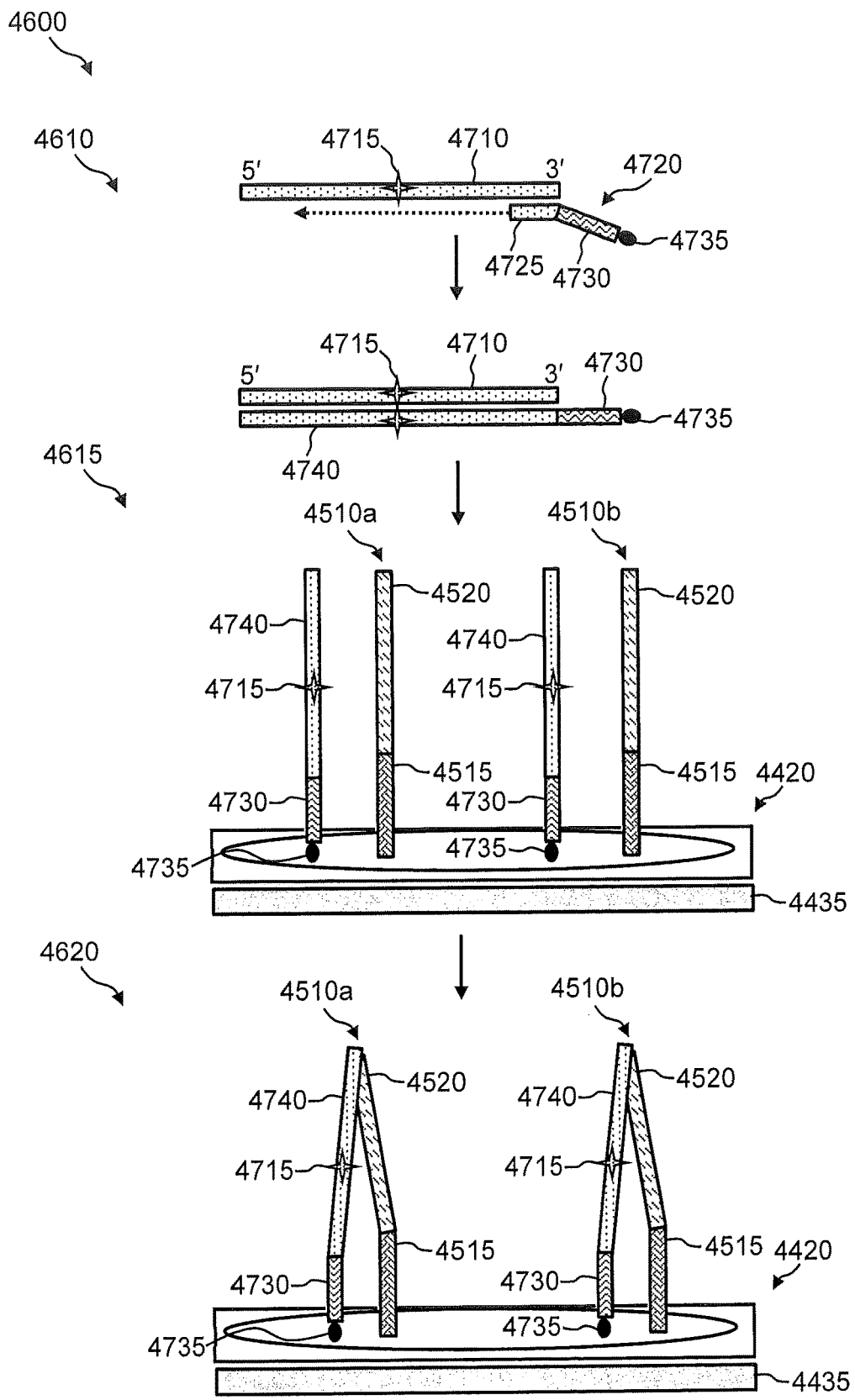
Figure 47B:
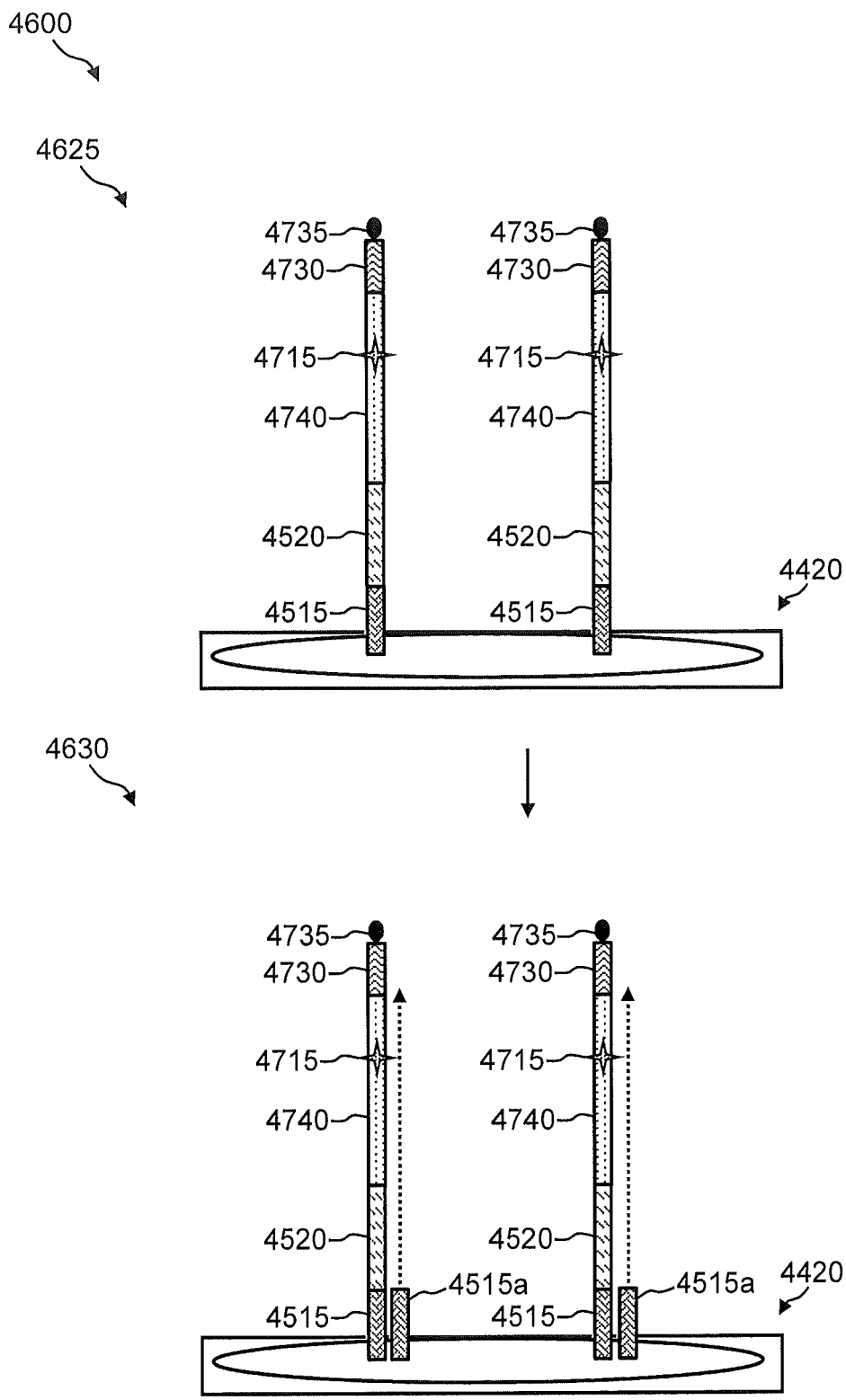
Figure 47C:
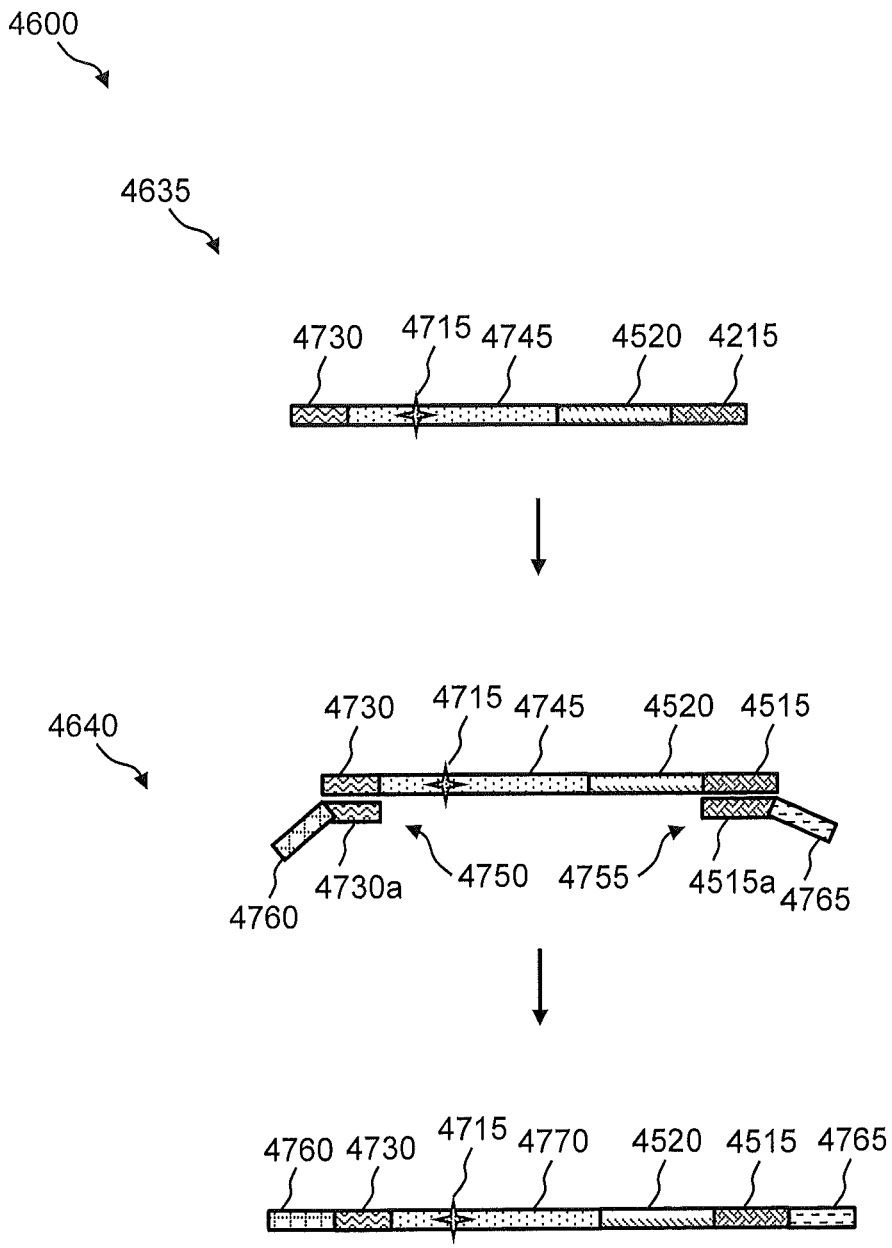

FIGS. 47A, 47B, and 47C show pictorially the steps of the method of FIG. 46.

Figure 48:
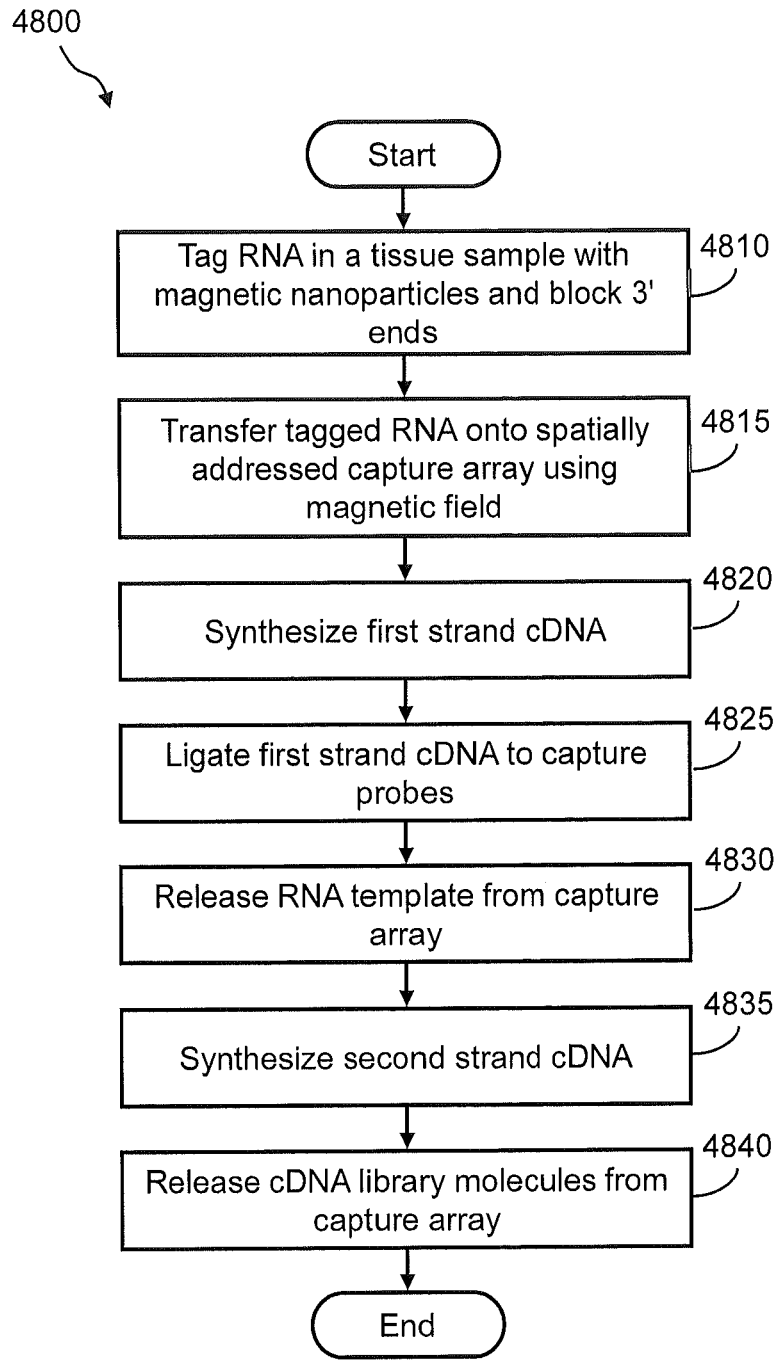

FIG. 48 illustrates a flow diagram of an example of a method of transferring RNA from a tissue sample to a capture array for generation of a spatially addressed sequencing library using the magnetic-based transfer system of FIG. 44.

Figure 49A:
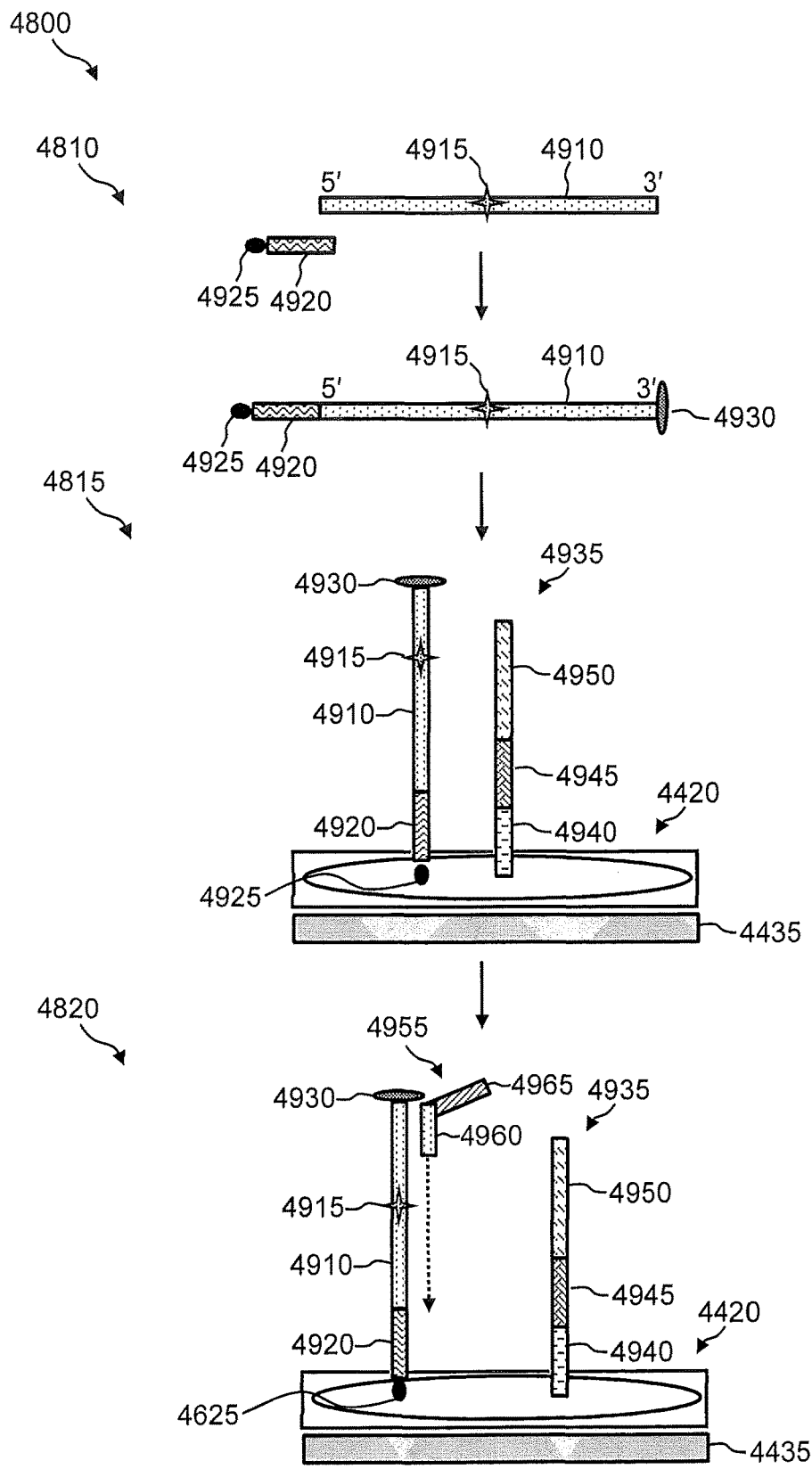
Figure 49B:
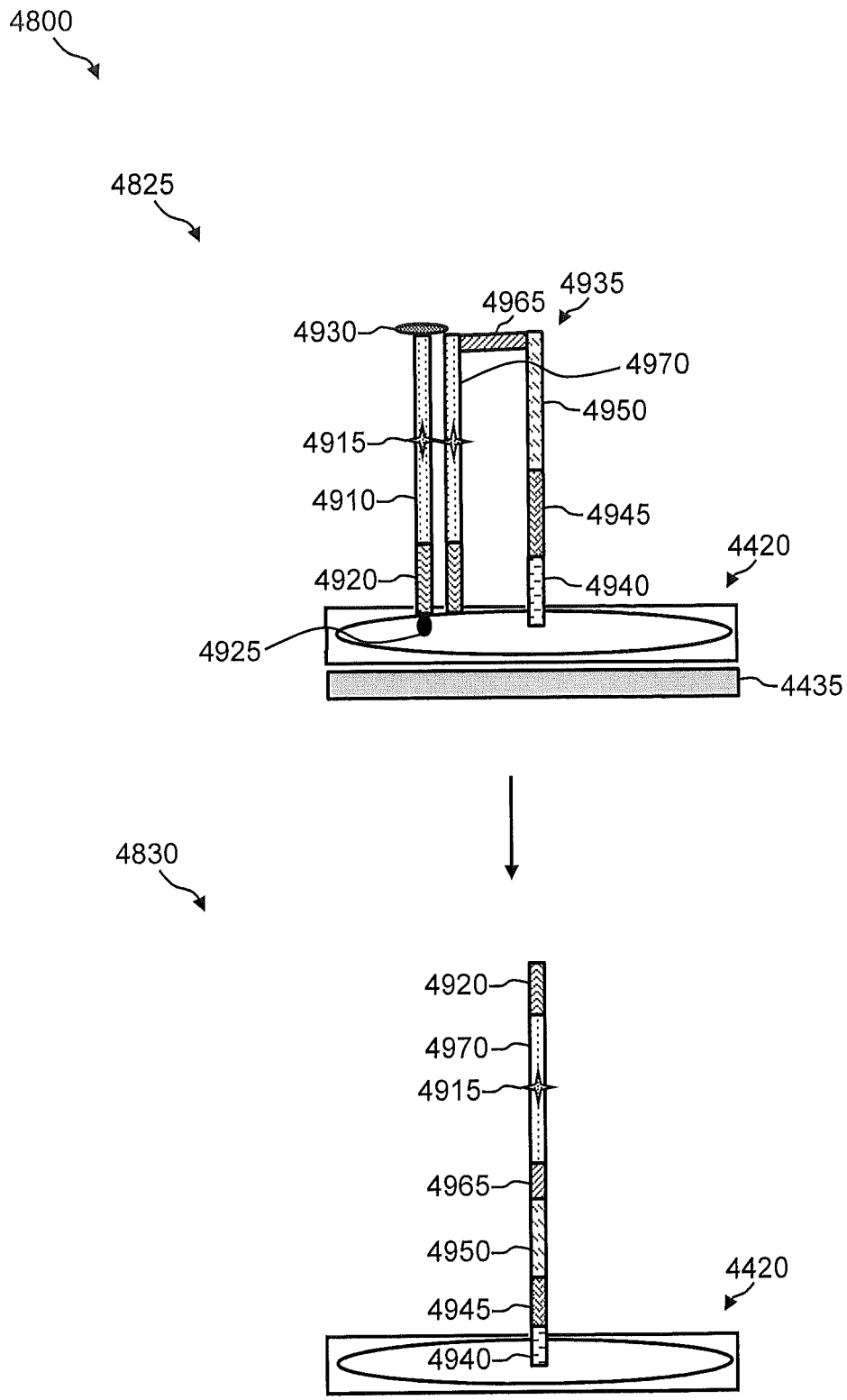
Figure 49C:
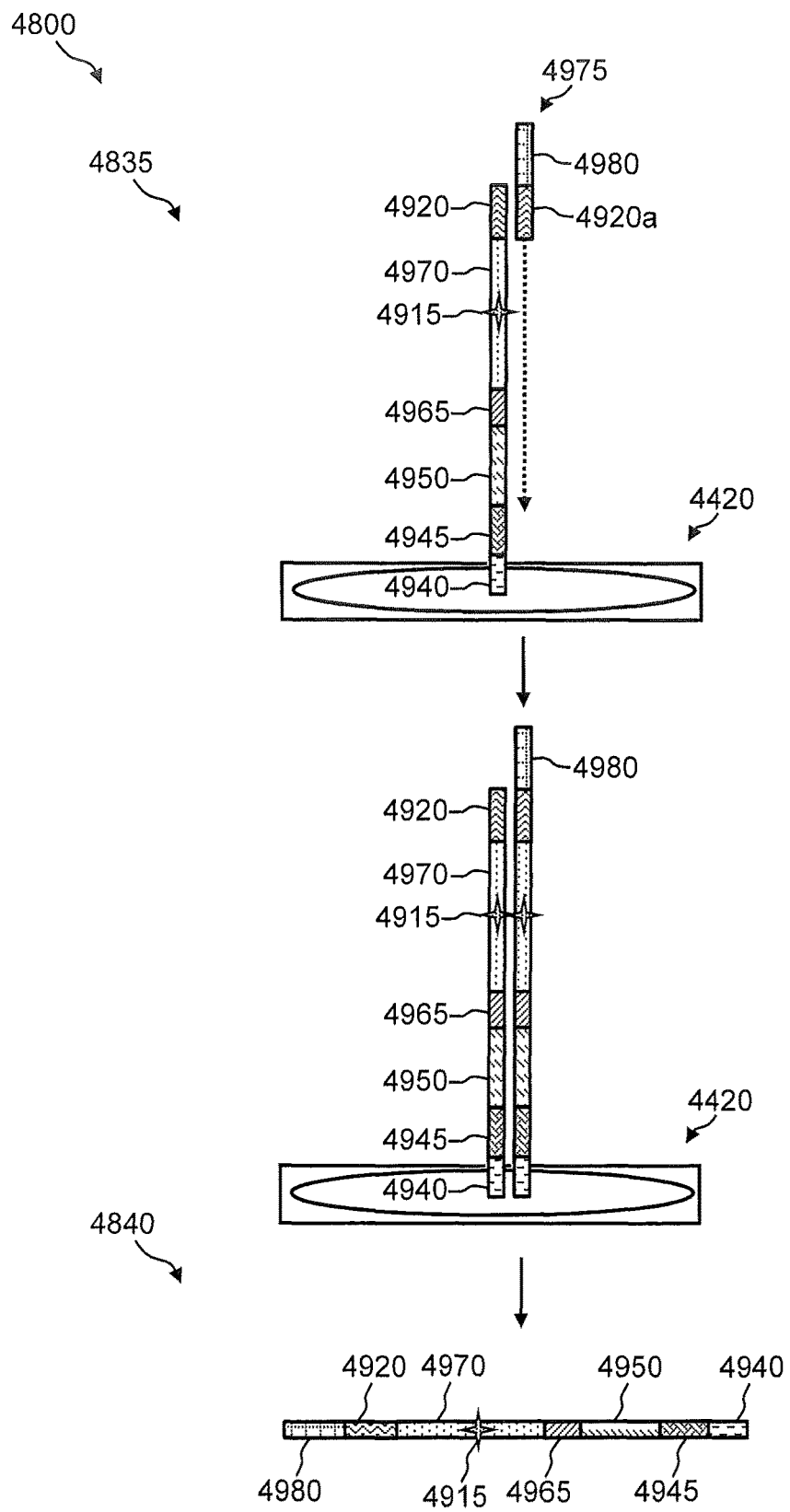

FIGS. 49A, 49B, and 49C show pictorially the steps of the method of FIG. 48.

Figure 50:
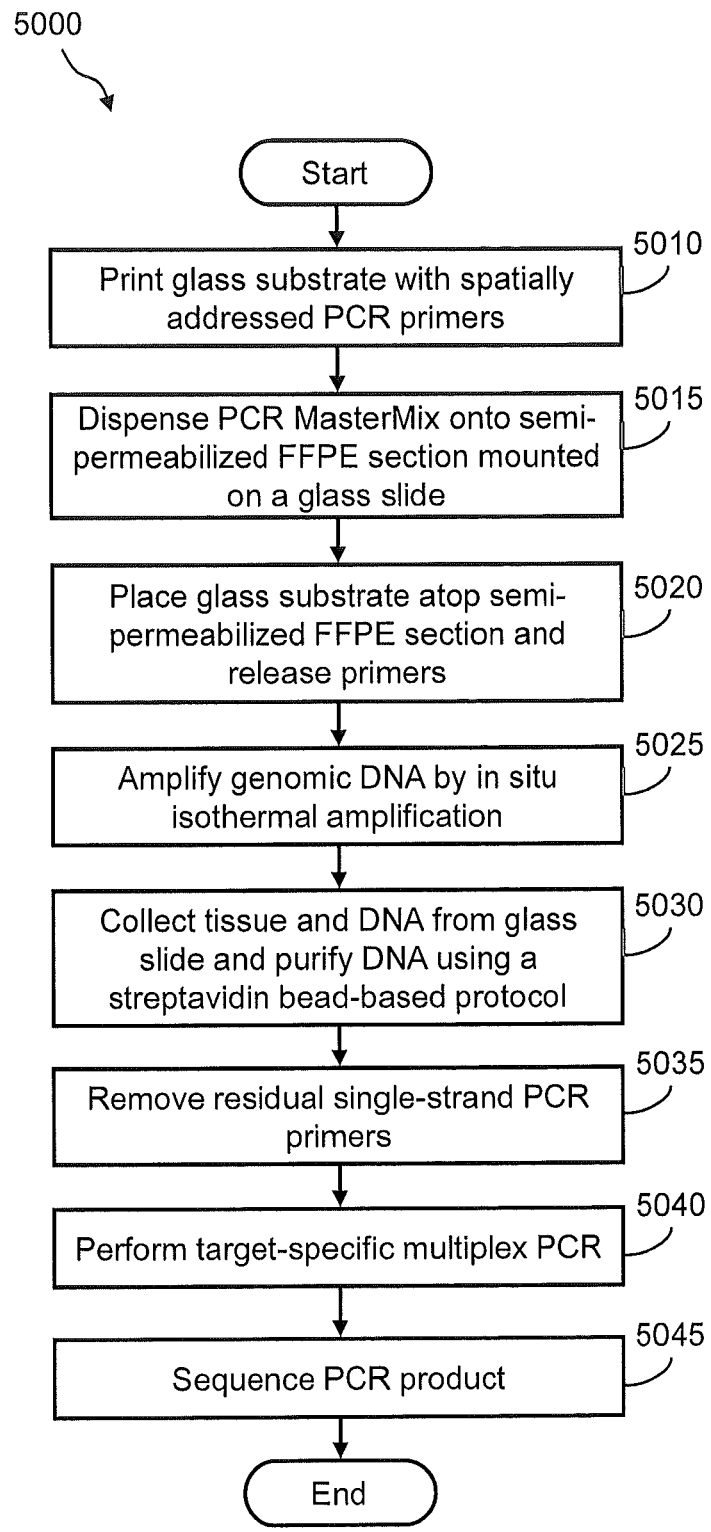

FIG. 50 illustrates a flow diagram of an example of a method of profiling genomic DNA in a tissue sample.

Figure 51:
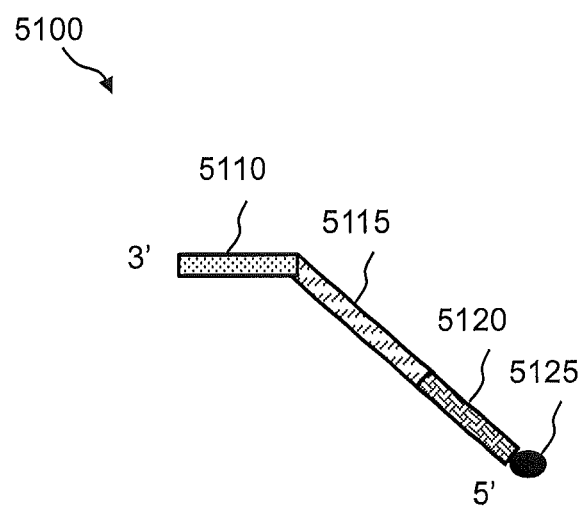

FIG. 51 illustrates a diagram of a spatially addressed PCR primer for pre-amplification and spatial indexing of whole genomic DNA.

Figure 52A:
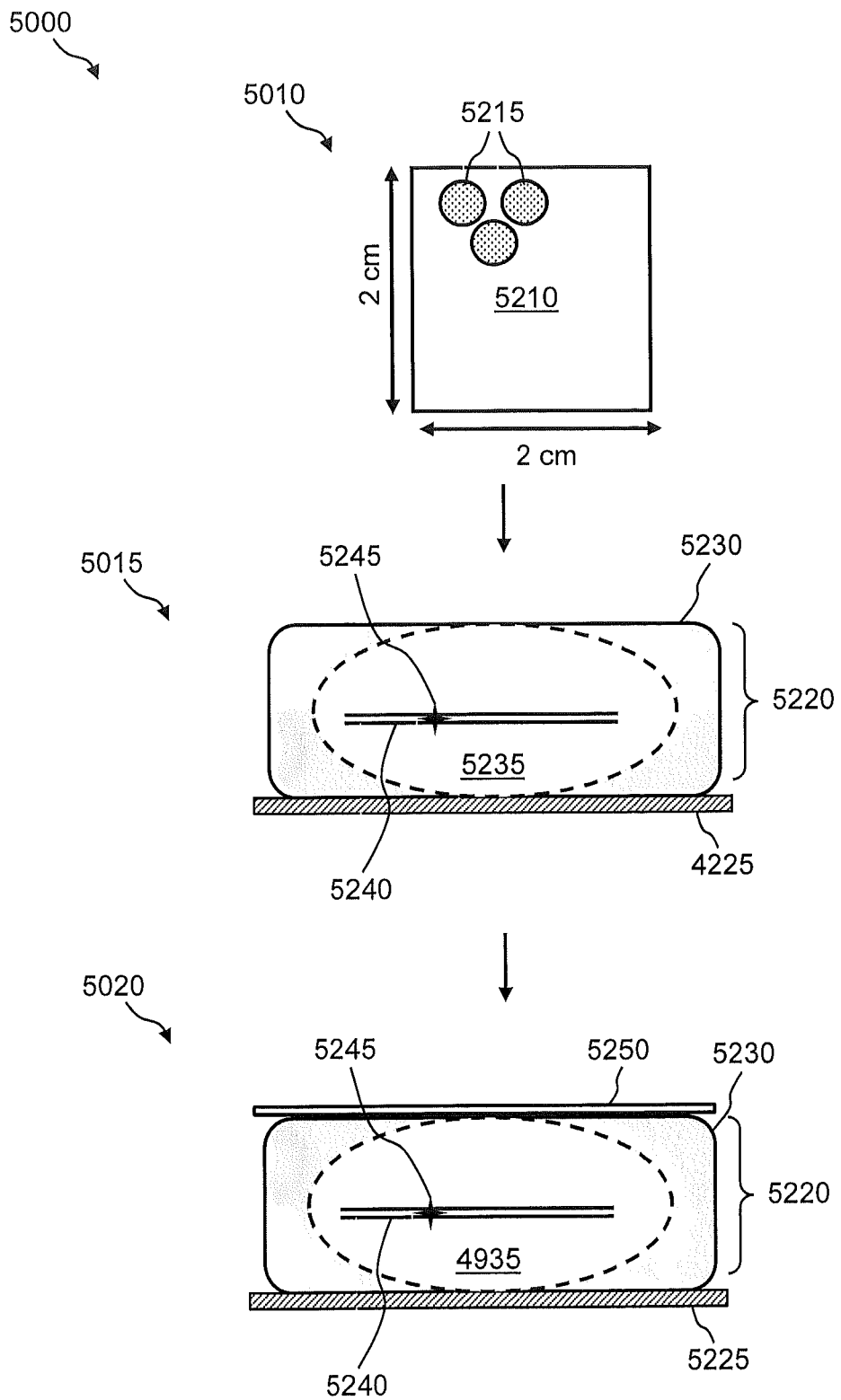
Figure 52B:
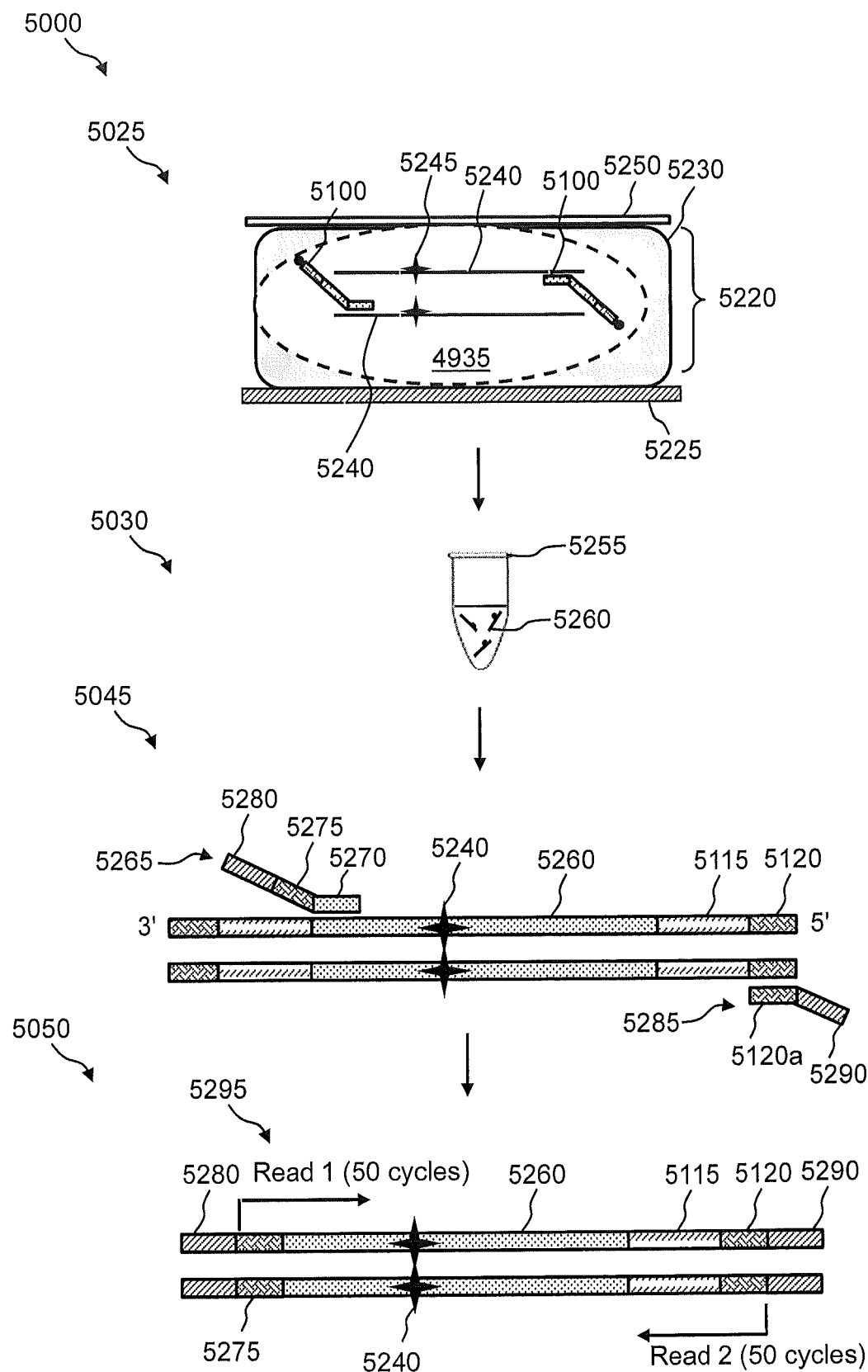

FIGS. 52A and 52B show pictorially the steps of the method of FIG. 50.

Figure 53:
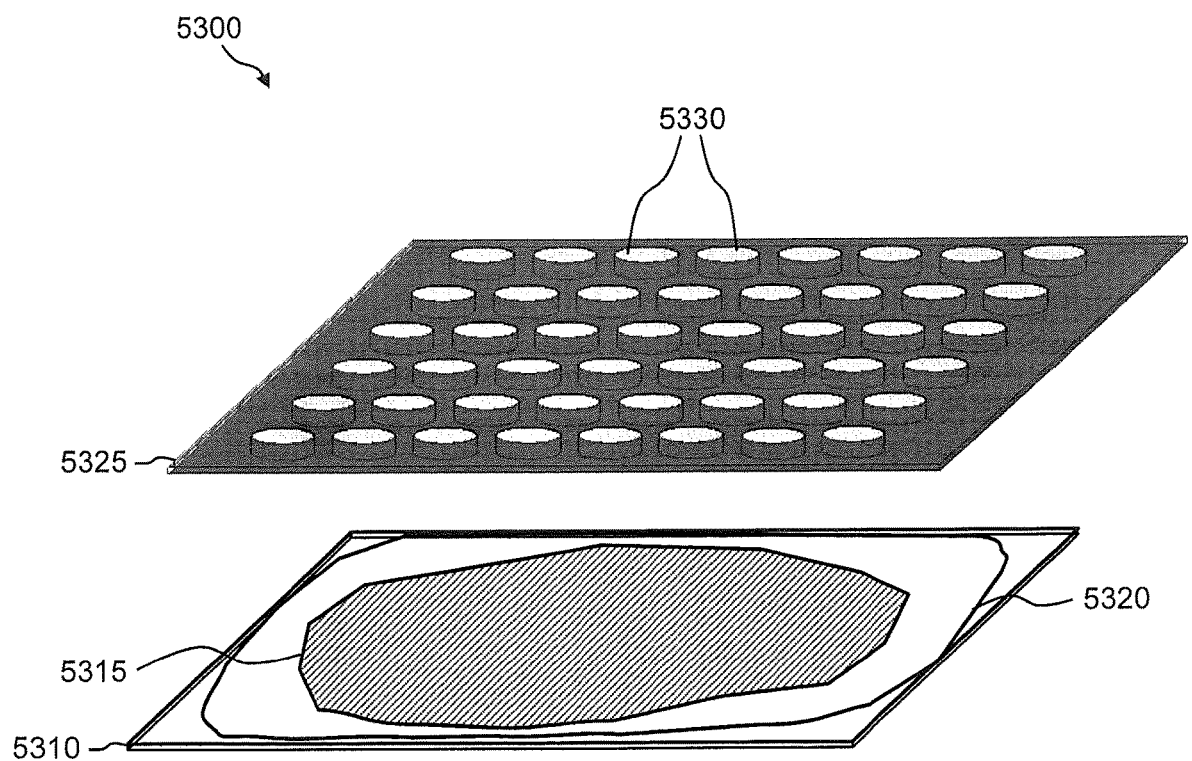

FIG. 53 illustrates a perspective view of an example of a microwell reactor overlay.

Figure 54:
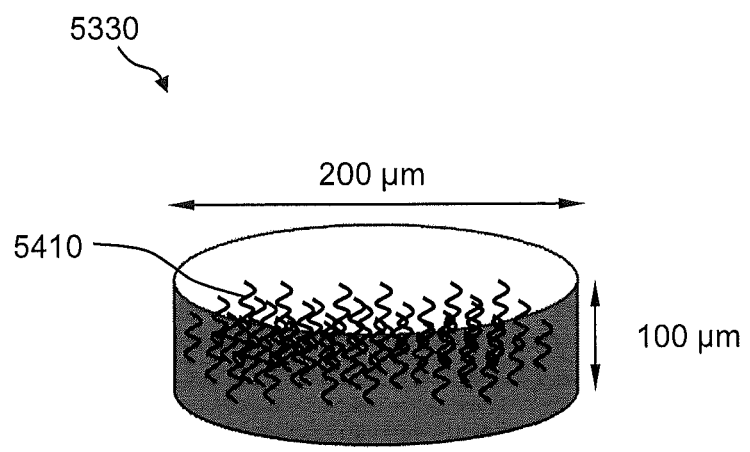

FIG. 54 illustrates a perspective view of a single microwell of FIG. 53.

Figure 55A:
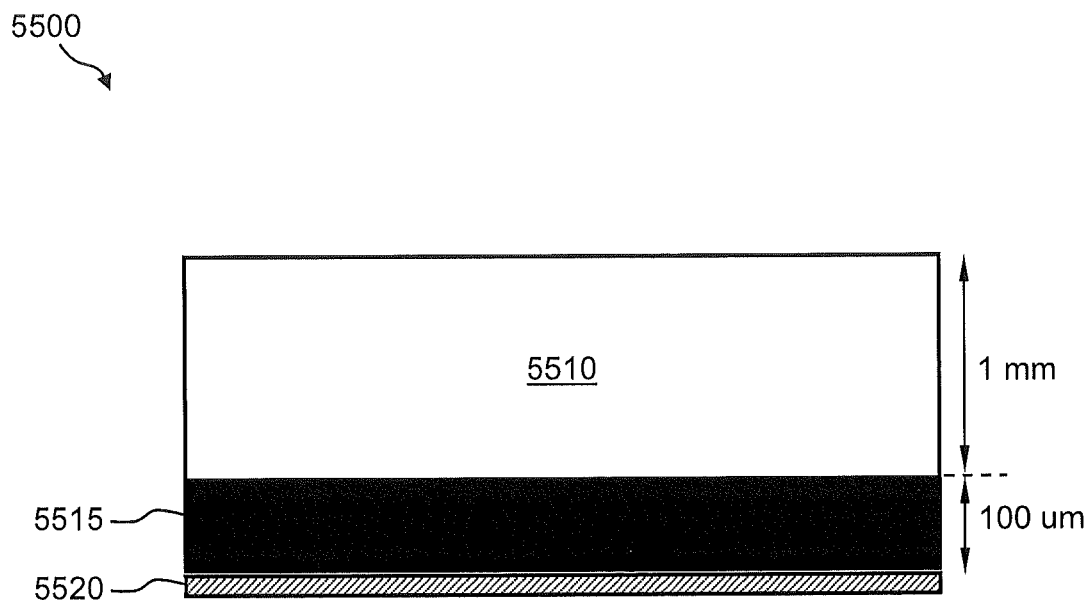
Figure 55B:
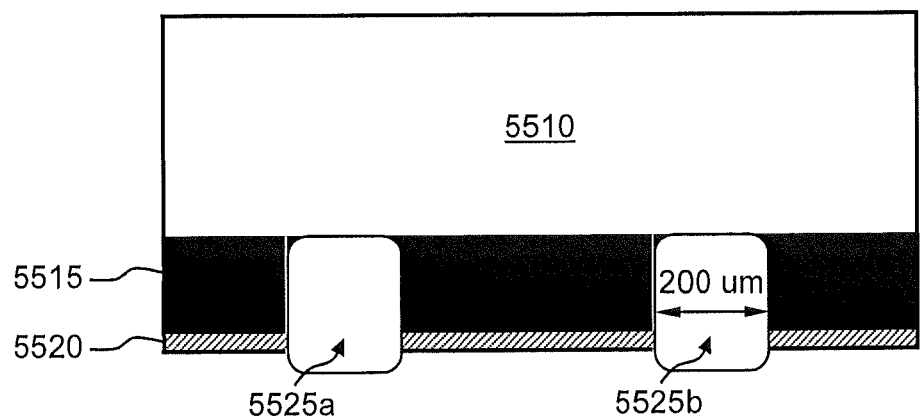

FIGS. 55A and 55B illustrate an example of a process of fabricating the microwell substrate of FIG. 53.

Figure 56:
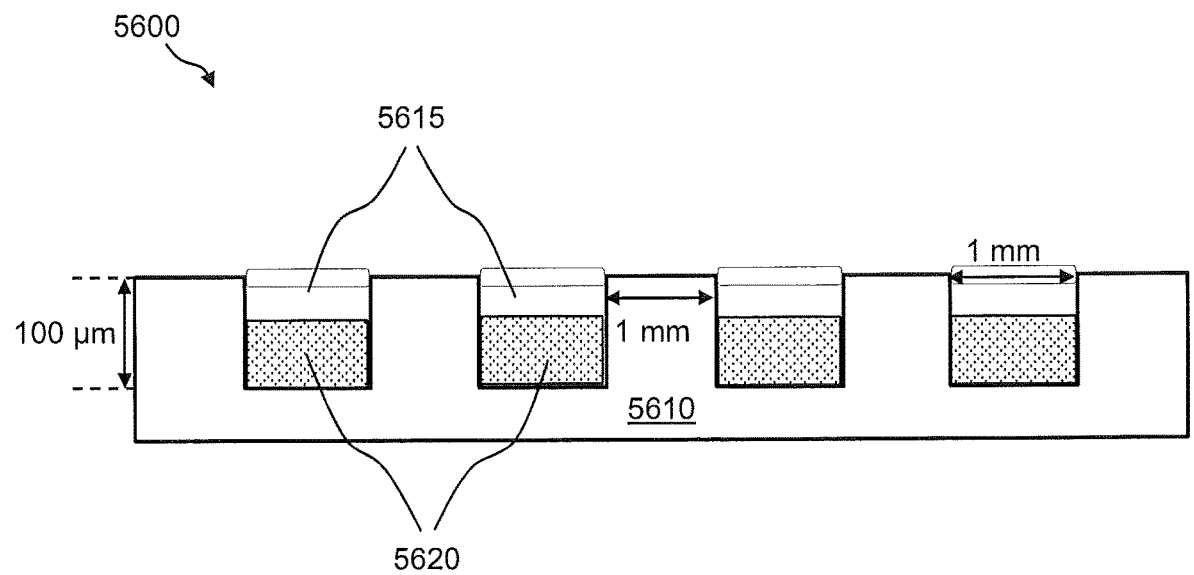

FIG. 56 illustrates a side view of an example of a microwell structure for capture and spatial compartmentalization of nucleic acids from a tissue sample.

Figure 57:
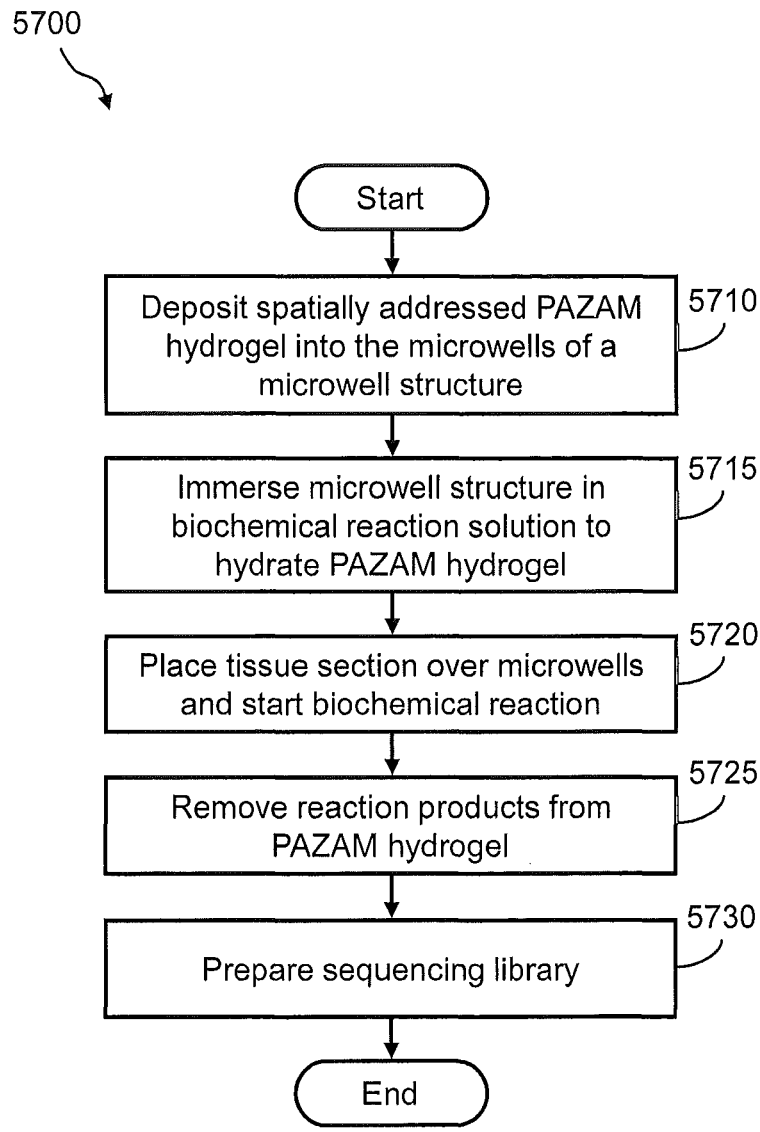

FIG. 57 illustrates a flow diagram of an example of a method of capturing nucleic acids from a tissue section using the microwell structure of FIG. 56 for preparation of a sequencing library.

Figure 58A:
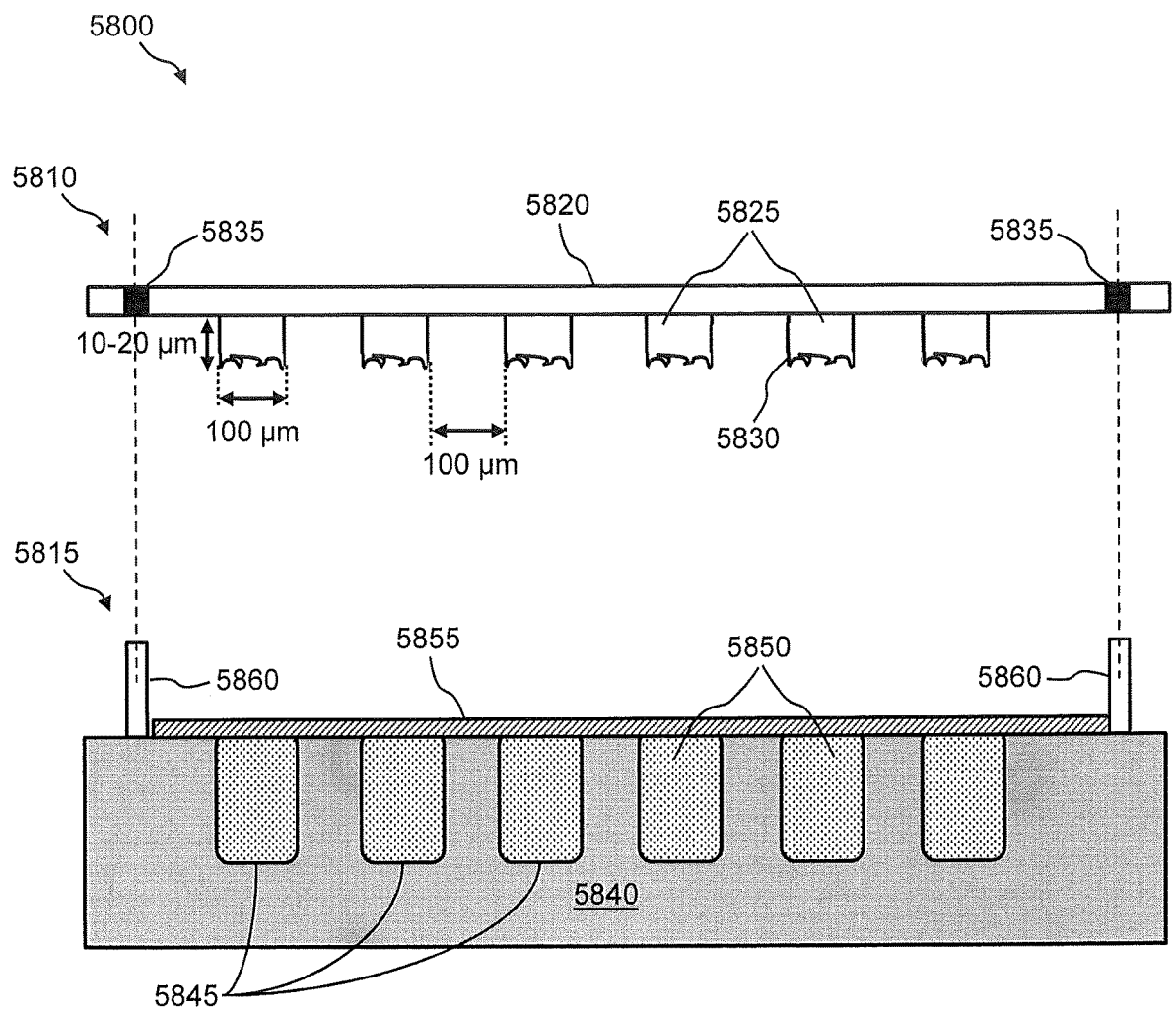

FIG. 58A illustrates a side view of an example of a pin system for tissue excision and preparation of a spatially addressed nucleic acid library.

Figure 58B:

FIG. 58B illustrates examples of different excision surfaces for the pins on the pin structure of FIG. 58A.

Figure 59:
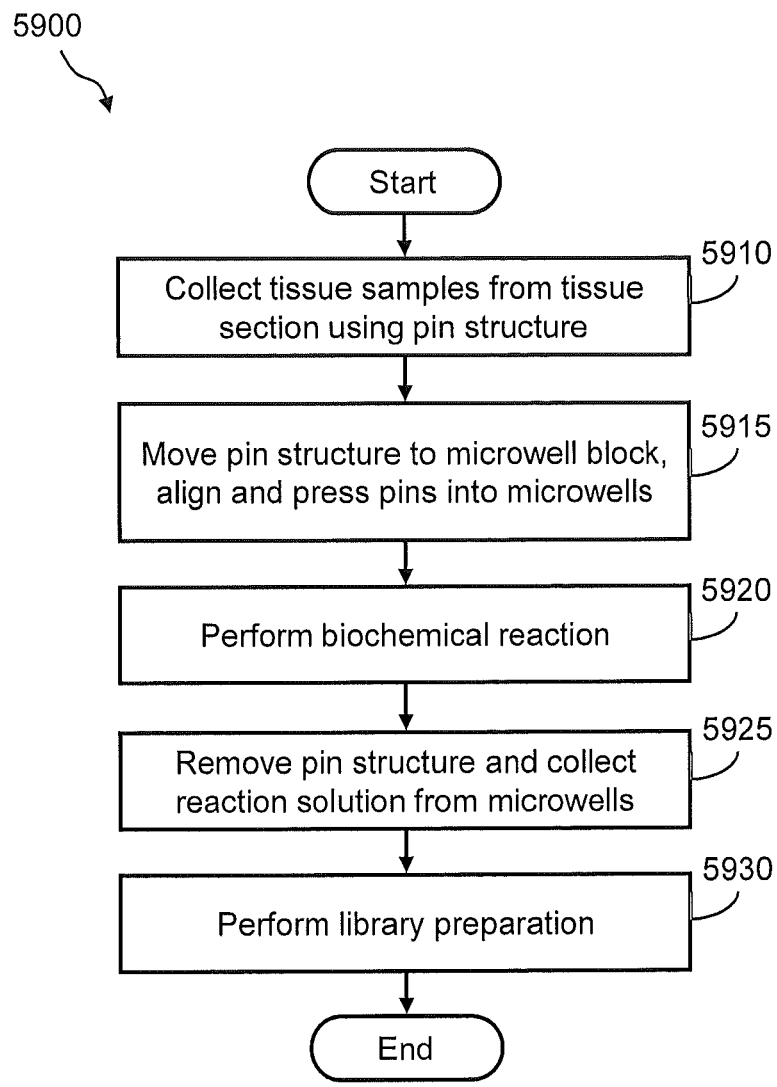

FIG. 59 illustrates a flow diagram of an example of a method of capturing nucleic acids from a tissue section using the pin system of FIG. 58 for preparation of a sequencing library.

Figure 60:
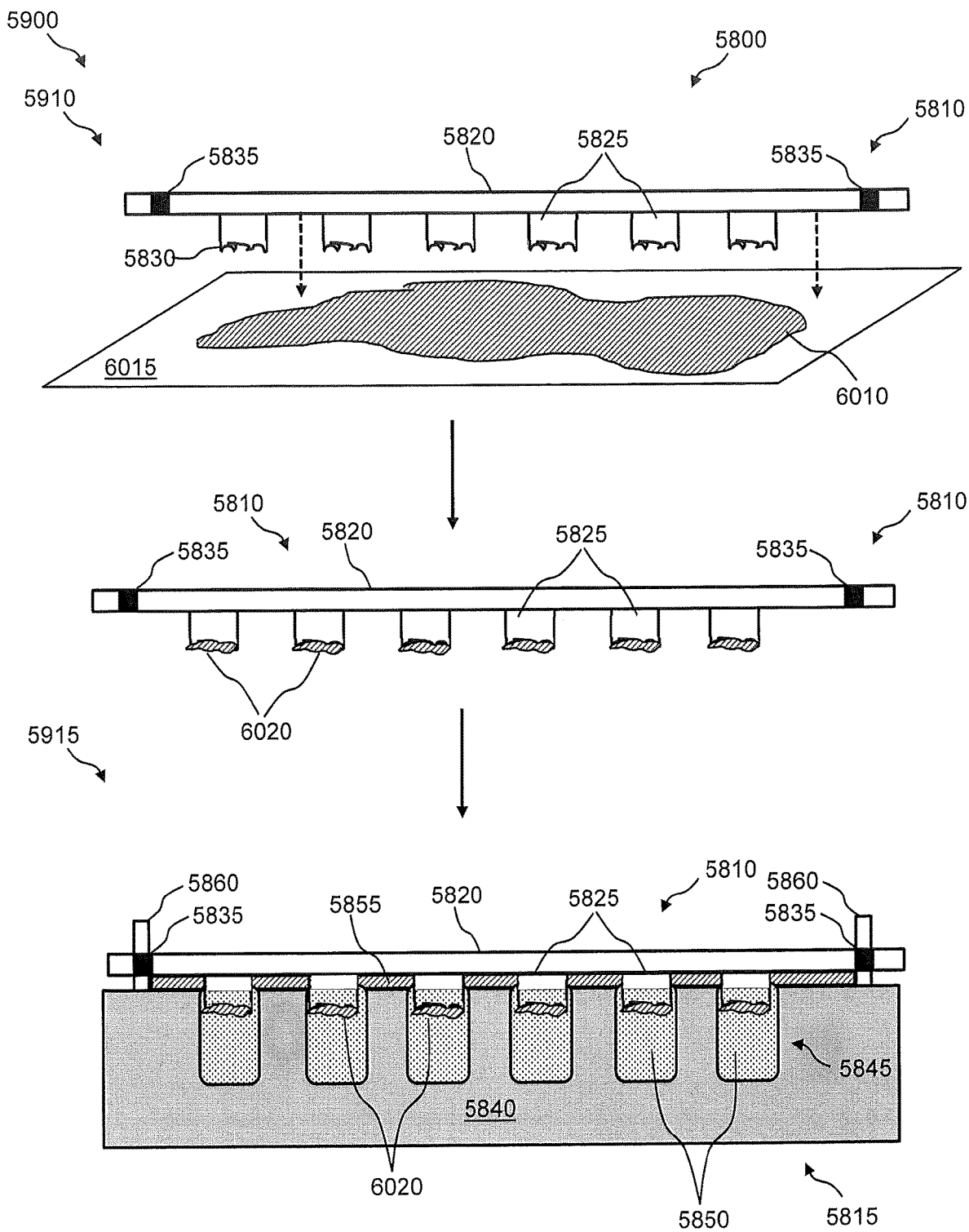

FIG. 60 illustrates side views of the pin system of FIG. 58 and shows pictorially the steps 5910 and 5915 of the method of FIG. 59.

Figure 61:
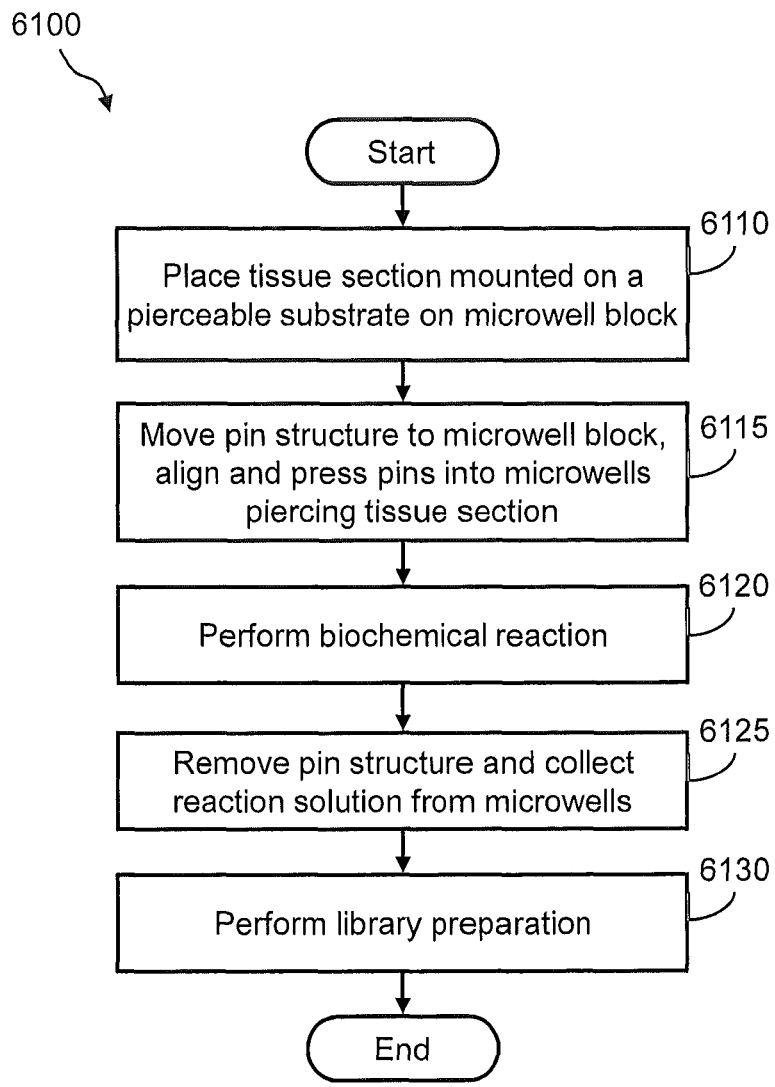

FIG. 61 illustrates a flow diagram of another example of a method of capturing nucleic acids from a tissue section using the pin system of FIG. 58 for preparation of a sequencing library.

Figure 62:
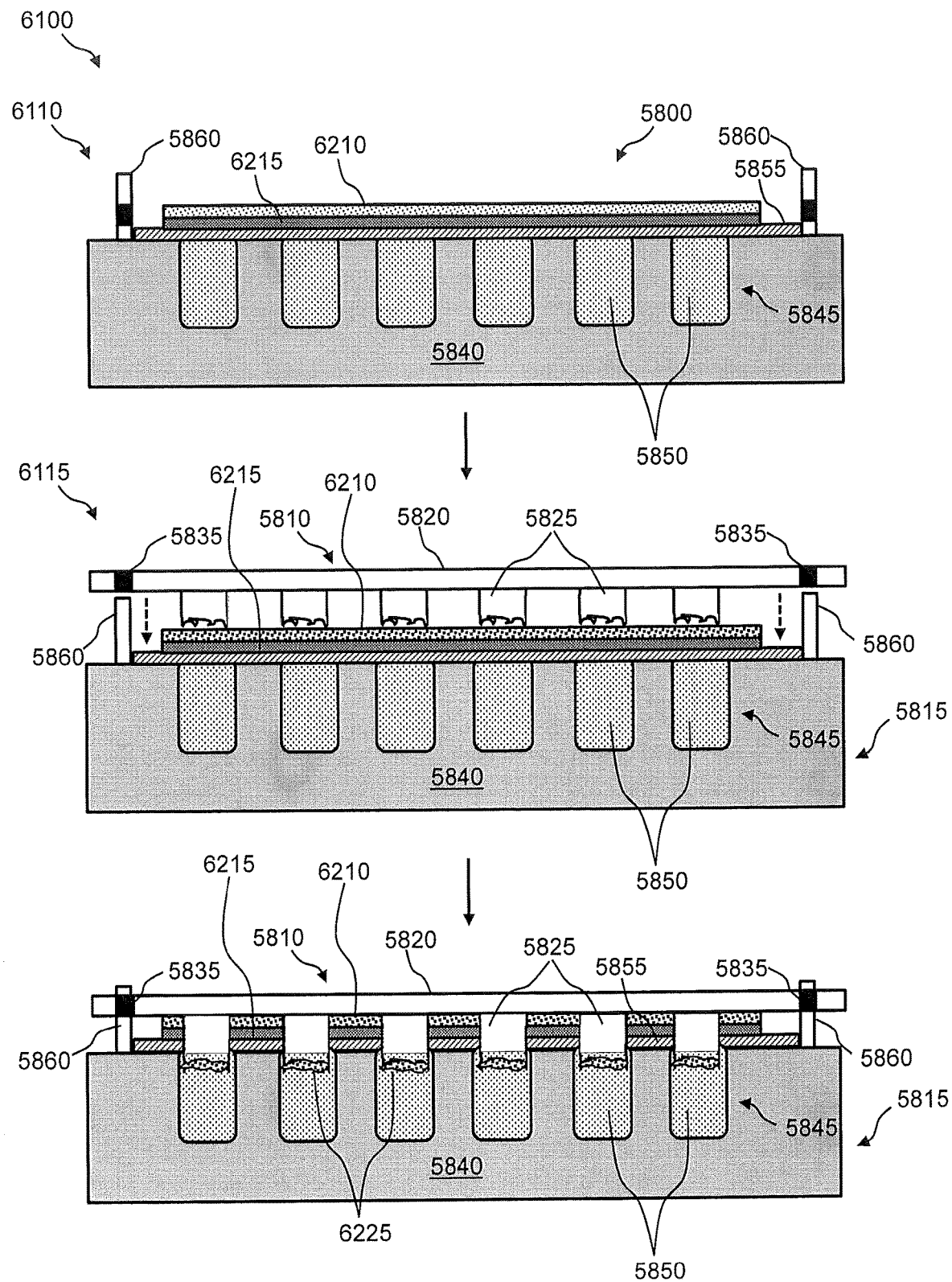

FIG. 62 illustrates side views of the pin system of FIG. 58 and shows pictorially the steps 6110 and 6115 of the method of FIG. 61.

Figure 63:
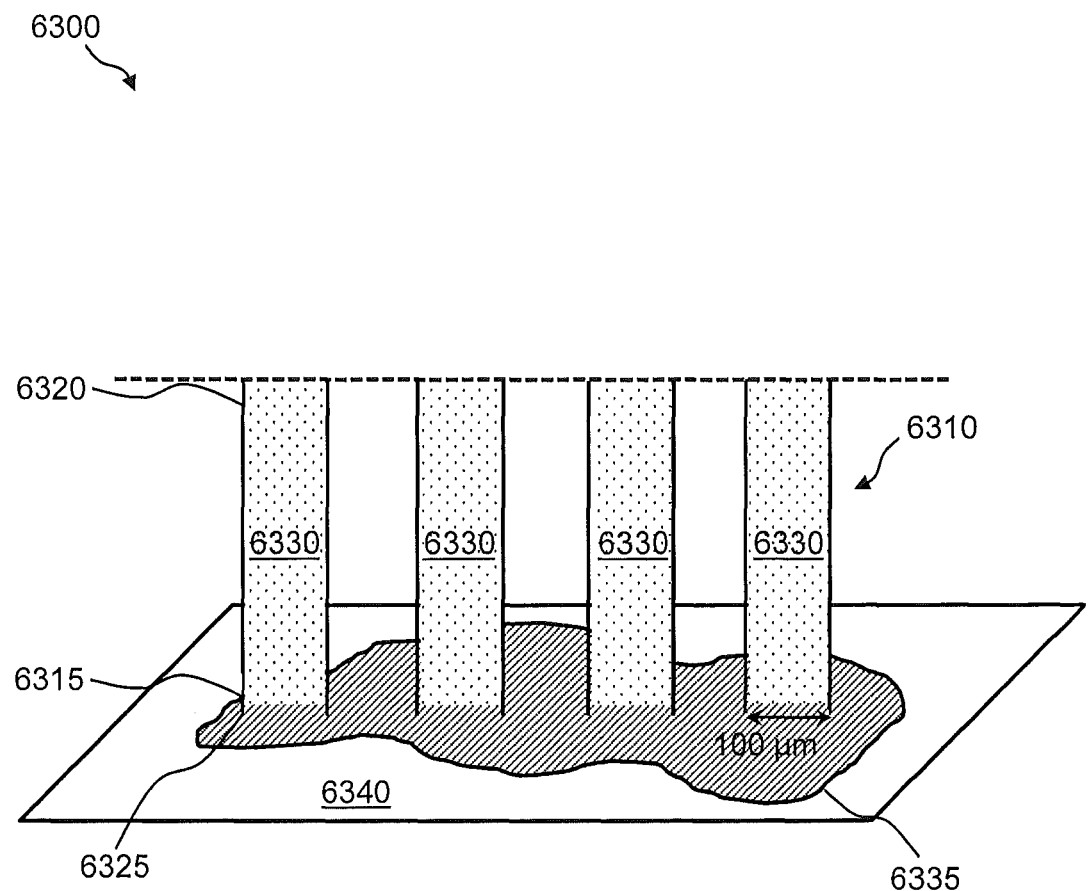
Figure 64:
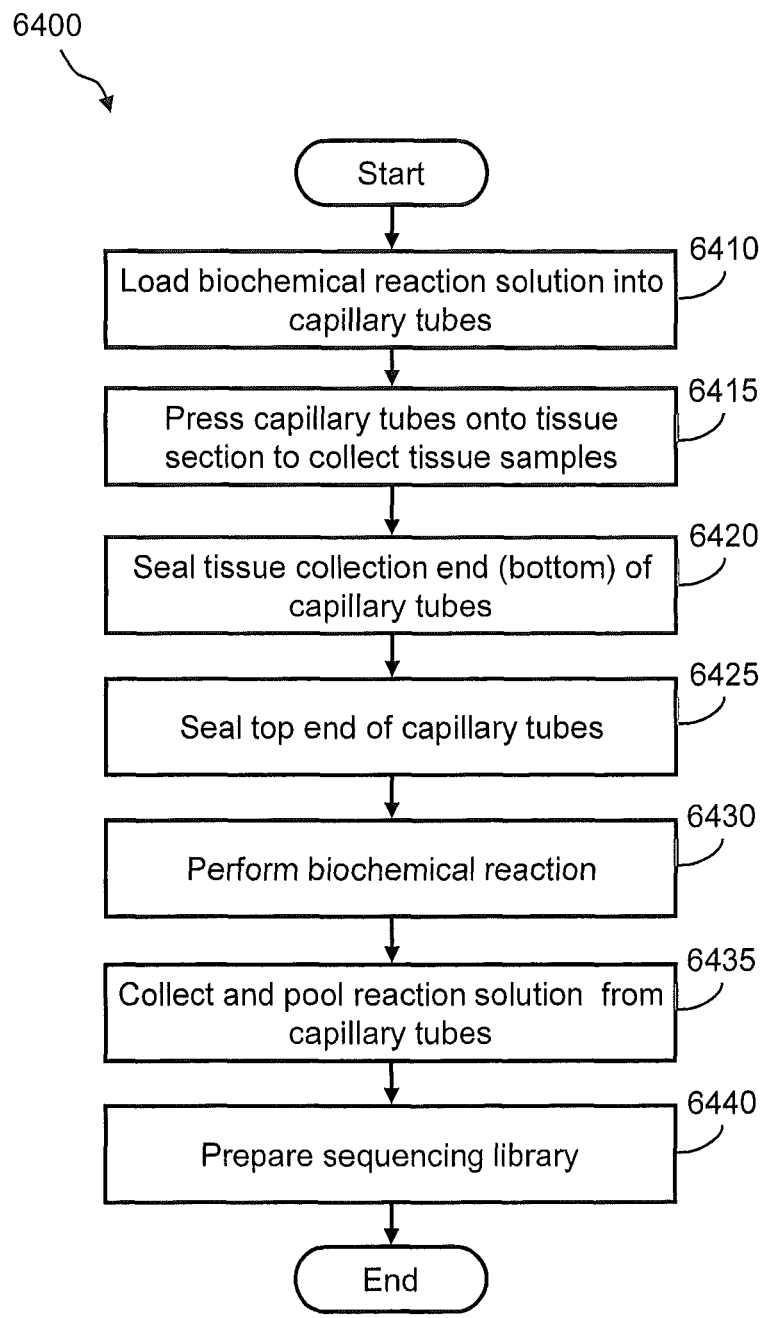

FIG. 63 illustrates a prespective view of a capillary "microreactor" system for capture of nucleic acids from a tissue section for preparation of a spatially addressed nucleic acid library FIG. 64 illustrates a flow diagram of an example of a method of capturing nucleic acids from a tissue section using the capillary microreactor system of FIG. 63 for preparation of a sequencing library.

Figure 65:
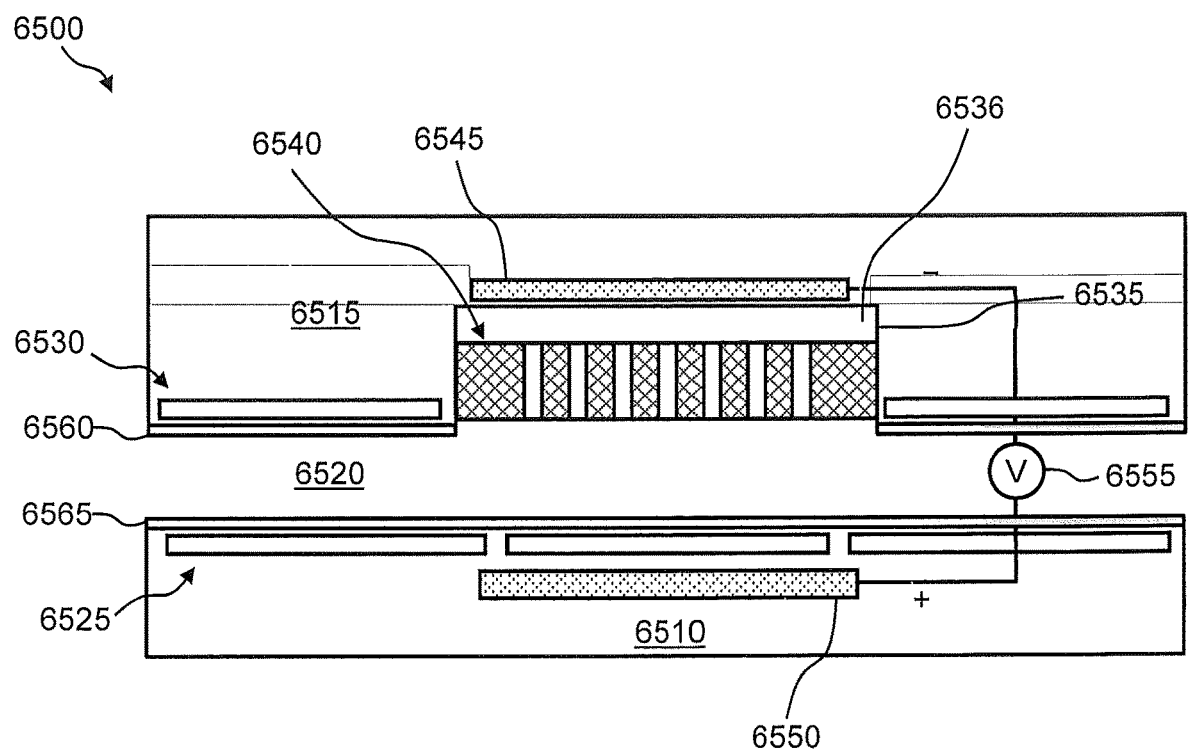

FIG. 65 illustrates a side view of a portion of a droplet actuator that is configured for spatial detection and analysis of nucleic acids in a tissue sample.

Figure 66:
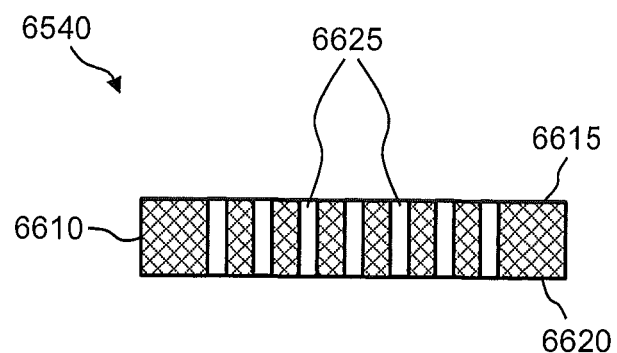

FIG. 66 illustrates a side view of the pore sheet of FIG. 65.

Figure 67A:
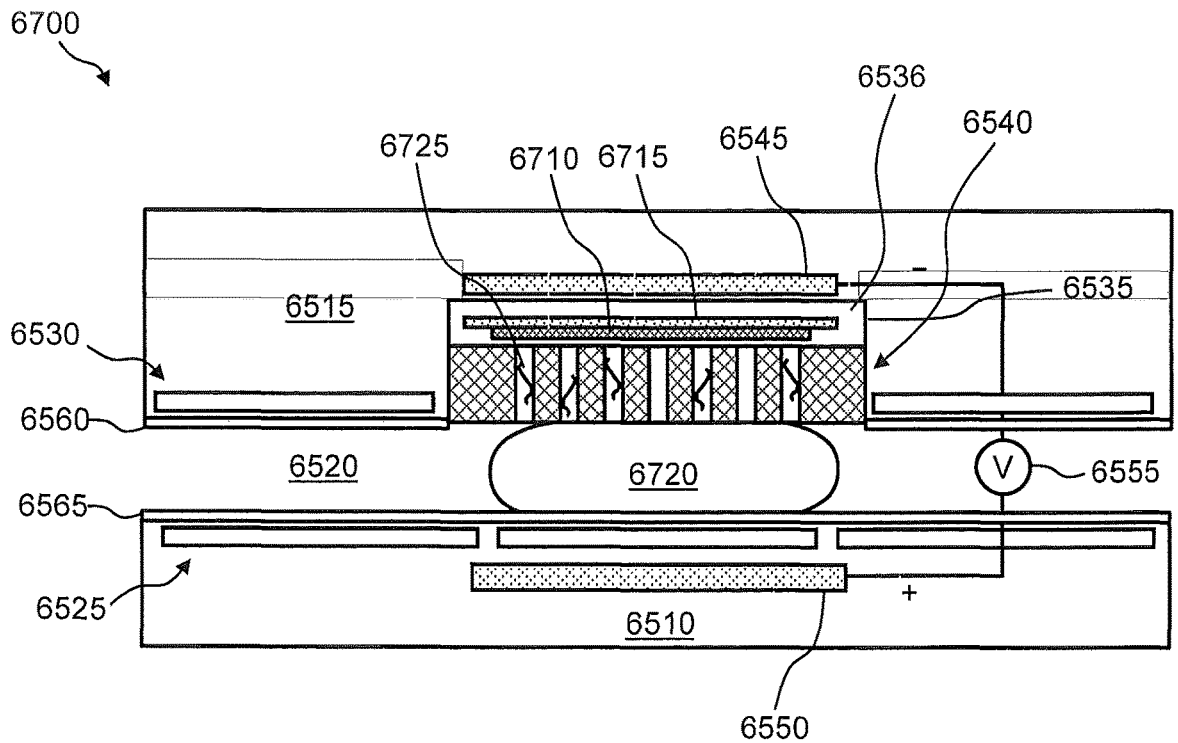
Figure 67B:
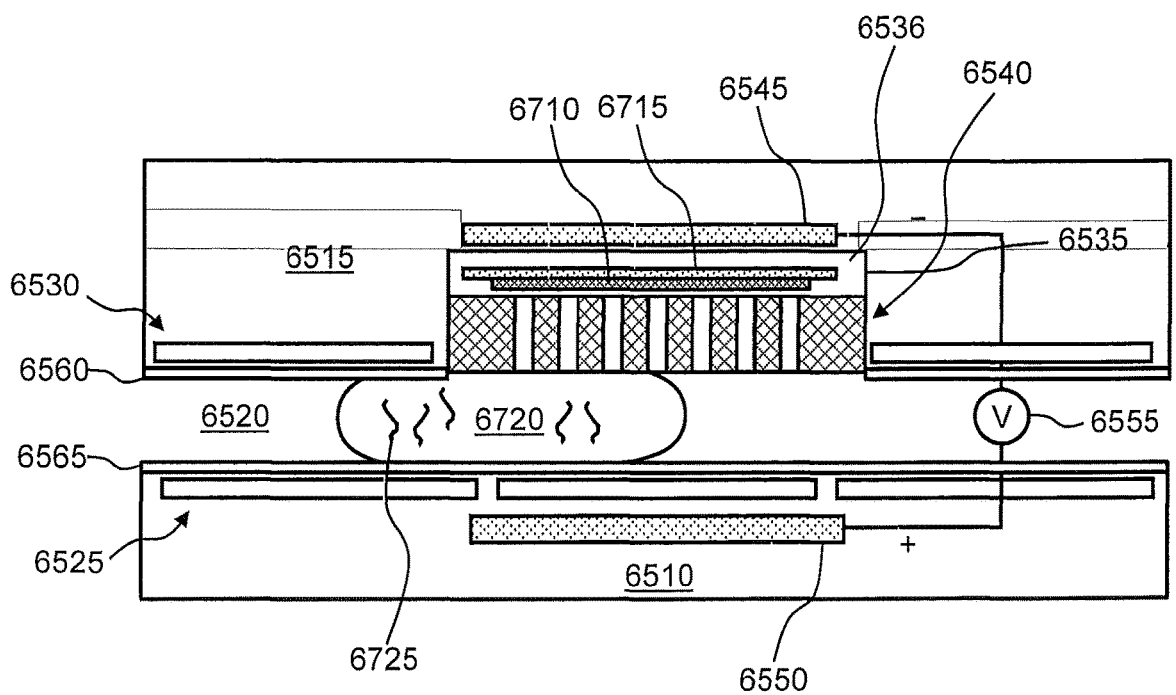

FIGS. 67A and 67B illustrate side views of the droplet actuator of FIG. 65 and show a process of isolating nucleic acid in a tissue sample for spatial detection and analysis.

Figure 68:
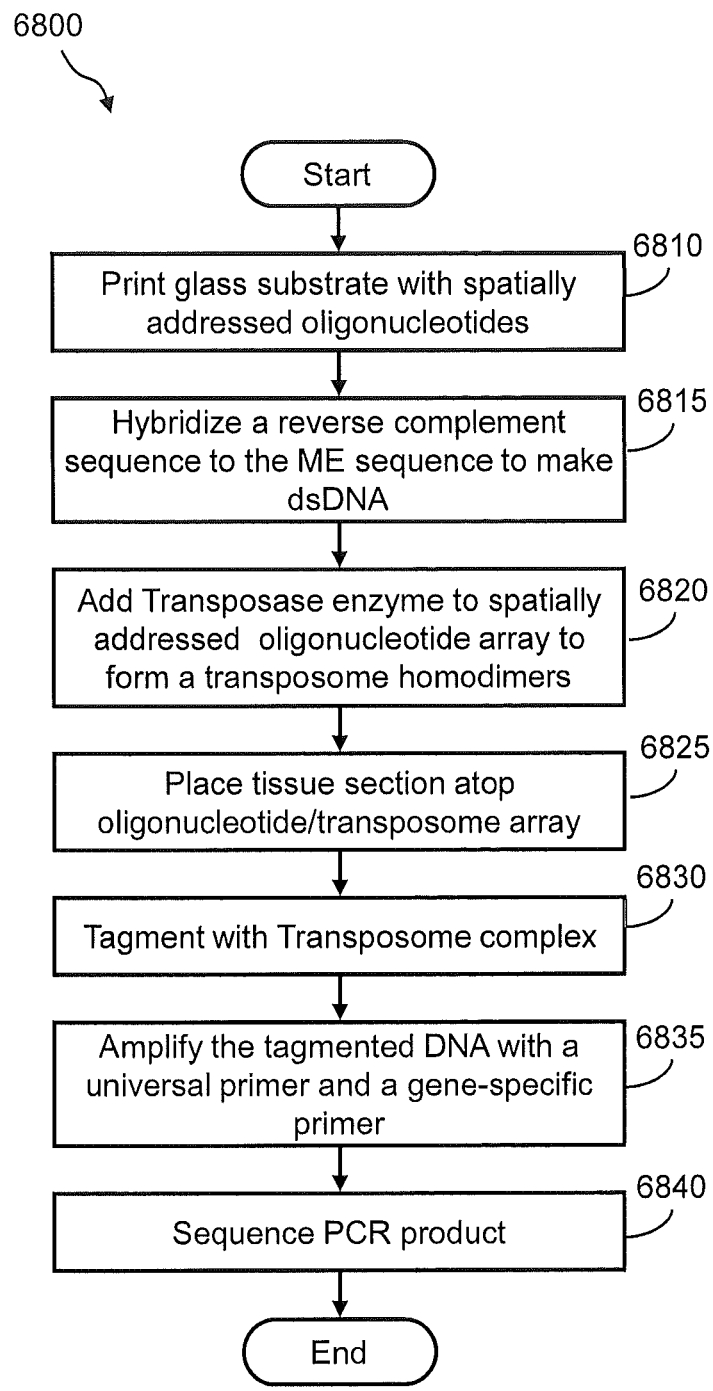

FIG. 68 illustrates an exemplary embodiments of a method of generating a spatially addressed genomic amplicon library using tagmentation of whole genomic DNA.

Figure 69A:
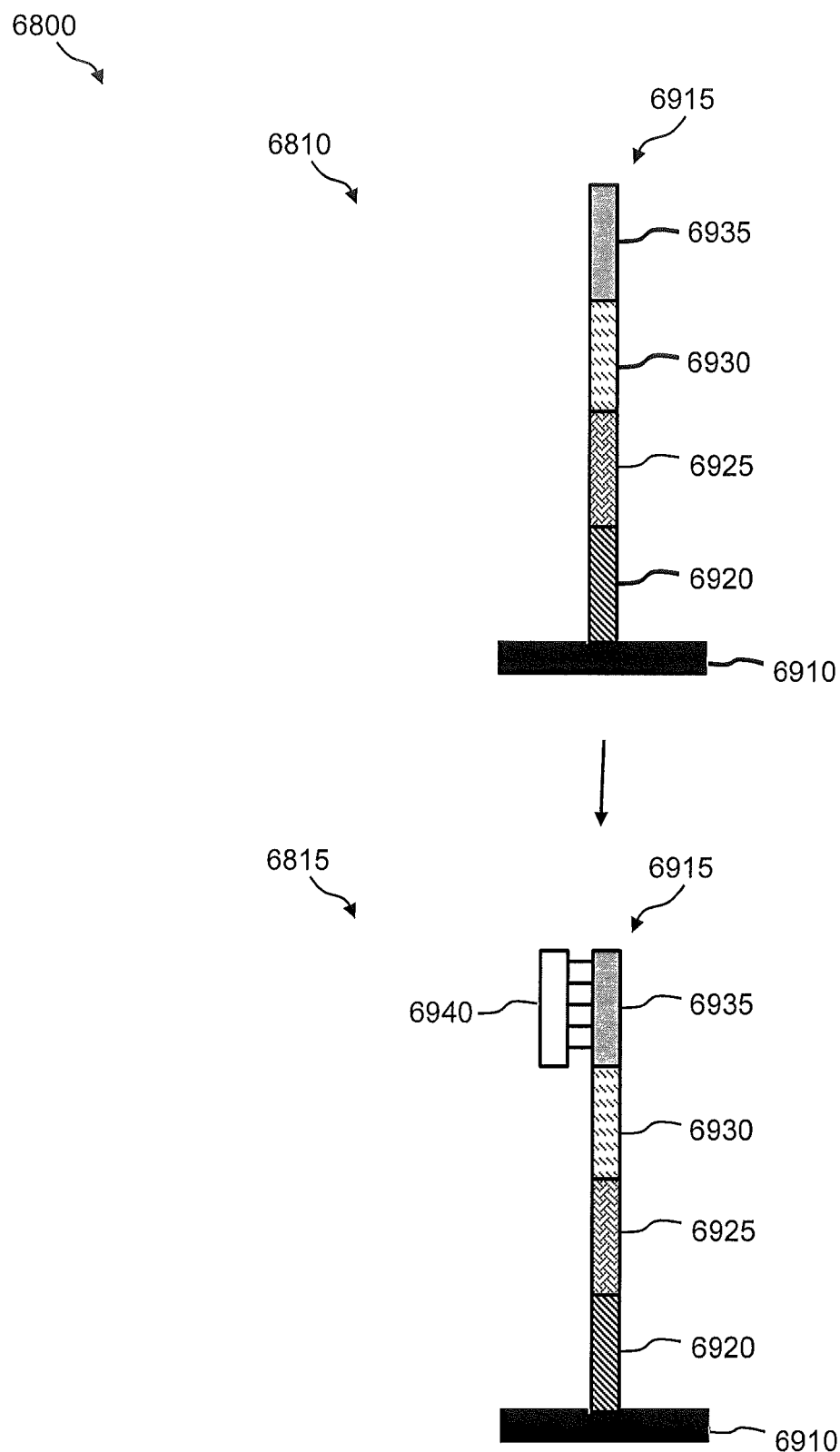
Figure 69B:
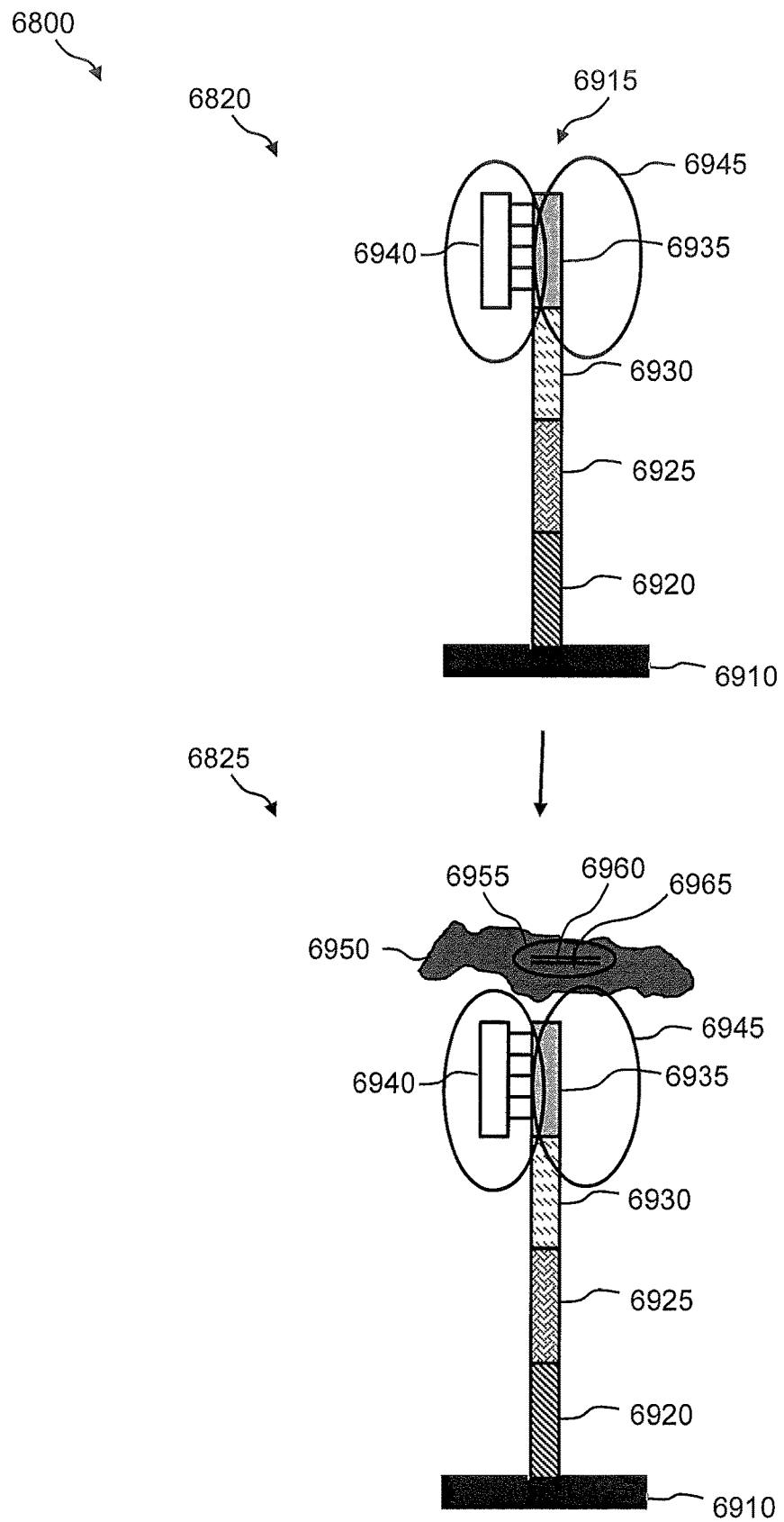
Figure 69C:
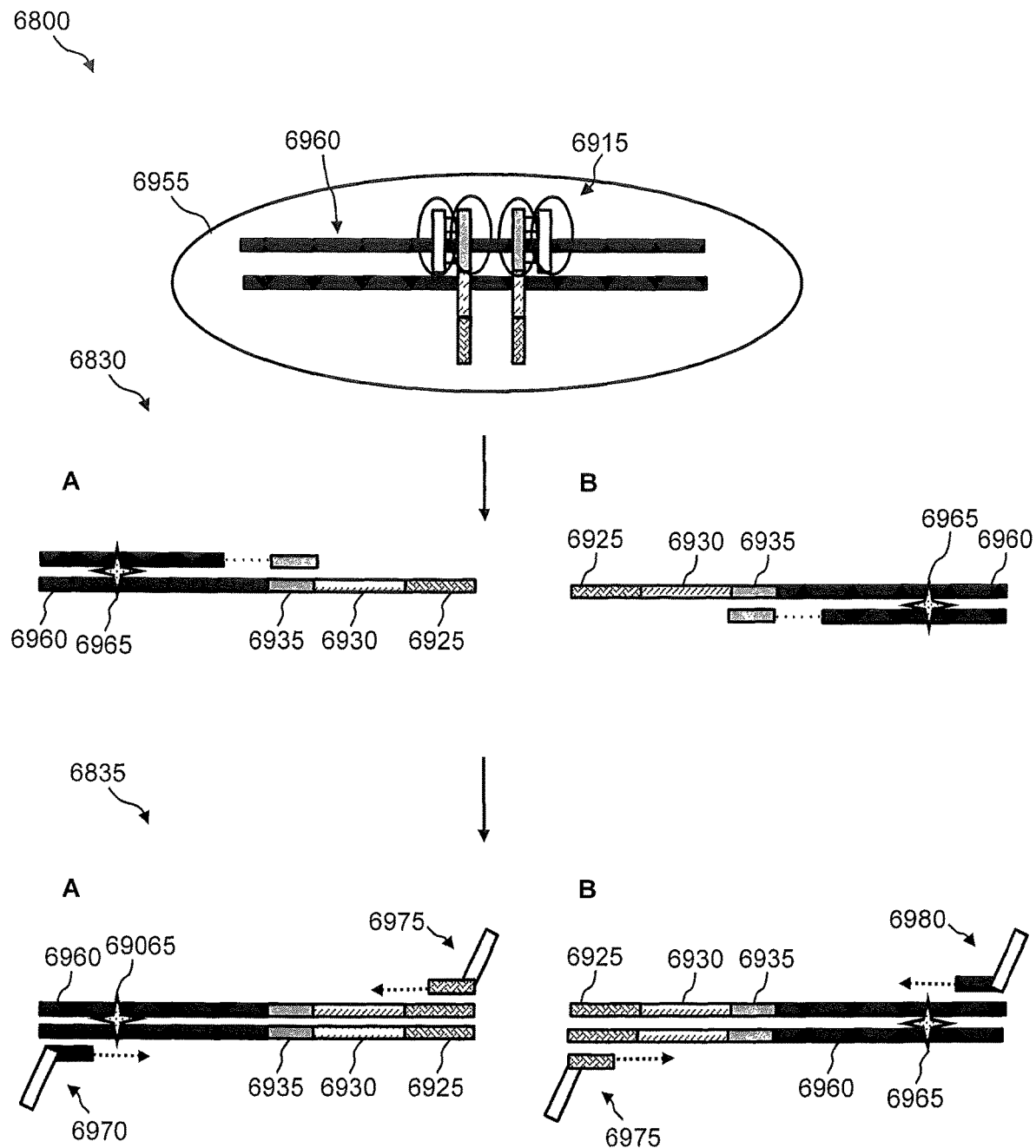

FIGS. 69A, 69B, and 69C illustrate the steps of a method of FIG. 68.

Figure 70:
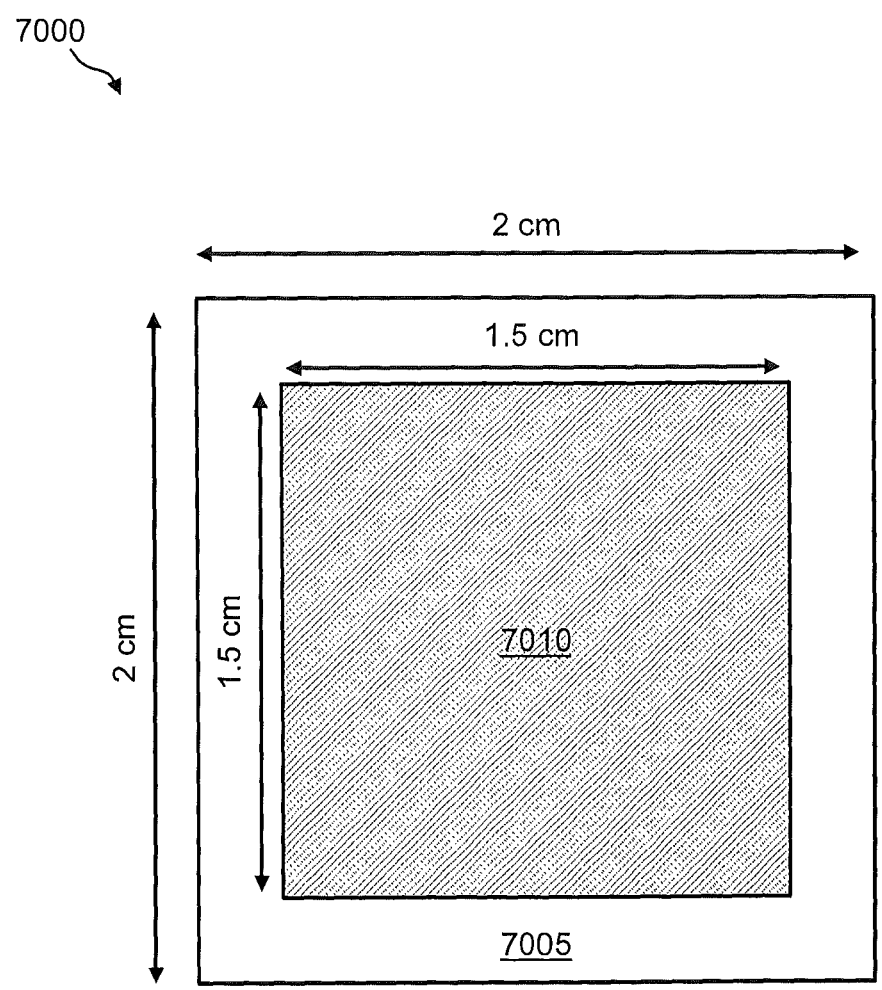

FIG. 70 illustrates a plan view of a spatial address overlay.

Figure 71:
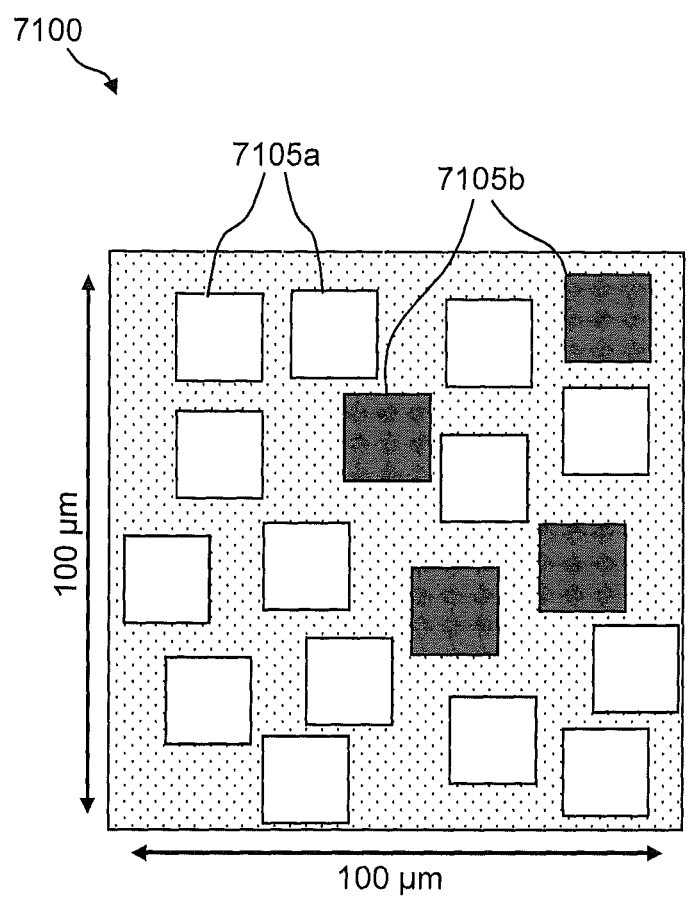

FIG. 71 illustrates a plan view of a single spatial feature on the substrate of FIG. 70.

4. DETAILED DESCRIPTION

Described herein are a variety of methods and compositions that allow for the characterization of analytes in tissues while preserving spatial information related to the origin of target analyte in the tissue. In various embodiments, an array includes a substrate on which a plurality of capture probes are immobilized such that each capture probe occupies a distinct position on the array. Each capture probe includes, among other sequences and/or molecules, a unique positional nucleic acid tag (i.e., a spatial address or indexing sequence). Each spatial address corresponds to the position of the capture probe on the array. The position of the capture probe on the array may be correlated with a position in the tissue sample.

Examples of analytes in a tissue sample include genomic DNA, methylated DNA, specific methylated DNA sequences, messenger RNA (mRNA), polyA mRNA, fragmented mRNA, fragmented DNA, mitochondrial DNA, viral RNA, microRNA, in situ synthesized PCR products, RNA/DNA hybrids, lipid, carbohydrate, protein, glycoprotein, lipoprotein, phosphoprotein, specific phosphorylated or acetylated variant of a protein, or viral coat proteins.

A nucleic acid tag encoding location (i.e., a spatial address or indexing sequence) can be coupled to a nucleic acid capture region or any other molecule that binds a target analyte. Examples of other molecules that may be coupled to a nucleic acid tag include antibodies, antigen binding domains, proteins, peptides, receptors, haptens, etc.

Described herein are a variety of methods and compositions that allow for the characterization of transcriptomes and/or genomic variation in tissues while preserving spatial information related to the origin of target nucleic acids in the tissue. For example, the methods disclosed herein can enable the identification of the location of a cell or a cell cluster in a tissue biopsy that carries an aberrant mutation. The methods provided herein can therefore be useful for diagnostic purposes, e.g., for the diagnosis of cancer, and possibly aid in the selection of targeted therapies.

The present disclosure is based, in part, on the realization that information related to the spatial origin of a nucleic acid in a tissue sample can be encoded in the nucleic acid in the process of preparing the nucleic acid for sequencing. For example, nucleic acids from a tissue sample can be tagged by probes including location-specific sequence information (a "spatial address"). Spatially addressed nucleic acid molecules from a tissue sample can then be sequenced in bulk. The sequence-identical nucleic acid molecules originating from different regions in a tissue sample can be distinguished based on their spatial address and can be mapped onto their regions of origin in the tissue sample.

The present disclosure is further based, in part, on the realization that distinguishing related nucleic acids based on their spatial origin in a tissue sample can increase the sensitivity of detection of rare mutations in a complex tissue. For example, it was found that spatial addressing of nucleic acids could increase the sensitivity of detection of single nucleotide variations (SNVs) in a tissue sample.

In some methods described herein probes for spatial tagging can include, e.g., combinations of spatial address regions and gene-specific capture regions. The spatially addressed and gene-specific probes can be contacted with the tissue sample as immobilized probes on a capture array. Alternatively, the spatially addressed probes can be released from the capture array and interact with the nucleic acids in solution in the tissue sample, e.g., in situ.

The present disclosure is further based, in part, on the realization that spatial tagging can be performed using probes that separate spatial address regions from gene-specific capture regions. The ability to separate capture regions from spatial address regions in two or more probe can increase the flexibility of sequencing library designs and of library preparation protocols.

The present disclosure is further based, in part, on the realization that the robustness and data quality of spatial transcriptomics experiments can be enhanced by facilitating the transfer of nucleic acids from a tissue sample onto a capture array, e.g., a capture array of spatially addressed capture probes. For example, electrophoretic transfer of nucleic acids can be used to improve transfer yields and transfer kinetics of nucleic acids. High-yield nucleic acid transfer from tissue samples onto capture arrays can facilitate the detection of rare SNVs. Fast transfer kinetics can be used limit nucleic acid diffusion during the transfer process and help increase the resolution of spatial addressing. Other methods described herein involve the use of intermediate nucleic acid substrates, such as particles (e.g., electromagnetic nanoparticles), membranes (e.g., nylon membranes) or microwell plates to facilitate nucleic acid capture in the tissue sample, to facilitate nucleic acid transfer onto capture arrays, and to limit diffusion and improve spatial resolution. Additional methods, involving, e.g., tagmentation of genomic DNA are described that can be used to efficiently add spatial addresses to nucleic acids, e.g., on the surface of a capture array.

The present disclosure is further based on the realization that spatial addressing of nucleic acids from a tissue sample can involve two-dimensional spatial addressing, e.g., to correlate the position of a nucleic acid on a two-dimensional capture array with the position of the nucleic acid in a two-dimensional tissue section. Spatial addressing can be performed also in additional dimensions. For example, spatial address sequences can be added to nucleic acids to describe the relative spatial position of a nucleic acid in a third or fourth dimension, e.g., by describing the position of a tissue section in a tissue biopsy, or the position of a tissue biopsy in a subject's organ. Temporal address sequences could be added to nucleic acids from a tissue sample to denote a timepoint in a timecourse experiment, e.g., inquiring into changes of gene-expression in a cell in response to a physical or chemical stimulus, such as a drug treatment during a clinical trial.

It must be noted that, as used in this specification and the appended claims, the singular forms "a", "an" and "the" include plural referents unless the content clearly dictates otherwise. Thus, for example, reference to "a capture probe" includes a mixture of two or more capture probes, and the like.

The term "about," particularly in reference to a given quantity, is meant to encompass deviations of plus or minus five percent.

As used herein, the terms "includes," "including," "includes," "including," "contains," "containing," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the terms "address," "tag," or "index," when used in reference to a nucleotide sequence is intended to mean a unique nucleotide sequence that is distinguishable from other indices as well as from other nucleotide sequences within polynucleotides contained within a sample. A nucleotide "address," "tag," or "index" can be a random or a specifically designed nucleotide sequence. An "address," "tag," or "index" can be of any desired sequence length so long as it is of sufficient length to be unique nucleotide sequence within a plurality of indices in a population and/or within a plurality of polynucleotides that are being analyzed or interrogated. A nucleotide "address," "tag," or "index" of the disclosure is useful, for example, to be attached to a target polynucleotide to tag or mark a particular species for identifying all members of the tagged species within a population. Accordingly, an index is useful as a barcode where different members of the same molecular species can contain the same index and where different species within a population of different polynucleotides can have different indices.

As used herein, a "spatial address," "spatial tag" or "spatial index," when used in reference to a nucleotide sequence, means an address, tag or index encoding spatial information related to the region or location of origin of an addressed, tagged, or indexed nucleic acid in a tissue sample.

As used herein, the term "substrate" is intended to mean a solid support. The term includes any material that can serve as a solid or semi-solid foundation for creation of features such as wells for the deposition of biopolymers, including nucleic acids, polypeptide and/or other polymers. A substrate as provided herein is modified, for example, or can be modified to accommodate attachment of biopolymers by a variety of methods well known to those skilled in the art. Exemplary types of substrate materials include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtiter plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

Those skilled in the art will know or understand that the composition and geometry of a substrate as provided herein can vary depending on the intended use and preferences of the user. Therefore, although planar substrates such as slides, chips or wafers are exemplified herein in reference to microarrays for illustration, given the teachings and guidance provided herein, those skilled in the art will understand that a wide variety of other substrates exemplified herein or well known in the art also can be used in the methods and/or compositions herein.

In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, the solid support includes a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S.

Ser. No. 13/661,524 or US Pat. App. Publ. No. 2012/0316086 A1, each of which is incorporated herein by reference.

As used herein, the term "interstitial region" refers to an area in a substrate or on a surface that separates other areas of the substrate or surface. For example, an interstitial region can separate one feature of an array from another feature of the array. The two regions that are separated from each other can be discrete, lacking contact with each other. In another example, an interstitial region can separate a first portion of a feature from a second portion of a feature. The separation provided by an interstitial region can be partial or full separation. Interstitial regions will typically have a surface material that differs from the surface material of the features on the surface. For example, features of an array can have an amount or concentration of capture agents or primers that exceeds the amount or concentration present at the interstitial regions. In some embodiments the capture agents or primers may not be present at the interstitial regions.

In some embodiments, the solid support includes an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g., microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, U.S. Prov. Pat. App. Ser. No. 61/753,833, which is incorporated herein by reference). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. App. Pub. No. 2011/0059865 A1, which is incorporated herein by reference) which is not covalently attached to any part of the structured substrate, can be used as the gel material.

In particular embodiments, a structured substrate can be made by patterning a solid support material with wells (e.g. microwells or nanowells), coating the patterned support with a gel material (e.g., PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g., a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nano-fabrication methods.

A patterned substrate can include, for example, wells etched into a slide or chip. The pattern of the etchings and geometry of the wells can take on a variety of different shapes and sizes so long as such features are physically or functionally separable from each other. Particularly useful substrates having such structural features are patterned substrates that can select the size of solid support particles such as microspheres. An exemplary patterned substrate having these characteristics is the etched substrate used in connection with BeadArray technology (Illumina, Inc., San Diego, Calif.). Further examples, are described in U.S. Pat. No. 6,770,441, which is incorporated herein by reference.

As used herein, the term "immobilized" when used in reference to a nucleic acid is intended to mean direct or indirect attachment to a solid support via covalent or non-covalent bond(s). In certain embodiments, covalent attachment can be used, but all that is required is that the nucleic acids remain stationary or attached to a support under conditions in which it is intended to use the support, for example, in applications requiring nucleic acid amplification and/or sequencing. Oligonucleotides to be used as capture primers or amplification primers can be immobilized such that a 3'-end is available for enzymatic extension and at least a portion of the sequence is capable of hybridizing to a complementary sequence. Immobilization can occur via hybridization to a surface attached oligonucleotide, in which case the immobilized oligonucleotide or polynucleotide can be in the 3'-5' orientation. Alternatively, immobilization can occur by means other than base-pairing hybridization, such as the covalent attachment set forth above.

Certain embodiments may make use of solid supports comprised of an inert substrate or matrix (e.g. glass slides, polymer beads etc.) which has been functionalized, for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814 and US 2008/0280773, the contents of which are incorporated herein in their entirety by reference. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

Exemplary covalent linkages include, for example, those that result from the use of click chemistry techniques. Exemplary non-covalent linkages include, but are not limited to, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "plurality" is intended to mean a population of two or more different members. Pluralities can range in size from small, medium, large, to very large. The size of small plurality can range, for example, from a few members to tens of members. Medium sized pluralities can range, for example, from tens of members to about 100 members or hundreds of members. Large pluralities can range, for example, from about hundreds of members to about 1000 members, to thousands of members and up to tens of thousands of members. Very large pluralities can range, for example, from tens of thousands of members to about hundreds of thousands, a million, millions, tens of millions and up to or greater than hundreds of millions of members. Therefore, a plurality can range in size from two to well over one hundred million members as well as all sizes, as measured by the number of members, in between and greater than the above exemplary ranges. An exemplary number of features within a microarray includes a plurality of about 500,000 or more discrete features within 1.28 cm'. Exemplary nucleic acid pluralities include, for example, populations of about $1\times10^5$, $5\times10^5$ and $1\times10^6$ or more different nucleic acid species. Accordingly, the definition of the term is intended to include all integer values greater than two. An upper limit of a plurality can be set, for example, by the theoretical diversity of nucleotide sequences in a nucleic acid sample.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. Particular forms of nucleic acids may include all types of nucleic acids found in an organism as well as synthetic nucleic acids such as polynucleotides produced by chemical synthesis. Particular examples of nucleic acids that are applicable for analysis through incorporation into microarrays produced by methods as provided herein include genomic DNA (gDNA), expressed sequence tags (ESTs), DNA copied messenger RNA (cDNA), RNA copied messenger RNA (cRNA), mitochondrial DNA or genome, RNA, messenger RNA (mRNA) and/or other populations of RNA. Fragments and/or portions of these exemplary nucleic acids also are included within the meaning of the term as it is used herein.

As used herein, the term "double-stranded," when used in reference to a nucleic acid molecule, means that substantially all of the nucleotides in the nucleic acid molecule are hydrogen bonded to a complementary nucleotide. A partially double stranded nucleic acid can have at least 10%, 25%, 50%, 60%, 70%, 80%, 90% or 95% of its nucleotides hydrogen bonded to a complementary nucleotide.

As used herein, the term "single-stranded," when used in reference to a nucleic acid molecule, means that essentially none of the nucleotides in the nucleic acid molecule are hydrogen bonded to a complementary nucleotide.

As used herein, the term "capture primers" is intended to mean an oligonucleotide having a nucleotide sequence that is capable of specifically annealing to a single stranded polynucleotide sequence to be analyzed or subjected to a nucleic acid interrogation under conditions encountered in a primer annealing step of, for example, an amplification or sequencing reaction. The terms "nucleic acid," "polynucleotide" and "oligonucleotide" are used interchangeably herein. The different terms are not intended to denote any particular difference in size, sequence, or other property unless specifically indicated otherwise. For clarity of description the terms can be used to distinguish one species of nucleic acid from another when describing a particular method or composition that includes several nucleic acid species.

As used herein, the term "gene-specific" or "target specific" when used in reference to a capture probe or other nucleic acid is intended to mean a capture probe or other nucleic acid that includes a nucleotide sequence specific to a targeted nucleic acid, e.g., a nucleic acid from a tissue sample, namely a sequence of nucleotides capable of selectively annealing to an identifying region of a targeted nucleic acid. Gene-specific capture probes can have a single species of oligonucleotide, or can include two or more species with different sequences. Thus, the gene-specific capture probes can be two or more sequences, including 3, 4, 5, 6, 7, 8, 9 or 10 or more different sequences. The gene-specific capture probes can comprise a gene-specific capture primer sequence and a universal capture probe sequence. Other sequences such as sequencing primer sequences and the like also can be included in a gene-specific capture primer.

In comparison, the term "universal" when used in reference to a capture probe or other nucleic acid is intended to mean a capture probe or nucleic acid having a common nucleotide sequence among a plurality of capture probes. A common sequence can be, for example, a sequence complementary to the same adapter sequence. Universal capture probes are applicable for interrogating a plurality of different polynucleotides without necessarily distinguishing the different species whereas gene-specific capture primers are applicable for distinguishing the different species.

In various embodiments, the capture elements (e.g., capture primers or capture probes or other nucleic acid sequences) can be spaced to A) spatially resolve nucleic acids within the geometry of a single cell, i.e., multiple capture sites per cell; B) spatially resolve nucleic acids at about the single cell level, i.e., about 1 capture site per cell. Additionally, capture elements may be spaced as in A or B above, and be: I) spaced to sample nucleic acids from a sample at regular intervals, e.g., spaced in a grid or pattern such that about every other or every $5^{th}$ or every $10^{th}$ cell is sampled, or about every other or every $5^{th}$ or every 10 gropu of 2, 3, 4, 5, 6, 7, 8, 9, 10 or more cells is sampled; II) spaced to capture samples from substantially all available cells in one or more regions of a sample, or III) spaced to capture samples from substantially all available cells in the sample.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid can be a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

The number of template copies or amplicons that can be produced can be modulated by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. The number of copies of a nucleic acid template can be at least 1, 10, 100, 200, 500, 1000, 2000, 3000, 4000, 5000, 6000, 7000, 8000, 9000 and 10,000 copies, and can be varied depending on the particular application.

As used herein, the term "each," when used in reference to a collection of items, is intended to identify an individual item in the collection but does not necessarily refer to every item in the collection unless the context clearly dictates otherwise.

Provided herein are arrays for and methods of spatial detection and analysis (e.g., mutational analysis or single nucleotide variation (SNV) detection) of nucleic acid in a tissue sample. The arrays described herein can comprise a substrate on which a plurality of capture probes are immobilized such that each capture probe occupies a distinct position on the array. Some or all of the plurality of capture probes can comprise a unique positional tag (i.e., a spatial address or indexing sequence). A spatial address can describe the position of the capture probe on the array. The position of the capture probe on the array can be correlated with a position in the tissue sample.

As used herein, the term "tissue sample" refers to a piece of tissue that has been obtained from a subject, fixed, sectioned, and mounted on a planar surface, e.g., a microscope slide. The tissue sample can be a formalin-fixed paraffin-embedded (FFPE) tissue sample or a fresh tissue sample or a frozen tissue sample, etc. The methods disclosed herein may be performed before or after staining the tissue sample. For example, following hematoxylin and eosin staining, a tissue sample may be spatially analyzed in accordance with the methods as provided herein. A method may include analyzing the histology of the sample (e.g., using hematoxylin and esoins staining) and then spatially analyzing the tissue.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a planar surface, e.g., a microscope slide.

In some embodiments, nucleic acids in a tissue sample are transferred to and captured onto an array. For example, a tissue section is placed in contact with an array and nucleic acid is captured onto the array and tagged with a spatial address. The spatially-tagged DNA molecules are released from the array and analyzed, for example, by high throughput next generation sequencing (NGS), such as sequencing-by-synthesis (SBS). In some embodiments, a nucleic acid in a tissue section (e.g., a formalin-fixed paraffin-embedded (FFPE) tissue section) is transferred to an array and captured onto the array by hybridization to a capture probe. In some embodiments, a capture probe can be a universal capture probe hybridizing, e.g., to an adaptor region in a nucleic acid sequencing library, or to the poly-A tail of an mRNA. In some embodiments, the capture probe can be a gene-specific capture probe hybridizing, e.g., to a specifically targeted mRNA or cDNA in a sample, such as a TruSeq™ Custom Amplicon (TSCA) oligonucleotide probe (Illumina, Inc.). A capture probe can be a plurality of capture probes, e.g., a plurality of the same or of different capture probes.

In some embodiments, a nucleic acid in a tissue section (e.g., an FFPE section) is transferred to an array and captured onto the array by single-strand ligation to a universal adaptor oligonucleotide. For example, universal adaptor oligonucleotides that include spatial addresses can be immobilized on a bead array. Single-stranded nucleic acid targets can be ligated to the adaptors for capture. The nucleic acid can comprise cDNA or genomic DNA amplicons. The universal adaptors can be used to capture gene-specific cDNA or DNA amplicons. The orientation of universal adaptors on the array (e.g., bead array) can be controlled to capture both 3' and 5' regions of target nucleic acids.

In some embodiments, a capture array (i.e., an array of capture sites) can be integrated with an electrophoretic system to facilitate the transfer of nucleic acid molecules from a tissue section onto a capture site on the array. Electrophoretic transfer of nucleic acids can maintain spatial resolution about the tissue context by limiting the diffusion of nucleic acid molecules away from their location of origin during transfer and by thereby reducing loss of nucleic acids between capture sites.

In some embodiments, a combinatorial indexing (addressing) system is used to provide spatial information for analysis of nucleic acids in a tissue sample. The combinatorial indexing system can involve the use of two or more spatial address sequences (e.g., two, three, four, five or more spatial address sequences).

In some embodiments, two spatial address sequences are incorporated into a nucleic acid during preparation of a sequencing library. A first spatial address can be used to define a certain position (i.e., capture site) in the X dimension on a capture array and a second spatial address sequence can be used define a position (i.e., a capture site) in the Y dimension on the capture array. During library sequencing, both X and Y spatial address sequences can be determined and the sequence information can be analyzed to define the specific position on the capture array.

In some embodiments, three spatial address sequences are incorporated into a nucleic acid during preparation of a sequencing library. A first spatial address can be used to define a certain position (i.e., capture site) in the X dimension on a capture array, a second spatial address sequence can be used define a position (i.e., a capture site) in the Y dimension on the capture array, and a third spatial address sequence can be used to define a position of a two-dimensional sample section (e.g., the position of a slice of a tissue sample) in a sample (e.g., a tissue biopsy) to provide positional spatial information in the third dimension (Z dimension) of a sample. During library sequencing, X, Y, and Z spatial address sequences can be determined and the sequence information can be analyzed to define the specific position on the capture array.

In some embodiments, a temporal address sequence (T) is optionally incorporated into a nucleic acid during preparation of a sequencing library. In some embodiments, the temporal address sequence can be combined with two or three spatial address sequences. The temporal address sequence can, for example, be used in the context of a time-course experiment for determining time-dependent changes in gene-expression in a tissue sample. Time-dependent changes in gene-expression can occur in a tissue sample, for example, in response to a chemical, biological or physical stimulus (e.g., a toxin, a drug, or heat). Nucleic acid samples obtained at different timepoints from comparable tissue samples (e.g., proximal slices of a tissue sample) can be pooled and sequenced in bulk. An optional first spatial address can be used to define a certain position (i.e., capture site) in the X dimension on a capture array, a second optional spatial address sequence can be used to define a position (i.e., a capture site) in the Y dimension on the capture array, and a third optional spatial address sequence can be used to define a position of a two-dimensional sample section (e.g., the position of a slice of a tissue sample) in a sample (e.g., a tissue biopsy) to provide positional spatial information in the third dimension (Z dimension) of the sample. During library sequencing, T, X, Y, and Z address sequences are determined and the sequence information is analyzed to define the specific X, Y (and optionally Z) position on the capture array for each timepoint (T).

The address sequences X, Y, and, optionally, Z and/or T, can be consecutive nucleic acid sequences or the address sequences can be separated by one or more nucleic acids (e.g., 2 or more, 3 or more, 10 or more, 30 or more, 100 or more, 300 or more, or 1,000 or more). In some embodiments, the X, Y, and optionally Z and/or T address sequences can each individually and independently be combinatorial nucleic acid sequences.

In some embodiments, the length of the address sequences (e.g., X, Y, Z, or T) can each individually and independently be 100 nucleic acids or less, 90 nucleic acids or less, 80 nucleic acids or less, 70 nucleic acids or less, 60 nucleic acids or less, 50 nucleic acids or less, 40 nucleic acids or less, 30 nucleic acids or less, 20 nucleic acids or less, 15 nucleic acids or less, 10 nucleic acids or less, 8 nucleic acids or less, 6 nucleic acids or less, or 4 nucleic acids or less. The length of two or more address sequences in a nucleic acid can be the same or different. For example, if the length of address sequence X is 10 nucleic acids, the length of address sequence Y can be, e.g., 8 nucleic acids, 10 nucleic acids, or 12 nucleic acids.

Address sequences, e.g., spatial address sequences such as X or Y, can be either partially or fully degenerate sequences.

In some embodiments, spatially addressed capture probes on an array can be released from the array onto a tissue section for generation of a spatially addressed sequencing library. In some embodiments, a capture probe comprises a random primer sequence for in situ synthesis of spatially-tagged cDNA from RNA in the tissue section. In some embodiments, a capture probe is a TruSeq™ Custom Amplicon (TSCA) oligonucleotide probe (Illumina, Inc.) for capturing and spatially tagging genomic DNA in the tissue section. The spatially-tagged nucleic acid molecules (e.g., cDNA or genomic DNA) are recovered from the tissue section and processed in single tube reactions to generate a spatially-tagged amplicon library.

In some embodiments, magnetic nanoparticles can be used to capture nucleic acid (e.g., in situ synthesized cDNA) in a tissue sample for generation of a spatially addressed library.

In some embodiments, spatial detection and analysis of nucleic acid in a tissue sample can be performed on a droplet actuator.

4.1 Generation of Arrays

In one aspect, provided herein are capture arrays comprising spatially encoded capture probes. The spatially encoded capture probes on the capture probes can be immobilized, e.g., on a planar glass substrate, or on a plurality of beads.

Figure 1A:
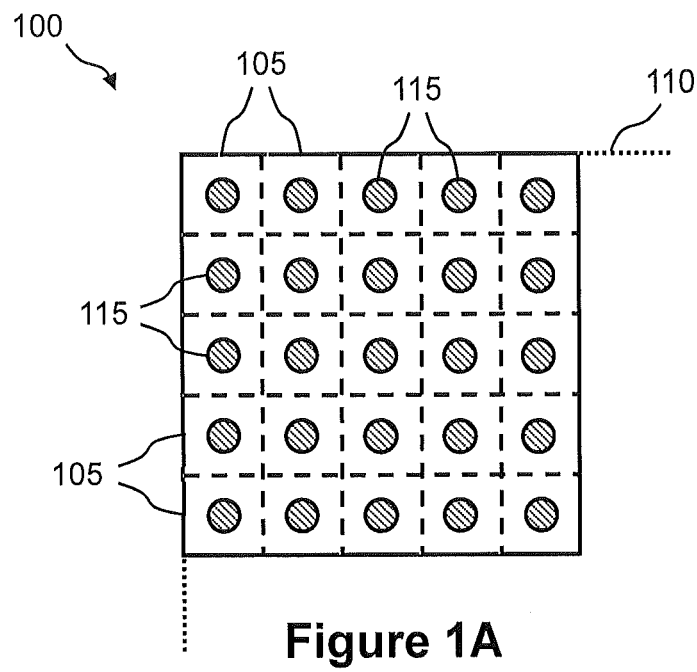
FIG. 1A illustrates a plan view of an exemplary embodiment of a capture array for capture of nucleic acid in a tissue sample.
Figure 1B:
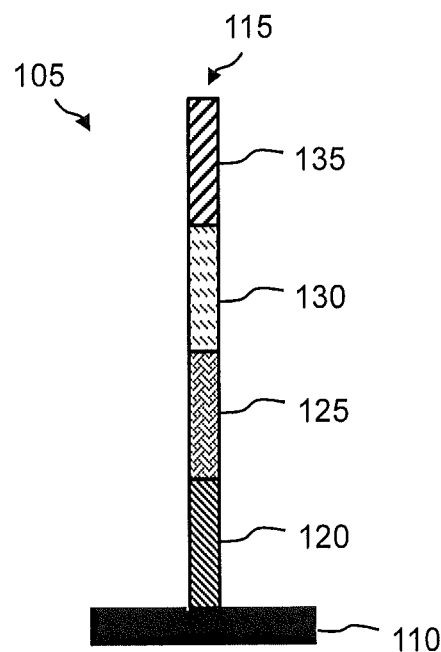
FIG. 1B illustrates a side view of one capture site of the capture array, wherein the one capture site comprises at least one capture probe for capture of nucleic acid in a tissue sample.

FIG. 1A illustrates a plan view of an exemplary embodiment of a capture array 100 for capture of nucleic acid in a tissue sample. Capture array 100 comprises an arrangement (e.g., rows and columns) of capture sites 105 on a solid support 110. In some embodiments, solid support 110 is a planar glass substrate. In some embodiments, solid support 110 is a bead (e.g., see FIG. 1C). At least one capture probe 115 is immobilized at each of the capture sites 105 of capture array 100, as shown in FIG. 1B. Namely, FIG. 1B illustrates a side view of one capture site 105 of capture array 100, wherein the one capture site 105 comprises at least one capture probe 115 for capture of nucleic acid in a tissue sample. FIG. 1B shows a capture probe 115 immobilized on the surface of solid support 110. In this embodiment, a single capture probe 115 is shown, but any number of capture probes 115 can be immobilized on solid support 110 at each capture site 105. Capture probe 115 may optionally comprise a cleavable sequence in a cleavable region 120, an SBS primer sequence in a SBS primer binding site 125, a spatial address sequence in a spatial address region 130, and a capture sequence in a capture region 135. Cleavable region 120 can be used to release captured nucleic acid from capture array 100 such that spatial address region 130 is included in the released nucleic acid and the nucleic acid is "tagged." SBS primer region 125 can comprise an SBS primer sequence (e.g., SBS12 or SBS3) that can be used in a sequencing-by-synthesis (SBS) process. Alternatively, SBS primer sequence 125 or some portion thereof may be added subsequently, e.g., by ligation or by PCR synthesis. SBS primer region 125 can also be used in an amplification reaction to generate a sequencing library as described in more detail with reference to FIG. 12 and FIG. 13. Spatial address region 130 corresponds to the position of capture probe 115 in capture array 100. Each capture probe 115 at a capture site 105 comprises a unique spatial address region 130. The position of capture probe 115 in capture array 100 can be correlated with a position in the tissue sample.

Capture region 135 can be, for example, a universal (general) capture region. In some embodiments, capture region 135 comprises a poly-T oligonucleotide that can be used to capture total mRNA in a tissue sample as described in more detail with reference to FIG. 3. In some embodiments, capture region 135 is a universal capture region that can be used to capture cDNA synthesized by in situ reverse transcription of RNA as describe in more detail with reference to FIG. 6. In some embodiments, capture region 135 is a universal capture region that can be used to capture genomic DNA amplicons as described in more detail with reference to FIG. 9 and FIG. 10.

In some embodiments, capture region 135 is a gene-specific or target-specific capture region that can be used to capture a specific nucleic acid in a tissue sample. Each capture probe 115 on capture array 100 can comprise one or more unique gene-specific capture region 135. U.S. Patent Pub. No. 2015148239, filed on Sep. 22, 2014 by Peter et al., and incorporated herein by reference, describes cleavable PCR primers in which each probe includes multiple cleavable primers, and which may be employed in this and other embodiments described herein. Different capture probes 115 on capture array 110 can have the same gene-specific capture region or they can be different gene-specific capture regions. In some embodiments, the nucleic acid in the tissue sample is a gene-specific mRNA as described in more detail with reference to FIG. 4. In some embodiments, the nucleic acid in the tissue sample is a gene-specific cDNA synthesized by in situ reverse transcription of RNA as described in more detail with reference to FIG. 7. In some embodiments (not shown), capture region 135 is a gene-specific region that can be used to capture genomic DNA amplicons.

The probes may be contacted with tissue by placing the tissue directly on the surface comprising the probes; placing the tissue on a substance, such as a filter or a gel or a thin buffer layer, separating the tissue from the probes such that the target nucleic acids may diffuse from the tissue, through the substance to the probes; placing the tissue on a substance such as a filter or a gel or a thin buffer layer separating the tissue from the probes such that the probes may diffuse from the surface comprising the probes, through the substance to the targets; extracting the targets from the tissue onto an intermediate substrate (e.g., a gel, filter, solid substrate, or combinations of the foregoing), which is then placed on the surface supporting the probes; and combinations of the foregoing. In each case, the technique is selected to substantially maintain information encoding the spatial orientation of the targets in the sample.

Figure 1C:
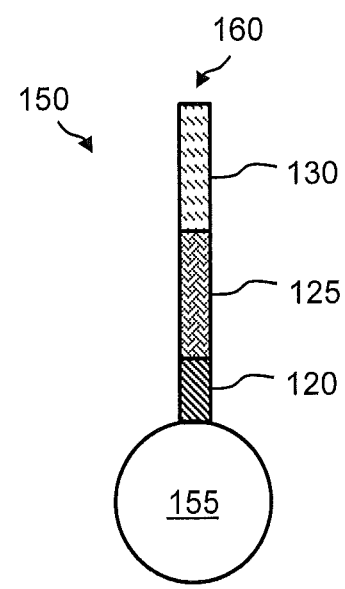
FIG. 1C illustrates a side view of an exemplary embodiment of a universal capture bead for capture of nucleic acid in a tissue sample.

FIG. 1C illustrates a side view of an embodiment of a universal capture bead 150 for capture of nucleic acid in a tissue sample. In some embodiments, there is a universal capture bead 150 at each of the capture sites 105 of capture array 100. For example, universal capture beads 150 can be deposited into wells on solid support 110 (e.g., a glass substrate). Universal capture bead 150 comprises a bead 155. A universal adaptor oligonucleotide 160 is immobilized on the surface of bead 155. Universal adaptor oligonucleotide 160 is essentially the same as capture probe 115 of FIG. 1B except that capture region 135 is omitted, i.e., universal adaptor oligonucleotide 160 comprises only cleavable region 120, SBS primer region 125, and spatial address region 130. SBS primer region 125 can comprise, for example, an SBS12 sequence or an SBS3 sequence. In this embodiment, a single universal adaptor oligonucleotide 160 is shown, but any number of universal adaptor oligonucleotides 160 can be immobilized on bead 155. Universal capture bead 150 can be used to capture nucleic acid in a tissue sample by single-strand ligation of target nucleic acid (e.g., cDNA or genomic DNA amplicons) to universal adaptor oligonucleotide 160 as described in more detail with reference to FIGS. 12 through 15.

A gene-specific capture array, such as a bead array with a plurality of gene-specific capture probes on each bead, can be produced using a ligation-based approach. For example, a bead array can be designed to have 1 million spatial addresses on a bead. The array can be designed to capture nucleic acid from 1,000 genes. To capture nucleic acid from 1,000 genes on a bead designed to have 1 million spatial addresses would require 1 billion capture probes (i.e., 1,000 genes×1 million spatial addresses=1 billion capture oligonucleotides). To avoid the synthesis of 1 billion capture probes, a pool of oligonucleotides representing gene-specific capture regions (e.g., capture region 135) can be ligated onto spatially addressed capture probes comprising cleavage region 120, SBS primer region 125, and spatial address region 130 (e.g., oligonucleotides representing 1,000 gene-specific capture regions+1 million spatial addressregions=1.1 million capture probes). In some embodiments, the pool of gene-specific capture regions is ligated to the spatially addressed capture probes using an enzymatic ligation approach. In some embodiments, the pool of gene-specific capture regions is ligated to the spatially addressed capture probes using a chemical ligation approach.

A ligation-based approach can also be used to produce a plurality of spatial addresses for a bead array. The current approach to produce a spatially-addressed bead array requires synthesis of each oligonucleotide independently for each distinct spatial address (e.g., 1 million spatial addresses requires synthesis of 1 million oligonucleotides). To avoid synthesizing 1 million oligonucleotides, a combinatorial approach can be used. For example, three distinct subsets of oligonucleotides with unique sequences (e.g., subset A with 100 unique sequence, subset B with 100 unique sequences, and subset C with 100 unique sequences) are synthesized and used in a combinatorial ligation reaction, e.g., 100 subset A×100 subset B×100 subset C=1 million oligonucleotides with distinct spatial addresses. The combinatorial approach requires the synthesis of only 300 different oligonucleotides.

In some embodiments, a hybridization and extension approach can be used to produce spatially addressed gene-specific capture probes. For example, a set "X" of 1,000 oligonucleotides with unique spatial addresses is synthesized. A second set "Y" of 1000 oligonucleotides that individually captures a unique gene and can hybridize to set "X" oligonucleotides is synthesized. Each individual oligo of set "Y" oligonucleotides are hybridized to set "X" oligonucleotides and an extension reaction is performed. Using this approach, synthesis of 2,000 oligonucleotides is required to generate 1 million different capture probes (1,000 unique spatial address sequence individually paired with 1,000 different gene-specific capture sequence). Using general oligonucleotide synthesis, the production of 1,000 gene-specific capture probes with each individually having 1,000 different spatial address would require the synthesis of 1 million oligonucleotide (1,000 genes×1,000 address).

The beads comprising the probes may be contacted with tissue by placing the tissue directly on the surface comprising the beads; placing the tissue on a substance, such as a filter or a gel or a thin buffer layer, separating the tissue from the beads such that the target nucleic acids may diffuse from the tissue, through the substance to the probes; placing the tissue on a substance such as a filter or a gel or a thin buffer layer separating the tissue from the probes such that the probes may diffuse from the beads, through the substance to the targets; extracting the targets from the tissue onto an intermediate substrate (e.g., a gel, filter, solid substrate, or combinations of the foregoing), which is then placed on the surface supporting the beads; depositing the beads directly into the tissue; and combinations of the foregoing. In each case, the technique is selected to substantially maintain information encoding the spatial orientation of the targets in the sample.

4.2 Spatial Detection and Analysis of Nucleic Acid in a Tissue Sample

In another aspect, provided herein is a method for spatial detection and analysis of nucleic acids in a sample.

Figure 2:
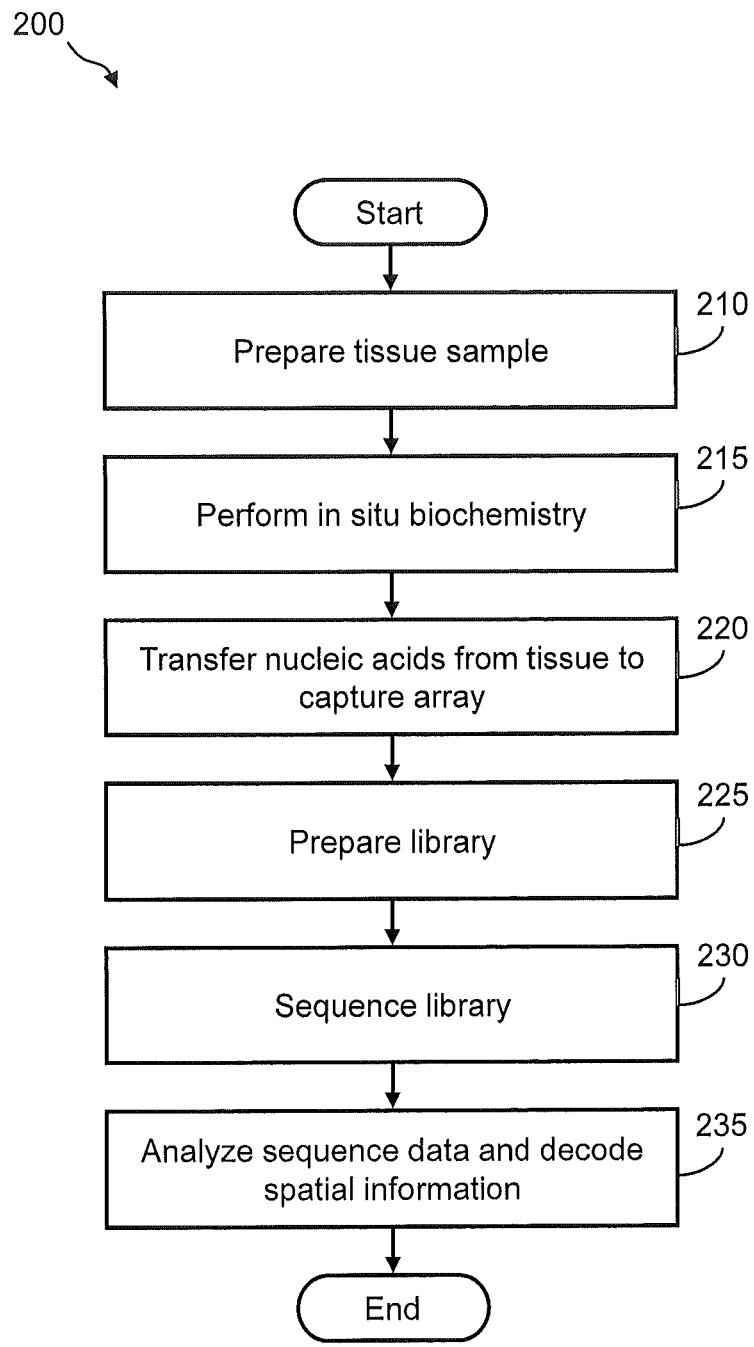
FIG. 2 illustrates a flow diagram of an exemplary embodiment of a method of spatial detection and analysis of nucleic acid in a tissue sample.

FIG. 2 illustrates a flow diagram of an embodiment of a method 200 of spatial detection and analysis of a nucleic acid in a tissue sample. Method 200 can include, but is not limited to, some or all of the following steps.

At a step 210, a tissue sample is prepared for analysis. In some embodiments, the tissue sample is a FFPE tissue sample that is sectioned onto a slide. Other examples include fresh tissue, frozen tissue, etc.

At a step 215, in situ biochemistry is performed on the tissue section to facilitate subsequent manipulation of a nucleic acid in the sample. In some embodiments, an in situ reverse transcription reaction is used to synthesize cDNA from targeted mRNA in the tissue sample. In some embodiments, an in situ amplification reaction can be used to produce multiple genomic DNA amplicons from targeted genes in the tissue sample. In some embodiments, there is no in situ biochemistry step, and synthesis of cDNA is performed after capture or extraction of the RNA from the tissue.

At a step 220, the target nucleic acid in the tissue section is transferred onto an array such that the position of a nucleic acid on the array can be correlated with a position in the tissue section. In some embodiments, the target nucleic acid comprises an mRNA. In some embodiments, the target nucleic acid comprises a cDNA synthesized in situ. In some embodiments, the nucleic acid comprises genomic DNA amplicons generated by in situ amplification. In some embodiments, the array is an array of capture sites, such as capture sites 105 of capture array 100 shown in FIG. 1A and FIG. 1B. In some embodiments, the array is an array of beads (e.g., universal capture beads 150 of FIG. 1C) that include a plurality of capture probes. Other examples of an array include an array of wells or pores or projections or a sequencing flow cell that includes a plurality of capture probes. The nucleic acid can be captured onto the array, for example, by hybridizing the nucleic acid to the capture probes on the array. In some embodiments, the nucleic acid can be captured onto the array by single-strand ligation of the nucleic acid onto universal adaptor oligonucleotides.

In this and other embodiments described herein, the probes may be contacted with target nucleic acid by placing the tissue directly on the surface comprising the probes; placing the tissue on a substance such as a filter or a gel or a thin buffer layer separating the tissue from the probes such that the target nucleic acid may diffuse from the tissue, through the substance to the probes; placing the tissue on a substance, such as a filter or a gel or a thin buffer layer separating the tissue from the probes such that the probes may diffuse from the surface comprising the probes, through the substance to the target nucleic acid; extracting the target nucleic acid from the tissue onto an intermediate substrate (e.g., a gel, filter, solid substrate, or combinations of the foregoing), which is then placed on the surface supporting the probes; and combinations of the foregoing. In each case, the technique is selected to substantially maintain information encoding the spatial orientation of the targets in the sample.

At a step 225, a sequencing library is prepared. In some embodiments, the sequencing library is prepared for sequencing-by-synthesis. Library preparation may be accomplished on the capture array substrate, or the nucleic acids may be cleaved from the substrate and pooled, so that library preparation can be accomplished separately, e.g., using a NeoPrep™ Library Prep System (Illumina, Inc., San Diego).

At a step 230, the library is sequenced. Sequencing may be accomplished using any sequencing technique. Examples of suitable sequencers include those available from, or being developed by, Illumina, Inc., F. Hoffmann-La Roche AG, Life Technologies, Inc., Beckman Coulter, Inc., Pacific Biosciences, Inc., Oxford Nanopore, Inc., and/or their affiliates.

At a step 235, the sequence data is analyzed (e.g., mutations and/or variant calling) and the spatial information is decoded. The spatial information can be used to provide information as to the location of the nucleic acid in the tissue section.

(a) Hybridization-Based Capture of Nucleic Acid

In some embodiments, hybridization-based capture is used to capture target nucleic acids in a tissue sample onto capture probes on an array. The array may be, for example, an array of beads or wells or pores or projections, a planar surface, or a sequencing flow cell that includes a plurality of capture probes. In one example, the tissue sample is contacted with capture probes that are fixed on the surface of the array. The tissue sample may be placed directly on the surface comprising the capture probes or the tissue sample may be placed on a substance such as a filter or a gel or a thin buffer layer separating the tissue sample from the capture probes such that the target nucleic acid may diffuse from the tissue through the substance to the capture probes.

In another example, the tissue sample is contacted with the array and the capture probes on the array are released into the tissue sample for hybridization to the nucleic acids in the tissue sample. The tissue sample may be placed directly on the surface comprising the capture probes or the tissue sample may be placed on a substance such as a filter or a gel or a thin buffer layer separating the tissue sample from the capture probes such that the released capture probes may diffuse from the array through the substance to the nucleic acid in the tissue sample. The capture probes may be anchored on the array using a releasable group or a selectively cleavable portion or linker. The capture probes may be released from the array using, for example, chemical cleavage, enzymatic cleavage or photo-cleavage. In another example, the capture probes may be printed onto the surface of the array and dried down. The capture probes may be released from the array by rehydration. In yet another example, the capture probes may be printed onto the array using a substance that dissolves in the presence of a certain treatment. The treatment to release the capture probes is then applied prior to the placement of the tissue sample onto the array.

In some embodiments, the nucleic acid is total mRNA. In some embodiments, the nucleic acid is gene-specific mRNA.

Figure 3:
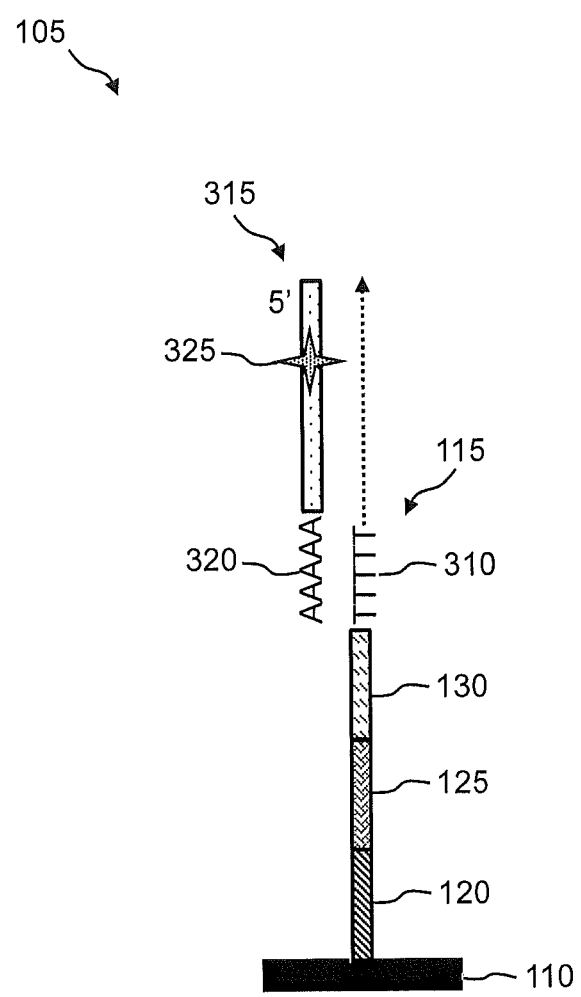
FIG. 3 illustrates a side view of the array of FIG. 1A and shows an exemplary embodiment of a process of capturing total mRNA in a tissue sample onto the array.

FIG. 3 illustrates a side view of another embodiment of a capture site 105 of capture array 100 of FIG. 1A and shows an embodiment of a process of capturing total mRNA in a tissue sample onto the array. In this embodiment, capture probe 115 comprises a poly-T capture region 310. A nucleic acid sample, such as a tissue sample or substrate comprising nucleic acid targets derived from a tissue sample (not shown), that includes a plurality of mRNA molecules 315 is contacted with the capture site 105. mRNA molecule 315 comprises a poly-A tail 320. A mutation 325 can be present in mRNA molecule 315. Mutation 325 can, for example, be a single nucleotide polymorphism (SNP). mRNA molecule 315 is captured on capture probe 115 by hybridization of poly-A tail 320 to poly-T capture region 310. Poly-T capture region 310 can also function as a reverse transcriptase primer for synthesis of first strand cDNA from captured mRNA molecule 315 (indicated by dashed arrow).

In this example, the tissue sample is contacted with a capture probe 115 that is fixed on the surface of capture site 105. mRNA molecule 315 is captured onto the array by hybridization to poly-T capture sequence 310. In another example (not shown), the tissue sample is contacted with the array and capture probe 115 is released from capture site 105 into the tissue sample by cleavage of optional cleavable sequence 120.

In some embodiments (not shown), capture region 310 is a random oligonucleotide ("randomer") capture region that can be used to capture a random pool of RNA molecules. The random oligonucleotide capture region can, for example, comprise a random sequence with reduced complexity such that capture of ribosomal RNA in the tissue sample is substantially reduced.

Figure 4:
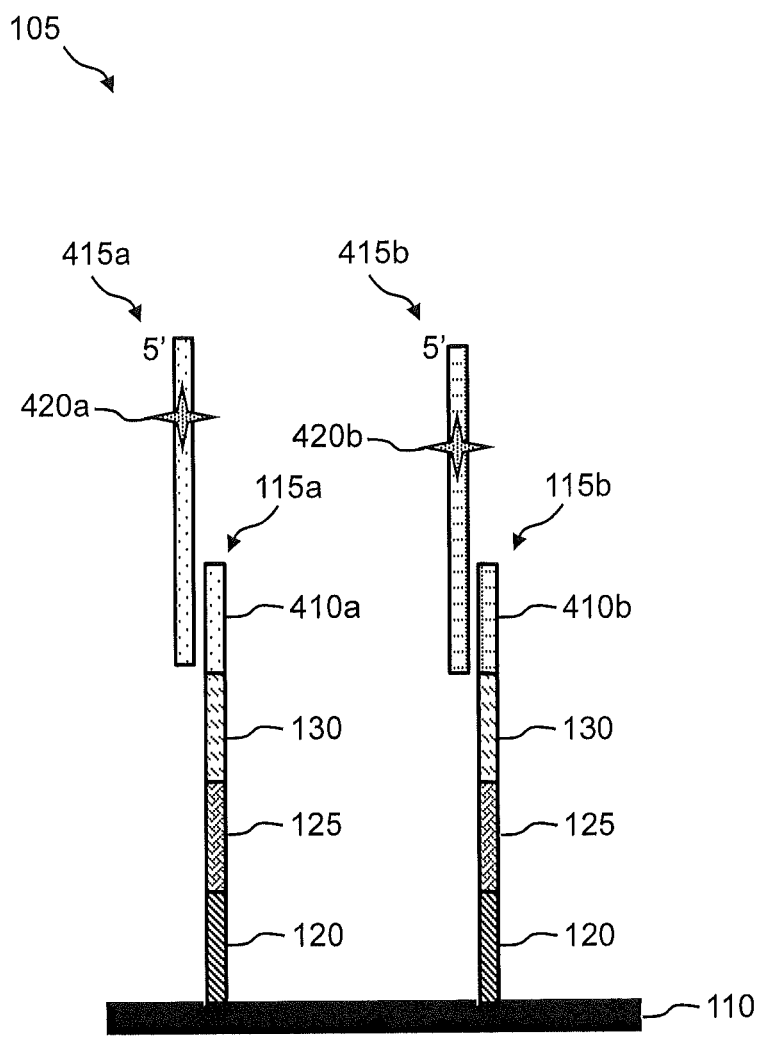
FIG. 4 illustrates a side view of the array of FIG. 1 and shows an exemplary embodiment of a process of capturing targeted mRNAs in a tissue sample onto the array.

FIG. 4 illustrates a side view of some embodiments of a capture site 105 of capture array 100 of FIG. 1A and shows an embodiment of a process of capturing individually targeted (i.e., gene-specific) mRNA in a tissue sample onto the array. In this embodiment, two capture probes 115, i.e., capture probe 115a and 115b, are shown. Capture probe 115a comprises a gene-specific capture region 410a. Similarly, capture probe 115b comprises a different gene-specific capture region 410b. A nucleic acid sample, such as a tissue sample or substrate comprising nucleic acid targets derived from a tissue sample (not shown), that comprises a plurality of different mRNA molecules 415 is contacted with the capture site 105. In this embodiment, a first mRNA molecule 415a is the transcript from a first gene and a second mRNA molecule 415b is the transcript from a second gene. mRNA molecule 415a can include a mutation 420a. mRNA molecule 415b can include a mutation 420b. Mutations 420 can, for example, be SNPs. mRNA molecule 415a is captured on capture probe 115a by hybridization of complementary mRNA sequences to gene-specific capture region 410a. Similarly, mRNA molecule 415b is captured on capture probe 115b by hybridization of a complementary mRNA molecule to gene-specific capture region 410b. Gene-specific capture region 410 can also function as reverse transcriptase primers for synthesis of first strand cDNA from captured mRNA molecule 415.

In this example, the tissue sample is contacted with capture probes 115 that is fixed on the surface of capture site 105. mRNA molecules 415 are captured onto the array by hybridization to gene-specific capture sequences 410. In another example (not shown), the tissue sample is contacted with the array and capture probes 115 are released from capture site 105 into the tissue sample by cleavage of optional cleavable sequence 120.

In some embodiments, hybridization-based capture is used to capture cDNA generated by in situ reverse transcription of RNA in a tissue sample onto an array.

Figure 5:
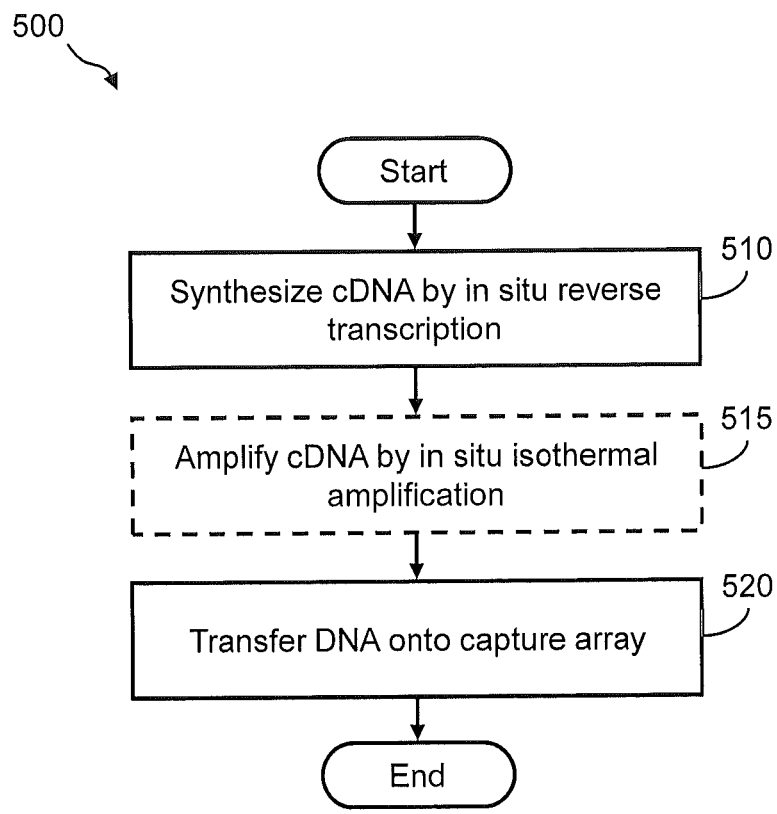
FIG. 5 illustrates a flow diagram of an exemplary embodiment of a method of generating cDNA by in situ reverse transcription of RNA in a tissue sample for capture onto an array.

FIG. 5 illustrates a flow diagram of an embodiment of a method 500 of generating cDNA by in situ reverse transcription of RNA in a tissue sample for capture onto an array (e.g., capture array 100 of FIG. 1A). Method 500 comprises, but is not limited to, some or all of the following steps.

At a step 510, gene-specific cDNA is synthesized from target mRNA in a tissue sample by in situ reverse transcription. For example, an oligonucleotide sequence that comprises a first gene-specific primer and a universal capture sequence can be used to prime first strand cDNA synthesis.

At an optional step 515, cDNA is amplified in the tissue sample by in situ isothermal amplification. For example, an oligonucleotide sequence that comprises a second gene-specific primer and an SBS primer sequence, e.g., SBS12, can be used for isothermal amplification.

At a step 520, the amplified cDNA is captured onto an array. The cDNA is captured onto the array by hybridizing the cDNA to capture probes on the array. In some embodiments the capture probes include a universal capture sequence and can be used to capture cDNA synthesized using a gene-specific primer that comprises a complementary capture sequence as described in more detail with reference to FIG. 6. In some embodiments, the capture probes include gene-specific capture sequences and can be used to capture cDNA synthesized using a pool of gene-specific primers or random primers that include an SBS primer sequence as described in more detail with reference to FIG. 7.

Figure 6:
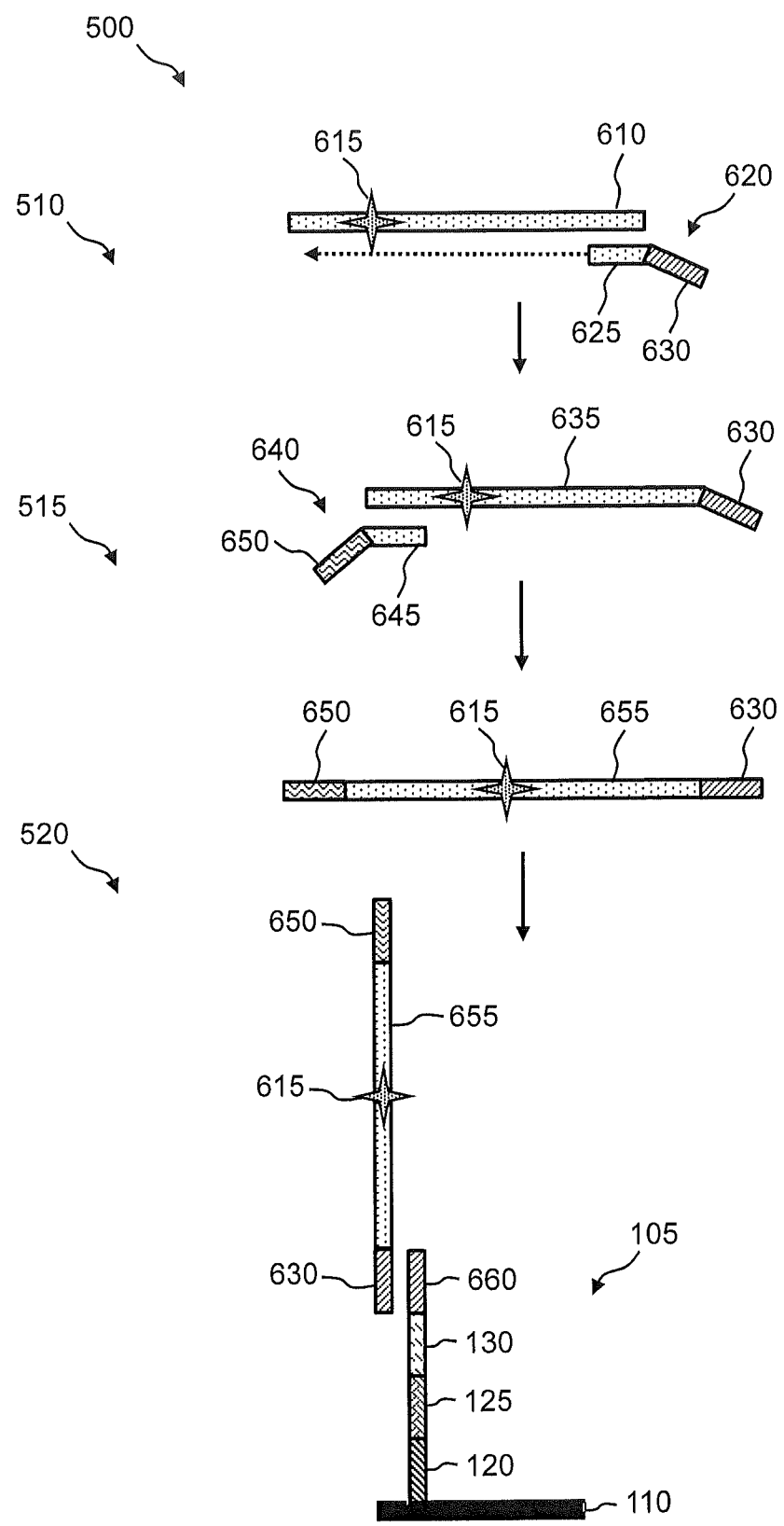
FIG. 6 illustrates an exemplary embodiment of the steps of a method of FIG. 5.

FIG. 6 illustrates an embodiment of the steps of a method 500 of FIG. 5. In this embodiment, an in situ isothermal amplification step (i.e., optional step 515) is used prior to transfer of DNA to an array. Namely, a tissue section (not shown) comprises a target mRNA molecule 610. Target mRNA molecule 610 can include a mutation 615. At step 510, target mRNA molecule 610 is reverse transcribed in situ using a reverse transcription (RT) primer 620. RT primer 620 comprises a first gene-specific primer region 625 and a universal capture region 630. RT primer 620 can also include a unique molecular identifier (UMI) region (not shown). A cDNA molecule 635 synthesized using RT primer 620 comprises universal capture region 630. At step 515, cDNA molecule 635 is amplified by in situ isothermal amplification using an amplification primer 640. Amplification primer 640 comprises a second gene-specific primer region 645 and an SBS sequencing primer region 650 comprising, e.g., a SBS12 sequence. A DNA molecule 655 generated using amplification primer 640 comprises universal capture region 630 and SBS sequencing primer 650. At step 520, DNA molecule 655 is captured onto the capture site 105. For example, the tissue sample containing DNA molecule 655 or a substrate comprising DNA molecule 655 derived from the tissue sample (not shown) is contacted with the capture site 105. In some embodiments, capture probe 115 on the capture site 105 comprises a capture region 660 that is complementary to universal capture region 630; SBS sequencing primer 130 is SBS3. DNA molecule 655 is captured onto the capture site 105 by hybridization of universal capture region 630 to capture region 660.

In this example, both capture region 660 and universal capture region 630 can also function as primers for an extension reaction. When capture region 660 is used as a primer, mutation 615 in DNA molecule 655 is copied. When universal capture region 630 is used as a primer, spatial address region 130 and SBS primer region 125 are copied. Both extension products can be used for downstream library generation.

In this example, the tissue sample is contacted with capture probe 115 that is fixed on the surface of capture site 105. DNA molecule 655 is captured onto the array by hybridization of universal capture region 630 to capture region 660. In another example (not shown), the tissue sample is contacted with the array and capture probes 115 are released from capture site 105 into the tissue sample by cleavage of optional cleavable sequence 120.

Figure 7:
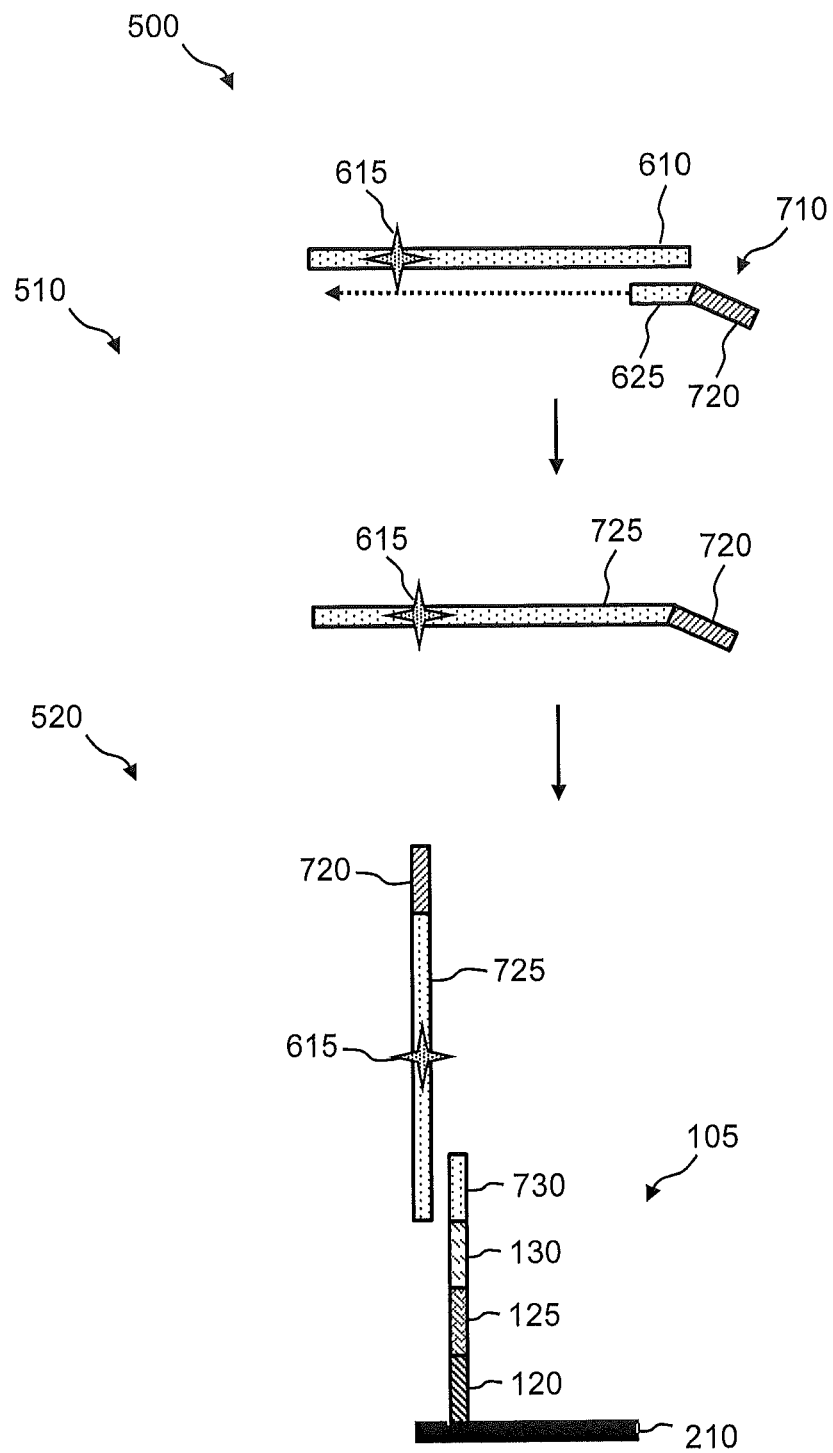
FIG. 7 illustrates another exemplary embodiment of the steps of a method of FIG. 5.

FIG. 7 illustrates an embodiment of the steps of a method 500 of FIG. 5. In this embodiment, a gene-specific capture probe is used to capture a specific cDNA and optional isothermal amplification step 515 of FIG. 5 is omitted. Namely, a tissue section (not shown) comprises target mRNA molecule 610. Target mRNA molecule 610 can include mutation 615. At step 510, target mRNA molecule 610 is reverse transcribed in situ using an RT primer 710. RT primer 710 comprises a gene-specific primer region 625 and an SBS primer region 720, e.g., SBS3. RT primer 710 can also include a UMI sequence (not shown). A cDNA molecule 725 synthesized using RT primer 710 comprises SBS primer region 720. At step 520, cDNA molecule 725 is captured onto the capture site 105. For example, the tissue sample containing DNA molecule 725 or a substrate comprising DNA molecule 725 derived from the tissue sample (not shown) is contacted with the capture site 105. In this embodiment, capture probe 115 on the capture site 105 comprises a gene-specific capture region 730 that is complementary to a sequences in the 3' end of cDNA molecule 725; SBS primer region 125 is SBS12. cDNA molecule 725 is captured on the capture site 105 by hybridization of capture region 730 to complementary sequences in the 3' end of cDNA molecule 725.

In some embodiments, hybridization-based capture can be used to transfer amplicons generated by in situ amplification of genomic DNA in a tissue sample to an array. In some embodiments, genomic DNA amplicons are generated using a "TSCA-like" amplification approach. In some embodiments, genomic DNA amplicons are generated using a DNA-Padlock approach.

Figure 8:
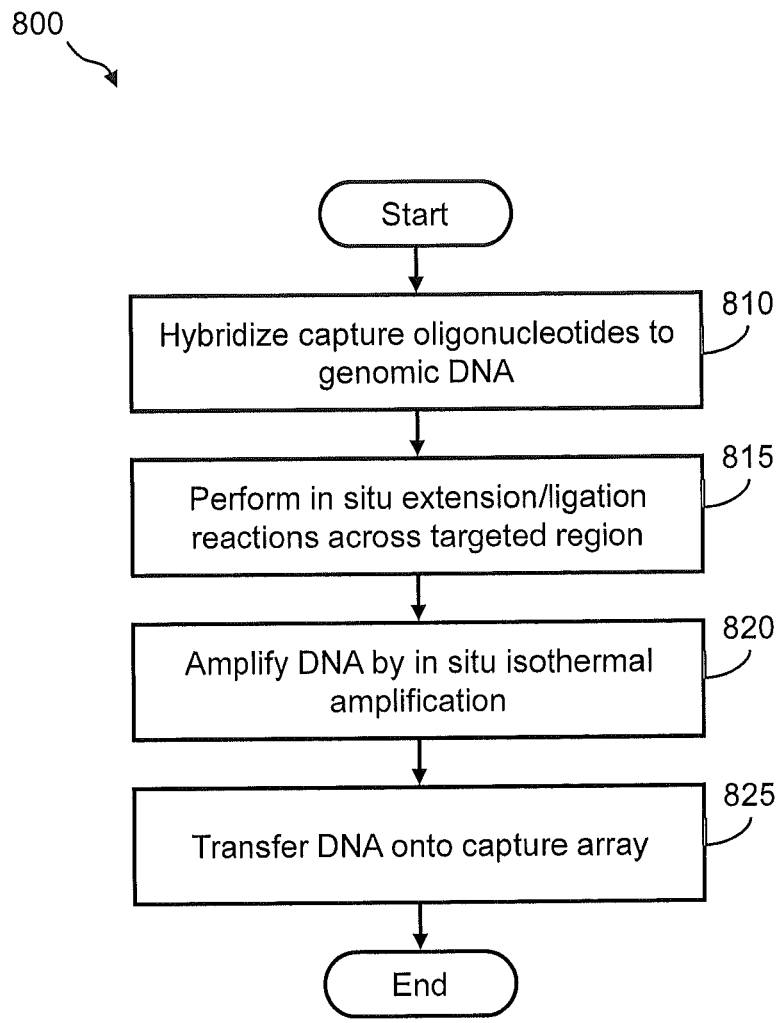
FIG. 8 illustrates a flow diagram of an exemplary embodiment of a method of capturing DNA amplicons onto an array, wherein the DNA amplicons are generated by in situ amplification of target nucleic acid.

FIG. 8 illustrates a flow diagram of an embodiment of a method 800 of capturing DNA amplicons onto an array (e.g., capture array 100 of FIG. 1A), wherein the DNA amplicons are generated by in situ amplification of target nucleic acid. In this embodiment, the amplification reaction is a TSCA-like amplification (TruSeq Custom Amplicon assembly, Illumina). Method 800 comprises, but is not limited to, some or all of the following steps.

At a step 810, a pair of gene-specific capture oligonucleotides that flank a region of interest are hybridized in situ to genomic DNA. For example, a first capture oligonucleotide that hybridizes 5' to a region of interest can comprise a gene-specific sequence and a universal capture sequence. A second capture oligonucleotide that hybridizes 3' to the region of interest can comprise a second gene-specific sequence and an SBS primer sequence (e.g., SBS12).

At a step 815, an in situ extension/ligation reaction is performed between the flanking capture oligonucleotides across the region of interest.

At a step 820, DNA flanked by capture oligonucleotides is amplified by in situ isothermal amplification to generate multiple copies of the region of interest, i.e., multiple genomic amplicons. Isothermal amplification can be performed, for example, using primer sequences that are complementary to the universal capture sequence and the SBS primer sequence.

At a step 825, the genomic amplicons are transferred onto an array and captured by hybridization to universal capture regions on the array.

Figure 9:
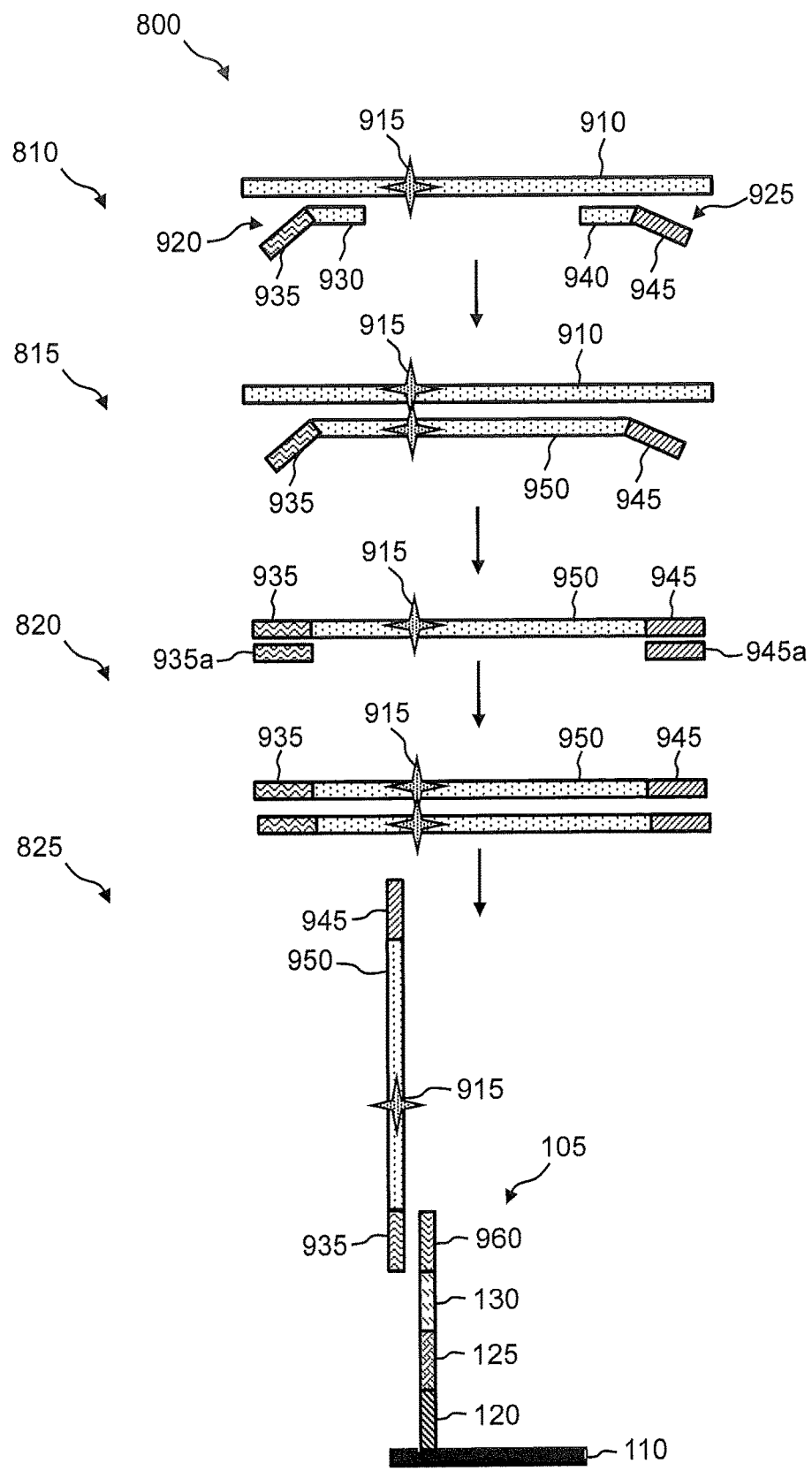
FIG. 9 illustrates an exemplary embodiment of the steps of a method of FIG. 8.

FIG. 9 illustrates an embodiment of the steps of a method 800 of FIG. 8. Namely, a tissue section (not shown) comprises a target genomic DNA molecule 910. Target DNA molecule 910 can include a mutation 915. At step 810, a first gene-specific capture oligonucleotide 920 and a second gene-specific capture oligonucleotide 925 that flank a region of interest are hybridized in situ to DNA molecule 910. Capture oligonucleotide 920 comprises a gene-specific region 930 and a universal capture region 935. Capture oligonucleotide 920 can also comprise a UMI region (not shown). Capture oligonucleotide 925 comprises a second gene-specific region 940 and an SBS primer region 945 (e.g., SBS12). At step 815, an extension/ligation reaction is performed in situ between the flanking capture oligonucleotides 920 and 925 across the region of interest. A DNA molecule 950 that is formed in the extension/ligation reaction comprises universal capture region 935 and SBS primer region 945. At step 820, DNA molecule 950 is amplified by in situ isothermal amplification to generate multiple copies (multiple amplicons) of the targeted region of interest. Isothermal amplification can be performed, for example, using a primer region 935a that is complementary to universal capture region 935 and a primer region 945a that is complementary to SBS primer region 945. At step 825, genomic amplicons 950 are captured onto the capture site 105. For example, the tissue sample containing genomic amplicons 950 or a substrate comprising genomic amplicons 950 derived from the tissue sample (not shown) is contacted with the capture site 105. In this example, capture probe 115 on the capture site 105 comprises a capture region 960 that is complementary to universal capture region 935; SBS primer region 130 is SBS3. DNA amplicons 950 are captured on the capture site 105 by hybridization of universal capture region 935 to capture region 960.

In this example, the tissue sample is contacted with capture probe 115 that is fixed on the surface of capture site 105. Genomic amplicon 950 is captured onto the array by hybridization of universal capture sequence 935 to capture sequence 960. In another example (not shown), the tissue sample is contacted with the array and capture probes 115 are released from capture site 105 into the tissue sample by cleavage of optional cleavable sequence 120.

Figure 10:
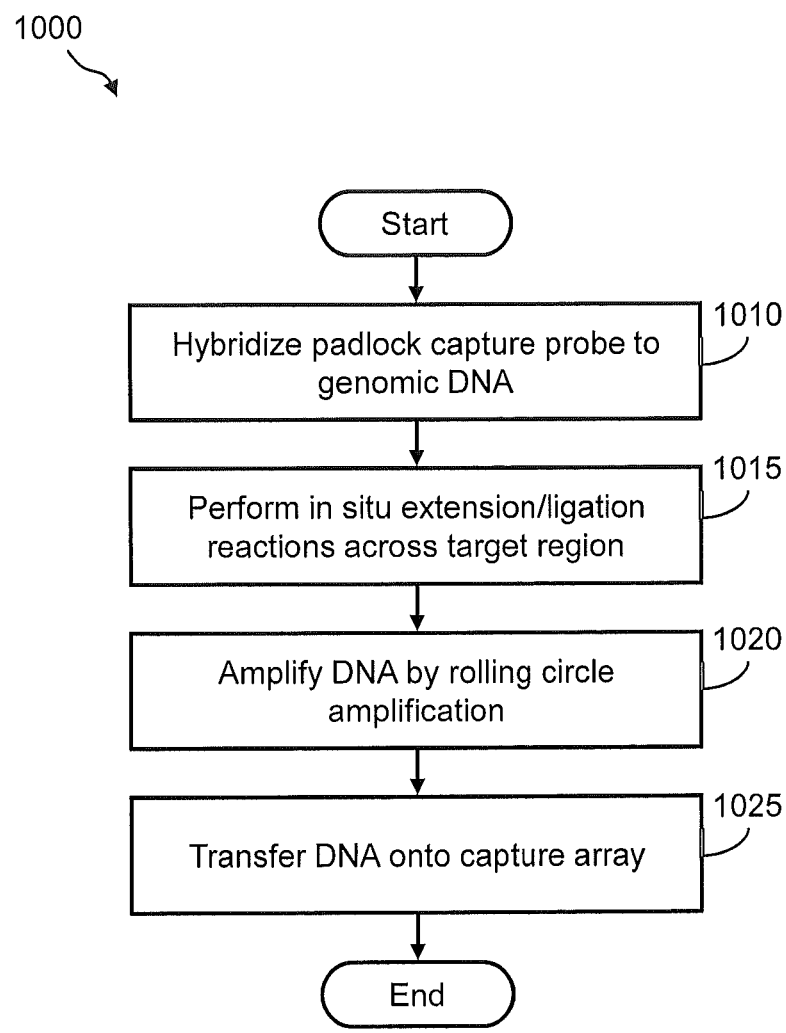
FIG. 10 illustrates a flow diagram of an exemplary embodiment of a method of capturing DNA amplicons onto an array, wherein the DNA amplicons are generated by in situ amplification of target nucleic acid.

FIG. 10 illustrates a flow diagram of embodiments of a method 1000 of capturing DNA amplicons onto an array (e.g., capture array 100 of FIG. 1A), wherein the DNA amplicons are generated by in situ amplification of target nucleic acid. In some embodiment, the amplification reaction can be a DNA padlock amplification. Method 1000 can comprise, but is not limited to, some or all of the following steps.

At a step 1010, a padlock capture probe is hybridized in situ to genomic DNA. For example, the padlock capture probe can comprise a first gene-specific sequence and a SBS primer sequence that are linked via a linker sequence to a universal capture sequence and a second gene-specific sequence. The first gene-specific sequence and the second gene-specific sequence flank a target region of interest in the genomic DNA.

At a step 1015, an in situ extension/ligation reaction is performed between the flanking gene-specific sequences in the padlock capture probe across the targeted region to generate a circular molecule.

At a step 1020, DNA flanked by the padlock capture probe is amplified by in situ rolling circle amplification to generate a concatamer of targeted amplicons. The rolling circle amplification can be performed, for example, using a primer sequence that is complementary to the SBS primer sequence in the padlock capture probe.

At a step 1025, targeted amplicon concatamers are captured onto an array that comprises a universal capture sequence.

Figure 11:
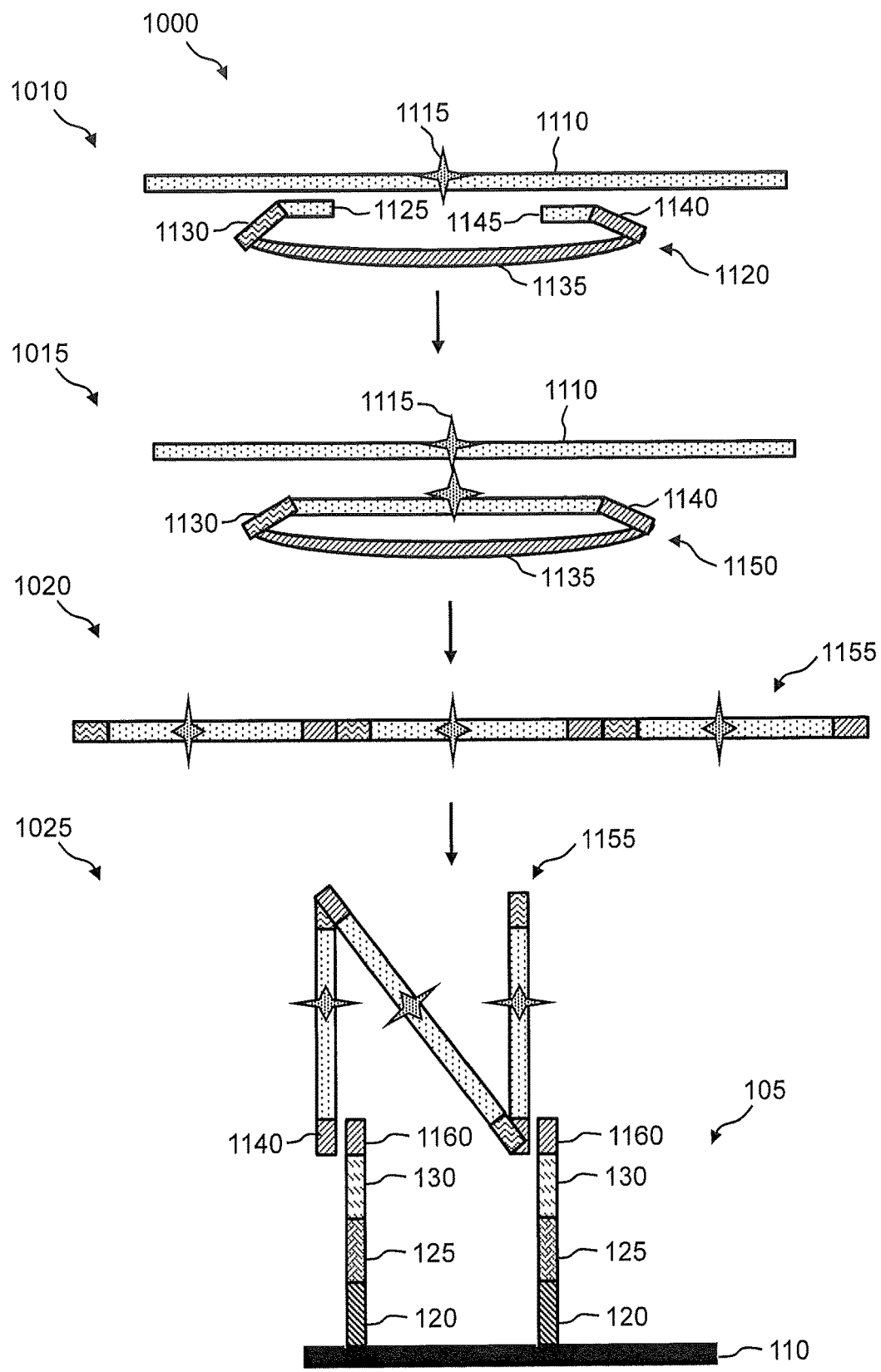
FIG. 11 illustrates the steps of a method of FIG. 10.

FIG. 11 illustrates the steps of a method 1000 of FIG. 10. Namely, a tissue section (not shown) comprises a target genomic DNA molecule 1110. Target DNA molecule 1110 can include a mutation 1115. At step 1010, a padlock capture probe 1120 is hybridized in situ to DNA molecule 1110. Padlock capture probe 1120 can comprise a first gene-specific region 1125 and an SBS primer region 1130 (e.g., SBS12) that can be linked via a linker region 1135 to a universal capture region 1140 and a second gene-specific region 1145. Padlock capture probe 1120 can also include a unique molecular identifier (UMI) region (not shown), to facilitate correction of sequencing errors. First gene-specific region 1125 and second gene-specific region 1145 flank a target region of interest in DNA molecule 1110. At a step 1015, an in situ extension/ligation reaction is performed between flanking first gene-specific region 1125 and second gene-specific region 1145 across the targeted region of interest to form a circular molecule 1150. In some embodiments, CircLigase™ (Epicentre, Illumina) can be used to ligate circular molecule 1150 prior to amplification. At a step 1020, circular molecule 1150 is amplified by in situ rolling circle amplification to generate a concatamer 1155 that comprises multiple copies of circular molecule 1150. The rolling circle amplification is performed using a primer sequence (not shown) that is complementary to SBS primer region 1130 on circular molecule 1150. At step 1025, concatamer 1155 is captured onto the capture site 105 that comprises cleavable region 120, SBS sequencing primer region 125 (e.g., SBS3), spatial address region 130, and capture region 135 (e.g., a universal capture sequence). For example, the tissue sample containing concatamer 1155 or a substrate comprising concatamer 1155 derived from the tissue sample (not shown) is contacted with the capture site 105. In some embodiments, capture probes 115 on capture site 105 comprises a capture region 1160 that is complementary to universal capture region 1140; SBS primer region comprises a SBS3 sequence. Concatamer 1155 is captured on the capture site 105 by hybridization of universal capture regions 1140 to capture regions 1160.

In this example, the tissue sample is contacted with capture probe 115 that is fixed on the surface of capture site 105. Concatamer 1155 is captured onto the array by hybridization of universal capture sequences 1140 to capture sequence 1160. In another example (not shown), the tissue sample is contacted with the array and capture probes 115 are released from capture site 105 into the tissue sample by cleavage of optional cleavable sequence 120.

(b) Ligation-Based Capture of Nucleic Acid

In some embodiments, a ligation-based capture is used to capture target nucleic acids in a tissue sample onto capture probes on an array. The array may be, for example, an array of beads or wells or pores or projections, a planar surface, or a sequencing flow cell that includes a plurality of capture probes. In one example, the tissue sample is contacted with capture probes that are fixed on the surface of the array. The tissue sample may be placed directly on the surface comprising the capture probes or the tissue sample may be placed on a substance such as a filter or a gel or a thin buffer layer separating the tissue sample from the capture probes such that the target nucleic acid may diffuse from the tissue through the substance to the capture probes.

In another example, the tissue sample is contacted with the array and the capture probes on the array are released into the tissue sample for hybridization to the nucleic acids in the tissue sample. The tissue sample may be placed directly on the surface comprising the capture probes or the tissue sample may be placed on a substance such as a filter or a gel or a thin buffer layer separating the tissue sample from the capture probes such that the released capture probes may diffuse from the array through the substance to the nucleic acid in the tissue sample. The capture probes may be anchored on the array using a releasable group or a selectively cleavable portion or linker. The capture probes may be released from the array using, for example, chemical cleavage, enzymatic cleavage or photo-cleavage. In another example, the capture probes may be printed onto the surface of the array and dried down. The capture probes may be released from the array by rehydration. In yet another example, the capture probes may be printed onto the array using a substance that dissolves in the presence of a certain treatment. The treatment to release the capture probes is then applied prior to the placement of the tissue sample onto the array.

In one example, the nucleic acid is cDNA synthesized by in situ reverse transcription of RNA in a tissue sample. In another example, the nucleic acid is DNA amplicons generated by in situ amplification of genomic DNA in a tissue sample.

Figure 12:
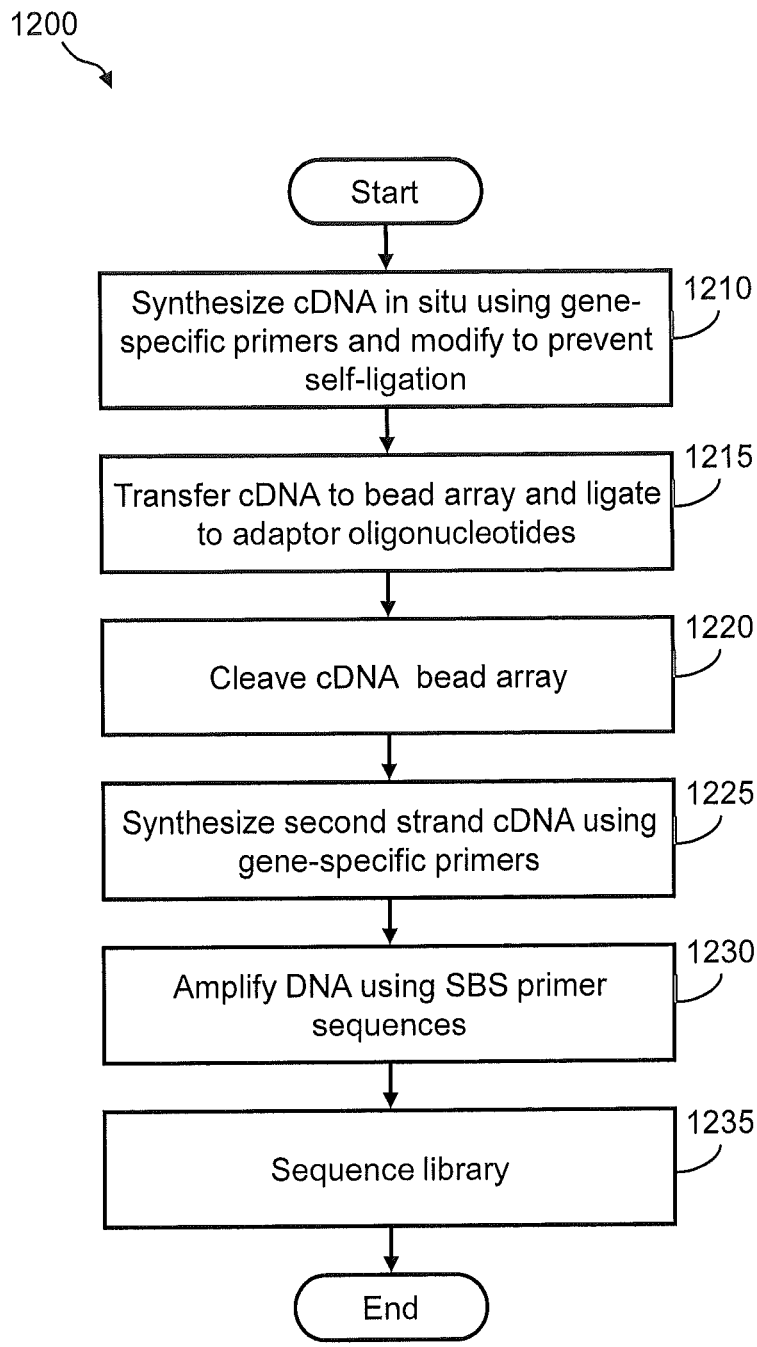
FIG. 12 illustrates a flow diagram of an exemplary embodiment of a method of capturing cDNA onto an array by single-strand ligation, wherein the cDNA is generated by in situ reverse transcription of target RNA molecules.

FIG. 12 illustrates a flow diagram of an embodiment of a method 1200 of capturing cDNA onto an array (e.g., capture array 100 of FIG. 1A) by single-strand ligation, wherein the cDNA is generated by in situ reverse transcription of target RNA molecules. Method 1200 comprises, but is not limited to, some or all of the following steps.

At a step 1210, cDNA is synthesized in situ using gene-specific primers. For example, a gene-specific reverse transcription primer (RT) that comprises a first gene-specific primer region and a unique molecular identifier (UMI) region can be used to prime first strand cDNA synthesis. The cDNA can be modified on the 5' or 3' end to prevent self-ligation. In some embodiments, a modification to prevent self-ligation of the cDNA can be pre-incorporated into the UMI sequence prior to in situ cDNA synthesis. In some embodiments, a modification such as the addition of a "tail" oligonucleotide region can be added post-cDNA synthesis to prevent self-ligation of the cDNA.

At a step 1215, the cDNA is transferred to a bead array and captured by ligating the cDNA to universal adaptor oligonucleotides on the bead array. The universal adaptor oligonucleotides can include a cleavable region, a SBS primer sequence (e.g., SBS3), and a spatial address as described with reference to FIG. 1A and FIG. 1C.

At a step 1220, the cDNA is cleaved from the bead array.

At a step 1225, second strand cDNA is synthesized using gene-specific primers. The gene-specific primers can include, for example, a gene-specific sequence and an SBS sequencing primer sequence (e.g., SBS12).

At a step 1230, the cDNA is amplified using a pair of SBS primers to generate a sequencing library. For example, a first SBS primer can comprise SBS12 complementary sequences and P7 sequences. A second SBS primer can comprise SBS3 complementary sequences and P5 sequences. The resulting library amplicons can be flanked on the 5' end by P7 sequence and SBS primer sequences and by UMI, spatial address, SBS sequencing primer, and P5 sequences on the 3' end. P7 and P5 sequences can be used to bind DNA amplicons to a flow cell surface for subsequent cluster amplification and sequencing.

At a step 1235, the library is sequenced.

Figure 13A:
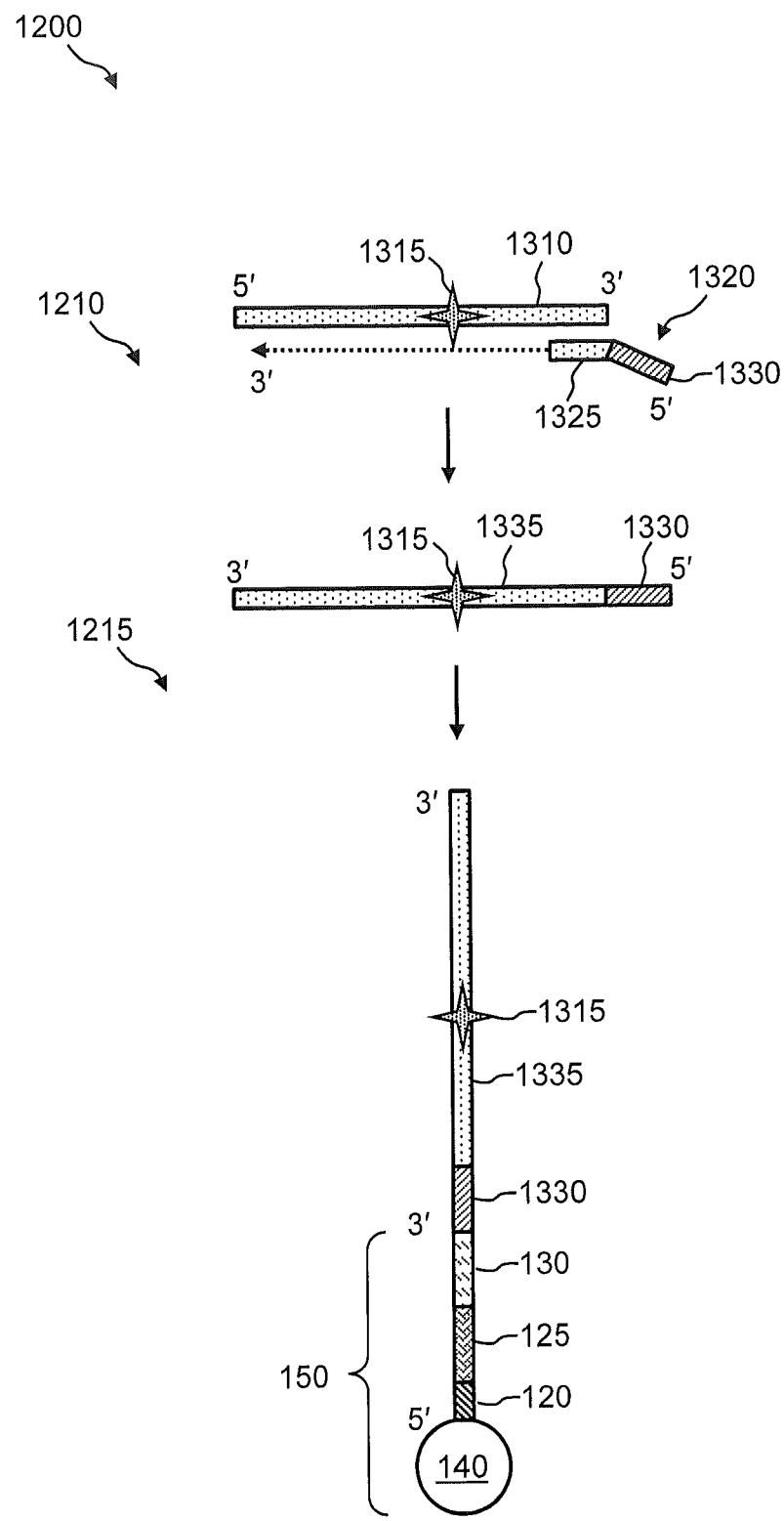
FIGS. 13A and 13B illustrates the steps of a method of FIG. 12.
Figure 13B:
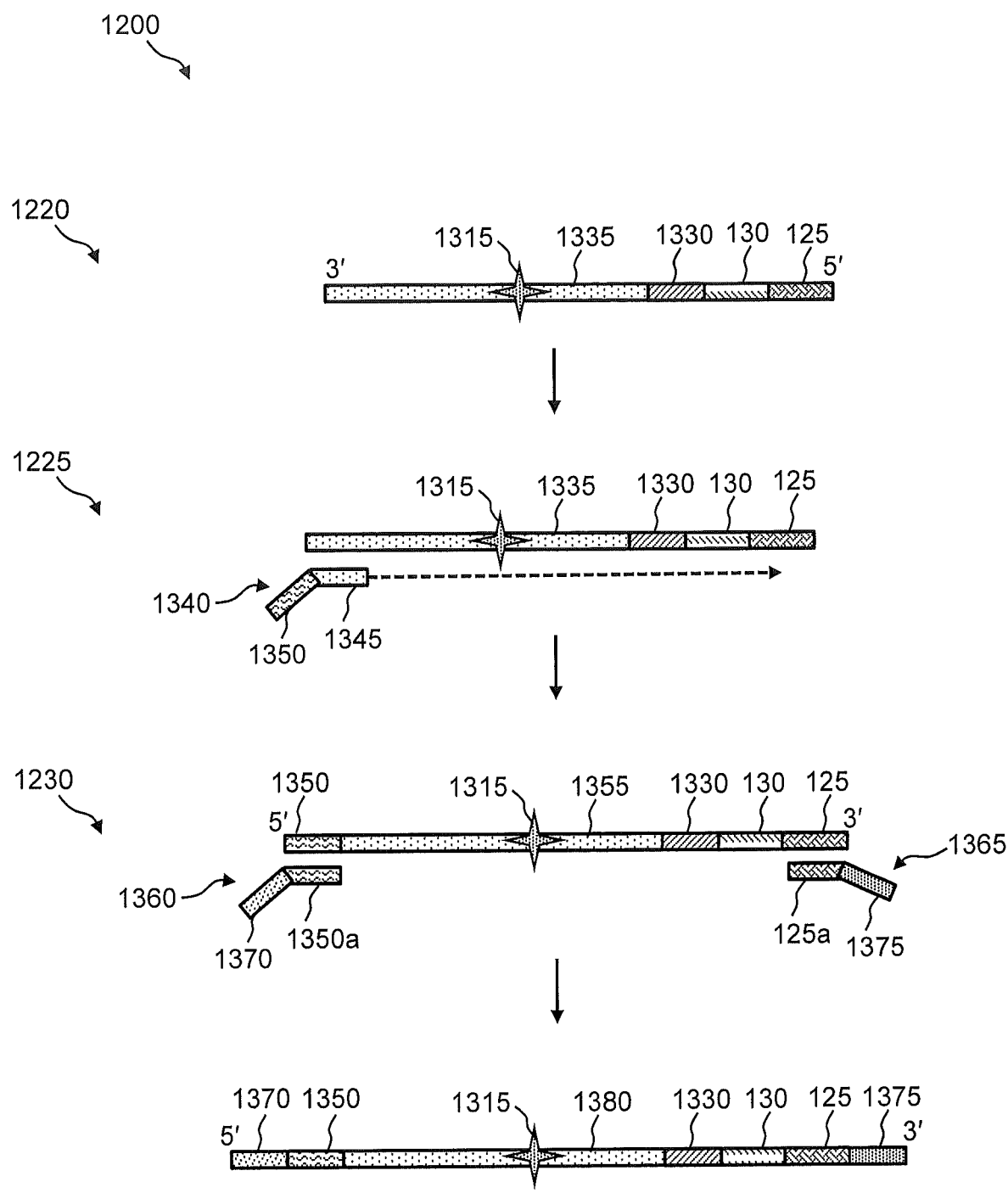

FIGS. 13A and 13B illustrate the steps of a method 1200 of FIG. 12. In some embodiments, cDNA synthesized in situ can be captured onto a bead array that comprises universal capture bead 150 of FIG. 1C. Namely, a tissue section (not shown) can comprise a target RNA molecule 1310. Target RNA molecule 1310 can include a mutation 1315. At step 1210, cDNA is synthesized in situ using a gene-specific RT primer 1320. RT primer 1320 can comprise a gene-specific region 1325 and a UMI region 1330. A cDNA molecule 1335 synthesized using RT primer 1320 comprises UMI region 1330. At step 1215, cDNA molecule 1335 is captured onto universal capture bead 150. For example, the tissue sample containing cDNA molecule 1335 or a substrate comprising cDNA molecule 1335 derived from the tissue sample (not shown) is contacted with universal capture bead 150. cDNA molecule 1335 is captured on universal capture bead 150 by ligation of UMI 1330 to spatial address region 130 in universal adaptor oligonucleotide 160. At step 1220, cDNA 1335 is cleaved from universal capture bead 150. cDNA molecule 1335 now comprises SBS primer region 125 (e.g., SBS3) and spatial address region 130. At step 1225, second strand cDNA is synthesized using a gene-specific primer 1340. Gene-specific primer 1340 comprises a gene-specific region 1345 and a SBS primer region 1350 (e.g., SBS12). A second strand cDNA molecule 1355 synthesized using gene specific primer 1340 comprises SBS sequencing primer region 1350, UMI region 1330, spatial address region 130, and SBS primer region 125. At step 1230, cDNA molecule 1355 is amplified using a first SBS primer 1360 and a second SBS primer 1365. SBS primer 1360 comprises an SBS complementary region 1350a that is complementary to SBS sequencing primer 1350 and a P7 primer region 1370. SBS primer 1365 comprises an SBS complementary region 125a that is complementary to SBS primer region 125 and a P5 primer region 1375. A library amplicon 1380 synthesized using SBS primers 1360 and 1365 is flanked on the 5' end by P7 primer region 1370 and SBS primer region 1350 and on the 3' end by UMI region 1330, spatial address region 130, SBS sequencing primer region 125, and P5 primer region 1375. At step 1235 (not shown), the library is sequenced.

In this example, the tissue sample is contacted with universal adaptor oligonucleotide 160 that is fixed on the surface of universal capture bead 150. cDNA molecule 1335 is captured onto the array by ligation of UMI 1330 to spatial address 130 in universal adaptor oligonucleotide 160. In another example (not shown), the tissue sample is contacted with the array and universal adaptor oligonucleotides 160 are released from the array into the tissue sample by cleavage of optional cleavable sequence 120.

In some embodiments, an anchor PCR step (not shown) to enrich for target cDNA sequences can be optionally performed prior to step 1225. For example, an anchor PCR amplification can be first performed using gene-specific primers without SBS primer sequence 1350. Following the anchor PCR amplification step, a second amplification can be performed using gene-specific primer 1340 that comprises gene-specific region 1345 and SBS sequencing primer region 1350.

FIG. 14 illustrates a flow diagram of embodiments of a method 1400 of capturing DNA amplicons onto an array (e.g., capture array 100 of FIG. 1A), wherein the DNA amplicons can be generated by in situ amplification of target nucleic acid. Method 1400 can comprise, but is not limited to, some or all of the following steps.

At a step 1410, a pair of gene-specific capture probes that flank a region(s) of interest are hybridized in situ to genomic DNA. For example, a first capture oligonucleotide that hybridizes 5' to a region of interest can comprise a first gene-specific sequence and a universal sequence. A second capture oligonucleotide that hybridizes 3' to a region of interest can comprise a second gene-specific sequence, a UMI, and a SBS primer sequence (e.g., SBS3).

At a step 1415, an in situ extension/ligation reaction is performed between the flanking capture probes across regions of interest.

At a step 1420, DNA flanked by capture probes is amplified by in situ isothermal amplification to generate multiple copies of the regions of interest, i.e., multiple amplicons. Isothermal amplification can be performed, for example, using primer sequences that are complementary to the universal sequence and the SBS primer sequence.

At a step 1425, a 3' tail oligonucleotide can be added onto the DNA amplicons to prevent self-ligation.

At a step 1430, DNA amplicons are transferred to a bead array (e.g., an array of universal capture beads 150 shown in FIG. 1C) and captured by ligation onto universal capture oligonucleotides on the bead array. For example, the DNA amplicons can be denatured, transferred to the bead array and ligated onto universal capture oligonucleotides. The universal capture oligonucleotides can include a cleavable sequence, an SBS primer sequence (e.g., SBS12), and a spatial address sequence as describe with reference to FIG. 1C. Both strands (i.e., top strand and bottom strand) of the denatured amplicons can ligate to the capture oligonucleotides on the bead array.

At a step 1435, DNA amplicons are cleaved from the bead array.

At a step 1440, DNA amplicons are amplified using a pair of SBS primers to generate a sequencing library. For example, a first SBS primer can comprise SBS12 complementary sequences and P7 sequences. A second SBS primer can comprise SBS3 complementary sequences and P5 sequences. In some embodiments, only targeted sequences that are flanked by SBS12 and SBS3 sequences are amplified (i.e., the top strand of the DNA amplicon). The resulting library amplicons are flanked on the 5' end by P7 and SBS12 primer sequences and by UMI, spatial address, SBS3 primer, and P5 sequences on the 3' end.

At a step 1445, the library is sequenced.

FIGS. 15A, 15B, and 15C illustrate the steps of a method 1400 of FIG. 14. Namely, a tissue section (not shown) comprises a targeted DNA region 1510. Target DNA molecule 1510 can include a mutation 1515. At step 1410, a first gene-specific capture probe 1520 and a second gene-specific capture probe 1525 that flank a region of interest are hybridized in situ to DNA molecule 1510. Gene-specific capture probe 1520 comprises a gene-specific region 1530 and a universal region 1535. Gene-specific capture probe 1525 can comprise a second gene-specific region 1540, a UMI region 1545, and an SBS primer region 1550 (e.g., SBS3). At step 1415, an in situ extension/ligation reaction is performed between the flanking gene-specific capture probes 1520 and 1525 across the region of interest to generate a DNA molecule 1555. DNA molecule 1555 comprises universal region 1535, UMI region 1545, and SBS primer region 1550. At step 1420, DNA 1555 is amplified (e.g., in situ isothermal amplification) to generate multiple copies (i.e., multiple amplicons) of the targeted region of interest. Amplification, e.g., isothermal amplification, is performed using a primer region 1535a that is complementary to universal region 1535 and a primer region 1550a that is complementary to SBS primer region 1550. At step 1425, a 3' tail oligonucleotide 1560 is added onto the DNA amplicons to prevent self-ligation. At step 1430, DNA molecule 1555 is denatured and transferred to universal capture bead 150. For example, the tissue sample containing DNA molecule 1555 or a substrate comprising DNA molecule 1555 derived from the tissue sample (not shown) is contacted with universal capture bead 150. Each strand (i.e., top strand "A" and bottom strand "B") of DNA molecule 1555 is captured on universal capture bead 150 by ligation of 3' tail oligonucleotide 1560 to spatial address region 130 in universal adaptor oligonucleotide 160. At Step 1435, DNA molecules 1555 are cleaved from universal capture bead 150. Two different configurations of DNA molecule 1555 are formed: A) a DNA molecule 1565 that comprises (in the 3' to 5' direction) SBS primer region 125 (e.g., SBS12), spatial address region 130, 3' tail oligonucleotide 1560, universal region 1535, DNA molecule 1555, UMI region 1545, and SBS primer region 1550 (e.g., SBS3) and B) a DNA molecule 1570 that comprises (in the 3' to 5' direction) SBS primer region 125 (e.g., SBS12), spatial address region 130, 3' tail oligonucleotide 1560, SBS primer region 1550 (e.g., SBS3), UMI region 1545, DNA molecule 1555, and universal region 1535. At step 1440, DNA molecules 1565 (A) and 1570 (B) are amplified using a first SBS primer 1575 and a second SBS primer 1580. First SBS primer 1575 comprises an SBS primer sequence 125a that is complementary to SBS primer sequence 125 and a P7 sequence 1585. Second SBS primer 1580 comprises a SBS primer sequence 1550a that is complementary to SBS primer sequence 1550 and a P5 sequence. A library amplicon 1595 amplified from DNA molecule 1565 using SBS primers 1575 and 1580 is flanked on the 3' end by P7 region 1585, SBS primer region 125 (e.g. SBS12), spatial address region 130, 3' tail oligonucleotide 1560, and universal region 1535 and on the 5' end by UMI region 1545, SBS primer region 1550 (e.g., SBS3), and P5 primer region 1590. Because of the configuration of the SBS sequences in DNA molecule 1570, DNA molecule 1570 is not amplified.

In this example, the tissue sample is contacted with universal adaptor oligonucleotide 160 that is fixed on the surface of universal capture bead 150. DNA molecule 1555 is captured on universal capture bead 150 by ligation of 3' tail oligonucleotide 1560 to spatial address 130. In another example (not shown), the tissue sample is contacted with the array and universal adaptor oligonucleotides 160 are released from the array into the tissue sample by cleavage of optional cleavable sequence 120.

4.3 Transfer of Nucleic Acids onto Capture Arrays

In some embodiments of the methods described herein nucleic acid molecules can be transferred from a sample, such as a tissue section, onto a capture array by passive diffusion.

In some embodiments, the transfer of nucleic acid molecules from a sample onto a capture array can be facilitated, e.g., through electrophoresis or centrifugation.

In some embodiments, nucleic acid molecules can be transferred directly from a sample, such as a tissue section, onto a capture array. For example, a tissue section can be placed directly onto a capture array.

In some embodiments, the nucleic acid molecules can be transferred indirectly from a sample, such as a tissue section, onto a capture array. For example, nucleic acids from a tissue section can be transferred first to one or more intermediate substrates, e.g., any substrate other than a capture array, such that the relative spatial orientation of nucleic acids on the intermediate substrate mirrors the relative spatial orientation in the tissue section. The nucleic acids can then be transferred from the intermediate substrate to the capture array, such that the relative spatial orientation of the nucleic acids on the capture array mirrors the relative spatial orientation of the nucleic acids in the tissue section. Indirect transfer can occur, e.g., through passive diffusion or through facilitated transfer (e.g., electrophoresis or centrifugation). The intermediate substrate can be, e.g., a membrane, such as a nylon membrane, or a gel, or a microwell plate. In some embodiments, the nucleic acids from a tissue sample can be transferred first to a gel, then to one or more membranes, and then to the capture array. In some embodiments, the intermediate substrate can be configured such that it stabilizes the separation of nucleic acids in different spatial regions of the tissue section. For example, nucleic acids in different spatial regions in the tissue section can be permanently separated from one another by placing different fragments of the tissue section (or of a gel or membrane comprising nucleic acids from the tissue section) into different wells of the microwell plate such that the relative spatial orientation of the tissue section fragments in the microwell plate can be correlated with the relative spatial orientation of the fragments in the tissue section. The nucleic acids in the tissue fragments in the microwell plate can subsequently be transferred from the microwell plate to the capture array.

In some embodiments, intermediate substrates can be used to produce two or more copies of nucleic acids whose relative spatial orientation can be correlated with their relative spatial orientation in a tissue section. For example, nucleic acids can be transferred from a tissue section onto several membranes, e.g., by placing the tissue section onto a membrane that forms the first layer of several layered membranes. Transfer from the tissue section can onto the two or more layered membranes can occur, e.g., through passive diffusion or it can be facilitated. The spatial orientation of the nucleic acids on each of the two or more layered membranes corresponds to the relative spatial orientation of the nucleic acids in the tissue section. The nucleic acids on the two or more layered membranes can subsequently be transferred to two or more capture arrays.

In some embodiments, the transfer of nucleic acid molecules from a sample onto a capture array can be facilitated using magnetically responsive nanoparticles (a) Facilitated Transfer of Nucleic Acids onto Capture Arrays In some embodiments, facilitated nucleic acid transfer can result in greater yields of nucleic acid transfer from the sample onto the capture array, compared to nucleic acid transfer by passive diffusion under otherwise comparable experimental condition (e.g., transfer temperature, transfer buffer, and the like). In some embodiments, facilitated nucleic acid transfer can result in at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater yields compared to nucleic acid transfer by passive diffusion. Methods for analyzing the efficiency of nucleic acid transfer are well known in the art, for example using radioisotope-labeled or fluorescently-labeled nucleic acids, or comparing yields or efficiencies of next-generation sequencing reactions.

In some embodiments, facilitated nucleic acid transfer can allow for a reduction of transfer times, compared to nucleic acid transfer by passive diffusion under otherwise comparable experimental conditions (e.g., a reduction of transfer times from more than 12 h, more than 24 h, more than 36 h, or more than 48 h to less than 6 h, less than 4 h, less than 2 h, or less than 1 h). In some embodiments, facilitated nucleic acid transfer can result in at least 2-fold, at least 3-fold, at least 4-fold, at least 5-fold, at least 6-fold, at least 7-fold, at least 8-fold, at least 9-fold, at least 10-fold reduction of transfer times, compared to nucleic acid transfer by passive diffusion. Methods for analyzing or comparing transfer times are well known in the art. For example, the transfer time can represent the time required to transfer a certain amount of nucleic acid from the sample to the capture array, as determined, e.g., through the use of radio-isotope-labeled or fluorescently-labeled nucleic acids, or by comparing yields or efficiencies of next-generation sequencing reactions.

In some embodiments, facilitated nucleic acid transfer can allow for the transfer of nucleic acids from larger samples, e.g., thicker tissue slices, onto a capture array, compared to nucleic acid transfer by passive diffusion under otherwise comparable experimental conditions. In some embodiments, facilitated nucleic acid transfer can allow for the transfer of nucleic acids from tissue slices having an at least 2-fold, at least 3-fold, at least 4-fold, at least 5-fold, at least 6-fold, at least 7-fold, at least 8-fold, at least 9-fold, or at least 10-fold larger thickness, compared to the thickness of samples typically applied when transferring nucleic acids by passive diffusion (e.g., from about 10 µm to about 100 µm in thickness). In some embodiments, the thickness of a tissue slice can be less than about 5 µm.

In some embodiments, nucleic acid transfer from a tissue sample can be facilitated with respect to certain capture sites on a capture array, whereas the nucleic acid transfer from a tissue sample can occur through passive diffusion with respect to certain other capture sites on the capture array. In some embodiments, nucleic acid transfer from a tissue sample onto a capture array can be facilitated with respect to a selected subset set capture sites, e.g., a subset of at least 1%, at least 3%, at least 5%, at least 10%, at least 20%, at least 30%, at least 40%, at least 50%, at least 60%, at least 70%, at last 80%, at least 90%, at least 95%, at least 98%, or at least 99% of capture sites.

(b) Electrophoretic System for Spatial Detection and Analysis of Nucleic Acids in a Tissue Sample In some embodiments, a capture array (i.e., an array of capture sites) can be integrated with an electrophoretic system to force nucleic acid molecules to move directly from a tissue section onto capture probes. In some embodiments, the nucleic acid is RNA. In some embodiments the nucleic acid is DNA (e.g., cDNA or DNA amplicons).

FIG. 16 illustrates a side view of a portion of an exemplary electrophoretic transfer system 1600 that is configured for spatial detection and analysis of nucleic acid in a tissue sample. Electrophoretic transfer system 1600 comprises a capture array 1610. Capture array 1610 can be capture array 100 of FIG. 1A. Capture array 1610 comprises a solid support 1615. In some embodiments, solid support 1615 is a planar glass substrate. An arrangement (e.g., rows and columns) of capture sites 1620 are formed on solid support 1615. In some embodiments, a row of six capture sites 1620 are shown (i.e., capture sites 1620a through 1620f), but any number and configuration of capture sites 1620 can be used. A plurality of oligonucleotides (not shown) are immobilized at each of the capture sites 1620. Associated with each capture site 1620 is a bottom electrode 1625 (e.g., six bottom electrodes 1625a through 1625f). In this example, one bottom electrode 1625 for each capture site 1620 is shown, but any number of bottom electrodes 1625 per capture site 1620 may be used. For example, capture array 1610 may include 2 bottom electrodes 1625 per capture site 1620, or 10 bottom electrodes 1625 per capture site 1620, or 100 bottom electrodes 1625 per capture site 1620, or any number of bottom electrodes 1625 per capture site 1620. A sample substrate 1630 is positioned atop capture array 1610. In one example, sample substrate 1630 is a planar glass substrate. Sample substrate 1630 includes an arrangement of top electrodes 1635. In this example, the arrangement of top electrodes 1635 corresponds to the arrangement of bottom electrodes 1625 on capture array 1610, i.e., one top electrode 1635 (e.g., top electrode s 1635a through 1635f) per bottom electrode 1625 (e.g., bottom electrodes 1625a through 1625f). In another example (not shown), sample substrate 1630 includes a single top electrode 1635. A tissue sample 1640 is mounted on the surface of sample substrate 1630 that is facing capture sites 1620 of capture array 1610.

Capture sites 1620, bottom electrodes 1625 and top electrodes 1635 are configured for electrophoretic transfer and capture of nucleic acids from a tissue sample such that spatial orientation is maintained and diffusion of nucleic acids from the tissue sample and loss of nucleic acids between capture sites 1620 is eliminated or substantially reduced. Each of the capture sites 1620 can be addressed (charged) individually or all or selected groups of the capture sites 1620 can be addressed in common as a single unit. A voltage source 1645 is connected across bottom electrodes 1625 and top electrodes 1635. In the presence of an electric field supplied by voltage source 1645, a plurality of nucleic acids 1650 are transferred from tissue sample 1640 to capture sites 1620. Nucleic acids 1650 are captured at capture sites 1620 by hybridization to capture probes (not shown) that are immobilized at capture sites 1620.

4.4 Spatial Detection and Analysis of Nucleic Acids in a Tissue Sample Using Capture Probe Sets.

According to the methods described herein, spatial detection and analysis of nucleic acids in a tissue sample can be performed using sets of two or more capture probes (e.g., 3 or more, 4 or more, 5 or more, 6 or more, 7 or more, 8 or more, 9 or more, or 10 or more capture probes). Typically at least a first capture probe in a set of capture probes is immobilized on a capture array. In some embodiments, a second capture probe can be immobilized on the same capture array as the first capture probe, e.g., in proximity to the first capture probe, e.g., in the same capture site. In some embodiments, a second capture probe can be immobilized on a particle, such as a magnetic particle or a magnetic nanoparticle. See, e.g., Section 5.6. In some embodiments, a second capture probe can be in solution, e.g., to be used to perform in situ reactions with a nucleic acid in a tissue sample.

The capture probes in the capture probe sets individually and independently can have a variety of different regions, e.g., a capture region (e.g., a universal or gene-specific capture region), a primer binding region (e.g., a SBS primer region, such as a SBS3 or SBS12 region, or another universal region, such as a P5 or P7 region), a spatial address region (e.g., a partial or combinatorial spatial address region), or a cleavable region.

In some embodiments, only one capture probe in a set of capture probes comprises a capture region. In some embodiments, two or more capture probes in a set of capture probes comprise as capture region.

In some embodiments, only one probe in a set of capture probes comprises a spatial address region, e.g., such as a complete spatial address region describing the position of a capture site on a capture array. In some embodiments, two or more probes in a set of capture probes can comprise a spatial address region, e.g., two or more probes can each comprise a partial spatial address region (i.e., combinatorial address region), wherein each partial address region describes the position of a capture site on a capture array, e.g., along the x-axis or the y-axis.

In some embodiments, a set of capture probes can comprise at least one capture probe comprising a capture region and a spatial address region (e.g., a complete or a partial spatial address region). In some embodiments, no capture probe in a set of capture probes comprises both a capture region and a spatial address region.

In another aspect, provided herein is a capture array for spatial detection and analysis of nucleic acids in a tissue sample, comprising a capture site comprising a set of capture probes. In some embodiments, the set of capture probes comprises at least two capture probes (i.e., at least a pair of capture probes). In some embodiments, the set of capture probes comprises three or more, four or more, five or more, six or more, seven or more, eight or more, nine or more, or ten or more capture probes. In some embodiments, the capture array can be integrated in an electrophoretic transfer system described herein. See, e.g., Section 5.3.

FIG. 17 illustrates a side view of one capture site 1700 on a capture array (e.g., capture array 100 of FIG. 1A), wherein the one capture site 1700 comprises two separate sets of immobilized capture probes. In some embodiments, a set of immobilized capture probes comprises two capture probes (i.e., a pair of capture probes). In some embodiments, a set of immobilized capture probes comprises three or more capture probes. By way of example, FIG. 17 shows capture site 1700 a of a capture array. A first set of capture probes 1710 comprises an SBS primer region 1715 (e.g., SBS3) and a spatial address region 1720. Each capture probe 1710 immobilized at capture site 1700a comprises the same unique spatial address region 1720. Capture probes 1710 immobilized at other capture sites 1700 (not shown), e.g., capture sites 1700b through 1700f, each include their own unique spatial address region 1720 (e.g., spatial address region 1720b through 1720f), i.e., each capture site 1700 has a unique spatial address region. A second set of capture probes 1725 comprises a second SBS primer region 1730 (e.g., SBS12) and a gene-specific capture region 1735, e.g., gene-specific capture region 1735a and gene-specific capture region 1735b. In some embodiments, the second set of capture probes does not comprise spatial address sequence. In this example, two spatially addressed capture probes 1710 and capture probes 1725 are shown, but any number of spatially addressed capture probes 1710 and capture probes 1725 can be immobilized at capture site 1700a. In some embodiments, the capture array illustrated in FIG. 17 can be integrated in an electrophoretic transfer system 1600 of FIG. 16.

Because at least two different sets of capture probes are used, e.g., in the embodiment illustrated in FIG. 17, the number of oligonucleotides required to achieve gene-specific capture is substantially reduced. For example, in a conventional approach, to RNA from 100 different genes at 20,000 capture sites, 2 million different spatially addressed capture oligonucleotides would be required. However, according to the methods described herein, to capture RNA from 100 different genes at 20,000 capture sites, only 20,000 spatially addressed oligonucleotides and 100 capture oligonucleotides are required.

In some embodiments, a capture array comprises a capture site (e.g., 1700a) comprising a pair of capture probes immobilized on a surface (e.g., 1710 and 1725a), wherein a first capture probe (e.g., 1710) of the pair of capture probes comprises a first primer binding region (e.g., SBS primer binding region 1715; e.g., SBS3) and a spatial address region (e.g., spatial address region 1720), and wherein a second capture probe (e.g., 1725a) of the pair of capture probes comprises a second primer binding region (e.g., SBS primer binding region 1730; e.g., SBS12) and a capture region (e.g., 1735a).

In some embodiments, the first capture probe does not comprise a gene-specific region.

In some embodiments, the second capture probe does not comprise a spatial address region.

In some embodiments, the capture site is a plurality of capture sites. In some embodiments, the plurality of capture sites is 2 or more, 10 or more, 30 or more, 100 or more, 300 or more, 1,000 or more, 3,000 or more, 10,000 or more, 30,000 or more, 100,000 or more, 300,000 or more, 1,000,000 or more 3,000,000 or more, or 10,000,000 or 1,000,000,000 or more capture sites.

In some embodiments, the capture array comprises a capture site density of 1 or more, 2 or more, 10 or more, 30 or more, 100 or more, 300 or more, 1,000 or more, 3,000 or more, 10,000 or more, 100,000 or more, 1,000,000 or more, capture sites per square centimeter ($cm^2$).

In some embodiments, the pair of capture probes in a capture site is a plurality of pairs of capture probes. In some embodiments, the plurality of capture probes is 2 or more, 10 or more, 30 or more, 100 or more, 300 or more, 1,000 or more, 3,000 or more, 10,000 or more, 30,000 or more, 100,000 or more, 300,000 or more, 1,000,000 or more 3,000,000 or more, or 10,000,000 or more, 100,000,000 or more, or 1,000,000,000 or more capture probes.

In some embodiments, the pair of capture probes in a capture site of a capture array is a plurality of pairs of capture probes. In some embodiments, each first capture probe in the plurality of pairs of capture probes within the same capture site comprises the same spatial address sequence. In some embodiments, each first capture probe in the plurality of pairs of capture probes in different capture sites comprises a different spatial address sequence.

In some embodiments, one or more capture sites of capture array have the same number of first capture probes and of second capture probes. In some embodiments, one or more capture sites have more first capture probes than second capture probes. For example, in some embodiments, one or more capture sites have at least 2-fold, at least 3-fold, at least 10-fold, at least 30-fold, at least 100-fold, at least 300-fold, at least 1,000-fold, at least 3,000-fold, or at least 10,000-fold more first capture probes than second capture probes. In some embodiments, one or more capture sites have more second capture probes than first capture probes. For example, in some embodiments, one or more capture sites have at least 2-fold, at least 3-fold, at least 10-fold, at least 30-fold, at least 100-fold, at least 300-fold, at least 1,000-fold, at least 3,000-fold, or at least 10,000-fold more second capture probes than first capture probes.

In some embodiments, the capture array is integrated into an electrophoresis system. In some embodiments, the electrophoresis system is an electrophoresis system as described in Section 5.3 (see, e.g., FIG. 16). In some embodiments, each capture site is independently electrically addressable in the electrophoresis system. In some embodiments, a capture site in the electrophoresis system is configured for transfer and capture of nucleic acids from a tissue sample such that diffusion of nucleic acids from the tissue sample and loss of nucleic acids between capture sites are substantially reduced relative to a passive nucleic acid transfer occurring under otherwise identical conditions in the absence of the electrophoresis system, e.g., by diffusion.

In some embodiments, the surface of the capture array is a planar surface, e.g., a glass surface. See, e.g., FIG. 1B. In some embodiments, the surface of the capture array comprises one or more wells. In some embodiments, the one or more wells correspond to one or more capture sites. In some embodiments, the surface of the capture array is a bead surface, e.g., as illustrated in FIG. 1C.

In some embodiments, the capture region in the second capture probe is a gene-specific capture region. In some embodiments, the gene-specific capture region in the second capture probe comprises the sequence of a TruSeq™ Custom Amplicon (TSCA) oligonucleotide probe (Illumina, Inc.). For example, the gene-specific capture regions in a plurality of second capture probes in a capture site can comprise a plurality of sequences of TSCA oligonucleotide probes.

In some embodiments, the capture region in the second capture probe is a universal capture region. In some embodiments, the universal capture region in the second capture probe comprises a random primer sequence. For example, the capture regions in a plurality of second capture probes in a capture site can comprise randomized sequences. In some embodiments, the universal capture region in a second capture probe comprises a poly-T capture sequence. For example, some or all of the universal capture sequences in a plurality of second capture probes in a capture site can comprise a poly-T capture sequence.

In some embodiments, the capture regions in one or more second capture probes of a capture site can be essentially the same capture regions in two or more capture sites of the capture array. In some embodiments, at least 1%, at least 5%, at least 10%, at least 15%, at least 20%, at least 25%, at least 30%, at least 40%, at least 50%, at least 60%, at least 70%, at least 80%, at least 90%, at least 95%, or at least 99% of second capture probes have the same capture regions in two or more capture sites of the capture array (e.g., in at least 1%, at least 5%, at least 10%, at least 15%, at least 20%, at least 25%, at least 30%, at least 40%, at least 50%, at least 60%, at least 70%, at least 80%, at least 90%, at least 95%, or at least 99% of capture sites on a capture array).

In some embodiments, the capture regions in the one or more second capture probes of a capture array can be essentially the same capture sequences in at least 1%, at least 5%, at least 10%, at least 15%, at least 20%, at least 25%, at least 30%, at least 40%, at least 50%, at least 60%, at least 70%, at least 80%, at least 90%, at least 95%, or at least 99% of capture sites on a capture array. In some embodiments, the capture regions in the one or more second capture probes of a capture array can be essentially the same capture sequences in essentially all capture sites on a capture array.

In some embodiments, the spatial address region comprises two or more partial spatial address regions (e.g., a first, a second, and, optionally, a third partial address region) that can be combined in a combinatorial manner (e.g., X*Y*Z). In some embodiments, the spatial address region comprises a first and a second partial address region to identify the position of a capture site on the capture array in the first (X) and second (Y) dimension. In some embodiments, the spatial address region further comprises a third partial address region to identify the location of a tissue slice (and of a nucleic acid transferred from the tissue slice) in the tissue sample in the third (Z) dimension.

In some embodiments, the first or second capture probe on the capture array further comprises a temporal address region (T) to identify the relative sequence of timepoints at which a sample was obtained in the course of a time-course experiment (e.g., a time-course experiment to determine changes of gene-expressions in a tissue over time in response to a chemical, biological, or physical stimulus).

In some embodiments, two or more address regions (e.g., spatial or temporal address regions) in a capture probe are consecutive. In some embodiments, two or more address regions are separated by one or more nucleic acids (e.g., by 2 or more, 3 or more, 10 or more, 30 or more, 100 or more, 300 or more, or 1,000 or more nucleic acids).

FIG. 18 illustrates a flow diagram of an embodiment of a method 1800 of transferring nucleic acids from a tissue sample to a capture array for generation of a spatially addressed sequencing library, wherein the capture array comprises capture sites that include separate pairs of immobilized capture probes, e.g., as shown in FIG. 17. In this embodiment, the nucleic acid is RNA. In some embodiments of the method illustrated in FIG. 18, the capture array is integrated into an electrophoretic transfer system, such as the electrophoretic transfer system 1600 of FIG. 16. Method 1800 comprises, but is not limited to, some or all of the following steps.

Optionally, at a step 1810, a nucleic acid from a tissue sample can be electrophoretically transferred to a capture array. For example and now referring to FIG. 16 and FIG. 17, sample substrate 1630 with tissue sample 1640 thereon can be placed atop capture array 1610. In this example, capture sites 1620 of capture array 1610 include separate pairs of immobilized capture probes, e.g., as shown in FIG. 17. An electric field is applied to capture sites 1620. As capture sites 1620 are activated, nucleic acids 1650 from tissue sample 1640 are transferred to capture array 1610 and hybridize to capture probes 1725 that are immobilized at capture sites 1620. In this embodiment, capture probes 1725 are gene-specific capture probes designed to capture specific mRNAs.

In some embodiments, at step 1810, the transfer of a nucleic acid from a sample, such as the tissue sample 1640, can occur by passive diffusion. In some embodiments, at step 1810, the transfer of a nucleic acid from a sample, such as the tissue sample 1640, is facilitated by a method other than electrophoresis.

At a step 1815, first strand cDNA is synthesized. For example, gene-specific capture regions 1735 can function as reverse transcriptase primers for synthesis of first strand cDNA from captured mRNA molecules.

At a step 1820, first strand cDNA is covalently linked to the second capture probe 1710 by single-strand ligation of cDNA to spatial address region 1720.

At a step 1825, second strand cDNA is synthesized using a primer that is complementary to SBS primer region 1715.

At a step 1830, second strand cDNA molecules are released from capture site 1700 by denaturation.

At a step 1835, the cDNA is amplified to generate a sequencing library. FIGS. 19A, 19B, 19C, and 19D show pictorially the steps of method 1800 of FIG. 18. Namely, at step 1810, a plurality of mRNA molecules 1910 are transferred (e.g., electrophoretically) from a tissue section (not shown) onto capture site 1700 and hybridize to capture probes 1725. In some embodiments, a first mRNA molecule 1910a is a transcript from a first gene and a second mRNA molecule 1910b is a transcript from a second gene. mRNA molecule 1910a can include a mutation 1915a. mRNA molecule 1910b can include a mutation 1915b. mRNA molecule 1910a is captured on capture probe 1725a by hybridization of complementary mRNA sequences to gene-specific capture region 1735a. Similarly, mRNA molecule

1910b is captured on capture probe 1725b by hybridization of complementary mRNA sequences to gene-specific capture region 1735b.

At step 1815, first strand cDNA is synthesized using gene-specific capture region 1735 as a primer. A cDNA molecule 1920 (i.e., cDNA molecules 1920a and 1920b) include SBS primer region 1730.

At step 1820, cDNA molecule 1920 is covalently linked to spatially addressed oligonucleotides 1710 by single-strand ligation of cDNA molecule 1920 to spatial address region 1720.

At step 1825, second strand cDNA is synthesized using a primer region 1715a that is complementary to SBS primer region 1715.

At step 1830, second strand cDNA molecules 1920 are released from capture site 1700 by denaturation. cDNA molecules 1920 now include SBS primer region 1715, spatial address region 1720, and SBS primer region 1730.

At step 1835, cDNA molecules 1920 are amplified to generate a sequencing library. In a first amplification reaction, cDNA molecules are amplified using a first SBS primer 1925. SBS primer 1925 comprises an SBS complementary region 1730a that is complementary to SBS primer region 1730 and a P7 region 1930. Amplicons 1935 (i.e., amplicons 1935a and 1935b) are flanked on the 5' end by P7 region 1930 and SBS primer region 1730 and on the 3' end by spatial address region 1720 and SBS primer region 1715. Amplicons 1935 are amplified using a second SBS primer 1940. SBS primer 1940 comprises an SBS complementary region 1715a that is complementary to SBS primer region 1715 and a P5 region 1945. Amplicons 1935 (i.e., amplicons 1935a and 1935b) are now flanked by P7 region 1930 and SBS primer region 1730 and by spatial address region 1720, SBS primer region 1715, and P5 region 1945.

In another aspect, provided herein is a method for spatial detection and analysis of nucleic acids in a tissue sample, comprising providing a capture array described herein. In some embodiments, the capture array comprises a capture site comprising a set of capture probes. In some embodiments, the set of capture probes comprises two capture probes (i.e., a pair of capture probes). In some embodiments, the set of capture probes comprises three or more, four or more, five or more, six or more, seven or more, eight or more, nine or more, or ten or more capture probes. In some embodiments, the capture array can be integrated in an electrophoretic transfer system described herein. See, e.g., Section 5.3.

In some embodiments, the method comprises (a) providing a capture array, comprising a capture site comprising a pair of capture probes (e.g., 1710 and 1725a) immobilized on a surface, wherein a first capture probe of the pair of capture probes comprises a first primer binding region (e.g., 1715) and a spatial address region (e.g., 1720), and wherein a second capture probe of the pair of capture probes comprises a second primer binding region (e.g., 1730) and a capture region (e.g., 1735a).

In some embodiments, the first capture probe does not comprise a capture region.

In some embodiments, the second capture probe does not comprise a spatial address region.

In some embodiments, the method further comprises any one or more of the following steps: (b) contacting the capture array with a tissue sample such that the position of a capture site on the array can be correlated with a position in the tissue sample; (c) allowing nucleic acids of the tissue sample to hybridize to the capture region of the second capture probe; (d) extending the capture region of the second capture probe to form an immobilized first complementary strand of the nucleic acid hybridized to the gene-specific sequence; (e) ligating the immobilized first complementary strand to the spatial address sequence of a first capture probe to immobilize the first complementary strand at both ends; (f) synthesizing a second complementary strand using a primer complementary to the first primer binding sequence of the first capture probe; (f) releasing the second complementary strand from the surface of the capture array; (g) analyzing the sequence of the released second complementary strand, and (h) correlating the sequence of the released second complementary stand to the position of the nucleic acid in the tissue sample.

In some embodiments, allowing nucleic acids of the tissue sample to hybridize to the capture region of the second capture probe comprises an electrophoretic transfer of the nucleic acids from the tissue sample onto the capture array.

In some embodiments, allowing the nucleic acids of the tissue sample to hybridize to the capture region of the second capture probe comprises passive diffusion of the nucleic acids from the tissue sample onto the capture array.

In some embodiments, analyzing the sequence of the released complementary strand comprises next-generation sequencing, e.g., by sequencing-by-synthesis.

In some embodiments, the nucleic acids of the tissue sample comprise a messenger ribonucleic acid (mRNA).

In some embodiments, the first or second primer binding region comprises a SBS primer sequence. In some embodiments, the SBS primer sequence is a SBS3 or SBS12 sequence.

In some embodiments, the capture region of the second capture probe comprises a single nucleotide variation (SNV). In some embodiments, the method has a sensitivity of SNV detection of at least 0.00025% SNV (1/400,000 cells). The sensitivity of spatial NGS for detection of single nucleotide variations is described in more detail with reference to Table 3 hereinbelow.

In some embodiments, the capture region in the second capture probe is a universal capture region. In some embodiments, the universal capture region in the second capture probe comprises a random primer sequence. In some embodiments, the capture regions in the plurality of second capture probes in a capture site comprise 10 or more, 100 or more, 1,000 or more, 10,000 or more, 100,000 or more, or 1,000,000 or more randomized capture sequences. In some embodiments, the universal capture region in the second capture probe comprises a poly-T capture sequence.

In some embodiments, the capture region in the second capture probe is a gene-specific capture region. In some embodiments, the gene-specific capture region in the second capture probe comprises the sequence of a TSCA oligonucleotide probe. In some embodiments, the capture regions in the plurality of second capture probes in a capture site comprise 10 or more, 100 or more, 1,000 or more, 10,000 or more, 100,000 or more, or 1,000,000 or more TSCA capture sequences.

In some embodiments, at least one capture probe in a set of capture probes is in solution, e.g., to hybridize with a nucleic acid in the tissue sample. FIG. 20 shows an exemplary embodiment of a process 2000 of capturing a nucleic acid in a tissue sample for subsequent anchoring onto an array. In this embodiment, a capture probe 2010 comprises a nucleic acid capture region 2015 and a universal array capture region 2020. In one example, nucleic acid capture region 2015 is a random primer sequence. In another example, nucleic acid capture region 2015 is a gene-specific primer sequence. Universal array capture region 2020 is a universal sequence that is used to anchor a nucleic acid molecule onto a capture array. Capture probe 2010 can be used in a solution-based hybridization reaction to capture a nucleic acid molecule 2025 in a tissue section. In one example, nucleic acid molecule 2025 is a genomic DNA molecule. Capture probe 2010 hybridizes to nucleic acid molecule 2025 from a tissue sample and is extended to form a nucleic acid complementary to nucleic acid molecule 2025 (indicated by the arrow) and incorporate universal array capture region 2020 into the complementary strand. Universal array capture region 2020 is then used to anchor the copied nucleic acid molecule onto a capture array (not shown). In another example, nucleic acid molecule 2025 is an RNA molecule. Capture probe 2010 hybridizes to nucleic acid molecule 2025 and is used as a primer in a reverse transcription reaction to synthesize first strand cDNA (indicated by the arrow) and incorporate universal array capture region 2020 into cDNA molecule. Universal array capture region 2020 is then used to anchor the cDNA molecule onto a capture array (not shown).

In some embodiments, the method comprises (a) providing a capture array, comprising a capture site comprising a first capture probe immobilized on a surface, wherein the capture probe comprises a cleavable region, a first primer binding region and a spatial address region.

In some embodiments, the first capture probe does not comprise a capture region.

In some embodiments, the method further comprises one or more of the following steps: (b) contacting a tissue sample with a second capture probe, wherein the second capture probe comprises a second primer binding region and a capture region (e.g., a gene specific or a universal capture region); (c) allowing nucleic acids of the tissue sample to hybridize to the capture region of the second capture probe; (d) extending the capture region of the second capture probe to form a first complementary strand of the nucleic acid hybridized to the nucleic acid.

In some embodiments, the second capture probe does not comprise a spatial address region.

In some embodiments, the method further comprises one or more of the following steps: (e) optionally, hybridizing a complementary oligonucleotide to the spatial address region of the capture probe to form a double-stranded spatial address region; (f) contacting the capture array with the tissue sample comprising the first complementary strand of the nucleic acid such that the position of a capture site on the array can be correlated with a position in the tissue sample; (g) allowing the first complementary strand of the nucleic acid to transfer from the tissue sample onto the capture array; (h) ligating the first complementary strand of the nucleic acid (that is optionally hybridized to the nucleic acid) to the first capture probe (e.g., by blunt end ligation, such as double stranded blunt end ligation) to form a spatially tagged double stranded nucleic acid comprising first and second primer binding sites and a cleavable domain; (g) releasing the double stranded nucleic acid from the surface of the capture array; (h) analyzing the sequence of the released double stranded nucleic acid, and (i) correlating the sequence of the released nucleic acid to the position of the nucleic acid in the tissue sample.

In some embodiments, allowing the first complementary strand of the nucleic acid to transfer from the tissue sample onto the capture array comprises an electrophoretic transfer of the nucleic acids from the tissue sample onto the capture array.

In some embodiments, allowing the first complementary strand of the nucleic acid to transfer from the tissue sample onto the capture array comprises passive diffusion of the nucleic acids from the tissue sample onto the capture array.

In some embodiments, of the released double stranded nucleic acid comprises next-generation sequencing, e.g., by sequencing-by-synthesis.

In some embodiments, the nucleic acids of the tissue sample comprise a messenger ribonucleic acid (mRNA).

In some embodiments, the first or second primer binding region comprises a SBS primer sequence. In some embodiments, the SBS primer sequence is a SBS3 or SBS12 sequence.

4.5 Combinatorial Indexing System

In another embodiment, a combinatorial indexing (addressing) system is used to provide spatial information for analysis of nucleic acids in a tissue sample. In this approach, two or more spatial address sequences are incorporated into a nucleic acid during preparation of a sequencing library. A first spatial address is used to define a certain position (i.e., capture site) in the X dimension on a capture array and a second spatial address sequence is used define a position (i.e., a capture site) in the Y dimension on the capture array. During library sequencing, both X and Y spatial address sequences are determined and the sequence information is analyzed to define the specific position on the capture array.

In one example, the tissue sample is contacted with capture probes that are fixed on the surface of the array. The tissue sample may be placed directly on the surface comprising the capture probes or the tissue sample may be placed on a substance such as a filter or a gel or a thin buffer layer separating the tissue sample from the capture probes such that the target nucleic acid may diffuse from the tissue through the substance to the capture probes.

FIGS. 21A and 21B show a grid array 2100 of a one-dimensional indexing scheme and a grid array 2105 of a two-dimensional indexing scheme, respectively, for spatial detection and analysis of nucleic acids in a tissue sample. Referring to FIG. 21A, to spatially address 100 positions in a one-dimensional indexing scheme, 100 unique spatial addresses are required. Referring now to FIG. 21B, to spatially address 100 positions in a two-dimensional indexing scheme, 10 unique spatial addresses are required for the X dimension and 10 unique spatial addresses are required for the Y dimension, i.e., the total unique spatial address sequences required is 20. Combinatorial indexing substantially reduces the number of spatial addresses that are needed for spatial detection and analysis of nucleic acids in a tissue sample.

In some embodiments, a capture site on an array comprises a first capture probe with a first spatial address sequence for the X dimension and a second capture probe with a second spatial address sequence for the Y dimension. In some embodiments, the first and second capture probes are oriented in opposite directions on the capture site such that both the 5' and 3' ends of a RNA molecule are captured. During subsequent library preparation steps, the first and second spatial address sequences are incorporated into library amplicons as described in more detail with reference to FIG. 22 and FIGS. 23A and 23B.

In some embodiments, the first and second capture probes are oriented in the same direction on the capture site such that only the 3' end of a mRNA molecule is captured. During subsequent library preparation steps, the first and second spatial address sequences are incorporated into library amplicons as described in more detail with reference to FIG. 24 and FIGS. 25A and 25B.

In some embodiments, two or more partial address region (e.g., a first and a second partial address region) can be incorporated into a single capture probe. The two or more partial address regions can form a consecutive region or be separated by one or more nucleic acids. For example, two or more partial address regions can be incorporated into a single first capture probe of a capture probe pair, according to the capture arrays and methods illustrated, e.g., in FIGS. 17-19.

FIG. 22 illustrates a flow diagram of an example of a method 2200 of using a combinatorial indexing system for generation of a spatially addressed cDNA sequencing library. Method 2200 comprises, but is not limited to, some or all of the following steps.

At a step 2210, a tissue sample that comprises a plurality of mRNA molecules is contacted with a capture array. The capture array can be, for example, capture array 100 of FIG. 1A. For each gene-specific (i.e., specifically targeted) mRNA molecule two capture probes are used, i.e., a first capture probe that comprises sequences specific for the 3' end of the mRNA molecule and a second capture probe that comprises sequences specific for the 5' end of the mRNA molecule. mRNA molecules are captured onto the array by hybridization of mRNA to the gene-specific capture regions on the capture probes. An example of the capture probes on capture array 100 are described in more detail with reference to FIG. 23A.

At a step 2215, first strand cDNA is synthesized. For example, gene-specific capture regions on the first capture probe are used as reverse transcriptase primers for synthesis of first strand cDNA from captured mRNA molecules. The cDNA molecule is then ligated to the 5' end of the second capture probe.

At a step 2220, the cDNA molecule is released from the capture array. For example, the cDNA molecule is released from the capture array using a cleavage reaction.

At a step 2225, the cDNA is amplified to generate a sequencing library.

FIGS. 23A and 23B illustrate the steps of method 2200 of FIG. 22. In this example, a single capture site 105 of capture array 100 of FIG. 1A is shown. Capture site 105 comprises a first capture probe 2310a and a second capture probe 2310b. Capture probes 2310 include a cleavable domain 2315, an SBS primer region 2320, a spatial address region 2325, a unique molecular identifier (UMI) 2330, and a capture region 2335. For example, capture probe 2310a comprises cleavable region 2315; SBS primer region 2320a, which comprises, e.g., a SBS3 sequence; spatial address region 2325a, which comprises a unique spatial address sequence for the X dimension; UMI region 2330a, which comprises a unique sequence for capture probe 2310a; and a gene-specific capture region 2335a, which is specific for the 3' end of a mRNA molecule. Capture probe 2320a is immobilized at capture site 105 in the 5' to 3' orientation (i.e., the 5' end of capture probe 2320a is attached to the surface of capture site 105). Similarly, capture probe 2310b comprises cleavable sequence 2315; SBS primer region 2320b, which comprises a SBS12 sequence; spatial address region 2325b, which comprises a unique spatial address region for the Y dimension; UMI region 2330b, which comprises a unique sequence for capture probe 2310b; and a gene-specific capture region 2335b, which is specific for the 5' end of the mRNA molecule. Capture probe 2320b is immobilized at capture site 105 in the 3' to 5' orientation (i.e., the 3' end of capture probe 2320a is attached to the surface of capture site 105).

At step 2210, a mRNA molecule 2340 in a tissue sample is captured on capture probes 2310. For example, the tissue sample containing mRNA molecule 2340 or a substrate comprising mRNA molecule 2340 derived from the tissue sample (not shown) is contacted with capture probes 2310. mRNA molecule 2340 can include a mutation 2345. mRNA molecule 2340 is captured at capture site 105 by hybridization of the 3' end of mRNA molecule 2340 to capture region 2335a and hybridization of the 5' end of mRNA molecule 2340 to capture region 2335b.

At step 2215, a cDNA molecule 2350 is synthesized using capture region 2335a as a primer in a reverse transcription reaction. The 3' end of cDNA molecule 2350 is then ligated to the 5' end of capture region 2335b.

At step 2220, cDNA molecule 2350 is released from capture site 105 by cleavage of cleavable region 2315. cDNA molecule 2350 comprises SBS primer region 2320a (i.e., SBS3), spatial address region 2325a (i.e., unique spatial address for the X dimension), UMI region 2330a, UMI region 2330b, spatial address region 2325b (i.e., unique spatial address for the Y dimension), and SBS primer region 2320b (i.e., SBS12).

At step 2225, cDNA molecule 2350 is amplified using an SBS primer 2355 and a second SBS primer 2360. SBS primer 2355 comprises an SBS sequence 2320a' that is complementary to SBS primer region 2320a and a P5 region 2365. SBS primer 2360 comprises an SBS region 2320b' that is complementary to SBS primer region 2320b and a P7 region 2370. A library amplicon 2375 synthesized using SBS primers 2355 and 2360 is flanked on the 5' end by P5 region 2365, SBS primer region 2320a (i.e., SBS3), spatial address region 2325a (i.e., unique spatial address for the X dimension), UMI region 2330a and on the 3' end by UMI region 2330b, spatial address region 2325b (i.e., unique spatial address for the Y dimension), SBS primer region 2320b (i.e., SBS12), and P7 region 2370.

FIG. 24 illustrates a flow diagram of an example of an alternative method 2400 of using a combinatorial indexing system for generation of a spatially addressed cDNA sequencing library. Method 2400 comprises, but is not limited to, some or all of the following steps.

At a step 2410, a tissue sample that comprises a plurality of mRNA molecules is contacted with a capture array. The capture array can be, for example, capture array 100 of FIG. 1A. For each gene-specific mRNA molecule two capture probes are used, i.e., a first capture probe that comprises sequences specific for the 3' end of the mRNA molecule and a second capture probe that comprises sequences specific for the 3' end of a corresponding first strand cDNA molecule. mRNA molecules are captured onto the array by hybridization of the 3' end of the mRNA to gene-specific regions on the first capture probe. An example of the capture probes on capture array 100 are described in more detail with reference to FIG. 25A.

At a step 2415, first strand cDNA is synthesized. For example, gene-specific capture regions on the first capture probe are used as reverse transcriptase primers for synthesis of first strand cDNA from captured mRNA molecules.

At a step 2420, first strand cDNA is captured on the second capture probe. First strand cDNA is captured on the second capture probe by hybridization of the 3' end of the cDNA to a gene-specific region on the second capture probe.

At a step 2425, second strand cDNA is synthesized. For example, gene-specific regions on the second capture probes are used as primers for synthesis of second strand DNA molecules.

At a step 2430, second strand cDNA molecules are released from the capture array. For example, cDNA molecules are released from the capture array using a cleavage reaction.

At a step 2435, cDNA molecules are amplified to generate a sequencing library.

FIGS. 25A, 25B, and 25C illustrate the steps of method 2400 of FIG. 24. In this example, a single capture site 105 of capture array 100 of FIG. 1A is shown. Capture site 105 is essentially the same as described above with reference to FIG. 23A except that capture probes 2310 are oriented in the same direction at capture site 105, i.e., both capture probe 2310a and capture probe 2310b are immobilized at capture site 105 in the 5' to 3' direction (i.e., the 5' end of capture probes 2310a and 2310b are attached to the surface of capture site 105). Capture region 2335a is specific for the 3' end of a mRNA molecule and capture region 2335b is specific for the 3' end of the corresponding first strand cDNA molecule.

At step 2410, a mRNA molecule 2510 in a tissue sample is captured on capture probe 2310a. For example, the tissue sample containing mRNA molecule 2510 or a substrate comprising mRNA molecule 2510 derived from the tissue sample (not shown) is contacted with capture probes 2310. mRNA molecule 2510 can include a mutation 2515. mRNA molecule 2510 is captured at capture site 105 by hybridization of the 3' end of mRNA molecule 2510 to capture region 2335a.

At step 2415, first strand cDNA is synthesized using capture region 2335a as a primer in a reverse transcription reaction.

At step 2420, a first strand cDNA molecule 2520 is captured on capture probe 2310b by hybridization of the 3' end of cDNA molecule 2520 to capture region 2335b.

At step 2425, second strand cDNA is synthesized in an extension reaction using capture region 2335b as a primer.

At step 2430, a cDNA molecule 2525 is released from capture site 105 by cleavage of cleavable region 2315. cDNA molecule 2525 comprises SBS primer region 2320a (i.e., SBS3), spatial address region 2325a (i.e., unique spatial address for the X dimension), UMI region 2330a, UMI region 2330b, spatial address region 2325b (i.e., unique spatial address for the Y dimension), and SBS primer region 2320b (i.e., SBS12).

At step 2435, cDNA molecule 2525 is amplified using an SBS primer 2530 and a second SBS primer 2535. SBS primer 2530 comprises an SBS region 2320a' that is complementary to SBS primer region 2320a and a P5 region 2540. SBS primer 2535 comprises an SBS region 2320b' that is complementary to SBS primer region 2320b and a P7 region 2545. A library amplicon 2550 synthesized using SBS primers 2530 and 2535 is flanked on the 5' end by P5 region 2540, SBS primer region 2320a (i.e., SBS3), spatial address region 2325a (i.e., unique spatial address for the X dimension), UMI region 2330a and on the 3' end by UMI region 2330b, spatial address region 2325b (i.e., unique spatial address for the Y dimension), SBS primer region 2320b (i.e., SBS12), and P7 region 2545.

In some embodiments, a combinatorial indexing system can involve use of two different arrays, i.e., a first array that comprises spatial address sequences for the X dimension and a second array that comprises spatial address sequences for the Y dimension. In one example, a first array can be used to deliver reverse transcription (RT) primers to a tissue sample for in situ synthesis of cDNA and a second array is used to capture the cDNA for generation of a spatially addressed sequencing library.

FIG. 26A illustrates a plan view of an example of an array 2600 for delivery of RT primers to a tissue sample for in situ synthesis of cDNA. Array 2600 comprises an arrangement, e.g., rows, of delivery sites 2605 on a solid support 2610. In this example, 10 delivery sites 2605 (e.g., delivery sites 2605a through 2605j) are arranged on solid support 2610. In one example, solid support 2610 is a glass coverslip. A plurality of RT primers 2615 is deposited (e.g., printed) in a stripe along the length of each delivery site 2605. RT primers 2615 are deposited at each delivery site 2605 such that they can be readily released from array 2600 onto a tissue sample.

FIG. 26B illustrates a side view of a portion of one delivery site 2605 of array 2600, wherein the portion of delivery site 2605 comprises at least one RT primer 2615 for synthesis of cDNA from mRNA in a tissue sample. In this example, a single RT primer 2615 is shown, but any number of RT primers 2615 can be deposited on solid support 2610 at each delivery site 2605. RT primer 2615 comprises an SBS primer region 2620 (e.g., SBS3), a spatial address region 2625 (i.e., unique spatial address for the X dimension), and a gene-specific primer region 2630. RT primer 2615 has a unique spatial address region 2625 for each delivery site 2605, i.e., delivery site 2605a has a unique spatial address region 2625a, delivery site 2605b has a unique spatial address region 2625b, etc. Gene-specific primer region 2630 can be the same gene-specific region or they can be different gene-specific sequences.

FIG. 27A illustrates a plan view of an example of a capture array 2700 for the capture of cDNA synthesized in situ using RT primers 2615 of FIG. 26B. Capture array 2700 comprises an arrangement, e.g., columns, of capture sites 2705 on a solid support 2710. In this example, 10 capture sites 2705 (e.g., capture sites 2705a through 2705j) are arranged on solid support 2710. In one example, solid support 2710 is a planar glass surface. A plurality of capture probes 2715 are deposited in a stripe along the length of each capture site 2705.

FIG. 27B illustrates a side view of a portion of one capture site 2705 of capture array 2700, wherein the portion of capture site 2705 comprises at least one capture probe 2715 for capture of cDNA synthesized in situ using RT primers 2615 of FIG. 26B. In this example, a single capture probe 2715 is shown, but any number of capture probes 2715 can be immobilized on solid support 2710 at each capture site 2705. Capture probe 2715 comprises a cleavable region 2720, an SBS primer region 2725 (e.g., SBS12), a spatial address region 2730, a unique molecular identifier (UMI) region 2735, and a gene-specific capture region 2740. Capture probe 2715 has a unique spatial address region 2730 for each capture site 2705, i.e., capture site 2705a has a unique spatial address region 2730a, capture site 2705b has a unique spatial address region 2730b, etc. Capture region 2740 is complementary to capture region 2630 of capture probe 2615 of FIG. 26B.

FIG. 28 illustrates a flow diagram of an example of a method 2800 of generating a spatially addressed sequencing library, wherein a first array is used for in situ synthesis of first strand cDNA and a second array is used to capture the cDNA for subsequent library generation. Method 2800 comprises, but is not limited to, the following steps.

At a step 2810, a tissue sample that comprises a plurality of mRNA molecules is contacted with a first array. The array is, for example, array 2600 of FIG. 26A that comprises a plurality of RT primers 2615. RT primers 2615 are released from array 2600 onto the tissue sample.

At a step 2815, first strand cDNA is synthesized in situ. For example, gene-specific primer sequences on the RT primers are used to prime first strand cDNA from targeted mRNA molecules in the tissue sample. After first strand cDNA synthesis, array 2600 is removed from the surface of the tissue sample.

At a step 2820, first strand cDNA is captured onto a second array and second strand cDNA is synthesized. For example, capture array 2700 of FIG. 27A that comprises a plurality of capture probes 2715 is contacted with the tissue sample. First strand cDNA is captured onto capture array 2700 by hybridization of the 3' end of the cDNA to gene-specific regions on capture probes 2715. Second strand cDNA is synthesized using gene-specific regions on capture probe 2715 as primers in an extension reaction.

At a step 2825, second strand cDNA molecules are released from the capture array. For example, cDNA molecules are released from the capture array using a cleavage reaction.

At a step 2830, cDNA molecules are amplified to generate a sequencing library.

FIGS. 29A and 29B illustrate the steps of method 2800 of FIG. 28. At step 2810, a tissue sample (not shown) that comprises a mRNA molecule 2910 is contacted with array 2600 (not shown). For example, the tissue sample containing mRNA molecule 2910 or a substrate comprising mRNA molecule 2910 derived from the tissue sample (not shown) is contacted with array 2600. mRNA molecule 2910 can include a mutation 2915. RT primers 2615 are released from array 2600 onto the tissue sample and hybridize to mRNA molecule 2910 via gene-specific region 2630.

At step 2815, a first strand cDNA molecule 2920 is synthesized in situ using gene-specific region 2630 as a primer in a reverse transcription reaction.

At step 2820, capture array 2700 of FIG. 27A that comprises a plurality of capture probes 2715 is contacted with the tissue sample. First strand cDNA 2920 is captured at capture site 2705 by hybridization of the 3' end of first strand cDNA 2920 to gene-specific capture region 2740. Second strand cDNA is synthesized in an extension reaction using gene-specific capture region 2740 as a primer.

At step 2825, a second strand cDNA 2925 is released from capture site 2705 by cleavage of cleavable region 2720. cDNA molecule 2925 comprises SBS primer region 2725 (SBS12), spatial address region 2730 (i.e., unique spatial address for the Y dimension), UMI region 2735, spatial address region 2625 (i.e., unique spatial address for the X dimension), and SBS primer region 2620 (SBS3).

At step 2830, cDNA molecule 2925 is amplified using an SBS primer 2930 and an SBS primer 2935. SBS primer 2930 comprises an SBS region 2725a that is complementary to SBS primer region 2725 and a P5 region 2940. SBS primer 2935 comprises an SBS region 2620a that is complementary to SBS primer region 2620 and a P7 region 2945. A library amplicon 2950 synthesized using SBS primers 2930 and 2935 is flanked on the 5' end by P5 region 2940, SBS primer region 2725 (i.e., SBS3), spatial address region 2730 (i.e., unique spatial address for the Y dimension), UMI region 2735 and on the 3' end by spatial address region 2625 (i.e., unique spatial address for the X dimension), SBS primer region 2620 (i.e., SBS3), and P7 region 2945.

In this example, the tissue sample is contacted with capture probes 2715 that are fixed on the surface of capture sites 2705. First strand cDNA 2920 is captured at capture site 2705 by hybridization of the 3' end of first strand cDNA 2920 to gene-specific capture sequence 2740. In another example (not shown), the tissue sample is contacted with capture array 2700 and capture probes 2715 are released from capture sites 2705 into the tissue sample by cleavage of cleavable sequence 2720. Second strand cDNA is synthesized in an extension reaction using gene-specific capture sequence 2740 as a primer.

4.5 Spatial Detection and Analysis of Nucleic Acid in a Tissue Sample Using Releasable Capture Probes In other embodiments, a spatially addressed array is used to release capture probes into a tissue section for generation of a spatially addressed sequencing library. In this approach, spatially addressed capture probes are deposited on the surface of a substrate (e.g., a glass coverslip) at distinct capture sites or "features." In one example, the spatially addressed capture probes are anchored onto the surface of the substrate by the formation of a cleavable bond. The spatially addressed capture probes are released into a tissue section by cleavage of the reversible bond and incorporated into the nucleic acid in subsequent biochemical processing steps. In some embodiments, the spatially addressed capture probes are deposited on the substrate suspended in a matrix such as a BioGel matrix. The spatially addressed capture probes suspended in the BioGel are released into a tissue section, for example, by application of a heat treatment or a chemical treatment. Immobilizing spatially addressed capture probes on a substrate surface using a cleavable bond or BioGel suspension obviates the need to capture nucleic acid (i.e., RNA, cDNA or genomic DNA) from a tissue section onto a substrate surface for generation of a spatially addressed library.

In one example, a spatially addressed capture probe comprises a random primer sequence that is used for in situ synthesis of cDNA from total RNA in a tissue sample.

FIG. 30 illustrates a flow diagram of an example of a method 3000 of generating a spatially addressed cDNA library using releasable capture probes. Method 3000 comprises, but is not limited to, the following steps.

At a step 3010, a coverslip is printed with spatially addressed capture probes to form an array of spatial features. In one example, the spatially addressed capture probes are printed on a 2 cm×2 cm coverslip to form an array of spatial features that are 100 μm in diameter with a pitch of 35 μm. The spatially addressed capture probes include a random primer sequence for synthesis of cDNA in a reverse transcription reaction, a spatial address sequence, and a biotinylated SBS primer sequence as described in more detail with reference to FIGS. 31A and 31B. The spatially addressed capture probes also include a modification at the 5' end of the molecule for reversible attachment to the coverslip. In one example, the spatially addressed capture probes include a 5' disulfide modification as described in more detail with reference to FIGS. 32A, 32B, and 32C. In some embodiments, the spatially addressed capture probes include a 5' photocleavable linker as described in more detail with reference to FIGS. 33A, 33B, and 33C.

At a step 3015, the coverslip is placed atop a semi-permeabilized FFPE tissue section mounted on a glass slide, such that the surface of the coverslip with the spatially addressed capture probes thereon is in contact with the tissue section.

At a step 3020, the spatially addressed capture probes immobilized on the coverslip are released from the surface of the coverslip into the cellular space of the tissue section. In one example, spatially addressed capture probes that include a 5' disulfide modification are released by flowing a solution of dithiothreitol (DTT) through the semi-permeabilized tissue section. In some embodiments, spatially addressed capture probes that include a 5' photocleavable linker are released using ultraviolet light irradiation.

At a step 3025, first strand cDNA is synthesized in situ using a reverse transcription reaction. For example, a reverse-transcription master mix solution is flowed between the coverslip and glass slide into the semi-permeabilized tissue section. The coverslip acts as a barrier to prevent evaporation during the reaction. Because of the internal biotin label in the spatially addressed capture probes used in the reverse transcription reaction, first strand cDNA is biotinylated.

At a step 3030, RNA:cDNA hybrids are dissociated and the cellular matrix disrupted. In one example, the RNA:cDNA duplexes are dissociated and the cellular matrix disrupted using a NaOH solution. In some embodiments, RNA:cDNA duplexes are dissociated and the cellular matrix disrupted using a heat treatment protocol.

At a step 3035, the semi-permeabilized tissue sample with RNA and cDNA therein is removed from the surface of glass slide and collected in a collection tube. In one example, the semi-permeabilized tissue sample with RNA and first strand cDNA therein is removed from the glass slide by scraping into an Eppendorf tube. In some embodiments, the semi-permeabilized tissue sample with RNA and first strand cDNA therein is removed from the glass slide by placing the slide into a 50 mL centrifuge tube and centrifuging to collect the material in a receptacle at the bottom of the tube.

At a step 3040, the biotinylated first strand cDNA is purified using two rounds of a streptavidin bead-based purification protocol. The purified first strand cDNA is collected in a PCR tube for subsequent processing steps. The cDNA molecule comprises an SBS primer sequence (e.g., SBS12), a spatial address sequence, and the random primer sequence.

At a step 3045, first strand cDNA is amplified in a multiplex reaction using a mix of forward and reverse primer pairs that flank, for example, one or more targeted SNVs. For example, a forward primer comprises a gene-specific sequence that targets a SNV of interest, an SBS primer sequence (e.g., SBS3), and P5 sequences. The gene-specific sequence is designed to be about 50 bp upstream of a targeted SNV. A reverse primer comprises SBS12 complementary sequences and P7 sequences.

At a step 3050, library amplicons are sequenced. For example, read 1 (e.g., from about 50 bp to about 75 bp) of an SBS reaction provides sequence information for the targeted SNV and read 2 (about 25 bp) provides sequence information for the spatial address.

FIGS. 31A and 31B illustrate schematic diagrams of a spatially addressed capture probe 3100 that comprises a 5' disulfide modification and a spatially addressed capture probe 3150 that comprises a 5' photocleavable linker, respectively. Referring to FIG. 31A, spatially addressed capture probe 3100 comprises a random primer region 3110, a spatial address region 3115, and an SBS primer region 3120 (e.g., SBS12). Random primer region 3110 can comprise, e.g., a 6 bp sequence that can be used to prime cDNA synthesis from the entire transcriptome of a cell in a reverse transcription reaction. Spatial address region 3115 comprises a unique sequence for each spatial feature on an array. SBS primer region 3120 comprises an internal biotin label 3125. Internal biotin label 3125 is used to purify the cDNA in subsequent processing steps. Spatially addressed capture probe 3100 also comprises a 5' disulfide modification 3130. Disulfide modification 3130 is used to reversibly anchor spatially addressed capture probe 3100 onto the surface of a glass substrate (e.g., glass coverslip) as described in more detail with reference to FIGS. 32A, 32B, and 32C.

Referring to FIG. 31B, spatially addressed capture probe 3150 is substantially the same as spatially addressed capture probe 3100 except that the 5' end of spatially addressed capture probe 3150 is modified with a photocleavable amino linker 3155. Photocleavable amino linker 3155 is used to reversibly anchor spatially addressed capture probe 3150 onto the surface of a glass substrate (e.g., glass coverslip) as described in more detail with reference to FIGS. 33A, 33B, and 33C.

FIGS. 32A, 32B, and 32C illustrate an example of a process of reversibly anchoring spatially addressed capture probe 3100 of FIG. 31A onto the surface of a glass coverslip.

In a first step and referring now to FIG. 32A, a glass coverslip 3210 functionalized with a plurality of thiol (SH) groups 3215 is provided. Thiol functionalized coverslips are commercially available.

In a next step and referring now to FIG. 32B, spatially addressed capture probes 3100 are deposited (e.g., printed) onto the surface of glass coverslip 3210.

In a next step and referring now to FIG. 32C, spatially addressed capture probes 3100 are anchored onto the surface of glass coverslip 3210 by formation of a disulfide bond in a thiol-disulfide exchange reaction between thiol groups 3215 and disulfide modifications 3130 on spatially addressed capture probes 3100. Spatially addressed capture probes 3100 can be subsequently released from glass coverslip 3210 by cleavage of the disulfide bond using a reducing agent. In one example, dithiothreital (DTT) is used to cleave the disulfide bond and release spatially addressed capture probes 3100.

FIGS. 33A, 33B, and 33C illustrate an example of a process of reversibly anchoring spatially addressed capture probes 3150 of FIG. 31B onto the surface of a glass coverslip.

In a first step and referring now to FIG. 33A, a glass coverslip 3310 functionalized with a plurality of aldehyde groups 3315 is provided. Aldehyde functionalized glass substrates are commercially available.

In a next step and referring now to FIG. 33B, spatially addressed capture probes 3150 are deposited onto the surface of glass coverslip 3310.

In a next step and referring now to FIG. 33C, spatially addressed capture probes 3150 are anchored onto the surface of glass coverslip 3310 by formation of a covalent bond between aldehyde groups 3315 and photocleavable amino linkers 3155 on spatially addressed capture probes 3150. Spatially addressed capture probes 3150 can be subsequently released from glass coverslip 3310 by cleavage of the covalent bond using ultraviolet light irradiation (e.g., 350 nm for about 5 minutes).

FIGS. 34A and 34B show pictorially the steps of method 3000 of FIG. 30. At step 3010, a coverslip 3410 is printed with spatially addressed capture probes (not shown) to form an array of spatial features 3415. In one example, the spatially addressed capture probes are printed on a 2 cm×2 cm coverslip to form an array of spatial features 3415 that are 100 μm in diameter with a pitch of 35 μm. The spatially addressed capture probes are, for example, spatially addressed capture probe 3100 of FIG. 31 that are used to capture the entire transcriptome of a cell.

At step 3015, coverslip 3410 is placed atop a semi-permeabilized tissue section 3420 that is mounted on a glass slide 3425. Tissue section 3420 comprises a plurality of cells 3430. Each cell contains one or more RNA molecules 3435. One or more RNA molecules 3435 can include a single nucleotide variation (SNV) 3440.

At step 3020, the spatially addressed capture probes (indicated by arrows) immobilized on coverslip 3410 are released from the surface of the coverslip into the cellular space.

At step 3025, first strand cDNA is synthesized in situ in a reverse transcription reaction using random primer sequences 3110 on spatially addressed capture probe 3100. For example, a reverse-transcription master mix solution (not shown) is flowed between coverslip 3410 and glass slide 3425 into semi-permeabilized tissue section 3420.

At step 3030, RNA:cDNA hybrids are dissociated and the cellular matrix in tissue sample 3420 is disrupted to release a cDNA molecule 3445. In one example, the RNA:cDNA duplexes are dissociated and the cellular matrix disrupted using a NaOH solution. In some embodiments, RNA:cDNA duplexes are dissociated and the cellular matrix disrupted using a heat treatment protocol.

At step 3035, semi-permeabilized tissue sample 3420 with cells 3430, RNA molecules 3435, and cDNA molecules 3445 therein are removed from the surface of glass slide 3425 and collected in a collection tube 3450. In one example, semi-permeabilized tissue sample 3420 with cells 3430, RNA molecules 3435, and cDNA molecules 3445 therein are removed from glass slide 3425 by scraping into an Eppendorf tube. In some embodiments, semi-permeabilized tissue sample 3420 with cells 3430, RNA molecules 3435, and cDNA molecules 3445 therein are removed from glass slide 3425 by placing glass slide 3425 into a 50 mL centrifuge tube and centrifuging to collect the material in a receptacle at the bottom of the 50 mL tube.

At step 3040, biotinylated cDNA molecules 3445 are purified using two rounds of a streptavidin bead-based purification protocol.

At step 3045, cDNA molecules 3445 are amplified in a multiplex reaction using a mix of forward and reverse primer pairs that flank targeted SNVs. For example, a forward primer 3455 comprises a gene-specific region 3460 that targets a SNV (e.g., SNV 3440) of interest, an SBS primer region 3465 (e.g., SBS3), and a P5 region 3470. Gene-specific region 3460 is designed to be about 50 bp upstream of a targeted SNV. A reverse primer 3475 comprises an SBS12 complementary region 3120a and a P7 region 3480. A library amplicon 3485 synthesized using forward primer 3455 and reverse primer 3475 comprises P5 region 3470, SBS primer region 3465, SNV 3440, random primer region 3110, spatial address region 3115, SBS primer region 3120, and P7 region 3480.

At step 3050, library amplicons are sequenced. For example, read 1 (e.g., from about 50 bp to about 75 bp) of an SBS reaction provides sequence information for the targeted SNV and read 2 (about 25 bp) provides sequence information for the spatial address.

In some embodiments, a spatially addressed capture probe comprises sequences for in situ targeted capture and amplification of genomic DNA in a tissue sample. In one example, the capture and amplification of targeted genomic DNA regions is performed using a TSCA-like approach (TruSeq Custom Amplicon assembly, Illumina). In the TSCA-like approach, a pair of capture probes that flank a targeted region of interest (e.g., an SNV) is used to capture genomic DNA. FIG. 35 illustrates a schematic diagram of an example of a capture probe pair 3500 for capturing a genomic DNA region of interest. Capture probe pair 3500 comprises a first capture probe 3510 that hybridizes 5' to a region of interest and a second capture probe 3515 that hybridizes 3' to the region of interest. First capture probe 3510 comprises an SBS primer region 3520a (e.g., SBS12), a spatial address region 3525, a gene-specific region 3530a. Second capture probe 3515 comprises an SBS primer region 3520b (e.g., SBS3) and a gene-specific region 3530b.

FIG. 36 illustrates a flow diagram of an example of a method 3600 of generating a spatially addressed genomic amplicon library using releasable capture probes. In this example, the capture and amplification of targeted genomic DNA regions is performed using a TSCA-like approach (TruSeq Custom Amplicon assembly, Illumina). Method 3600 comprises, but is not limited to, the following steps.

At a step 3610, a coverslip with spatially addressed capture probes thereon is placed atop a semi-permeabilized FFPE tissue section mounted on a glass slide. In one example, the spatially addressed capture probes are suspended in a BioGel matrix that is deposited onto the surface of the coverslip. The spatially addressed capture probes are a pair of probes that include DNA sequences that flank a region of interest (e.g., a SNV) in the genomic DNA. The capture probes also include sequences for subsequent PCR amplification (e.g., SBS3 and SBS12 sequences) as described above with reference to FIG. 35. One (or both) of the capture probes can also include an internal biotin label for subsequent purification of the targeted DNA region. The capture probes are released from the BioGel matrix onto the tissue section using, for example, a heat treatment protocol.

At a step 3615, the capture probes are hybridized to genomic DNA and an in situ extension/ligation reaction is performed between the flanking capture probes across the targeted region of interest.

At a step 3620, the extension/ligation products are purified. For example, the tissue sample with extension/ligation products therein is removed from the surface of the glass slide and collected in a collection tube. The extension/ligation products are then purified using one or more rounds of a purification protocol, such as a streptavidin bead-based purification protocol.

At a step 3625, the extension/ligation products are PCR amplified to add indices and sequencing primers.

At a step 3630, library amplicons are sequenced.

FIG. 37 illustrates the steps of method 3600 of FIG. 36. At step 3610, a coverslip 3710 with spatially addressed capture probes in a BioGel matrix thereon is placed atop a semi-permeabilized FFPE tissue section 3715 mounted on a glass slide 3720. Tissue section 3715 comprises a cell 3725. Cell 3725 comprises a region of targeted genomic DNA 3730. Genomic DNA 3730 can include a SNV 3735. First capture probe 3510 and second capture probe 3515 are released into tissue section 3715 using a heat treatment protocol.

At step 3615, first capture probe 3510 and second capture probe 3515 are hybridized to genomic DNA and an in situ extension/ligation reaction is performed between the flanking capture probes across the targeted region of interest to generate an extension/ligation product 3740.

At step 3620, the extension/ligation product 3740 is purified. For example, the tissue sample with extension/ligation product 3740 therein is removed from the surface of the glass slide and collected in a collection tube 3745. Extension/ligation product 3740 is then purified using one or more rounds of a purification protocol, such as a streptavidin bead-based purification protocol.

At step 3625, extension/ligation product 3740 is PCR amplified using a forward primer 3750 and a reverse primer 3755 to add sequencing adapters. Forward primer 3750 comprises an SBS region 3520b' that is complementary to SBS primer region 3520b and a P5 region 3760. Reverse primer 3755 comprises an SBS region 3520a' that is complementary to 3520a and a P7 region 3765.

4.6 Particle-Based Capture of Nucleic Acids

In some embodiments, nucleic acids in tissue samples can be first captured by probes immobilized on particles, such as nanoparticles, and then transferred to a capture array described herein. The particle based transfer of nucleic acids can increase the efficiency, e.g., the yield or the kinetics, of the nucleic acid transfer from the tissue sample to the capture array.

Nucleic acids can be transferred from a tissue sample to a capture array by transferring particles comprising the nucleic acids from the tissue sample to the capture array. Particle transfer can be facilitated, e.g., by using magnetically responsive particles, such as magnetically responsive nanoparticles, and by applying a magnetic field to the tissue sample and the capture array to facilitate the transfer of the magnetically responsive nanoparticles from the tissue sample to the capture array. In some embodiments, particle transfer from the tissue sample to the capture array can be facilitated, e.g., by using a molecular interaction, such as a ligand-binding interaction (e.g., a streptavidin-biotin interaction). For example, particle transfer can be facilitated, e.g., by using streptavidin-coated particles, such as streptavidin-coated nanoparticles, and a biotin-coated capture array. Alternatively, any protein-protein, protein-small-molecule, or nucleic acid-nucleic acid interaction, or any specific chemical reaction (e.g., "click chemistry") can be used to facilitate rapid or complete transfer of nucleic acid comprising particles from the tissue sample to the capture array.

A variety of probes can be immobilized on the particles to capture nucleic acids from the tissue sample and combined with a variety of probes on a capture array described herein. In some embodiments, the probes on the particles consist essentially of capture regions to capture the nucleic acids from the tissue sample (besides, e.g., additional elements to immobilize the probes to the particle). In some embodiments, the probes on the particles can comprise a capture region and a spatial address region (e.g., a partial or combinatorial spatial address region, or a complete spatial address region). The probe-coated particles described herein can be used in combination, e.g., with capture arrays comprising capture sites having probes comprising essentially a cleavable region, or a cleavable region and a spatial address region (e.g., a partial or combinatorial spatial address region, or a complete spatial address region), or a cleavable region, a spatial address region and a capture region (e.g., a region to capture the nucleic acids on the particles), or any other combination of regions.

In some embodiments, magnetically responsive nanoparticles are used to capture nucleic acid (e.g., in situ synthesized cDNA) in a tissue sample for generation of a spatially addressed library.

In some embodiments, the magnetically responsive nanoparticles can comprise immobilized probes comprising essentially a capture region (e.g., a gene-specific or a universal capture region). In some embodiments, the probes can further comprise a SBS primer region (e.g., a SBS3 or SBS12 region) or other universal regions, such as P5 or P7 regions. In some embodiments the nanoparticles are used in combination with a capture array comprising capture probes comprising a cleavable region, a spatial address region, and a capture region (e.g., a gene-specific capture region). In some embodiments, the probes on the capture array further comprise a SBS primer region (e.g., a SBS 3 or SBS12 region) or other universal regions, such as P5 or P7 regions.

FIG. 38 illustrates a flow diagram of an example of a method 3800 of generating a spatially addressed sequencing library using particles, such as magnetically responsive nanoparticles, to capture nucleic acid from a tissue sample.

At a step 3810, cDNA is synthesized from target mRNA in a tissue sample by in situ reverse transcription. In some embodiments, the cDNA is a gene-specific (i.e., targeted) cDNA. In some embodiments, the cDNA is a random cDNA or a cDNA representing bulk mRNA. For example, in some embodiments, a gene-specific RT primer bound to the surface of a particle, such as a magnetically responsive nanoparticle, can be used to prime first strand cDNA synthesis in a reverse transcription reaction.

At a step 3815, first strand cDNA bound to the surface of, e.g., a magnetically responsive nanoparticle is captured onto an array. The array is, for example, a glass substrate that is printed with spatially addressed capture probes to form an array of capture sites. The spatially addressed capture probes can comprise, e.g., a cleavable polylinker sequence, a spatial address sequence, and a gene-specific capture sequence that is complementary to a sequence in the first strand cDNA. The spatially addressed capture probes can be attached to the glass substrate via the cleavable polylinker sequence. The spatial address sequence is typically a unique sequence for each spatial feature on the array. Each spatial feature can include a plurality of spatially addressed capture probes with different gene-specific capture sequences. A magnet can be placed in proximity to the array. The reaction can be heated to an incubation temperature of about 95° C. for about 1 minute to denature RNA:cDNA hybrids. In the proximity of the magnet, first strand cDNA bound to the surface of a magnetically responsive nanoparticle can be anchored onto the surface of the array. First strand cDNA molecules can be captured onto the array by hybridization (e.g., at about 60° C. for about 10 minutes) to the gene-specific capture sequences in the spatially addressed capture probes.

At a step 3820, second strand cDNA can be synthesized. For example, the magnet is removed from the proximity of the array and first strand cDNA molecules that are not hybridized to gene-specific capture sequences in the spatially addressed capture probes can be removed by washing. Second strand cDNA is synthesized in an extension reaction using the second gene-specific capture sequence as a primer.

At a step 3825, the double-stranded cDNA can be released from the capture array by cleavage of the cleavable polylinker sequence.

At a step 3830, double-stranded cDNA can optionally be end repaired and ligated to sequencing adapters to generate a sequencing library. In embodiments where the RT primer and the capture primer on the capture array comprise SBS primer regions, end repair.

FIG. 39 illustrates the steps of an exemplary method 3800 of FIG. 38. Namely, a tissue section (not shown) comprises a target RNA molecule 3910. Target RNA molecule 3910 can include a mutation 3915. At step 3810, cDNA is synthesized in situ using a gene-specific RT primer 3920 in a reverse transcription reaction. RT primer 3920 is attached to the surface of a magnetically responsive nanoparticle 3925. A cDNA molecule 3930 synthesized using RT primer 3920 is attached to magnetically responsive nanoparticle 3925.

At step 3815, cDNA molecules 3930 are captured onto an array that comprises a plurality of capture sites 3935. In this example, a single capture site 3935 is shown. Capture site 3935 comprises a spatially addressed capture probe 3940. Spatially addressed capture probe 3940 comprises a cleavable polylinker region 3945, a spatial address region 3950, and a gene-specific capture region 3955 that is complementary to a sequence in the first strand cDNA. Spatially addressed capture probe 3940 is attached to capture site 3935 via cleavable polylinker region 3945. A magnet 3960 is placed in proximity to capture site 3935. The reaction is heated to an incubation temperature of about 95° C. for about 1 minute to denature RNA:cDNA hybrids. In the proximity of magnet 3960, first strand cDNA molecules 3930 bound to the surface of magnetically responsive nanoparticle 3925 are anchored onto the surface capture site 3935. First strand cDNA molecules 3930 are captured onto the capture site 3935 by hybridization (e.g., at about 60° C. for about 10 minutes) to gene-specific capture region 3955 in spatially addressed capture probe 3940.

At step 3820, second strand cDNA is synthesized. For example, magnet 3960 is removed from the proximity of capture site 3935 and first strand cDNA molecules 3930 that are not hybridized to gene-specific capture sequence 3955 in spatially addressed capture probe 3940 are removed by washing. Second strand cDNA is synthesized in an extension reaction using gene-specific capture region 3955 as a primer.

At step 3825, a double-stranded cDNA molecule 3965 that now comprises spatial address region 3950 is released from capture site 3935 by cleavage of cleavable polylinker region 3945.

At step 3830 (not shown in FIG. 39), double-stranded cDNA molecule 3965 is optionally end repaired and ligated to sequencing adapters to generate a spatially addressed sequencing library.

In some embodiments, the RT primer and the capture primer on the capture array can optionally and independently comprise additional regions, such as SBS primer regions (e.g., SBS3 or SBS12 regions) or universal regions (e.g., P5 or P7 regions) that can, e.g., be incorporated into the double stranded cDNA molecule 3965.

In another aspect, provided herein is a method for spatial detection and analysis of nucleic acids in a tissue sample, comprising providing a magnetically responsive nanoparticle (e.g., 3925) comprising an immobilized capture probe comprising a capture region (e.g., 3920).

In some embodiments, the capture region is a gene-specific capture region (comprising, e.g., a TSCA sequence). In some embodiments, the capture region is a universal capture region (comprising, e.g., a poly-T sequence or a randomized nucleic acid sequence).

In some embodiments, the immobilized capture probe does not include a spatial addressing region.

In some embodiments, the method further comprises contacting the magnetically responsive nanoparticle with a tissue sample, such that the position of the magnetically responsive nanoparticle on the tissue sample can be correlated with the position of a nucleic acid in the tissue sample, and allowing the nucleic acid to hybridize to the capture region of the immobilized capture probe.

In some embodiments, the method further comprises extending the capture region of the immobilized capture probe to form an immobilized first complementary strand of the nucleic acid hybridized to the capture region (e.g., 3930).

In some embodiments, the method further comprises contacting the tissue sample with a capture array, such that the position of a capture site on the capture array can be correlated with a position in the tissue sample, wherein the capture array comprises a capture site (e.g., 3935) comprising a capture probe immobilized on a surface (e.g., 3940), wherein the capture probe comprises a cleavable region (e.g., 3945), a spatial address region (e.g., 3950) and a gene-specific region (e.g., 3955).

In some embodiments, the method further comprises applying a magnetic field to the capture array and tissue sample to transfer the magnetically responsive nanoparticle with the immobilized first complementary strand to the capture array and allowing the immobilized first complementary strand to hybridize to the capture region of the capture probe on the capture array.

In some embodiments, the method further comprises extending the capture region of the capture probe on the capture array to form an immobilized second complementary strand of the nucleic acid (e.g., newly synthesized strand of 3965).

In some embodiments, the method further comprises cleaving the capture probe on the capture array at the cleavable domain to release a spatially tagged second complementary strand from the surface of the capture array.

In some embodiments, the method further comprises, analyzing the sequence of the released spatially tagged second complementary strand.

In some embodiments, the method further comprises correlating the sequence of the released spatially tagged second complementary stand to the position of the nucleic acid in the tissue sample.

In some embodiments, particle (e.g., nanoparticle) associated probes can be hybridized to a nucleic acid from a tissue sample prior to immobilizing the probe to the nanoparticle and the probe-nucleic acid hybrid can then be immobilized to the nanoparticle. In some embodiments, a probe hybridized to a nucleic acid from the tissue sample can be extended to form a nucleic acid complementary to the nucleic acid from the tissue sample, and the complementary nucleic acid can then be immobilized to the nanoparticle. In some embodiments, the probes can comprise a linker element for linking a probe-nucleic acid hybrid or a complementary nucleic acid to the nanoparticle.

FIGS. 40A and 40B illustrate an example of a process 4000 of using a capture probe to form a complementary nucleic acid in a tissue sample and subsequently immobilizing the complementary nucleic acid to a nanoparticle.

In a first step and referring now to FIG. 40A, a capture probe 4010 is hybridized to a nucleic acid 4015 from a tissue sample. Capture probe 4010 includes a capture region 4015 and a linker element 4020. In one example capture region 4015 comprises a random primer sequence. In another example, capture region 4015 comprises a gene-specific primer sequence. Linker element 4020 is an element for linking a probe-nucleic acid hybrid or complementary nucleic acid to a nanoparticle. In one example, nucleic acid molecule 4025 is a genomic DNA molecule. In another example, nucleic acid molecule 4025 is an RNA molecule. Capture probe 4010 hybridizes to nucleic acid molecule 4025 from a tissue sample and is extended to form a complementary nucleic acid molecule 4025a.

In a next step and referring now to FIG. 40B, complementary nucleic acid 4025a is immobilized to a nanoparticle 4030 via linker element 4020 in capture probe 4010. In one example, nanoparticle 4030 is a magnetically responsive nanoparticle.

In another aspect, provided herein is a method for spatial detection and analysis of nucleic acids in a tissue sample, comprising providing a primer comprising a capture region and a linker element (e.g., a biotin group, a thiol, group, or another chemical linker).

In some embodiments, the capture region is a gene-specific capture region (comprising, e.g., a TSCA sequence). In some embodiments, the capture region is a universal capture region (comprising, e.g., a poly-T sequence or a randomized nucleic acid sequence).

In some embodiments, the method further comprises contacting a tissue sample with the primer and allowing the primer to hybridize to a nucleic acid from the tissue sample.

In some embodiments, the method further comprises extending the primer to form an immobilized first complementary strand of the nucleic acid hybridized to the primer.

In some embodiments, the method further comprises contacting the tissue sample with a magnetically responsive nanoparticle (e.g., a streptavidin coated magnetically responsive nanoparticle), such that the position of the magnetically responsive nanoparticle on the tissue sample can be correlated with the position of the extended primer in the tissue sample, and immobilizing the extended primer comprising the first immobilized strand of the nucleic acid to the magnetically responsive nanoparticle at the linker element.

In some embodiments, the method further comprises contacting the tissue sample with a capture array such that the position of a capture site on the capture array can be correlated with a position in the tissue sample, wherein the capture array comprises a capture site comprising a capture probe immobilized on a surface, wherein the capture probe comprises a cleavable region, a spatial address region and a gene-specific region.

In some embodiments, the method further comprises applying a magnetic field to the capture array and the tissue sample to transfer the magnetically responsive nanoparticle with the immobilized first complementary strand to the capture array and allowing the immobilized first complementary strand to hybridize to the gene-specific region of the capture probe on the capture array.

In some embodiments, the method further comprises extending the gene-specific region of the capture probe on the capture array to form an immobilized second complementary strand of the nucleic acid.

In some embodiments, the method further comprises cleaving the capture probe on the capture array to release a spatially tagged second complementary strand from the surface of the capture array.

In some embodiments, the method further comprises, analyzing the sequence of the released spatially tagged second complementary strand.

In some embodiments, the method further comprises correlating the sequence of the released spatially tagged second complementary stand to the position of the nucleic acid in the tissue sample In some embodiments, a particle (e.g., a magnetically responsive nanoparticle) can comprise an immobilized probe comprising a capture region (e.g., a gene-specific or a universal capture region) and a first partial address region. In some embodiments, the particle associated probe can further comprise a SBS primer region (e.g., a SBS3 or SBS12 region) or another universal region, such as a P5 or P7 region. In some embodiments the particles can be used in combination with a capture array comprising a capture probe comprising a cleavable region, a second spatial address region, and a capture region (e.g., a gene-specific capture region). In some embodiments, the probe on the capture array can further comprise an SBS primer region (e.g., an SBS 3 or SBS12 region) or another universal region, such as a P5 or P7 region.

FIGS. 41A and 41B illustrate schematic diagrams of an example of a particle-associated capture probe comprising a first partial spatial address region and a second array capture probe comprising a second partial address region, respectively, for spatial detection and analysis of nucleic acids in a tissue sample. Referring now to FIG. 41A, a particle-associated capture probe 4110 comprises a capture region 4115 (e.g., a gene-specific or a universal capture region) and a first partial address region 4120 immobilized on a particle 4125. In one example, particle 4125 is a magnetically responsive nanoparticle. Capture probe 4110 hybridizes to a nucleic acid molecule 4130 from a tissue section and is extended (indicated by the arrow) to form a nucleic acid complementary to nucleic acid molecule 4130. The complementary nucleic acid comprises first partial address region 4120 and particle 4125. First partial address region 4120 identifies the position of a capture site along a first dimension of a capture array. In some embodiments, a magnetic field is used to facilitate transfer of the complementary nucleic acid molecule comprising particle 4125 onto an array comprising an array capture probe.

Referring now to FIG. 41B, an array capture probe 4135 comprises a capture region 4140 (e.g., a gene-specific capture region), a second partial address region 4145, and SBS region 4150, and a cleavable region 4155. Array capture probe 4135 can be immobilized on the surface of a capture array (not shown) via cleavable region 4155. Array capture probe 4135 on a capture array (not shown) can be contacted with a tissue sample comprising nucleic acid molecules labeled with first partial address region 4120 of FIG. 41A such that the position of array capture probe 4135 can be correlated with a position in the tissue sample. Second partial address region 4145 identifies the position of a capture site along a second dimension of a capture array.

In another aspect, provided herein is a method for spatial detection and analysis of nucleic acids in a tissue sample, comprising providing a magnetically responsive nanoparticle comprising an immobilized capture probe comprising a capture region and a first partial spatial address region.

In some embodiments, the capture region is a gene-specific capture region (comprising, e.g., a TSCA sequence). In some embodiments, the capture region is a universal capture region (comprising, e.g., a poly-T sequence or a randomized nucleic acid sequence).

In some embodiments, the first partial spatial address region identifies the position of a capture site along a first dimension of a capture array.

In some embodiments, the method further comprises contacting the magnetically responsive nanoparticle with a tissue sample, such that the position of the magnetically responsive nanoparticle on the tissue sample can be correlated with the position of a nucleic acid in the tissue sample, and allowing the nucleic acid to hybridize to the capture region of the immobilized capture probe.

In some embodiments, the method further comprises extending the capture region of the immobilized capture probe to form an immobilized first complementary strand of the nucleic acid hybridized to the capture region, wherein the immobilized first complementary strand comprises the first partial address region.

In some embodiments, the method further comprises contacting the tissue sample with a capture array such that the position of a capture site on the capture array can be correlated with a position in the tissue sample, wherein the capture array comprises a capture site comprising a capture probe immobilized on a surface, wherein the capture probe comprises a cleavable region, a second partial address region and a gene-specific region.

In some embodiments, the second partial spatial address region identifies the position of a capture site along a second dimension of a capture array.

In some embodiments, the method further comprises applying a magnetic field to the capture array and tissue sample to transfer the magnetically responsive nanoparticle with the immobilized first complementary strand to the capture site of a capture array and allowing the immobilized first complementary strand to hybridize to the capture region of the capture probe on the capture site of the capture array.

In some embodiments, the method further comprises extending the capture region of the capture probe on the capture site to form an immobilized second complementary strand of the nucleic acid, wherein the second complementary strand of the nucleic acid comprises the first and second partial spatial address regions.

In some embodiment, the combination of the first and second partial spatial address region defines the position of the capture site on the capture array.

In some embodiments, the method further comprises cleaving the capture probe on the capture array at the cleavable domain to release a spatially tagged second complementary strand from the surface of the capture array.

In some embodiments, the method further comprises, analyzing the sequence of the released spatially tagged second complementary strand.

In some embodiments, the method further comprises correlating the sequence of the released spatially tagged second complementary stand to the position of the nucleic acid in the tissue sample.

In another aspect, provided herein is a method for spatial detection and analysis of nucleic acids in a tissue sample, comprising providing a magnetically responsive nanoparticle comprising an immobilized capture probe comprising a capture region.

In some embodiments, the immobilized capture probe does not comprise a spatial address region.

In some embodiments, the capture region is a gene-specific capture region (comprising, e.g., a TSCA sequence). In some embodiments, the capture region is a universal capture region (comprising, e.g., a poly-T sequence or a randomized nucleic acid sequence).

In some embodiments, the method further comprises contacting the magnetically responsive nanoparticle with a tissue sample, such that the position of the magnetically responsive nanoparticle on the tissue sample can be correlated with the position of a nucleic acid in the tissue sample, and allowing the nucleic acid to hybridize to the capture region of the immobilized capture probe.

In some embodiments, the method further comprises extending the capture region of the immobilized capture probe to form an immobilized first complementary strand of the nucleic acid hybridized to the capture region.

In some embodiments, the immobilized first complementary strand does not comprise a spatial address region.

In some embodiments, the method further comprises contacting the tissue sample with a capture array such that the position of a capture site on the capture array can be correlated with a position in the tissue sample, wherein the capture array comprises a capture site comprising a probe immobilized on a surface, wherein the probe comprises a spatial address region.

In some embodiments, the probe does not comprise a capture region.

In some embodiments, the method further comprises applying a magnetic field to the capture array and tissue sample to transfer the magnetically responsive nanoparticle with the immobilized first complementary strand to the capture site of a capture array and ligating the immobilized first complementary strand to the spatial address region of the probe on the capture array to immobilize the first complementary strand on both ends on the capture array and on the magnetically responsive nanoparticle.

FIGS. 42A and 42B illustrate schematic diagrams of an example of a particle-associated capture probe and a second array capture probe comprising a spatial address region, respectively, for spatial detection and analysis of nucleic acids in a tissue sample. Referring now to FIG. 42A, a particle-associated capture probe 4210 comprises a capture region 4215 (e.g., a gene-specific or a universal capture region) immobilized on a magnetically responsive nanoparticle 4220. Capture probe 4210 hybridizes to a nucleic acid molecule 4225 from a tissue section and is extended (indicated by the arrow) to form a nucleic acid complementary to nucleic acid molecule 4225. The complementary nucleic acid comprises magnetically responsive nanoparticle 4220. In some embodiments, a magnetic field is used to facilitate the transfer of the complementary nucleic acid molecule comprising magnetically responsive nanoparticle 4220 onto an array comprising an array capture probe.

Referring now to FIG. 42B, an array capture probe 4230 comprises a spatial address region 4235 a cleavable region 4240. Array capture probe 4230 can be immobilized on the surface of a capture array (not shown) via cleavable region 4240. Array capture probe 4230 on a capture array surface (not shown) can be contacted with a tissue sample comprising the complementary nucleic acid molecules tagged with magnetically responsive nanoparticle 4220 of FIG. 42A such that the position of array capture probe 4230 can be correlated with a position in the tissue sample. The complementary nucleic acids comprising magnetically responsive nanoparticle 4220 can be captured on to capture probe 4230 by ligation to spatial address region 4235. Spatial address region 4240 identifies the position of a capture site on the array.

In some embodiments, the first complementary strand comprises a spatial address region when immobilized on both ends on the capture array and on the magnetically responsive nanoparticle.

In some embodiments, the immobilized capture probe on the magnetically responsive nanoparticle and the spatial address region optionally each further comprise a primer binding region (e.g., a SBS primer binding region, such as a SBS3 or SBS12 region). In some embodiments, the method further comprises synthesizing a second complementary strand using a primer pair complementary to the primer binding regions in the first complementary strand, wherein the second complementary strand comprises the spatial address region, and releasing the second complementary strand from the surface of the capture array. In some embodiments, the method further comprises analyzing the sequence of the released second complementary strand and correlating the sequence of the released second complementary stand to the position of the nucleic acid in the tissue sample.

In some embodiments, the immobilized capture probe on the magnetically responsive nanoparticle and the spatial address region optionally each further comprise a cleavable region (e.g., the same cleavable region or different cleavable regions). In some embodiments, the method further comprises releasing the immobilized first complementary strand by cleaving the cleavable regions in the immobilized first complementary strand. In some embodiments, the method further comprises analyzing the sequence of the released first complementary strand and correlating the sequence of the released second complementary stand to the position of the nucleic acid in the tissue sample.

In some embodiments, a particle (e.g., a magnetically responsive nanoparticle) can comprise an immobilized probe comprising a capture region (e.g., a gene-specific or a universal capture region), a first primer binding region (e.g., an SBS primer region, such as an SBS3 or SBS12 region) and a spatial address region. In some embodiments, the particle associated probe can further comprise another universal region, such as a P5 or P7 region. In some embodiments the particles can be used in combination with a capture array comprising a capture probe comprising essentially a second primer binding region (e.g., an SBS primer region, such as an SBS 3 or SBS12 region) and, optionally another universal region, such as a P5 or P7 region.

FIGS. 43A and 43B illustrate schematic diagrams of an example of a particle-associated capture probe and a second array capture probe, respectively, for spatial detection and analysis of nucleic acids from a tissue sample. Referring now to FIG. 43A, a particle-associated capture probe 4310 comprises a capture region 4315 (e.g., a gene-specific or a universal capture region), a spatial address region 4320, and a first primer binding site 4325 (e.g., an SBS primer region SBS3) immobilized on a magnetically responsive nanoparticle 4330. Capture probe 4310 can be contacted with a tissue sample (not shown), such that the position of capture probe 4310 on the tissue sample can be correlated with the position of a nucleic acid molecule 4335 in the tissue sample. Capture probe 4310 hybridizes to nucleic acid molecule 4335 from the tissue section and is extended (indicated by the arrow) to form a nucleic acid complementary to nucleic acid molecule 4335. The complementary nucleic acid (not shown) comprises spatial address region 4320, first primer binding site 4325, and magnetically responsive nanoparticle 4330. In some embodiments, a magnetic field generated by a magnet (not shown) is used to facilitate the transfer of the complementary nucleic acid molecule comprising magnetically responsive nanoparticle 4330 onto an array comprising an array capture probe.

Referring now to FIG. 43B, an array capture probe 4340 comprises a second primer binding site 4325a (e.g., an SBS primer region SBS12) that is different from first primer binding site 4325 of FIG. 43A. Array capture probe 4340 can be immobilized on the surface of a capture array (not shown). Array capture probe 4340 on a capture array surface (not shown) can be contacted with a tissue sample comprising the complementary nucleic acid molecules tagged with magnetically responsive nanoparticle 4330 of FIG. 43A. The complementary nucleic acid comprising magnetically responsive nanoparticle 4330 can be captured onto capture probe 4340 by ligation to second primer binding site 4325a.

In another aspect, provided herein is a method for spatial detection and analysis of nucleic acids in a tissue sample, comprising providing a magnetically responsive nanoparticle comprising an immobilized capture probe comprising a capture region, a first primer binding region and a spatial address region.

In some embodiments, the capture region is a gene-specific capture region (comprising, e.g., a TSCA sequence). In some embodiments, the capture region is a universal capture region (comprising, e.g., a poly-T sequence or a randomized nucleic acid sequence).

In some embodiments, the method further comprises contacting the magnetically responsive nanoparticle with a tissue sample, such that the position of the magnetically responsive nanoparticle on the tissue sample can be correlated with the position of a nucleic acid in the tissue sample, and allowing the nucleic acid to hybridize to the capture region of the immobilized capture probe.

In some embodiments, the method further comprises extending the capture region of the immobilized capture probe to form an immobilized first complementary strand of the nucleic acid hybridized to the capture region, wherein the immobilized first complementary strand comprises the spatial address region.

In some embodiments, the method further comprises contacting the tissue sample with a capture array such that the position of a capture site on the capture array can be correlated with a position in the tissue sample, wherein the capture array comprises a capture site comprising a capture probe immobilized on a surface, wherein the capture probe comprises essentially a second primer binding region (e.g., an SBS primer region, such as an SBS3 or SBS12 region).

In some embodiments, the method further comprises applying a magnetic field to the capture array and tissue sample to transfer the magnetically responsive nanoparticle with the immobilized first complementary strand to the capture site of a capture array and ligating the immobilized first complementary strand to the capture probe on the capture site of the capture array to immobilize the first complementary strand at both ends.

In some embodiments, the method further comprises synthesizing a second complementary strand using a primer complementary to the first primer binding sequence of the first capture probe and releasing the second complementary strand from the surface of the capture array.

In some embodiments, the method further comprises analyzing the sequence of the released second complementary strand and correlating the sequence of the released second complementary stand to the position of the nucleic acid in the tissue sample.

FIG. 44 illustrates a perspective view of a magnetic-based transfer system 4400 that is configured for spatial detection and analysis of nucleic acid in a tissue sample. Magnetic-based transfer system 4400 includes capture array 4410. Capture array 4410 includes a solid support 4415. In one example, solid support 4415 is a planar glass substrate. Printed on the surface of solid support 4415 are a plurality of distinct capture sites ("spatial features") 4420, which are regions containing spatially addressed oligonucleotides. An example of a single capture site 4420 is described in more detail with reference to FIG. 45. Overlaid on capture array 4410 is a sample substrate 4425. In one example, sample substrate 4425 is a glass slide. A tissue sample 4430 is mounted on the surface of sample substrate 4425 that is facing capture sites 4420 on capture array 4410. In one example, tissue section 4430 is an FFPE tissue section. Nucleic acid (not shown) in tissue sample 4430 is tagged with a magnetically responsive nanoparticle. Positioned below and in proximity to capture array 4410 is a magnet 4435. Magnet 4435 may be a permanent magnet or an electromagnet. In one example, magnet 4435 is a movable magnet. Namely, magnet 4435 may be moved in proximity to or away from capture array 4410. A magnetic field generated by magnet 4435 is used to attract the nanoparticle-tagged nucleic acid molecules (not shown) from tissue section 4430 onto capture sites 4420 on capture array 4410. The magnetic field generated by magnet 4435 is configured such that transfer of nucleic acids from the tissue sample and loss of nucleic acids between capture sites 4420 is eliminated or substantially reduced.

In another embodiment (not shown), capture sites 4420 are microwells in solid support 4415. Printed on the bottom surface of each microwell are the spatially addressed oligonucleotides. In the presence of a magnetic field, the microwells function to trap the nanoparticle-tagged nucleic acid and eliminate or substantially reduce aggregation of the magnetically responsive nanoparticles.

FIG. 45 illustrates a side view of one capture site 4420 on capture array 4410, wherein the one capture site 4420 includes a plurality of capture probes. In one example, a plurality of capture probes 4510 includes an SBS primer sequence 4515 (e.g., SBS3) and a spatial address sequence 4520. In another example (not shown), capture 4510 includes a P7 sequence, an SBS primer sequence (e.g., SBS12), and a spatial address sequence as described in more detail with reference to FIG. 49A. Each capture probe 4510 immobilized at a single capture site 4420 includes the same unique spatial address sequence 4520 (e.g., spatial address sequence 4520*a*). For example, in FIG. 45, both capture probe 4510*a* and capture probe 4510*b* have the same unique spatial address sequence 4520*a*. Other capture sites 4420 (not shown) each include their own unique spatial address sequence 4520 (e.g., spatial address sequences 4520*b*, 4520*c*, 4520*d*, 4520*e*, and so on). Accordingly, capture probes 4510 immobilized at other capture sites 4420 each include their own unique spatial address sequence 4520. SBS primer sequence 4515 is used in subsequent processing steps for library preparation.

FIG. 46 illustrates a flow diagram of an example of a method 4600 of transferring cDNA from a tissue sample to a capture array for generation of a spatially addressed sequencing library using magnetic-based transfer system 4100 of FIG. 44 and FIG. 45. Method 4600 includes, but is not limited to, the following steps.

At a step 4610, first strand cDNA is synthesized in situ from RNA in a tissue sample in a reverse transcription (RT) reaction. For example, an RT primer bound to the surface of a magnetically responsive nanoparticle is used to prime first strand cDNA from mRNA in tissue sample 4430 mounted on sample substrate 4425. In one example, the RT primer includes a gene-specific primer sequence and an SBS primer sequence (e.g., SBS3). In another example, the RT primer includes random primer sequences and an SBS primer sequence (e.g., SBS3). Because the RT primer is bound to the surface of a magnetically responsive nanoparticle, first strand cDNA is tagged with the magnetically responsive nanoparticle.

At a step 4615, first strand cDNA is transferred onto a spatially addressed capture array using a magnetic field. For example, sample substrate 4425 with tissue sample 4430 thereon is placed atop capture array 4410. Magnet 4435 is positioned in close proximity to capture array 4410. The magnetic field generated by magnet 4435 is used to attract the nanoparticle-tagged first strand cDNA from tissue section 4430 onto capture sites 4420 on capture array 4410. Accordingly, first strand cDNA is immobilized at capture sites 4420 by magnet 4435.

At a step 4620, first strand cDNA is covalently linked to capture probes 4510 by single-strand ligation of the 3' end of the cDNA to spatial address sequence 4520.

At a step 4625, magnet 4435 is moved away from capture array 4410 such that capture array 4410 is no longer within the magnetic field of magnet 4435. As the magnetic field at capture array 4410 diminishes, the 5' end of the first strand cDNA molecule is released from capture site 4420. The first strand cDNA is now anchored at capture site 4420 via capture probe 4510.

At a step 4630, second strand cDNA is synthesized using a primer that is complementary to SBS primer sequence 4515 on capture probes 4510.

At a step 4635, the second strand cDNA is released from capture site 4420. In one example, the second strand cDNA is released from capture site 4420 using a heat denaturation protocol. In another example, the second strand cDNA is released using a chemical (e.g., NaOH) denaturation protocol.

At a step 4640, the second strand cDNA is amplified to generate a sequencing library.

FIGS. 47A, 47B, and 47C show pictorially the steps of method 4600 of FIG. 46. Namely, a tissue section (not shown) includes an RNA molecule 4710. RNA molecule 4710 may include a mutation 4715. At step 4610, first strand cDNA is synthesized in situ using an RT primer 4720. RT primer 4720 includes a random primer sequence 4725 and an SBS primer sequence 4730 (e.g., SBS3). RT primer 4720 is bound to the surface of a magnetically responsive nanoparticle 4735. A first strand cDNA molecule 4740 synthesized using RT primer 4720 includes SBS primer sequence 4730 and magnetically responsive nanoparticle 4735.

At step 4615, first strand cDNA molecules 4740 are transferred from the tissue section (not shown) onto capture site 4420. Magnet 4435 is positioned in close proximity to capture array 4410. The magnetic field generated by magnet 4435 is used to attract nanoparticle-tagged first strand cDNA molecules 4740 from the tissue section (not shown) onto capture site 4420. Accordingly, first strand cDNA molecules 4740 are immobilized at capture sites 4420 by magnet 4435.

At step 4620, first strand cDNA molecules 4740 are covalently linked to capture probes 4510 by single-strand ligation of cDNA molecules 4740 to spatial address sequences 4520.

At step 4625, magnet 4435 is moved away from capture array 4410 such that capture array 4410 is no longer within the magnetic field of magnet 4435. As the magnetic field at capture array 4410 diminishes, the 5' end of first strand cDNA molecules 4740 are released from capture site 4420. First strand cDNA molecules 4740 are now anchored at capture site 4420 via capture probe 4510.

At step 4630, a second strand cDNA molecule 4745 is synthesized using a primer 4515*a* that is complementary to SBS primer sequence 4515 on capture probes 4510.

At step 4635, second strand cDNA molecule 4745 is released from capture site 4420. Second strand cDNA molecule 4745 includes SBS primer sequence 4730 (e.g., SBS3), mutation 4715, spatial address sequence 4520, and SBS primer sequence 4515 (e.g., SBS12).

At step 4640, second strand cDNA molecule 4745 is amplified using a first SBS primer 4750 and a second primer 4755 to generate a sequencing library. First SBS primer 4750 includes an SBS complementary sequence 4730*a* that is complementary to SBS primer sequence 4730 and a P5 sequence 4760. Second SBS primer 4755 includes an SBS complementary sequence 4515*a* that is complementary to SBS primer sequence 4515 and a P7 sequence 4765. A library amplicon 4770 synthesized using SBS primers 4750 and 4755 includes P5 sequence 4760, SBS primer sequence 4730 (e.g., SBS3), mutation 4715, spatial address sequence 4520, SBS primer sequence 4515 (e.g., SBS12), and P7 sequence 4765.

In another embodiment, RNA in a tissue sample (e.g., an FFPE tissue sample) is tagged in situ with magnetically responsive nanoparticles and subsequently transferred to a capture array for generation of a spatially addressed cDNA library.

FIG. 48 illustrates a flow diagram of an example of a method 4800 of transferring RNA from a tissue sample to a capture array for generation of a spatially addressed sequencing library using magnetic-based transfer system 4400 of FIG. 44. Method 4800 includes, but is not limited to, the following steps.

At a step 4810, RNA in a tissue sample is tagged with magnetically responsive nanoparticles. For example, an SBS primer oligonucleotide bound to the surface of a magnetically responsive nanoparticle is ligated to the RNA in a tissue sample. The 3' end of the RNA molecules are then modified (i.e., blocked) to prevent unwanted ligation in a subsequent processing step.

At a step 4815, the tagged RNA is transferred onto capture site 4420 using a magnetic field as described above for cDNA in step 4615 of method 4600 of FIG. 46.

At a step 4820, first strand cDNA is synthesized from the transferred RNA in a RT reaction. For example, an RT primer that includes a gene-specific primer sequence and a ligation oligonucleotide is used to prime the first strand cDNA. In another example, an RT primer that includes random primer sequences and a ligation oligonucleotide is used to prime the first strand cDNA.

At a step 4825, the first strand cDNA is covalently linked to capture probes on capture site 4420 by single-strand ligation. The capture probes are described in more detail with reference to FIG. 49A.

At a step 4830, the RNA template used to generate the cDNA is released from capture site 4420. For example, magnet 4435 is moved away from capture array 4410. Thereby diminishing the magnetic field at capture site 4420 and releasing the magnetically responsive nanoparticle from the surface capture sites 4420. RNA:cDNA duplexes are dissociated using a heat treatment protocol. The first strand cDNA is anchored at capture site 4420 via ligation to the capture probes.

At a step 4835, second strand cDNA is synthesized in an extension reaction. For example, a primer that includes a sequence that is complementary to the SBS primer sequence in the cDNA and a P5 sequence is used to primer the second strand cDNA synthesis.

At a step 4840, cDNA library molecules are released from capture site 4420 by denaturation.

FIGS. 49A, 49B, and 49C show pictorially the steps of method 4800 of FIG. 48. Namely, a tissue section (not shown) includes an RNA molecule 4910. RNA molecule 4910 may include a mutation 4915. At step 4810, an SBS primer oligonucleotide 4920 bound to the surface of a magnetically responsive nanoparticle 4925 is ligated in situ to RNA molecule 4910. The 3' end of RNA molecule 4910 is then modified (i.e., blocked) to prevent unwanted ligation in a subsequent processing step.

At step 4815, RNA molecule 4910 with magnetically responsive nanoparticle 4925 thereon is transferred from the tissue section (not shown) onto capture site 4420 using a magnetic field as described above for cDNA in step 4615 of method 4600 of FIG. 46. In this example, capture site 4420 includes a capture probe 4935. Capture probe 4935 includes a P7 sequence 4940, an SBS primer sequence 4945 (e.g., SBS12), and a spatial address sequence 4950.

At step 4820, cDNA is synthesized from RNA molecule 4910 in a RT reaction. For example, an RT primer 4955 that includes a gene-specific primer sequence 4960 and a ligation oligonucleotide 4965 is used to prime first strand cDNA.

At step 4825, a cDNA molecule 4970 that includes SBS primer sequence 4920 (e.g., SBS3) and ligation oligonucleotide 4965 is covalently linked to capture probe 4935 by single-strand ligation of ligation oligonucleotide 4965 to spatial address sequence 4950.

At step 4830, RNA molecule 4910 is released from capture site 4420. For example, magnet 4435 is moved away from capture site 4420. Thereby diminishing the magnetic field at capture site 4420 and releasing magnetically responsive nanoparticle 4925 bound to RNA molecule 4910 from the surface capture site 4420. The RNA:cDNA duplex (i.e., RNA molecule 4910:cDNA molecule 4970 duplex) is then dissociated using a heat treatment protocol. cDNA molecule 4970 is now anchored at capture site 4420 by capture probe 4935.

At step 4835, cDNA molecule 4970 is copied in an extension reaction. For example, a primer 4975 that includes a sequence 4920a that is complementary to SBS primer sequence 4920 (e.g., SBS3) and a P5 sequence 4980 is used to primer second strand cDNA synthesis. cDNA molecule 4970 now includes P7 sequence 4940, SBS primer sequence 4945 (e.g., SBS12), spatial address sequence 4950, ligation oligonucleotide 4965, mutation 4915, SBS primer sequence 4920 (e.g., SBS3), and P5 sequence 4980.

At step 4840, a cDNA molecule 4970 is released from capture site 4420 by denaturation (e.g., heat or chemical denaturation). cDNA molecule 4970 is now ready for sequencing.

4.7 Spatial Tissue Profiling Based on DNA

The disclosed techniques provide methods of spatial detection and analysis (e.g., mutational analysis or single nucleotide variation (SNV) detection) of genomic DNA in a tissue sample. In one example, the tissue sample is an FFPE tissue sample. Spatial detection and analysis of the DNA in a tissue sample (e.g., an FFPE sample) has several advantages compared to spatial detection and analysis of RNA in a tissue sample: (1) DNA is more stable than RNA; (2) DNA fragments in an FFPE tissue sample are longer (e.g., 300-400 bp) compared to RNA fragments in an FFPE tissue sample (e.g., 100-200 bp); (3) RNA molecules expressed at a relatively low level may be undetectable; and (4) changes in tumor suppressor genes are detected in DNA while they are not detected in RNA.

A disadvantage of using DNA for spatial tissue profiling is that for most genes there may be only 2 copies of a gene per cell. The methods disclosed herein include an initial in situ whole genome pre-amplification step that is used to increase gene copy number prior performing other biochemical process steps.

FIG. 50 illustrates a flow diagram of an example of a method 5000 of profiling genomic DNA in a tissue sample. In one example, method 5000 is used for profiling SNVs of interest in genomic DNA. Method 5000 includes, but is not limited to, the following steps.

At a step 5010, a glass substrate is printed with spatially addressed PCR primers to form an array of spatial features. In one example, the spatially addressed PCR primers are printed on a 2 cm×2 cm coverslip to form an array of spatial features that are 100 µm in diameter on a pitch of 35 µm. In another example, the spatially addressed PCR primers are printed in microwells fabricated on the surface of a glass slide. The spatially addressed PCR primers are printed on a coverslip or glass slide using, for example, commercially available printing technologies. The spatially addressed PCR primers include a random primer sequence, a spatial address sequence, an SBS primer sequence and a biotin label as described in more detail with reference to FIG. 51. The spatially addressed PCR primers may also include a modification at the 5' end of the molecule for reversible attachment to the coverslip. In one example, the spatially addressed PCR primers may include a 5' disulfide modification as described for spatially addressed capture probe 3100 of process 3200 of FIGS. 32A, 32B, and 32C. In another example, the spatially addressed PCR primers may include a 5' photocleavable linker as described for spatially addressed capture probe 3100 of process 3300 of FIGS. 33A, 33B, and 33C.

At a step 5015, a PCR master mix solution is dispensed onto the surface of a semi-permeabilized FFPE tissue section mounted on a glass slide. The PCR master mix solution includes, for example, dNTPs, DNA polymerase, $MgCl_2$, and reaction buffers.

At a step 5020, the glass substrate with spatially addressed PCR primers thereon is placed atop the semi-permeabilized FFPE tissue section, such that the surface of the glass substrate with the spatially addressed PCR primers thereon is in contact with the tissue section. The spatially addressed PCR primers are released from the surface of the glass substrate into the cellular space of the tissue section.

At a step 5025, genomic DNA is amplified by in situ isothermal amplification. In one example, the amplification reaction is a recombinase polymerase amplification (RPA) reaction. Table 1 below shows other examples of isothermal DNA amplification methods that may be used to amplify the genomic DNA. In another example, a conventional PCR-based whole genome amplification reaction is used to amplify the genomic DNA. In one example, the conventional PCR-based method is improved primer extension pre-amplification PCR (iPEP PCR). In another example, the conventional PCR-based method is degenerate oligonucleotide-primed PCR (DOP-PCR; e.g., Rubicon Picoplex kit).

At a step 5035, residual single-stranded PCR primers are removed by digestion using a 3' to 5' exonuclease.

At a step 5040, the DNA is amplified in a multiplex PCR reaction targeting SNVs of interest. For example, a forward primer includes a gene-specific sequence that targets an SNV of interest, an SBS primer sequence (e.g., SBS3), and a P5 sequence. A reverse primer includes SBS12 complementary sequences and a P7 sequence. In another example, a TSCA-like approach is used to target DNA regions of interest.

At a step 5045, the PCR product is sequenced.

FIG. 51 illustrates a diagram of a spatially addressed PCR primer 5100 for pre-amplification and spatial indexing of whole genomic DNA. Spatially addressed PCR primer 5100 includes a random primer sequence 5110, a spatial address sequence 5115, and an SBS primer sequence 5120 (e.g., SBS12). Random primer sequence 5110 is a 9 bp sequence that is used to amplify genomic DNA in a whole genome pre-amplification reaction. Spatial address sequence 5115 is

TABLE 1

Summary of isothermal nucleic acid amplification methods

| Method* | Amplification time | Reaction volume | Target | Detection limit |
|---------|-------------------|-----------------|--------|-----------------|
| LAMP | within 1 h | 25 μL | Hepatitis B virus (HBV) DNA | 50 copies/25 μL |
|  | within 15 min | 10 μL | Prostate-specific antigen gene | 23 fg/μL |
|  | within 1 h | 5 μL | Pseudorabies virus (PRV) DNA | 10 fg |
|  | within 1 h | — | λ DNA | two molecule |
|  | 1 h 35 min | 35 μL | E. coli genomic DNA | 24 colony forming units (CFU)/mL 48 CRU/mL |
| HDA | 2 h | 150 μL | N. gonorrhoeae genomic DNA | 1 ng |
|  |  |  | Methicillin resistant S. aureus genomic DNA | 250 pg |
|  | 0.5 h | ~5 μL/192 nL | BNI-1 fragment of SARS cDNA | 0.01 ng/μL |
|  | 0.5 h | 25 μL | E. coli genomic DNA | 10 CFU |
| RCA | within 65 min | 10 μL | Genomic DNA for V. cholera | 25 ng |
|  | 4 h | 2 pL | pIVEX2.2EM-lacZ plasmid | 0.07 pg/μL |
|  | 2.5 h | pL | Human-malaria-causing Plasmodium parasites | less than one parasite/μL |
| MDA | 10-16 h | 60 nL | E. coli genomic DNA | — |
| RPA | within 20 min | 10 μL | mecA gene of Staphylococcus aureus | less than 10 copies |
|  | 1 h | 9 nL | Methicillin-resistant Staphylococcus aureus genomic DNA | 300 copies/mL |

*LAMP = loop-mediated isothermal amplification; HDA = helicase dependent amplification; MDA = multiple displacement amplification; RCA = rolling circle amplification; RPA = recombinase polymerase amplification At a step 5030, the semi-permeabilized tissue sample with the amplified genomic DNA therein is removed from the surface of the glass slide and collected in a collection tube. In one example, the semi-permeabilized tissue sample with the amplified genomic DNA therein is removed from the glass slide by scraping into an Eppendorf tube. Because of the biotin label on the PCR primer used in the amplification reaction, the amplified DNA is biotinylated. The amplified biotinylated DNA is purified using a streptavidin bead-based purification protocol.

a unique sequence for each capture site (spatial feature) on an array. SBS primer sequence 5120 includes biotin label 5125. Biotin label 5125 is used to purify the amplified DNA in subsequent processing steps.

FIGS. 52A and 52B show pictorially the steps of method 5000 of FIG. 50. At step 5010, a glass substrate 5210 is printed with spatially addressed PCR primers (not shown) to form an array of spatial features 5215. In this example, glass substrate 5210 is a 2 cm×2 cm coverslip with spatial features that are 100 µm in diameter. The spatially addressed PCR primers are, for example, spatially addressed PCR primer 5100 of FIG. 51.

At step 5015, a semi-permeabilized tissue section 5220 mounted on a glass slide 5225 is overlaid with a PCR master mix solution 5230. Semi-permeabilized tissue sample 5220 includes a cell 5235. Cell 5235 includes a genomic DNA molecule 5240. Genomic DNA molecule 5240 may include a single nucleotide variation (SNV) 5245.

At step 5020, glass substrate 5210 is placed atop tissue section 5220 and PCR master mix solution 5230 such that the surface glass substrate 5210 with spatially addressed PCR primers 5100 thereon (not shown) is in contact with tissue section 5220. PCR primers 5100 (not shown) are released from the surface of glass substrate 5210 into the cellular space of tissue section 5220.

At step 5025, genomic DNA is amplified by in situ isothermal amplification using PCR primers 5100.

At step 5030, tissue section 5220 with amplified DNA 5260 therein is removed from the surface of glass slide 5225 and collected in a collection tube 5255. In one example, collection tube 5255 is an Eppendorf tube. Because of biotin label 5125 on PCR primer 5100, amplified DNA 5260 is biotinylated.

At step 5035 (not shown in FIG. 52), amplified DNA 5260 is purified using a streptavidin bead-based purification protocol.

At step 5040 (not shown in FIG. 52), residual single-stranded PCR primers 5100 are removed by digestion using a 3' to 5' exonuclease.

At step 5045, DNA molecules 5260 are amplified in a target-specific multiplex PCR reaction. For example, a forward primer 5265 includes a gene-specific sequence 5270 that targets SNV 5240, an SBS primer sequence 5275 (e.g., SBS3), and a P5 sequence 5280. A reverse primer 5285 includes a SBS12 complementary sequence 5120a and a P7 sequence 5290. A library amplicon 5295 synthesized using forward primer 5265 and reverse primer 5285 includes P5 sequence 5285, SBS primer sequence 5275, SNV 5240, spatial address sequence 5115, SBS primer sequence 5120, and P7 sequence 5290.

4.8 Spatial Compartmentalization

To limit the diffusion of spatially addressed oligonucleotides (and other reaction components or products) on a tissue section and maintain spatial resolution, compartmentalization of biochemical reactions in "microwell reactors" or "microreactors" may be used. Spatial compartmentalization can be combined with any of the biochemistry techniques described herein for characterization of transcriptomes and/or genomic variation in tissues while preserving spatial information related to the origin of target nucleic acids in the tissue.

FIG. 53 illustrates a perspective view of an example of a microwell reactor overlay 5300. Microwell reactor overlay 5300 includes a glass slide 5310. Mounted atop glass slide 5310 is a tissue section 5315. In one example, tissue section 5315 is an FFPE tissue section. A reaction fluid 5320 is dispensed onto glass slide 5310 such that tissue section 5315 is covered by reaction fluid 5320. In one example, reaction fluid 5320 is a PCR master mix solution used in an amplification reaction. In another example, reaction fluid 5320 is a reverse transcription mix solution. A microwell substrate 5325 is placed atop reaction fluid 5320 and tissue section 5315 on glass slide 5320. Microwell substrate 5325 includes a plurality of microwells 5330. Printed on the bottom surface of each microwell 5330 is a plurality of spatially addressed oligonucleotides (not shown). Microwells 5330 function as compartmentalized reaction chambers for performing a biochemical reaction (e.g., PCR amplification). Microwells 5330 are described in more detail with reference to FIG. 54.

FIG. 54 illustrates a perspective view of a single microwell 5330 of microwell reactor overlay 5300 of FIG. 53. In this example, microwell 5330 has a diameter of about 200 µm and a height of about 100 µm. The volume of microwell 5350 is about 3 nL. Printed on the bottom surface of microwell 5350 is a plurality of spatially addressed oligonucleotides 5410. Spatially addressed oligonucleotides 5410 include a unique spatial address sequence for each microwell 5330.

FIGS. 55A and 55B illustrate an example of a process 5500 of fabricating microwell substrate 5325 of microwell reactor overlay 5300 of FIG. 53. In this example only a portion of microwell substrate 5325 is shown.

In a first step and referring now to FIG. 55A, microwell substrate 5325 includes a glass substrate 5510. In one example, glass substrate 5510 is a hydrophilic glass substrate that is about 1 mm thick. A polyimide layer 5515 is disposed on the surface of glass substrate 5510. In one example, polyimide layer 5515 is a black Kapton layer that is about 100 µm thick. A hydrophobic layer 5520 is disposed on the surface of polyimide layer 5515. In one example, hydrophobic layer 5520 is formed by silanizing polyimide layer 5515.

In a next step and referring now to FIG. 55B, a plurality of microwells 5525 are formed in polyimide layer 5515. In this example, two microwells 5525 are shown, but any number and arrangement of microwells 5525 may be used. In one example, microwells 5525 are formed in polyimide layer 5515 using precise ultraviolet laser ablation to remove portions of polyimide layer 5515 and hydrophobic layer 5520. In this example, microwells 5525 are about 200 µm in diameter. Table 2 below shows other examples of suitable dimensions for microwell 5525. Microwells 5525 are hydrophilic regions that function as reaction chambers for performing biochemical reactions. Because of the presence of hydrophobic layer 5520 in the interstitial regions between microwells 5525, lateral diffusion of reaction components or products is eliminated or substantially reduced. The relatively small volume of microwell 5525 provide for small reaction volume and higher efficiency reactions. Compartmentalization (confinement) of spatially addressed oligonucleotides within microwells 5525 also obviates the need for process steps that may be required to release printed oligonucleotides from the surface of a glass substrate.

TABLE 2

| Microwell dimensions | | |
| --- | --- | --- |
| Diameter (µm) | Height (µm) | Volume (nL) |
| 200 | 100 | 3.1 |
| 500 | 100 | 19.6 |
| 1000 | 100 | 78.6 |

FIG. 56 illustrates a side view of an example of a microwell structure 5600 for capture and spatial compartmentalization of nucleic acids from a tissue sample. Microwell structure 5600 includes a substrate 5610. In one example, substrate 5610 is a glass slide. Substrate 5610 includes an array of microwells 5615. In one example, microwells 5615 are formed in substrate 5610 using an etching process, such as by precise ultraviolet laser ablation. Microwells 5615 are hydrophilic regions, while the interstitial regions between microwells 5615 are hydrophobic regions. Microwells 5615 function as reaction chambers for performing biochemical reactions (e.g., reverse transcription of RNA to cDNA, amplification of genomic DNA). Because the interstitial regions between microwells 5615 are hydrophobic, lateral diffusion of reaction components or products away from microwells 5615 is eliminated or substantially reduced. In one example, microwells 5615 have a diameter of about 1 mm and a height of about 100 µm. The spacing between microwells 5615 is about 1 mm.

Deposited in each microwell 5615 is a quantity of gel material 5620. The quantity of gel material 5620 deposited in each microwell 5615 is selected such that as gel material 5620 is subsequently hydrated, gel material 5620 swells to fill and protrude from microwells 5615 without contacting adjacent microwells 5615. In one example, gel material 5620 is a hydrogel material such as poly(N-(5-azidoacetamidylpentyl)acrylamide-co-acrylamide) (PAZAM) that is functionalized with covalently linked, spatially addressed capture oligonucleotides (not shown). The spatially addressed capture oligonucleotides (not shown) include a spatial address sequence that is unique for each microwell 5615. The spatially addressed capture oligonucleotides also include a capture sequence for capture of nucleic acids (e.g., RNA or genomic DNA) from a tissue section. The capture sequence can be, for example, a gene-specific capture sequence or a universal capture sequence. Gel material 5620 can be deposited in each microwell 5615 by printing (e.g., contact printing or piezoelectric printing).

FIG. 57 illustrates a flow diagram of an example of a method 5700 of capturing nucleic acids from a tissue section using microwell structure 5600 of FIG. 56 for preparation of a sequencing library. Method 5700 includes, but is not limited to, the following steps.

At a step 5710, a quantity of gel material 5620 is deposited in each microwell 5615 of microwell structure 5600, such that each microwell 5615 includes gel material 5620 that has a unique spatial address sequence therein. In some embodiments, microwell structure 5600 that has gel material 5620 deposited therein can be stored for a period of time prior to use.

At a step 5715, at time-of-use, microwell structure 5600 is immersed in a biochemical reaction solution to hydrate gel material 5620. In some embodiments, the biochemical reaction solution includes reverse transcriptase and reaction components to synthesize cDNA from targeted RNA in a tissue sample. In some embodiments, the biochemical reaction solution includes DNA polymerase and reaction components to produce multiple genomic DNA amplicons from targeted genes in a tissue sample. Microwell structure 5600 is immersed in the biochemical reaction solution for a period of time sufficient for hydration of gel material 5620. As gel material 5620 is hydrated, gel material 5620 swells to fill and protrude from microwells 5615. Microwell structure 5600 is then removed from the biochemical reaction solution. Because the interstitial region between microwells 5615 is hydrophobic, no biochemical reaction solution remains between microwells 5615. The spatially addressed capture oligonucleotides covalently bound to gel material 5620 are localized at each microwell 5615.

At a step 5720, a tissue section is placed atop microwell structure 5600 such that the tissue section is in contact with the hydrated gel material 5620 that has spatially addressed capture oligonucleotides therein. In one example, the tissue section is a semi-permeablized FFPE tissue section. As the tissue section contacts hydrated gel material 5620 that has spatially addressed capture oligonucleotides thereon, the biochemical reaction is initiated. Because the interstial regions between microwells 5615 are hydrophobic, reaction components and products are localized at each microwell 5615.

At a step 5725, the reaction products (e.g., cDNA or DNA) are removed from gel material 5620. The reaction products may be purified from the PAZAM using bead purification methods. At a step 5730, a sequencing library is prepared.

FIG. 58A illustrates a side view of an example of a pin system 5800 for tissue excision and preparation of a spatially addressed nucleic acid library. Pin system 5800 includes a pin structure 5810 and a microwell block 5815. Pin structure 5810 includes a substrate 5820. In one example, substrate 5820 is a glass substrate. Protruding from substrate 5820 is an array of pins 5825. In one example, pins 5825 are formed of a glass material. In one example, pins 5825 have a diameter of about 100 µm and a height of from about 10 µm to about 20 µm. The spacing between pins 5825 is about 100 µm. At the end of each pin 5825 is an excision surface 5830. Excision surface 5830 can be any shape that facilitates removal of a tissue sample from a tissue section. Examples of different excision surfaces are described in more detail with reference to FIG. 58B. Pins 5825 can be coated with a substance (not shown) to facilitate adherence of the tissue to pins 5825. In one example, pins 5825 can be coated with poly-lysine. In another example, pins 5825 are coated with an adhesive material. In yet another example, pins 5825 are coated with PAZAM. Substrate 5820 also includes alignment holes 5835. In this example, two alignment holes 5835 are shown, but any number of alignment holes 5835 may be used. Alignment holes 5835 are used to align pin structure 5810 with microwell block 5815.

Microwell block 5815 includes a substrate 5840. Substrate 5840 includes an array of microwells 5845. Microwells 5845 are arranged to align with pins 5825 in pin structure 5810. Microwells 5845 are loaded with a quantity of a biochemical reaction mixture 5850. In various embodiments, biochemical reaction mixture 5850 includes spatially addressed capture oligonucleotides for targeting and tagging nucleic acids in a tissue sample. The spatially addressed capture oligonucleotides (not shown) in biochemical reaction mixture 5850 include a spatial address sequence that is unique for each microwell 5845. In some embodiments, biochemical reaction mixture 5850 includes spatially addressed capture oligonucleotides, reverse transcriptase and reaction components to synthesize cDNA from targeted RNA in a tissue sample. In some embodiments, biochemical reaction mixture 5850 includes spatially addressed capture oligonucleotides, DNA polymerase and reaction components to produce multiple genomic DNA amplicons from targeted genes in a tissue sample. In some embodiments, biochemical reaction mixture 5850 is a solution of about 1 uL in volume. In some embodiments, biochemical reaction mixture 5850 is a dehydrated reaction mixture or portion thereof that is rehydrated prior to using microwell block 5815. Microwells 5845 with biochemical reaction mixture 5850 therein are covered with a pierceable film 5855, such as foil. Microwell block 5815 also includes alignment pins 5860. In this example, two alignment pins 5860 are shown, but any number of alignment pins 5860 may be used. Microwell block 5815 is aligned with pin structure 5810 by fitting alignment pins 5860 of microwell block 5815 into alignment holes 5835 of pin structure 5810.

FIG. 58B illustrates examples of different excision surfaces 5830 for pins 5825 on pin structure 5810 of FIG. 58A. In one example, excision surface 5830a is concave in shape. In another example, excision surface 5830b is "v" shaped. In yet another example, excision surface 5830c has a relatively shallow jagged edge shape. In yet another example, excision surface 5830d has a relatively deep jagged edge shape.

FIG. 59 illustrates a flow diagram of an example of a method 5900 of capturing nucleic acids from a tissue section using pin system 5800 of FIG. 58A for preparation of a sequencing library. In this example, pin structure 5810 is used as a "touch" pin structure to contact a tissue section mounted on a solid substrate and remove tissue samples for subsequent delivery to microwell block 5815 for capture of nucleic acids. Method 5900 includes, but is not limited to, the following steps.

At a step 5910, tissue samples from a tissue section are collected using pin structure 5810. For example, a tissue section on a glass slide is contacted with pins 5825 such that samples of tissue adhere to excision surfaces 5830. As pin structure 5810 is removed from the surface of the tissue section, adherent tissue samples are removed from the tissue section. In one example, the tissue section is a semi-permeablized FFPE tissue section.

At a step 5915, pin structure 5810 that has tissue samples thereon is moved to microwell block 5815. For example, pin structure 5810 is aligned with and mated to microwell block 5815. In so doing, pierceable film 5855 is ruptured and pins 5825 that have tissue samples thereon are immersed in biochemical reaction mixture 5850 within microwells 5845.

At a step 5920, in an incubation period, the biochemical reaction is performed.

At a step 5925, pin structure 5810 is removed from microwell block 5815 and the biochemical reaction mixture that has reaction products (e.g., cDNA or genomic DNA amplicons) therein is collected from microwells 5845.

At a step 5930, a sequencing library is prepared.

FIG. 60 illustrates side views of pin system 5800 of FIG. 58A and shows pictorially the step 5910 and 5915 of method 5900 of FIG. 59. Namely, at step 5910 a tissue section 6010 (e.g., an FFPE tissue section) atop a glass slide 6015 is contacted with pin structure 5815 of pin system 5800. Tissue in contact with excision surfaces 5830 adhere to pins 5825. As pin structure 5815 is removed from the surface of tissue section 6010, adherent tissue samples 6020 are removed from the tissue section.

At step 5915, pin structure 5810 that has tissue samples 6020 thereon is moved to microwell block 5815. For example, pin structure 5810 is aligned with and mated to microwell block 5815. In so doing, pierceable film 5855 is ruptured and pins 5825 that have tissue samples 6020 thereon are immersed in biochemical reaction mixture 5850 within microwells 5845.

FIG. 61 illustrates a flow diagram of another example of a method 6100 of capturing nucleic acids from a tissue section using pin system 5800 of FIG. 58A for preparation of a sequencing library. In this example, pin structure 5810 is used as a "push" pin structure to contact a tissue section mounted on a pierceable substrate and push tissue samples directly into microwells 5845 for capture of nucleic acids. Method 6100 includes, but is not limited to, the following steps.

At a step 6110, a tissue section mounted on a pierceable substrate is placed on microwell block 5815; namely, atop pierceable film 5855 of microwell block 5815. In one example, the tissue section is a semi-permeablized FFPE tissue section.

At a step 6115, pin structure 5810 is moved to microwell block 5815. For example, pin structure 5810 is aligned with and mated to microwell block 5815. In so doing, both the pierceable substrate that has the tissue section thereon and pierceable film 5855 are ruptured and pins 5825 that have tissue samples thereon are immersed in biochemical reaction mixture 5850 within microwells 5845.

At a step 6120, in an incubation period, the biochemical reaction is performed.

At a step 6125, pin structure 5810 is removed from microwell block 5815 and the biochemical reaction mixture with reaction products (e.g., cDNA or genomic DNA amplicons) therein is collected from microwells 5845.

At a step 6130, a sequencing library is prepared.

FIG. 62 illustrates side views of pin system 5800 of FIG. 58A and shows pictorially the steps 6110 and 6115 of method 6100 of FIG. 61. Namely, at step 6110, a tissue section 6210 (e.g., an FFPE tissue section) mounted on a pierceable substrate 6215 is placed atop microwell block 5815. At step 6115, pin structure 5810 is moved to microwell block 5815. For example, pin structure 5810 is aligned with and mated to microwell block 5815. In so doing, both pierceable substrate 6215 that has tissue section 6210 thereon and pierceable film 5855 are ruptured and pins 5825 that have tissue samples 6225 thereon are immersed in biochemical reaction mixture 5850 within microwells 5845.

FIG. 63 illustrates a prespective view of a capillary "microreactor" system 6300 for capture of nucleic acids from a tissue section for preparation of a spatially addressed nucleic acid library. Capillary microreactor system 6300 includes a plurality of capillary tubes 6310. In one embodiment, the capillary tubes 6310 may used individually to collect and process a sample or may be bundled in an array and used as a unit. In this example, 4 capillary tubes 6310 are shown, but any number of capillary tubes 6310 may be used. Capillary tubes 6310 have a sample contact end 6315 and a non-contact end 6320. Sample contact end 6315 of each capillary tube 6310 includes a small protrusion 6325. In one example, capillary tubes 6310 are about 100 μm in diameter. Dried on the inner surface of each capillary tube 6310 is a quantity of spatially addressed capture oligonucleotides (not shown) for targeting and tagging nucleic acids from a tissue section. The spatially addressed capture oligonucleotides (not shown) include a spatial address sequence that is unique for each capillary tube 6310. The spatially addressed capture oligonucleotides also include a capture sequence for capture of nucleic acids (e.g., RNA or genomic DNA) from a tissue section. The capture sequence can be, for example, a gene-specific capture sequence or a universal capture sequence.

At point-of-use, capillary tubes 6310 are filled with a biochemical reaction solution 6330. In one example, capillary tubes 6310 are filled with biochemical reaction solution 6330 by "wicking" or capillary action. In some embodiments, biochemical reaction solution 6330 includes reverse transcriptase and reaction components to synthesize cDNA from targeted RNA in a tissue sample. In some embodiments, biochemical reaction solution 6330 includes DNA polymerase and reaction components to produce genomic DNA amplicons from targeted genes in a tissue sample.

Capillary tubes 6310 are "stamped" onto and press into a tissue section 6335 mounted on a substrate 6340. In one example, tissue section 6335 is a semi-permeablized FFPE tissue section. As capillary tubes 6310 are pressed into tissue section 6335, a sample of tissue is pressed into capillary tube 6310 via protrusion 6325. In some embodiments, an inert substrate (not shown) is positioned between tissue section 6335 and substrate 6340. The inert substrate is used to seal sample contact ends 6315 of capillary tubes 6310.

FIG. 64 illustrates a flow diagram of an example of a method 6400 of capturing nucleic acids from a tissue section using capillary microreactor system 6300 of FIG. 63 for preparation of a sequencing library. Method 6400 includes, but is not limited to, the following steps.

At a step 6410, at point-of-use, biochemical reaction solution 6330 is loaded via capillary action into capillary tubes 6310.

At a step 6415, capillary tubes 6310 that have biochemical reaction solution 6330 therein are stamped onto and pressed into tissue section 6335 mounted on substrate 6340 to collect tissue samples.

At a step 6420, capillary tubes 6310 are removed from substrate 6340 and sealed at sample contact end 6315 to prevent evaporation. In some embodiments, capillary tubes 6310 are removed from substrate 6340 and sample contact ends 6315 are stamped onto an inert substrate to seal against evaporation. In some embodiments, an inert substrate is positioned between tissue section 6335 and substrate 6340. As capillary tubes 6310 are pressed into and through tissue section 6335, sample contact ends 6315 are pressed into the inert substrate and sealed against evaporation.

At a step 6425, non-contact ends 6320 of capillary tubes 6310 are sealed against evaporation. In some embodiments, non-contact ends 6320 are stamped onto an inert substrate to seal against evaporation.

At a step 6430, in an incubation period, the biochemical reaction is performed.

At a step 6435, the biochemical reaction solution with reaction products (e.g., cDNA or genomic DNA amplicons) therein is collected from capillary tubes 6310 and pooled.

At a step 6440, a sequencing library is prepared.

4.9 Serial Section DNA/RNA Workflow

A pool of spatially addressed random primer oligonucleotides may be used in a serial DNA/RNA workflow for spatial detection and analysis of DNA and RNA in a tissue sample. For example, a spatially addressed random primer oligonucleotide may include a random primer sequence, a spatial address sequence, an SBS primer sequence and a biotin label as described above for spatially addressed PCR primer 5100 of FIG. 51. A pool of spatially addressed random primer oligonucleotides is used in an in situ whole genomic DNA amplification reaction to amplify and spatially index DNA in one serial section of the tissue sample. The amplified and spatially indexed DNA is then used to generate a sequencing library. The same pool of spatially addressed random primer oligonucleotides is used in an in situ RT reaction to synthesize and spatially index cDNA from RNA in a second serial section of the tissue sample. The spatially indexed cDNA is then used to generate a second sequencing library. The combined DNA/RNA workflow provides for increased data output from a single tissue sample.

4.10 Droplet Actuator Configured for Spatial Detection and Analysis of Nucleic Acids FIG. 65 illustrates a side view of a portion of droplet actuator 6500 that is configured for spatial detection and analysis of nucleic acids in a tissue sample. Droplet actuator 6500 includes a bottom substrate 6510 that is separated from a top substrate 6515 by a droplet operations gap 6520. Droplet operations are conducted in droplet operations gap 6520 on a droplet operations surface. Bottom substrate 6510 includes an arrangement of droplet operations electrodes 6525 (e.g., electrowetting electrodes). Droplet operations are conducted atop droplet operations electrodes 6525 on a droplet operations surface. Top substrate 6515 includes a reference electrode 6530. Top substrate 6515 also includes a recessed area 6535 that is of sufficient size and shape to accommodate a pore sheet 6540. Pore sheet 6540 is described in more detail with reference to FIG. 66. Associated with recessed area 6535 is an electrophoresis electrode 6545. Bottom substrate 6510 includes a corresponding electrophoresis electrode 6550. Electrophoresis electrodes 6545 and 6550 are connected to a voltage source 6555. Pore sheet 6540, electrophoresis electrodes 6545 and 6550 are configured for electrophoretic transfer and capture of nucleic acids in a tissue sample such that spatial orientation is maintained. Further, pore sheet 6540 is installed in recessed area 6535 such that there is a certain amount of space 6536 between the top of pore sheet 6540 and electrophoresis electrode 6545.

A hydrophobic layer 6560 is disposed on the surface of top substrate 6515 that is facing droplet operations gap 6520. Similarly, another hydrophobic layer 6565 is disposed on the surface of bottom substrate 5610 that is facing droplet operations gap 6520.

FIG. 66 illustrates a side view of pore sheet 6540 of droplet actuator 6500 of FIG. 65. Pore sheet 6540 includes a substrate 6610 that has a top surface 6615 and a bottom surface 6620. Substrate 6610 includes an array of pores 6625. Pores 6625 are through-holes (e.g., micro-pores) in substrate 6610 that extent through substrate 6610 from top surface 6615 to bottom surface 6620. Each pore 6625 is filled with a gel or a solution or a reaction matrix that includes a plurality of unique spatially addressed capture probes (not shown). Each spatial address corresponds to the position of the capture probes on pore sheet 6540. The position of each pore 6625 may be correlated with a position in a tissue sample. Bottom surface 6620 of substrate 6610 may include a hydrophobic layer (not shown) to facilitate transport of a droplet to pore sheet 6540 and away from pore sheet 6540.

FIGS. 67A and 67B illustrate side views of droplet actuator 6500 of FIG. 65 and show a process 6700 of isolating nucleic acid in a tissue sample for spatial detection and analysis. Process 6700 is an example of a nucleic acid isolation protocol wherein nucleic acids in a tissue sample are electrophoretically transferred to an array of micro-pores containing unique spatially addressed capture probes, tagged with the unique spatial address sequence and transferred to a droplet for subsequent processing on the droplet actuator. Process 6700 includes, but is not limited to, the following steps.

In one step and referring now to FIG. 67A, a tissue sample 6710 mounted on a sample substrate 6715 is positioned in recessed area 6535; namely, in space 6536 atop pore sheet 6540. In one example, tissue sample 6710 is an FFPE tissue section. In one example, tissue sample 6710 is placed directly on the surface of pore sheet 6540. In another example, tissue sample 6710 is placed on a substance (not shown) such as a gel or a thin buffer layer separating tissue sample 6710 from pore sheet 6540 to facilitate electrophoretic transfer of nucleic acids from tissue sample 6710 into pore sheet 6540. A droplet 6720 is transported using droplet operations to a certain droplet operations electrode 6525 aligned with pore sheet 6540. A voltage is applied from voltage source 6555 to electrophoresis electrodes 6545 and 6550, creating an electric field. In the presence of the electric field, a plurality of nucleic acids 6725 are transferred from tissue sample 6710 into pores 6625 of pore sheet 6540. Nucleic acid 6725 in each pore 6625 of pore sheet 6540 is tagged with a spatial address sequence (not shown) that corresponds to the position of each pore 6625 on pore sheet 6540.

In another step and referring now to FIG. 67B, after a period of time sufficient for capture of nucleic acids 6725 onto spatially addressed capture probes contained in each pore 6625, nucleic acids 6725 are electrophoretically transferred into droplet 6720. Droplet 6720 with tagged nucleic acids 6725 therein is transported using droplet operations away from pore sheet 6540 for subsequent processing steps on droplet actuator 6500. For example, droplet actuator 6500 may include a reaction zone (not shown) for performing processing steps in a sequencing library preparation protocol (e.g., reverse transcription of RNA to cDNA, exonuclease I digestion, PCR amplification, and Nextera library preparation). Droplet actuator 6500 may also include a sequencing zone (not shown) for performing a DNA sequencing protocol (e.g., an SBS protocol). The sequencing zone may be, for example, a sequencing flow cell.

4.11 Spatial Tissue Profiling Based on DNA Tagmentation

"Tagmentation," as used herein, is a process of transposase mediated fragmentation and tagging. Tagmentation often involves the modification of DNA by a transposome complex comprising transposase enzyme complexed with adaptors comprising a transposon end sequence. Tagmentation results in the simultaneous fragmentation of DNA and ligation of the adapters to the 5' ends of both strands of DNA duplex fragments.

This disclosure is based, in part, on the realization that tagmentation can be efficiently used to spatially address nucleic acids from a tissue sample on a capture array.

FIG. 68 illustrates a flow diagram of an example of a method 6800 of profiling genomic DNA in a tissue sample using tagmentation of the DNA. In this example, method 6800 is used for profiling SNVs of interest in genomic DNA. Method 6800 can comprise, but is not limited to, some or all of the following steps.

At a step 6810, a glass substrate is printed with spatially addressed oligonucleotides to form an array of spatial features. In some embodiments, the spatially addressed oligonucleotides can be printed on a 2 cm×2 cm coverslip to form an array of spatial features that are 100 μm in diameter on a pitch of 35 μm. In some embodiments, the spatially addressed oligonucleotides can be printed in microwells fabricated on the surface of a glass slide. The spatially addressed oligonucleotides can be printed on a coverslip or glass slide using, for example, commercially available printing technologies. The spatially addressed oligonucleotides can comprise a linker sequence, an SBS primer sequence, a spatial address sequence, and a 19 bp Mosaic End (ME) sequence as described in more detail with reference to FIG. 69A. In some embodiments, the ME sequence is a Tn5 transposase recognition sequence. In some embodiments, the ME sequence is a Mu transposase recognition sequence. The spatially addressed oligonucleotides can further comprise a modification at the 5' end of the molecule for reversible attachment to the coverslip. In some embodiments, the spatially addressed oligonucleotides can comprise a 5' disulfide modification as described for spatially addressed capture probe 3100 of process 3200 of FIGS. 32A, 32B, and 32C. In some embodiments, the spatially addressed PCR primers can include a 5' photocleavable linker as described for spatially addressed capture probe 3100 of process 3300 of FIGS. 33A, 33B, and 33C.

At a step 6815, a reverse complement oligonucleotide sequence is hybridized to the ME sequence to form a region of double stranded DNA.

At a step 6820, a transposase enzyme solution is added onto the surface of the spatially addressed oligonucleotide array to form a transposome homodimer at each region of double stranded DNA. In some embodiments, the transposase enzyme solution comprises Tn5. In some embodiments, the transposase enzyme solution comprises Mu.

At a step 6825, a tissue section is placed on the array, such that the surface of the array substrate with the spatially addressed oligonucleotides and transposome homodimers thereon is in contact with the tissue section. In one example, the tissue section is an FFPE tissue section.

At a step 6830, the double stranded DNA is tagmented with a transposome complex. Methods, compositions, and kits for treating nucleic acid, and in particular, methods and compositions for fragmenting and tagging DNA using transposon compositions are described in detail, for example, in US2010/0120098 and US2011/0287435, which are hereby incorporated by reference in their entireties.

At a step 6835, the tagmented DNA is amplified using a gene specific primer and a universal primer that includes a complementary region to the SBS primer sequence to a generate tagmented genomic DNA library.

At a step 6840, the tagmented genomic DNA library is sequenced.

FIGS. 69A, 69B, and 69C illustrate the steps of the method 6800 of FIG. 68. At step 6810 (see FIG. 69A), an array surface 6910 is printed with spatially addressed oligonucleotides 6915 for spatial indexing and tagmentation of whole genomic DNA. In this example, a single spatially addressed oligonucleotide 6915 is shown, but any number of 6915 oligonucleotides can be immobilized on the array surface 6010, Spatially addressed oligonucleotide 6015 includes a linker region 6920, an SBS primer region 6925, a spatial address region 6930, and a ME region 6935. Spatial address region 6930 comprises a unique sequence for each capture site (spatial feature) on an array. The 19 bp ME sequence of ME region 6935 or the transposon end is described in detail, e.g., in US2010/0120098 and US2011/0287435. Methods, compositions, and kits for treating nucleic acid, and in particular, methods and compositions for fragmenting and tagging DNA using transposon compositions are described in detail, e.g., in US2010/0120098 and US2011/0287435.

The linker region 6920 in this example comprises a cleavable sequence that can be used to release captured nucleic acid from array surface 6910 such that spatial address region 6930 is included in the released nucleic acid and the nucleic acid is "tagged." SBS primer region 6925 comprise an SBS primer sequence (e.g., SBS12 or SBS3) that can be used in a sequencing-by-synthesis (SBS) process. SBS primer region 6925 can also be used in an amplification reaction to generate a sequencing library as described in more detail with reference to FIG. 12 and FIG. 13.

At step 6815 (see FIG. 69A), an ME reverse complement sequence 6940 is hybridized to the ME region 6935.

At step 6820 (see FIG. 69B), a transposase enzyme solution (not shown) is added onto the array surface 6910 to form a transposome homodimer 6945 at each region of double stranded DNA. In some embodiments, the transposome ends comprise Mu transposome ends and the transposase is Mu transposase. In some embodiments, the transposome ends comprise Tn5 transposome ends and the transposase is Tn5 transposase.

At step 6825 (see FIG. 69B), a tissue section 6950 is placed atop the array surface 6910 such that the spatially addressed oligonucleotides 6915 and transposome homodimers 6945 thereon is in contact with the tissue section 6950. In some embodiments, tissue section 6950 is an FFPE tissue section. Tissue section 6950 includes a cell 6955. Cell 6955 includes a genomic DNA molecule 6960. Genomic DNA molecule 6960 may include a single nucleotide variation (SNV) 6965.

At step 6830 (see FIG. 69C), genomic DNA 6960 is tagmented. For example, genomic DNA 6960 is tagmented such that SNV 6965 is "A" upstream of a tagmentation event or "B" downstream of a tagmentation event.

At step 6835 (see FIG. 69C), tagmented genomic DNA 6960 is amplified. For example, if SNV 6965 is "A" upstream of a tagmentation event, genomic DNA 6960 is amplified using a gene-specific primer 6970 and a universal primer 6975 that includes a complementary region to the SBS primer region 6925. If SNV 6965 is "B" downstream of a tagmentation event, genomic DNA 6960 is amplified using a gene-specific primer 6980 and the universal primer 6975.

At step 6840 (not shown in FIGS. 69A, 69B, and 69C), the PCR product is sequenced.

In another aspect, provided herein is a capture array for spatial detection and analysis of nucleic acids in a tissue sample, comprising a capture site comprising a capture probe (e.g., 6915) comprising a spatial address region (e.g., 6930), and a transposon end (TE) region (e.g., 6935). In some embodiments, the capture probe further comprises a cleavable region (e.g., 6920) and an SBS primer binding region (e.g., 6925). In some embodiments, the transposon end region is hybridized to a reverse-complementary oligonucleotide (e.g., 6940) to form a double-stranded transposon end region. In some embodiments, the TE region comprises an ME sequence.

In some embodiments, the capture array further comprises a transposase to form a transposome (e.g., 6945).

In some embodiments the transposome ends comprise Mu transposome ends and the transposase is Mu transposase. In some embodiments the transposome ends comprise Tn5 transposome ends and the transposase is Tn5 transposase.

In another aspect, provided herein is a method for spatial detection and analysis of nucleic acids in a tissue sample, comprising providing a capture array described herein. In some embodiments, the capture array comprises a capture site comprising a capture probe (e.g., 6915) comprising a spatial address region (e.g., 6930), and a transposon end (TE) region (e.g., 6935). In some embodiments, the capture probe further comprises a cleavable region (e.g., 6920) and an SBS primer binding region (e.g., 6925).

In some embodiments, the method further comprises contacting the capture array with an oligonucleotide that is a reverse-complement of the TE region (e.g., 6940) to form a double-stranded transposon end region.

In some embodiments, the method further comprises contacting the capture array with a transposase to form a transposome (e.g., 6945). In some embodiments the transposome ends comprise Mu transposome ends and the transposase is Mu transposase. In some embodiments the transposome ends comprise Tn5 transposome ends and the transposase is Tn5 transposase.

In some embodiments, the method further comprises contacting the capture array with a tissue sample such that the position of a capture site on the array can be correlated with a position in the tissue sample; and allowing a tagmentation reaction to occur between the genomic DNA of the tissue sample and the transposome at the capture site. In some embodiments, the genomic DNA comprises a SNV.

In some embodiments, the method further comprises analyzing the sequence of the tagmented DNA. In some embodiments, sequencing the tagmented DNA comprises performing a sequencing reaction using a combination of a gene-specific primer and a universal primer. IN some embodiments, analyzing the sequence of the tagmented DNA comprises detecting the SNV.

In some embodiments, the method further comprises correlating the sequence of the tagmented DNA to the position of the genomic DNA in the tissue sample. In some embodiments, correlating the sequence of the tagmented DNA comprises correlating the SNV with a position in the tissue sample.

4.12 Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer can be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference. This approach is being commercialized by Solexa (now Illumina Inc.), and is also described in International Patent Pub. No. WO 91/06678 and International Patent Pub. No. WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Pub. No. 2007/0166705, U.S. Patent Pub. No. 2006/0188901, U.S. Pat. No. 7,057, 026, U.S. Patent Pub. No. 2006/0240439, U.S. U.S. Patent Pub. No. 2006/0281109, International Patent Pub. No. WO 05/065814, U.S. Patent Pub. No. 2005/0100900, International Patent Pub. No. WO 06/064199, International Patent Pub. No. WO 07/010,251, U.S. U.S. Patent Pub. No. 2012/ 0270305 and U.S. Patent Pub. No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Pub. No. 2013/0079232. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal.

As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated materials of U.S. Patent Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Pub. No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Patent Pub. No. 2009/0026082; U.S. Patent Pub. No. 2009/0127589; U.S. Patent Pub. No. 2010/0137143; or U.S. Patent Pub. No. 2010/0282617, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Patent Pub. No. 2010/0111768 A1 and U.S. patent application Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. patent application Ser. No. 13/273,666, which is incorporated herein by reference. For example, the MiSeq™ platform may be implemented with capture probes 5' CAACGATCGTCGAAATTCGC[target primer] 3' and 5' [target primer]AGATCGGAAGAGCGTCGTGTA3' where [target primer] is a sequence which is complimentary to a target nucleic acid.

4.13 Concluding Remarks

The foregoing detailed description of embodiments refers to the accompanying drawings, which illustrate specific embodiments of the present disclosure. Other embodiments having different structures and operations do not depart from the scope of the present disclosure. This specification is divided into sections for the convenience of the reader only. Headings should not be construed as limiting of the scope of the disclosure provided herein. The definitions are intended as a part of the disclosure provided herein. It will be understood that various details of the present disclosure can be changed without departing from the scope of the disclosed embodiments. Furthermore, the foregoing description is for the purpose of illustration only, and not for the purpose of limitation.

5. EXAMPLES 5.1 Sensitivity of Spatial NGS for Detection of Single Nucleotide Variations This example demonstrates that sensitivity of SNV detection can be substantially increased using spatially addressed sequencing compared to bulk sequencing.

The sensitivity of SNV detection using bulk sequencing or spatially addressed sequencing data was evaluated using simulated data sets. The calculations used to derive a bulk sequencing data set was based on the following assumptions: (1) a typical FFPE section is 1.5 cm×1.5 cm, which is about 225,000,000 μm$^2$; (2) a typical cell is 20×20 μm, which has an area of about 400 μm$^2$; (3) the number of cells in a typical FFPE section is about 563,000 (i.e., 225,000,000 μm$^2$ FFPE block÷400 μm$^2$ cell=~563K cells per section); and (4) the packing density of cells in an FFPE section is about 70%, then the number of cells in a typical FFPE section is about 400,000. Table 3 below shows simulated data for the sensitivity of SNV detection in bulk sequencing. To identify rare populations of clonally mutated cells using bulk sequencing, the variant frequency (% SNV) needs to be above the sequencing error rate, which is about 1%. For example, 1 variant cell ("Localized mutated cells") in a FFPE section has a variant frequency (% SNV) of 0.00025 (i.e., (1 cell÷400,000 cells in FFPE section)×100)= 0.00025% SNV), which is well below the sequencing error rate and is therefore not detectable in bulk sequencing data. At least about 4000 cells are required to detect an SNV in bulk sequencing data, e.g., 4096 cells÷400,000 cells in FFPE section)×100)=1.024, which is above the sequencing error rate.

TABLE 3

Sensitivity of SNV detection in bulk sequencing

| Localized mutated cells | % SNV (bulk sequence data) | SNV detection sensitivity above sequencing error*? |
| --- | --- | --- |
| 1 | 0.00025 | No |
| 4 | 0.001 | No |
| 16 | 0.004 | No |
| 64 | 0.016 | No |
| 256 | 0.064 | No |
| 1024 | 0.256 | No |
| 2048 | 0.512 | No |
| 4096 | 1.024 | Yes |
| 8192 | 2.048 | Yes |

*1% sequencing error rate

It was found that sensitivity of SNV detection can be substantially increased using spatially addressed sequencing as exemplified using a simulated data set based on a 1.5 cm×1.5 cm tissue section overlaid on a 2 cm×2 cm array. FIG. 70 illustrates a plan view of a spatial address overlay 7000. Spatial address overlay 7000 comprises a substrate 7005. In one example, substrate 7005 is a planar glass substrate such as a coverslip that is 2 cm×2 cm in size. Printed on the surface of substrate 7005 are a plurality of distinct features (not shown) which are regions containing spatially addressed oligonucleotides. An example of a single spatial feature is described in more detail with reference to FIG. 71. Overlaid on substrate 7005 is a tissue section 7010. In one example, tissue section 7005 is an FFPE tissue section that is 1.5 cm×1.5 cm in size.

FIG. 71 illustrates a plan view of a single spatial feature 7100 on substrate 7005 of FIG. 70. In this example, spatial feature 7100 is a 100 μm×100 μm square (area=10,000 μm$^2$). Spatial feature 7100 is of sufficient size to encompass a plurality of cells 7105 contained in a tissue sample. Cells 7105 can be normal cells (e.g., 7105a) or variant (mutated) cells (e.g., 7105b). In one example, cells 7105 are 20 μm×20 μm in size (area=400 μm$^2$) and the cell packing density in the tissue section is about 70%. Based on these parameters, the number of cells 7105 that are encompassed in spatial feature 7100 is about 18 (i.e., (10,000 μm$^2$÷400*0.7)=~18).

Table 4 below shows the simulated data for the sensitivity of SNV detection in spatially addressed sequencing data based on spatial address overlay 7000 of FIG. 70 and FIG. 71. For example, 1 variant cell ("Localized mutated cells) in a single spatial feature 3000 has a variant frequency (% SNV) of about 6 (i.e., (1 cell÷18 cells per spatial feature)*100=6% SNV), which is above the 1% sequencing error rate and is therefore detectable in spatially addressed sequencing data. In comparison, about 4000 cells or more are required for SNV detection in bulk sequencing data.

TABLE 4

Comparison of sensitivity of SNV detection between spatially indexed and bulk sequencing data

| | Sequence data tagged by spatial index | | Bulk sequencing | |
|---|---|---|---|---|
| Localized mutated cells† | % SNV (spatial indexing) | SNV detection sensitivity above sequencing error*? | % SNV (spatial indexing) | SNV detection sensitivity above sequencing error? |
| 1 | 6 | Yes | 0.00025 | No |
| 2 | 11 | Yes | 0.0005 | No |
| 4 | 22 | Yes | 0.001 | No |
| 16 | 89 | Yes | 0.004 | No |
| 32 | ~2 spatial index regions | Yes | 0.008 | No |
| 64 | ~4 spatial index regions | Yes | 0.016 | No |
| 128 | ~7 spatial index regions | Yes | 0.032 | No |
| 256 | ~14 spatial index regions | Yes | 0.064 | No |
| ... | ... | ... | ... | ... |
| 4000 | ~220 spatial index regions | Yes | 1 | Yes |

†Cells per spatial feature;
*1% sequencing error rate

The number (x) of spatial features 7100 on substrate 7005 required to achieve a desired level of detection sensitivity can be calculated as follows: (X+Y array length)=(spatial feature edge×x)+((x−1)×spatial feature spacing)), where the array length is 20,000 μm, the spatial feature edge is 100 μm, and the spatial feature spacing is, for example, 50 μm; then x=133 spatial features for X dimension and 133 spatial features for Y dimension. The total number of features on substrate 7005 (2 cm×2 cm) is 133×133=~17,689.

What is claimed is:

1. A method, comprising:
   (a) providing a capture array comprising a plurality of capture sites, wherein each capture site of the plurality of capture sites comprises:
       a pair of probes that are separately immobilized on a surface at each capture site, wherein a first probe of the pair of probes comprises a first primer binding region sequence and a spatial address region sequence and does not comprise a poly-T capture sequence, wherein the spatial address region sequence of the first probe comprises a sequence of nucleic acids unique to each capture site such that the spatial address region sequence of each capture site of the plurality of capture sites is different relative to one another, wherein a second probe of the pair of probes comprises a second primer binding region sequence and the poly-T capture sequence and does not comprise the spatial address region sequence and wherein the second probe is a same sequence at each of the plurality of capture sites, wherein the poly-T capture sequence is configured to hybridize to a target nucleic acid comprising a poly-A tail;
   (b) contacting the plurality of capture sites of the capture array with a tissue sample such that a position of each capture site on the capture array can be correlated with a position in the tissue sample;
   (c) subsequent to the contacting, allowing target nucleic acids of the tissue sample, the target nucleic acids comprising the poly-A tail, to hybridize to respective poly-T capture sequences of the second probe of the plurality of capture sites to form hybridized second probes;
   (d) extending the poly-T capture region sequence of the hybridized second probes to form first complementary strands of the sample nucleic acids; and
   (e) linking ends of the first complementary strands to the first probes at each capture site to form immobilized first complementary strands and such that the immobilized first complementary strand comprises the unique spatial address region sequence of the first capture probe associated with each respective capture site and such that immobilized first complementary strands at different capture sites comprise different spatial address region sequences.

2. The method of claim 1, further comprising wherein (e) comprises ligating the immobilized first complementary strands to the spatial address region sequence of the first probes at each capture site to immobilize the first complementary strands at both ends; (f) releasing the first complementary strands from the surface of the capture array and amplifying the first complementary strands to generate second complementary strands; (g) analyzing a sequence of the second complementary strands; and (h) correlating the sequence of the second complementary strands to the position of the target nucleic acid in the tissue sample.

3. The method of claim 1, wherein allowing nucleic acids of the tissue sample to hybridize to the poly-T capture region of the second probe comprises an electrophoretic transfer of the nucleic acids from the tissue sample onto the capture array.

4. The method of claim 1, wherein the first primer binding region sequence and the second primer binding sequence are different.

5. The method of claim 1, where in the first probe further comprises a universal adaptor oligonucleotide; and
   wherein the (e) comprises linking the immobilized first complementary strand to the spatial address sequence of the first probe to immobilize the first complementary strand at both ends via the universal adapter oligonucleotide.

6. The method of claim 1, wherein the linking comprises linking a 3' end of the complementary strand to a 5' end of the first capture probe.

7. The method of claim 1, wherein the first complementary strand comprises a cDNA molecule.

* * * * *

UNITED STATES PATENT AND TRADEMARK OFFICE
CERTIFICATE OF CORRECTION

PATENT NO. : 10,913,975 B2  
APPLICATION NO. : 15/747670  
DATED : February 9, 2021  
INVENTOR(S) : Alex So et al.

Page 1 of 1

It is certified that error appears in the above-identified patent and that said Letters Patent is hereby corrected as shown below:

In the Claims

1. In Column 88, Line 27, in Claim 5, replace "where in" with --wherein--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*